US012703747B2

(12) United States Patent
Sabzevari et al.

(10) Patent No.: US 12,703,747 B2
(45) Date of Patent: Aug. 11, 2026

(54) FUSION CONSTRUCTS AND METHODS OF USING THEREOF

(71) Applicant: PRECIGEN, INC., Germantown, MD (US)

(72) Inventors: Helen Sabzevari, Germantown, MD (US); Simon Metenou, Germantown, MD (US); ChangHung Chen, Germantown, MD (US); Rutul R. Shah, Germantown, MD (US)

(73) Assignee: PRECIGEN, INC., Germantown, MD (US)

( * ) Notice: Subject to any disclaimer, the term of this patent is extended or adjusted under 35 U.S.C. 154(b) by 403 days.

(21) Appl. No.: 18/058,364

(22) Filed: Nov. 23, 2022

(65) Prior Publication Data

US 2024/0141045 A1 May 2, 2024

Related U.S. Application Data

(62) Division of application No. 16/506,981, filed on Jul. 9, 2019, now Pat. No. 11,535,669.

(60) Provisional application No. 62/866,420, filed on Jun. 25, 2019, provisional application No. 62/864,367, filed on Jun. 20, 2019, provisional application No. 62/863,710, filed on Jun. 19, 2019, provisional application No. 62/695,623, filed on Jul. 9, 2018, provisional application No. 62/695,627, filed on Jul. 9, 2018.

(51) Int. Cl.

| | |
|---|---|
| ***C07K 16/28*** | (2006.01) |
| ***A61K 39/00*** | (2006.01) |
| ***A61K 40/11*** | (2025.01) |
| ***A61K 40/31*** | (2025.01) |
| ***A61K 40/36*** | (2025.01) |
| ***A61K 40/42*** | (2025.01) |
| ***A61P 35/00*** | (2006.01) |
| ***C07K 14/71*** | (2006.01) |
| ***C07K 16/22*** | (2006.01) |

(52) U.S. Cl.

CPC .......... *C07K 16/2818* (2013.01); *A61K 40/11* (2025.01); *A61K 40/31* (2025.01); *A61K 40/36* (2025.01); *A61K 40/4202* (2025.01); *A61K 40/421* (2025.01); *A61K 40/4211* (2025.01); *A61K 40/4214* (2025.01); *A61K 40/4229* (2025.01); *A61K 40/4276* (2025.01); *A61P 35/00* (2018.01); *C07K 14/71* (2013.01); *C07K 16/22* (2013.01); *A61K 2039/505* (2013.01); *A61K 2239/50* (2023.05); *A61K 2239/59* (2023.05); *C07K 2317/56* (2013.01); *C07K 2317/92* (2013.01); *C07K 2319/00* (2013.01)

(58) Field of Classification Search

CPC ............ C07K 16/2896; C07K 2319/00; C07K 14/71; A61K 10/36; A61K 40/4229

See application file for complete search history.

(56) References Cited

U.S. PATENT DOCUMENTS

| | | | | |
|---|---|---|---|---|
| 5,595,756 | A * | 1/1997 | Bally | A61K 9/1272 264/4.1 |
| 5,968,780 | A | 10/1999 | Fan et al. | |
| 7,595,048 | B2 | 9/2009 | Honjo et al. | |
| 8,354,509 | B2 | 1/2013 | Carven et al. | |
| 9,180,185 | B2 | 11/2015 | Bauss et al. | |
| 9,629,877 | B2 | 4/2017 | Cooper et al. | |
| 9,676,863 | B2 | 6/2017 | Lo | |
| 9,758,582 | B2 | 9/2017 | Govindappa et al. | |
| 9,809,637 | B2 | 11/2017 | Kumar et al. | |
| 9,850,306 | B2 | 12/2017 | Bedi et al. | |
| 9,987,500 | B2 | 6/2018 | Parapdopoulos et al. | |
| 12,194,094 | B2 | 1/2025 | Sabzevari et al. | |
| 2005/0203022 | A1 | 9/2005 | Gotwals et al. | |
| 2009/0217401 | A1 | 8/2009 | Korman et al. | |
| 2011/0245174 | A1 | 10/2011 | Artymiuk et al. | |
| 2015/0086584 | A1 | 3/2015 | Gilboa et al. | |
| 2016/0193334 | A1 | 7/2016 | Strack et al. | |
| 2016/0272960 | A1 | 9/2016 | Thanos et al. | |
| 2016/0340430 | A1 * | 11/2016 | Bedi | A61K 39/39558 |
| 2017/0233747 | A1 | 8/2017 | Govindappa et al. | |
| 2018/0118832 | A1 | 5/2018 | Lo et al. | |
| 2018/0134766 | A1 | 5/2018 | Larson et al. | |
| 2018/0140686 | A1 | 5/2018 | Varadarajan et al. | |

(Continued)

FOREIGN PATENT DOCUMENTS

| | | | |
|---|---|---|---|
| CN | 109913425 | A | 6/2019 |
| EP | 2542590 | B1 | 5/2017 |

(Continued)

OTHER PUBLICATIONS

Greenspan et al. 1999. Defining epitopes: It's not as easy as it seems; Nature Biotechnology, 17:936-937 (Year: 1999).*
Topalian et al. Safety, Activity, and Immune Correlates of Anti-PD-1 Antibody in Cancer. New England Journal of Medicine. 2012; 366(26): 2443-2454 (Year: 2012).*
Metropulos et al. The difficulty in translating the preclinical success of combined TGFβ and immune checkpoint inhibition to clinical trial. eBioMedicine. Nov. 28, 2022;86:104380 (Year: 2022).*
Heppner et al. Tumor heterogeneity: biological implications and therapeutic consequences. Cancer Metastasis Review 2:5-23; 1983 (Year: 1983).*
Sporn et al. Chemoprevention of Cancer. Carcinogenesis, vol. 21 (2000), 525-530 (Year: 2000).*

(Continued)

*Primary Examiner* — Vanessa L. Ford
*Assistant Examiner* — Sandra Carter
(74) *Attorney, Agent, or Firm* — Gene J. Yao; Barnes & Thornburg LLP

(57) ABSTRACT

Provided herein is a composition comprising a fusion protein or a fragment or a variant thereof comprising an anti-PD1 antibody or a fragment/variant thereof and a TGF-β trap. Provided herein is a composition comprising a fusion protein or a fragment thereof or a variant thereof comprising an anti-PD1 antibody or a fragment/variant thereof and a ADA2 polypeptide. Also provided herein are methods of using the composition in treating cancer.

17 Claims, 52 Drawing Sheets

Specification includes a Sequence Listing.

(56) References Cited

U.S. PATENT DOCUMENTS

2018/0179261 A1 6/2018 Kumar et al.
2018/0327477 A1 11/2018 Kumar et al.
2019/0048085 A1 2/2019 Dotti et al.
2019/0390186 A1 12/2019 Rosbash et al.
2020/0048351 A1 2/2020 Sabzevari et al.

FOREIGN PATENT DOCUMENTS

WO 2011109789 A2 9/2011
WO WO-2013169693 A1 * 11/2013 ............ A61K 38/20
WO WO-2015118175 A2 * 8/2015 ................ A61P 5/00
WO 2015164594 A1 10/2015
WO 2016061286 A2 4/2016
WO 2018129331 A1 7/2018
WO 2018/208720 A1 11/2018
WO 2018205985 A1 11/2018
WO 2019/211489 A1 11/2019
WO 2020/118094 A9 6/2020
WO 2020/263796 A1 12/2020

OTHER PUBLICATIONS

Auerbach et al. Angiogenesis assays: problems and pitfalls. Cancer and Metastasis Reviews, 2000, 19: 167-172 (Year: 2000).*
Gura T. Systems for Identifying New Drugs Are Often Faulty. Science, 1997, 278(5340): 1041-1042 (Year: 1997).*
Jain RK. Barriers to Drug Delivery in Solid Tumors. Scientific American, Jul. 1994,58-65 (Year: 1994).*
Hait. Anticancer drug development: the grand challenges. Nature Reviews/Drug Discovery, 2010, 9, pp. 253-254 (Year: 2010).*
Gravanis et al. The changing world of cancer drug development: the regulatory bodies' perspective. Chin Clin Oncol, 2014, 3, pp. 1-5 (Year: 2014).*
Beans. Targeting metastasis to halt cancer's spread. PNAS 2018; 115(50): 12539-12543 (Year: 2018).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis The 70% Hurdle. Genome Research, 2000, 10:398-400 (Year: 2000).*
David, Justin M., et al., A novel bifunctional anti-PD-L 1/TGF-13 Trap fusion protein (M7824) efficiently reverts mesenchymalization of human lung cancer cells, Oncoimmunology, 2017, vol. 6, No. 10, e1349589, pp. 1-15.
Lan, Yan et al., Enhanced preclinical antitumor activity of M7824, a bifunctional fusion protein simultaneously targeting PD-L 1 and TGF-!3., Sci. Transl. Med. 10, eaan5488 (2018), pp. 1-15.
Qian et al., Binding Affinity of Transforming Growth Factor-b for it's Type II Receptor is Determined by the C-Terminal Region of the Molecule, J Biol Chem, Nov. 29, 1996, vol. 271, No. 48, pp. 30656-30662.
Ravi, Rajani et al., Bifunctional immune checkpoint-targeted antibody-ligand traps that simultaneously disable TGFI3 enhance the efficacy of cancer immunotherapy, Nature Communications I (2018), 9:741, pp. 1-14.
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).
Strauss et al., Clinical Cancer Research, 24:1287-1295 (2018).
Shuguang Tan et al., An Unexpected N-Terminal Loop in PD-1 Dominates Binding by Nivolumab, 8 Nat. Commc'ns, No. 1, art. 14369 (2017).
Shoichiro Horita et al., High-Resolution Crystal Structure of the Therapeutic Antibody Pembrolizumab Bound to Human PD-1, 6 Sci. Rep., art. 35297 (2016).
Jianzhi Zhang, Rates of Conservative and Radical Nonsynonymous Nucleotide Substitutions in Mammalian Nuclear Genes, 50 J. Mol. Evol. 56 (2000).
Pauline C. Ng & Steven Henikoff, Predicting Deleterious Amino Acid Substitutions, 11 Genome Res. 863 (2001).
Jason Baardsnes et al., TβR-II Discriminates the High- and Low-Affinity TGF-β Isoforms via Two Hydrogen-Bonded Ion Pairs, 48 Biochemistry 2146 (2009) (Author Manuscript).
Mary E. Keir et al., PD-1 and Its Ligands in Tolerance and Immunity, 26 Ann. Rev. Immunol. 677 (2008).
D.T. Jones, Critically Assessing the State-of-the-Art in Protein Structure Prediction, 1 Nat. Rev. Mol. Cell Biol. 116 (2000).
S.C.E. Tosatto & S. Toppo, Large-Scale Prediction of Protein Structure and Function from Sequence, 12 Curr. Pharm. Des. 2067 (2006).
Joan Massagué, TGFβ Signalling in Context, 13 Nat. Rev. Mol. Cell Biol. 616 (2012).
Michael Pickup et al., The Roles of TGFβ in the Tumour Microenvironment, 13 Nat. Rev. Cancer 788 (2013).
Philipp Holliger & Peter J. Hudson, Engineered Antibody Fragments and the Rise of Single Domains, 23 Nat. Biotechnol. 1126 (2005).
Megha Garg et al., Rilonacept Maintains Long-Term Inflammatory Remission in Patients with Deficiency of the IL-1 Receptor Antagonist, 2 JCI Insight, e94838 (2017).
Weiping Zou, Immunosuppressive Networks in the Tumour Environment and Their Therapeutic Relevance, 5 Nat. Rev. Cancer 263 (2005).
Sanjeev Mariathasan et al., TGFβ Attenuates Tumour Response to PD-L1 Blockade by Contributing to Exclusion of T Cells, 554 Nature 544 (2018).
M. Brown et al., Tolerance of Single, but Not Multiple, Amino Acid Replacements in Antibody VH CDR2: A Means of Minimizing B Cell Wastage from Somatic Hypermutation?, 156 J. Immunol. 3285 (1996).
C. Lloyd et al., Modelling the Human Immune Response: Performance of a 1011 Human Antibody Repertoire Against a Broad Panel of Therapeutically Relevant Antigens, 22 Protein Eng'g, Des. & Selection 159 (2009).
Bryan M. Edwards et al., The Remarkable Flexibility of the Human Antibody Repertoire: Isolation of Over One Thousand Different Antibodies to a Single Protein, BLyS, 334 J. Mol. Biol. 103 (2003).
Detlef Gossow & Gerhard Seemann, Humanization of Monoclonal Antibodies, in 203 Methods Enzymology 99 (1991).
Karsten Winkler et al., Changing the Antigen Binding Specificity by Single Point Mutations of an Anti-p24 (HIV-1) Antibody, 165 J. Immunol. 4505 (2000).
Jeffrey Skolnick & Jacquelyn S. Fetrow, From Genes to Protein Structure and Function: Novel Applications of Computational Approaches in the Genomic Era, 18 Trends Biotechnol. 34 (2000).

* cited by examiner

| | Protein | $IC_{50}$ (nM) |
|---|---|---|
| ■ | Anti-PD1 hIgG1-TGFbRII | 9.5 |
| □ | Anti-PD1 hIgG4-TGFbRII | 13.4 |

| | Protein | $IC_{50}$ (pM) |
|---|---|---|
| ■ | Anti-PD1 hIgG1-TGFbRII | 12.7 |
| | Anti-PD1 IgG4-TGFbRII | 14.9 |

| | Protein | $IC_{50}$ (pM) |
|---|---|---|
| ■ | Anti-PD1 hIgG1-TGFbRII | 5.3 |
| | Anti-PD1 hIgG4-TGFbRII | 6.7 |

| Protein | $EC_{50}$ (nM) |
|---|---|
| Anti-PD1 (VH7/VL6) | 2.7 |
| Anti-PD1 (VH7/VL6)-wtADA2 | 1.5 |
| Anti-PD1 (VH7/VL6)-mutADA2 | 1.7 |

| Protein | $EC_{50}$ (nM) |
|---|---|
| Anti-PD1 (VH6/VL5) | 6.0 |
| Anti-PD1 (VH6/VL5)-wtADA2 | 2.8 |
| Anti-PD1 (VH6/VL5)-mutADA2 | 4.7 |

| Protein | $LogEC_{50}$ (fM) |
|---|---|
| Anti-PD1 | 6.2 |
| Anti-PD1-wtADA2 | 6.2 |

| | Anti-PD1(VH6/VL5)-wtADA2 | Anti-PD1(VH6/VL5)-mutADA2 |
|---|---|---|
| Km | 179.3 | 23.54 |

FUSION CONSTRUCTS AND METHODS OF USING THEREOF

CROSS REFERENCE TO RELATED APPLICATIONS

The present application is a division of U.S. application Ser. No. 16/506,981, filed Jul. 9, 2019, which in turn claims the benefit of U.S. Provisional Patent Application Nos. 62/695,623 filed on Jul. 9, 2018, 62/695,627 filed on Jul. 9, 2018, 62/863,710 filed Jun. 19, 2019, 62/864,367 filed Jun. 20, 2019 and 62/866,420 filed Jun. 25, 2019. Each of these applications is hereby incorporated by reference in their entireties.

REFERENCE TO SEQUENCE LISTING

The present application contains a Sequence Listing that has been submitted electronically in XML format and is hereby incorporated by reference in its entirety. The XML copy, created on Jul. 25, 2023, is named 75594-371757_SL.xml and is 400,232 bytes in size.

BACKGROUND OF THE DISCLOSURE

Recently, monoclonal antibody-based cancer immunotherapy based on the interruption of suppressive signals that are delivered to the adaptive immune system has shown promise in the clinic. With the FDA approval of CTLA-4 antibody inhibitor (e.g., ipilimumab) and PD-1 inhibitors (e.g., pembrolizumab, nivolumab), more treatment options are now available to treat solid tumors including lung cancer, renal cell cancer, and ovarian cancer. However, in the majority of indications where PD-1/PD-L1 and TGF-β are co-expressed (e.g., ovarian, gastric and colorectal) little to no response to immune checkpoint inhibitors has been observed. Accordingly, there is a continuing need in the art to obtain safer and more effective treatments for cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a fusion protein comprising, (a) an antibody or a fragment of said antibody or a variant of said antibody that binds to programmed cell death protein-1 (PD-1), and (b) a Transforming growth factor beta (TGF-β) cytokine trap; wherein one or more polypeptides of the fusion protein are connected by a linker.

In one embodiment, said linker comprises (G4S)n, wherein n is 2, 3, 4, 5, or 6. In one embodiment, said linker comprises (Gly)n, wherein n is 6, 7, or 8. In one embodiment, said linker comprises (EAAAK)n, wherein n is 1, 2, 3, 4, 5, or 6. In one embodiment, said linker comprises $A(EAAAK)_4ALEA(EAAAK)_4A$. In one embodiment, said linker comprises a sequence as shown in any one of SEQ ID NOs: 17-34. In one embodiment, said TGF-β cytokine trap comprises transforming growth factor receptor (TGFβR), or a functional fragment thereof, an anti-TGF-β antibody or an antigen binding fragment thereof, a TGF-β1 inhibitory peptide or a variant thereof.

In one embodiment, said TGFβR is transforming growth factor beta receptor II (TGFβRII) or said functional fragment thereof. In one embodiment, said functional fragment of TGFβRII is a TGFβRII extracellular domain (ECD). In one embodiment, said ECD binds TGF-β1. In one embodiment, said ECD binds TGF-β3. In one embodiment, said ECD binds TGF-β1 and TGF-β3. In one embodiment, said ECD binds TGF-β1 and TGF-β3 but not TGF-β2. In one embodiment, said TGF-β cytokine trap comprises a sequence at least 80% identical to a sequence as shown in SEQ ID NO: 14, SEQ ID NO. 141, or SEQ ID NO: 142. In one embodiment, said TGF-β cytokine trap comprises a sequence as shown in SEQ ID NO: 14, SEQ ID NO. 141, or SEQ ID NO: 142.

In one embodiment, said TGF-β cytokine trap comprises a sequence as shown in SEQ ID NO: 14. In one embodiment, said antibody (anti-PD1) is immunoglobulin G (IgG) antibody. In one embodiment, said IgG is IgG1, IgG2, IgG3, or IgG4. In one embodiment, said IgG4 comprises a mutation at position 108 of SEQ ID NO 146 or SEQ ID NO: 292. In one embodiment, said mutation is S108P mutation. In one embodiment, said IgG4 is connected to said TGF-β cytokine trap by said linker. In one embodiment, said fragment of said antibody is a Fab, $(Fab)_2$, $(Fab')_2$, Fv, $(Fv)_2$, or scFv.

In one embodiment, said antibody comprises a variable region of heavy chain ($V_H$) and a variable region of light chain ($V_L$) of said antibody. In one embodiment, said linker connects said variable region of heavy chain ($V_H$) to said TGF-β cytokine trap. In one embodiment, said linker connects said variable region of light chain ($V_L$) to said TGF-β cytokine trap. In one embodiment, said variable region of heavy chain ($V_H$) is connected to said variable region of light chain ($V_L$) by a second linker in said fusion protein. In one embodiment, said second linker comprises a sequence as shown in any one of SEQ ID NOs: 17-34. In one embodiment, said variable region of heavy chain ($V_H$) is at least 80% identical to a sequence as shown in any one of SEQ ID NOs: 1-7 and 149-164.

In one embodiment, said variable region of light chain ($V_L$) is at least 80% identical to a sequence as shown in any one of SEQ ID NOs: 8-13 and 148. In one embodiment, said variable region of heavy chain ($V_H$) comprises a sequence as shown in any one of SEQ ID NOs: 1-7 and 149-164. In one embodiment, said variable region of light chain ($V_L$) comprises a sequence as shown in any one of SEQ ID NOs: 8-13 and 148. In one embodiment, said variable region of heavy chain ($V_H$) is at least 90% identical to a sequence as shown in SEQ ID NO: 6 and said variable region of light chain ($V_L$) is at least 90% identical to a sequence as shown in SEQ ID NO: 12. In one embodiment, said variable region of heavy chain ($V_H$) comprises a sequence as shown in SEQ ID NO: 6 and said variable region of light chain ($V_L$) comprises a sequence as shown in SEQ ID NO: 12.

In one embodiment, said fusion protein comprises a sequence as shown in SEQ ID NO: 15 and a sequence as shown in SEQ ID NO: 16. In one embodiment, said fusion protein comprises a sequence as shown in SEQ ID NO: 15 and a sequence as shown in SEQ ID NO: 143. In one embodiment, said variable region of heavy chain (VH) is at least 90% identical to a sequence as shown in SEQ ID NO: 7 and said variable region of light chain is at least 90% identical to a sequence as shown in SEQ ID NO: 13. In one embodiment, said variable region of heavy chain ($V_H$) comprises a sequence as shown in SEQ ID NO: 7 and said variable region of light chain ($V_L$) comprises a sequence as shown in SEQ ID NO: 13.

In one embodiment, said fusion protein comprises a sequence as shown in SEQ ID NO: 296 and a sequence as shown in SEQ ID NO: 145. In one embodiment, said fusion protein comprises a sequence as shown in SEQ ID NO: 296 and a sequence as shown in SEQ ID NO: 144. In one embodiment, said antibody further comprises fragment crystallizable region ($F_C$). In one embodiment, said $F_C$ is human $F_C1$, $F_C2$, $F_C3$, $F_C4$, or a fragment thereof. In one embodiment, said $F_C$ further comprises one or more mutations. In one embodiment, said antibody comprises said scFv and said $F_C$ fragment. In one embodiment, said TGF β cytokine trap comprises said anti-TGF β antibody or said antigen binding fragment thereof. In one embodiment, the anti-TGF β antibody comprises VH encoded by SEQ ID NOs: 166, 168, 169, 171, 173, 175, or 177, and VL encoded by SEQ ID NOs: 165, 167, 170, 172, 174, 176, or 178.

In one embodiment, said TGF β cytokine trap comprises said TGF β inhibitory peptides or said variant thereof. In one embodiment, the TGF β inhibitory peptides comprises sequence set forth in any one of SEQ ID NOs. 193-227.

Provided herein is a polynucleotide encoding the fusion protein disclosed herein.

Provided herein is an expression vector comprising a polynucleotide encoding the fusion protein disclosed herein, wherein said polynucleotide is operably linked to a promoter. In one embodiment, said promoter is a constitutive promoter, a tissue specific promoter, or an inducible promoter. In one embodiment, said inducible promoter is a small molecule ligand-inducible two polypeptide ecdysone receptor-based gene switch. In one embodiment, said vector is an adenoviral vector.

Provided herein is a pharmaceutical composition, comprising: (a) the fusion protein disclosed herein, (b) a polynucleotide encoding the fusion protein disclosed herein, or (c) the expression vector disclosed herein, and (d) a pharmaceutically acceptable excipient.

Provided herein is a method of treating cancer, comprising: contacting a cell with (a) the fusion protein disclosed herein, (b) a polynucleotide encoding the fusion protein disclosed herein, or (c) the expression vector disclosed herein. In one embodiment, said cell is a cancer cell. In one embodiment, said cell is a mammalian cell.

Provided herein is a method of treating a subject with a cancer, the method comprising: administering a composition comprising a fusion protein comprising (a) an antibody or a fragment or a variant of said antibody that binds to programmed cell death protein-1 (PD-1), and (b) a transforming growth factor receptor (TGFβR) or a functional fragment thereof, an anti-TGF-β antibody or an antigen binding fragment thereof, a TGF-β1 inhibitory peptide or a variant thereof; wherein one or more polypeptides of the fusion protein are connected by a linker.

In one embodiment, said linker comprises (G4S)n, wherein n is 2, 3, 4, 5, or 6. In one embodiment, said linker comprises (Gly)n, wherein n is 6, 7, or 8. In one embodiment, said linker comprises (EAAAK)n, wherein n is 1, 2, 3, 4, 5, or 6. In one embodiment, said linker comprises A(EAAAK)4ALEA(EAAAK)4A. In one embodiment, said linker comprises a sequence as shown in any one of SEQ ID NOs: 17-34. In one embodiment, said transforming growth factor receptor protein is TGFβRII. In one embodiment, said functional fragment of said TGFβRII is TGFβRII extracellular domain (ECD). In one embodiment, said TGF-β cytokine trap comprises a sequence at least 80% identical to a sequence as shown in SEQ ID NO: 14, SEQ ID NO: 141, or SEQ ID NO: 142. In one embodiment, said TGF-β cytokine trap comprises a sequence as shown in SEQ ID NO: 14, SEQ ID NO: 141, or SEQ ID NO: 142.

In one embodiment, said antibody is immunoglobulin G (IgG) antibody. In one embodiment, said IgG is IgG1, IgG2, IgG3, or IgG4. In one embodiment, said IgG4 comprises a mutation at position 108 of SEQ ID NO: 146 or SEQ ID NO: 292. In one embodiment, said mutation is S108P mutation. In one embodiment, said fragment of said antibody is a Fab, (Fab)2, (Fab')2, Fv, (Fv)2, or scFv of said antibody. In one embodiment, said antibody or a fragment of said antibody or a variant of said antibody comprises a variable region of heavy chain ($V_H$) and a variable region of light chain ($V_L$). In one embodiment, said linker connects said variable region of heavy chain ($V_H$) to said TGF-β cytokine trap. In one embodiment, said linker connects said variable region of light chain ($V_L$) and to said TGF-β cytokine trap.

In one embodiment, said variable region of heavy chain ($V_H$) is connected to said variable region of light chain ($V_L$) by a second linker. In one embodiment, said variable region of heavy chain ($V_H$) is at least 80% identical to a sequence as shown in any one of SEQ ID NOs: 1-7 and 149-164. In one embodiment, said variable region of light chain ($V_L$) is at least 80% identical to a sequence as shown in any one of SEQ ID NOs: 8-13 and 148. In one embodiment, said variable region of heavy chain ($V_H$) comprises a sequence as shown in any one of SEQ ID NOs: 1-7 and 149-164

In one embodiment, said variable region of light chain ($V_L$) comprises a sequence as shown in any one of SEQ ID NOs: 8-13 and 148. In one embodiment, said variable region of heavy chain ($V_H$) is at least 90% identical to a sequence as shown in SEQ ID NO: 6 and said variable region of light chain ($V_L$) is at least 90% identical to a sequence as shown in SEQ ID NO: 12. In one embodiment, said variable region of heavy chain ($V_H$) comprises a sequence as shown in SEQ ID NO: 6 and said variable region of light chain ($V_L$) comprises a sequence as shown in SEQ ID NO: 12. In one embodiment, said fusion protein comprises a sequence as shown in SEQ ID NO: 15 and a sequence as shown in SEQ ID NO: 16.

In one embodiment, said fusion protein comprises a sequence as shown in SEQ ID NO: 15 (VL5 Igg4) and a sequence as shown in SEQ ID NO: 143. In one embodiment, said variable region of heavy chain (VH) is at least 90% identical to a sequence as shown in SEQ ID NO: 7 and said variable region of light chain ($V_L$) is at least 90% identical to a sequence as shown in SEQ ID NO: 13. In one embodiment, said variable region of heavy chain comprises a sequence as shown in SEQ ID NO: 7 and said variable region of light chain comprises a sequence as shown in SEQ ID NO: 13. In one embodiment, said fusion protein comprises a sequence as shown in SEQ ID NO: 296 and a sequence as shown in SEQ ID NO: 145. In one embodiment, said fusion protein comprises a sequence as shown in SEQ ID NO: 296 and a sequence as shown in SEQ ID NO: 144.

In one embodiment, said antibody further comprises fragment crystallizable region ($F_C$). In one embodiment, said $F_C$ is human $F_C1$, $F_C2$, $F_C3$, $F_C4$, or a fragment thereof. In one embodiment, said $F_C$ further comprises one or more mutations. In one embodiment, said antibody comprises said scFv and said $F_C$ fragment. In one embodiment, said cancer is a refractory cancer. In one embodiment, said subject is non-responsive to a treatment with a PD-1 antibody or a CTLA-4 antibody. In one embodiment, the method further comprises administering one or more additional anti-cancer agent. In one embodiment, said additional anti-cancer agent is a PD-1 inhibitor, PD-L1 inhibitor or a CTLA-4 inhibitor.

In one embodiment, said PD-1 inhibitor is an anti-PD-1 antibody or a fragment or a variant thereof.

In one embodiment, said CTLA-4 inhibitor is an anti-CTLA-4 antibody or a fragment or a variant thereof. In one embodiment, the method further comprises administering one or more cytokines. In one embodiment, said subject is a mammalian subject. In one embodiment, said subject is a human. In one embodiment, said cancer is mesothelioma, glioblastoma, endometrial cancer, colorectal cancer, gastric cancer, cervical cancer, ovarian cancer, pancreatic cancer, prostate cancer, breast cancer, stomach cancer, bladder cancer, liver cancer, Hodgkin's lymphoma, lung cancer, skin cancer, renal cancer or head and neck cancer.

In one embodiment, the skin cancer is cutaneous squamous-cell carcinoma, melanoma or basal cell cancer. In one embodiment, the lung cancer is non small cell lung cancer (NSLC) or small cell lung cancer (SCLC). In one embodiment, the breast cancer is triple negative breast cancer (TNBC). In one embodiment, the method further comprises administering an effective amount of T cells engineered to express an exogenous receptor. In one embodiment, the exogenous receptor is a chimeric antigen receptor. In one embodiment, the chimeric antigen receptor is an engineered T-cell receptor.

In one embodiment, the chimeric antigen receptor comprises an antigen binding domain that binds to an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, MUC-1, MUC-4, MUC-16, MAGE-A1, h5T4, PSMA, TAG-72, EGFR, CD20, EGFRvIII, CD123 or VEGF-R2. In one embodiment, the antigen binding domain comprises a sequence selected from SEQ ID NOs: 37-56. In one embodiment, the antigen binding domain comprises a sequence selected from SEQ ID NOs: 35-36.

In one embodiment, an effective amount of engineered T-cells is at least $10^2$ cells/kg. In one embodiment, an effective amount of engineered T-cells is at least $10^4$ cells/kg. In one embodiment, an effective amount of engineered T-cells is at least $10^5$ cells/kg. In one embodiment, the engineered T cells further express a cytokine. In one embodiment, the cytokine is a fusion protein comprising IL-15 and IL-15Rα.

Provided herein is a method of treating cancer in a subject in need thereof comprising (a) administering a composition comprising a fusion protein comprising an antibody or a fragment of said antibody or a variant of said antibody that binds to programmed cell death protein-1 (PD-1); and a transforming growth factor receptor (TGFβR) protein or a functional fragment thereof; wherein one or more polypeptides of the fusion protein are connected by a linker; and (b) administering to the subject one or more doses of an effective amount of engineered T-cells, wherein the engineered T-cells comprise a chimeric receptor and membrane bound IL-15.

In one embodiment, said fusion protein comprises a sequence as shown in SEQ ID NO: 15 and a sequence as shown in SEQ ID NO: 294. In one embodiment, said fusion protein comprises a sequence as shown in SEQ ID NO: 296 and a sequence as shown in SEQ ID NO: 295. In one embodiment, said fusion protein comprises a sequence as shown in SEQ ID NO: 15 and a sequence as shown in SEQ ID NO: 294. In one embodiment, said fusion protein comprises a sequence as shown in SEQ ID NO: 13 and a sequence as shown in SEQ ID NO: 295.

Disclosed herein are, inter alia, fusion proteins comprising: (a) an antibody or a fragment of said antibody or a variant of said antibody that binds to programmed cell death protein-1 (PD-1); and (b) an adenosine deaminase (ADA) protein or a functional fragment thereof; wherein one or more polypeptides of the fusion protein are connected by a linker. In one embodiment, the linker comprises (G4S)n, wherein n is 2, 3, 4, 5, or 6. In some embodiments, the linker comprises (Gly)n, wherein n is 6, 7, or 8. In another embodiment, the linker comprises (EAAAK)n, wherein n is 1, 2, 3, 4, 5, or 6. In certain embodiments, the linker comprises A(EAAAK)4ALEA(EAAAK)4A. In certain embodiments, the linker comprises a sequence as shown in any one of SEQ ID NOs: 17-34.

In one embodiment, the adenosine deaminase protein is adenosine deaminase 2 (ADA2) or a mutant thereof or a variant thereof. In another embodiment, the adenosine deaminase (ADA) protein comprises any one of ADA2 mutant 1 (SEQ ID NO: 273), ADA2 mutant 2 (SEQ ID NO: 274), ADA2 mutant 3 (SEQ ID NO 275), ADA2 mutant 4 (SEQ ID NO: 276), ADA2 mutant 5 (SEQ ID NO: 277), or ADA2 mutant 6 (SEQ ID NO: 278), ADA2 mutant 7 (SEQ ID NO: 279), or wild type ADA2 (SEQ ID NO: 284). In other embodiment, the adenosine deaminase (ADA) protein comprises a sequence at least 80% identical to a sequence as shown in any one of SEQ ID NOs: 284 or 273-279. In certain embodiments, the adenosine deaminase (ADA) protein comprises a sequence as shown in any one of SEQ ID NOs: 284 or 273-279.

In one embodiment, the antibody is immunoglobulin G (IgG) antibody. In certain embodiments, the IgG is IgG1, IgG2, IgG3, or IgG4. In one embodiment, the IgG4 comprises a mutation at position 108 of SEQ ID NOs: 146 or 292. In some embodiments, the mutation is S108P mutation. In some examples, the fragment of the antibody is a Fab, (Fab)2, (Fab')2, Fv, (Fv)2, or scFv of the antibody. In one embodiment, the antibody or a fragment of the antibody or a variant of the antibody comprises a variable region of heavy chain ($V_H$) and a variable region of light chain ($V_L$). In one embodiment, the linker connects the variable region of heavy chain ($V_H$) to adenosine deaminase 2 (ADA2) or a mutant thereof or a variant thereof. In another embodiment, the linker connects the variable region of light chain ($V_L$) to the adenosine deaminase 2 (ADA2) or a mutant thereof or a variant thereof.

In one example, the variable heavy region ($V_H$) is connected to the variable light region ($V_L$) by a second linker. In one embodiment, the variable region of heavy chain ($V_H$) is at least 80% identical to a sequence as shown in any one of SEQ ID NOs: 1-7 and 149-164. In another example, the variable region of light chain ($V_L$) is at least 80% identical to a sequence as shown in any one of SEQ ID NOs: 8-13 and 148. In a further embodiment, the variable region of heavy chain ($V_H$) comprises a sequence as shown in any one of SEQ ID NOs: 1-7 and 149-164. In a further embodiment, the variable region of light chain ($V_L$) comprises a sequence as shown in any one of SEQ ID NOs: 8-13 and 148. In one embodiment, the variable region of heavy chain (VH) is at least 90% identical to a sequence as shown in SEQ ID NO: 6 (VH6) and the variable region of light chain (VL) is at least 90% identical to a sequence as shown in SEQ ID NO: 12 (VL5). In an embodiment, the variable region of heavy chain ($V_H$) comprises a sequence as shown in SEQ ID NO: 6 and said variable region of light chain ($V_L$) comprises a sequence as shown in SEQ ID NO: 12.

In one example, the fusion protein comprises a sequence as shown in SEQ ID NO: 12 (VL5) and a sequence as shown in SEQ ID NO: 280 (VH6 IgG4 (mut)– ADA2 wt). In another example, the fusion protein comprises a sequence as shown in SEQ ID NO: 12 (VL5) and a sequence as shown in SEQ ID NO: 281 (VH6 igG4 (mut) ADA2 mut 7). In one example, the variable region of heavy chain ($V_H$) is at least 90% identical to a sequence as shown in SEQ ID NO: 7 (VH7) and said variable region of light chain ($V_L$) is at least 90% identical to a sequence as shown in SEQ ID NO: 13 (VL6). In one example, the variable region of heavy chain (VH) comprises a sequence as shown in SEQ ID NO: 7 (VH7) and the variable region of light chain ($V_L$) comprises a sequence as shown in SEQ ID NO: 13 (VL6). In another example, the fusion protein comprises a sequence as shown in SEQ ID NO: 13 (VL6), and a sequence as shown in SEQ ID NO: 282 (VH7 igG4 (mut) ADA2 wt). In one example, the fusion protein comprises a sequence as shown in SEQ ID NO: 13 (VL6), and a sequence as shown in SEQ ID NO: 283 (VH7 igG4 (mut) ADA2 mut 7).

Provided herein is a polynucleotide encoding the fusion protein. Further provided herein is an expression vector comprising a polynucleotide encoding the fusion protein of any one of aspects above, wherein the polynucleotide is operably linked to a promoter. In some embodiments, the promoter is a constitutive promoter, a tissue specific promoter, or an inducible promoter. In some embodiments, the inducible promoter is a small molecule ligand-inducible two polypeptide ecdysone receptor-based gene switch. In some embodiments, the vector is an adenoviral vector.

Provided herein is a method of treating cancer, comprising: contacting a cell with the fusion protein, a polynucleotide encoding the fusion protein, or the expression vector. In some embodiments, the cell is a cancer cell. In some embodiments, the cell is a mammalian cell.

Further provided herein are a pharmaceutical compositions comprising the fusion protein; or a polynucleotide encoding the fusion protein; or the expression vector and, a pharmaceutically acceptable excipient.

Provided herein is a method of treating a subject with a cancer, the method comprising administering a composition comprising a fusion protein comprising an antibody or a fragment of said antibody or a variant of said antibody that binds to programmed cell death protein-1 (PD-1); and an adenosine deaminase protein or a functional fragment thereof; wherein one or more polypeptides of the fusion protein are connected by a linker. In certain cases, the adenosine deaminase protein is adenosine deaminase 2 (ADA2). In other embodiments, the adenosine deaminase (ADA) protein comprises any one of ADA2 mutant 1 (SEQ ID NO: 273), ADA2 mutant 2 (SEQ ID NO: 274), ADA2 mutant 3 (SEQ ID NO 275), ADA2 mutant 4 (SEQ ID NO: 276), ADA2 mutant 5 (SEQ ID NO: 277), or ADA2 mutant 6 (SEQ ID NO: 278), ADA2 mutant 7 (SEQ ID NO: 279), or wild type ADA2 (SEQ ID NO: 284).

In certain cases the linker comprises (G4S)n, wherein n is 2, 3, 4, 5, or 6. In some embodiments, the linker is (Gly)n, wherein n is 6, 7, or 8. In some embodiments, the linker comprises (EAAAK)n, wherein n is 1, 2, 3, 4, 5, or 6. In some embodiments, the linker comprises $A(EAAAK)_4ALEA(EAAAK)_4A$. In some cases, the linker comprises a sequence as shown in any one of SEQ ID Nos: 17-34.

Provided herein is a method of treating a subject with a cancer. In certain cases, the cancer is mesothelioma, glioblastoma, endometrial cancer, colorectal cancer, gastric cancer, cervical cancer, ovarian cancer, pancreatic cancer, prostate cancer, breast cancer, stomach cancer, bladder cancer, liver cancer, Hodgkin's lymphoma, lung cancer, skin cancer, renal cancer or head and neck cancer. In certain cases, the skin cancer is cutaneous squamous-cell carcinoma, melanoma or basal cell cancer. In other cases, the lung cancer is non small cell lung cancer (NSLC) or small cell lung cancer (SCLC). In some cases, the breast cancer is triple negative breast cancer (TNBC).

In another embodiment, there is a method of treating a subject with a cancer, the method comprising administering a composition comprising a fusion protein comprising an antibody or a fragment of said antibody or a variant of said antibody that binds to programmed cell death protein-1 (PD-1); and an adenosine deaminase protein or a functional fragment thereof; wherein one or more polypeptides of the fusion protein are connected by a linker. In a further embodiment, the method of treating a subject with cancer further comprises administering an effective amount of T cells engineered to express an exogenous receptor.

In some cases, the exogenous receptor is a chimeric antigen receptor. In other cases, the chimeric antigen receptor is an engineered T-cell receptor. In one case, the chimeric antigen receptor comprises an antigen binding domain that binds to an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, MUC-1, MUC-4, MUC-16, MAGE-A1, h5T4, PSMA, TAG-72, EGFR, CD20, EGFRvIII, CD123 or VEGF-R2. In some embodiments, the antigen binding domain comprises sequence selected from SEQ ID NOs: 37-56 In other embodiments, the antigen binding domain comprises sequence selected from SEQ ID NOs: 35-36.

In one embodiment, an effective amount of engineered T-cells is at least $10^2$ cells/kg. In another embodiment, an effective amount of engineered T-cells is at least $10^4$ cells/kg. In a further embodiment, the effective amount of engineered T-cells is at least $10^5$ cells/kg.

In a further embodiment, the engineered T cells further express a cytokine. In another embodiment, the cytokine is a fusion protein comprising IL-15 and IL-15Rα.

Provided herein is a method of treating cancer in a subject in need thereof comprising administering a composition comprising a fusion protein comprising an antibody or a fragment of said antibody or a variant of said antibody that binds to programmed cell death protein-1 (PD-1); and an adenosine deaminase protein or a functional fragment thereof; wherein one or more polypeptides of the fusion protein are connected by a linker, and administering to the subject one or more doses of an effective amount of engineered T-cells, wherein the engineered T-cells comprise a chimeric receptor and membrane bound IL-15.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
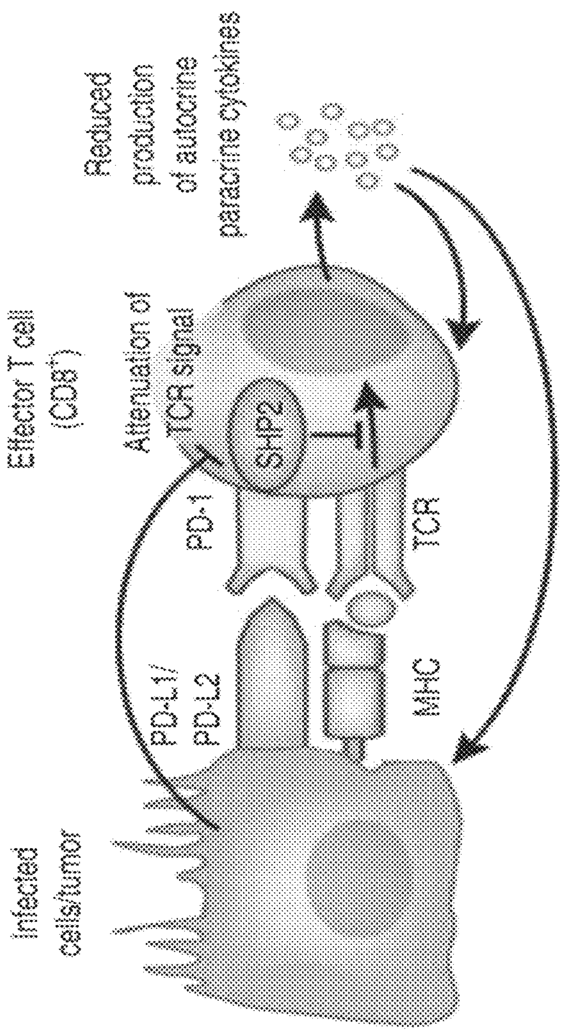
FIG. 1 is a schematic of PD-1/PD-L1 in immunosuppression.

The following description and examples illustrate embodiments of the present disclosure in detail.

It is to be understood that the present disclosure is not limited to the particular embodiments described herein and as such can vary. Those of skill in the art will recognize that there are variations and modifications of the present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Polynucleotide" or "oligonucleotide" as used herein refers to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Transfection," "transformation," or "transduction" as used herein refer to the introduction of one or more exogenous polynucleotides into a host cell by using physical or chemical methods. The polynucleotide sequences and vectors disclosed or contemplated herein can be introduced into a cell by, for example, transfection, transformation, or transduction. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

"Polypeptide", "peptide", and their grammatical equivalents as used herein refer to a polymer of amino acid residues. The polypeptide can optionally include glycosylation or other modifications typical for a given protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides or proteins described herein in an engineered cell can be associated with post-translational modifications of one or more amino acids of the polypeptide or protein. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

The terms "identical" and its grammatical equivalents as used herein or "sequence identity" in the context of two nucleic acid sequences or amino acid sequences of polypeptides refer to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, Gene, 73:237-244 (1988) and Higgins and Sharp, *CABIOS,* 5:151-153 (1989); Corpet et al., *Nucleic Acids Res.,* 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, the percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In some embodiments, the substantial identity exists over a region of the sequences that is at least about 50 residues in length, over a region of at least about 100 residues, and in some embodiments, the sequences are substantially identical over at least about 150 residues. In some embodiments, the sequences are substantially identical over the entire length of the coding regions.

"Homology" is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available. Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed "homologs." For example, any naturally occurring proteins can be modified by any available mutagenesis method. When expressed, this mutagenized nucleic acid encodes a polypeptide that is homologous to the protein encoded by the original nucleic acid.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

The term "coding sequence" as used herein refers to a segment of a polynucleotide that encodes for protein or polypeptide. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "induce", "induction" and its grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

The term "antibody", also known as immunoglobulin (Ig), as used herein can be monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. The antibodies can be from any animal origin. An antibody can be IgG (including IgG1, IgG2, IgG3, and IgG4), IgA (including IgA1 and IgA2), IgD, IgE, or IgM, and IgY. In some embodiments, the antibody can be whole antibodies, including single-chain whole antibodies. In some embodiments, the antibody can be a fragment of an antibody, which can include, but are not limited to, a Fab, a Fab', a $F(ab')_2$, a Fd (consisting of $V_H$ and CH1), a Fv fragment (consisting of $V_H$ and $V_L$), a single-chain variable fragment (scFv), a single-chain antibody, a disulfide-linked variable fragment (dsFv), and fragments comprising either a $V_L$ or $V_H$ domain. A whole antibody typically consists of four polypeptides: two identical copies of a heavy (H) chain polypeptide and two identical copies of a light (L) chain polypeptide. Each of the heavy chains contains one N-terminal variable ($V_H$) region and three C-terminal constant (CH1, CH2 and CH3) regions, and each light chain contains one N-terminal variable ($V_L$) region and one C-terminal constant ($C_L$) region. The variable regions of each pair of light and heavy chains form the antigen binding site of an antibody. The $V_H$ and $V_L$ regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

The terms "fragment of an antibody," "antibody fragment," "fragment of an antibody," "antigen-binding portion" or its grammatical equivalents are used interchangeably herein to mean one or more fragments or portions of an antibody that retain the ability to specifically bind to an antigen (see, generally, Holliger et al., Nat. Biotech., 23(9): 1126-1129 (2005)). The antibody fragment desirably comprises, for example, one or more CDRs, the variable region (or portions thereof), the constant region (or portions thereof), or combinations thereof. Non-limiting examples of antibody fragments include (1) a Fab fragment, which is a monovalent fragment consisting of the $V_L$, $V_H$, $C_L$, and CH1 domains; (2) a F(ab')2 fragment, which is a bivalent fragment comprising two Fab fragments linked by a disulfide bridge at the stalk region; (3) a Fv fragment consisting of the $V_L$ and $V_H$ domains of a single arm of an antibody; (4) a single chain Fv (scFv), which is a monovalent molecule consisting of the two domains of the Fv fragment (i.e., $V_L$ and $V_H$) joined by a linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (5) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Pat. No. 8,603,950.

"Antigen recognition moiety," "antigen recognition domain," "antigen binding domain," or "antigen binding region" refers to a molecule or portion of a molecule that specifically binds to an antigen. In one embodiment, the antigen recognition moiety is an antibody, antibody like molecule or fragment thereof.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein.

The term "proliferative disease" as referred to herein refers to a unifying concept in which excessive proliferation of cells and/or turnover of cellular matrix contributes significantly to the pathogenesis of the disease, including cancer. In some embodiments, the proliferative disease is cancer.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to cancer.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment", "treating", or its grammatical equivalents refers to obtaining a desired pharmacologic and/or physiologic effect. In embodiments, the effect is therapeutic, i.e., the effect partially or completely cures a disease and/or adverse symptom attributable to the disease. In some embodiments, the term "treating" can include "preventing" a disease or a condition.

As used herein, a "treatment interval" refers to a treatment cycle, for example, a course of administration of a therapeutic agent that can be repeated, e.g., on a regular schedule. In embodiments, a dosage regimen can have one or more periods of no administration of the therapeutic agent in between treatment intervals. For example, a treatment interval can include one dose of a fusion protein administered in combination with (prior, concurrently or after) administration of a second therapeutic agent, e.g. CAR-T cells.

The terms "administered in combination" or "co-administration" or "co-administering" or "co-providing" as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the first treatment and second treatment can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, treatment. The order of administration of the first and secondary treatment can also be reversed.

The term "therapeutically effective amount", therapeutic amount", "immunologically effective amount", "anti-tumor effective amount", "tumor-inhibiting effective amount" or its grammatical equivalents refers to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

Programmed Cell Death Protein and Other Check Point Inhibitors

Programmed cell death protein 1, also known as PD-1 or CD279 (cluster of differentiation 279), is an immune checkpoint protein. The PD-1/PD-L1 signaling axis can promote tumor mediated immune evasion. In some cases, PDL-1 can be over-expressed by tumor cells, accessory cells, such as myeloid-derived suppressor cell (MDSCs), tumor associated macrophages (TAMs), antigen presenting cells (APCs), in the tumor microenvironment. In some cases, PD-1 can be upregulated by "exhausted" T cells and can signal to suppress effector T cells function upon binding to its ligand (PDL-1, PDL2, and CD80). Blockade of the PD-1/PD-L1 pathway by anti-PD-1 or anti-PD-L1 can restore the function of exhausted T cells and promote tumor cell killing (FIG. 1).

In some embodiments, the fusion protein comprising a PD-1 inhibitor and TGF-β trap can comprise, but not limited to, a full length nivolumab (anti-PD-1), MK-3945 (anti-PD-1), pembrolizumab (anti-PD-1), pidilizumab (anti-PD-1), REGN2810 (anti-PD-1), AMP-224 (anti-PD-1), MEDI0680 (anti-PD-1), PDR001 (anti-PD-1), CT-001 (anti-PD-1), or a functional fragment or a variant thereof. In some embodiments, the PD-1 inhibitor is nivolumab. In some embodiments, the PD-1 inhibitor is pembrolizumab.

Fusion Proteins

In some embodiments, the fusion protein or a fragment thereof or a variant thereof provided herein comprises the PD-1 inhibitor or antibody fused to a cytokine trap via a linker.

In some embodiments, the PD-1 inhibitor can be an antibody or a fragment of the antibody or a variant of the antibody that targets PD-1. In some embodiments, the fusion protein comprising prembrolizumab can be fused to a cytokine trap (e.g., TGF-β trap). In some embodiments, the fusion protein comprising nivolumab can be fused to a cytokine trap (e.g., TGF-β trap).

In some embodiments, the fusion protein or a fragment thereof or a variant thereof described herein comprises a cytokine trap as described above and an antibody, a fragment or a variant of the antibody that targets immune checkpoint genes. In some embodiments, an antibody or a fragment of the antibody or a variant of the antibody that target immune checkpoints, such as cytotoxic T lymphocyte associated protein-4 (CTLA-4) and programmed cell death-ligand-1 (PDL1), can be fused to a TGF-β trap molecule via a linker. In some embodiments, the PD-L1 inhibitor is atezolizumab.

In some embodiments, the fusion protein or a fragment thereof or a variant thereof provided herein comprises the PD1 inhibitor or antibody fused to an adenosine deaminase (e.g., ADA2) described herein or a functional variant or derivative thereof.

Cytokine Trap

Cytokines have an impact on many biological processes. Inhibiting cytokines can have clinical benefits for example, in cancer. Several cytokines have been shown to be causative agents in a variety of diseases. Such cytokines, include but are not limited to IL-1, IL-4, 11-6, TNF-α, TGF-beta and its various isoforms. The term "cytokine trap" as used herein refers to blockers or neutralizers of cytokine action. Examples of such cytokine traps can include but are not limited to extracellular domains of the cytokine receptors, antibodies that bind to cytokines, and peptides that bind to the cytokines (e.g. inhibitory peptides). In one embodiment, the cytokine is TGF-β. In one embodiment, the cytokine is TGF-β1. In one embodiment, the cytokine is TGF-β3. In one embodiment, the cytokine is TGF-β1 and TGF-β3. In further embodiments, cytokine traps that target TGF-β (e.g. TGF-β trap) can include the extracellular domain of TGF-βRII or its variants thereof (for example, SEQ ID NO 141 and 142), anti-TGF-β antibodies and inhibitory peptides of TGF-β1, TGF-β2 and/or TGF-β3.

Transforming Growth Factor

Transforming growth factor-β (TGF-β) is a multifunctional set of peptides that can control proliferation, differentiation, and other functions in many cell types. TGF-β can act synergistically with TGF-α in inducing transformation. It also can act as a negative autocrine growth factor. Dysregulation of TGF-β activation and signaling can result in apoptosis. Many cells can synthesize TGF-β and almost all of them have specific receptors for this peptide. TGF-β1, TGF-β2, and TGF-β3 all can function through the same receptor signaling systems. TGF-β1 can play an important role in controlling the immune system, and can show different activities on different types of cell, or cells at different developmental stages. Most immune cells (or leukocytes) can secrete TGF-β1. TGF-β1 is a peptide of 112 amino acid residues derived by proteolytic cleavage from the C-terminal of a precursor protein. TGF-β, a small secreted polypeptide, can signal through the type II serine/threonine kinase dimeric receptor (TGFβRII) that can recruit and phosphorylate the type I dimeric receptor (TGFβRI). TGFβRI can phosphorylate and activate SMADs which can be transcription factors regulating genes involved in cell proliferation, differentiation, apoptosis and growth. Many advanced stage cancers are known to over-express both the TGF-β and TGFβR promoting aggressive tumor formation. Inhibiting the TGFB signaling pathway can be a key therapeutic strategy in treating cancer.

Figure 2:
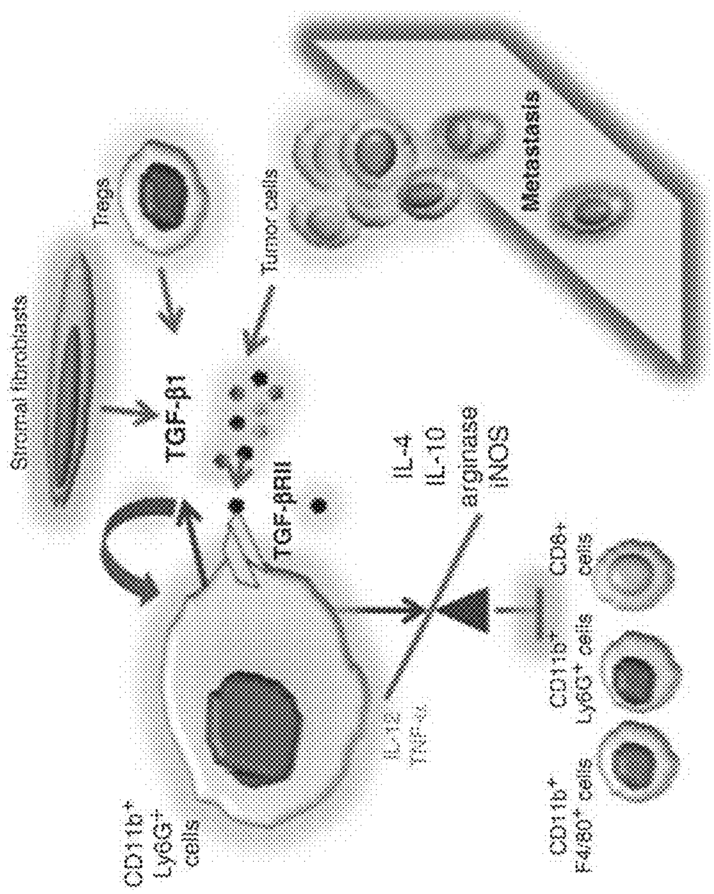
FIG. 2 is a schematic of TGF-β in immunosuppression.
Figure 3:
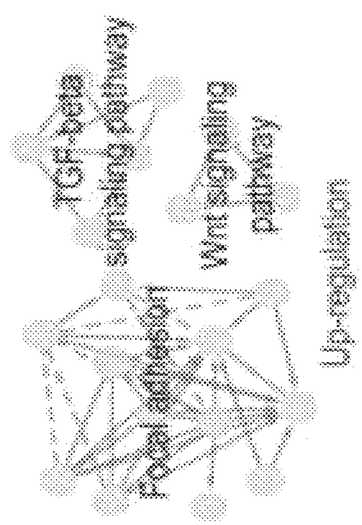
FIG. 3 shows TGF-β associated gene cluster correlated with metastatic disease and poor prognosis in subset of ovarian cancer patients (enriched in Stage III/IV).

Some T cells (e.g., regulatory T cells) can release TGF-β1 to inhibit the actions of other T cells. IL-1 and IL-2 dependent proliferation of activated T cells, and the activation of quiescent helper T cells and cytotoxic T cells can be prevented by the activity of TGF-β1. Similarly, TGF-β1 can inhibit the secretion and activity of many other cytokines including, but not limited to, interferon-γ, tumor necrosis factor alpha (TNF-α) and various interleukins. It can also decrease the expression levels of cytokine receptors, such as the IL-2 receptor, to down-regulate the activity of immune cells. However, TGF-β1 can also increase the expression of certain cytokines in T cells and can promote their proliferation, particularly if the cells are immature (FIG. 2).

TGF-β1 can have similar effects on B cells that vary according to the differentiation state of the cell. It can inhibit proliferation and can stimulate apoptosis of B cells, and can play a role in controlling the expression of antibody, transferrin, and MHC class II proteins on immature and mature B cells.

The effects of TGF-β1 on macrophages and monocytes can be predominantly suppressive; this cytokine can inhibit the proliferation of these cells and can prevent their production of reactive oxygen (e.g., superoxide (02)) and nitrogen (e.g., nitric oxide (NO)) intermediates. However, as with other cell types, TGF-β1 can also have the opposite effect on cells of myeloid origin. For example, TGF-β1 can act as a chemoattractant, directing an immune response to some pathogens; macrophages and monocytes can respond to low levels of TGF-β1 in a chemotactic manner. Furthermore, the expression of monocytic cytokines (including IL-1α, IL-β, and TNF-α), and phagocytic killing by macrophages can be increased by the action of TGF-β1 (FIG. 2).

Transforming Growth Factor—Beta III (TGF-β3), a subset of a cytokine family, is responsible for a plethora of functions including cellular proliferation, embryogenesis, immune system regulation, and differentiation.

Transforming Growth Factor-β Receptor II (TGFβRII)

TGF-β receptors (TGFβR) are single pass serine/threonine kinase receptors. They can exist in several different isoforms that can be homodimeric or heterodimeric. The number of characterized ligands in the TGF-β superfamily can far exceed the number of known receptors, suggesting the promiscuity between the ligand and receptor interactions. Three TGF-β superfamily receptors (TGFβR) specific for TGF-β can be distinguished by their structural and functional properties. TGFβRI (ALK5) and TGFβRII can have similar ligand-binding affinities and can be distinguished from each other only by peptide mapping. Both TGFβRI and TGFβRII can have a high affinity for TGF-β1 and low affinity for TGF-β2. TGFβRIII (0-glycan) can have a high affinity for both homodimeric TGF-β1 and TGF-β2 and in addition the heterodimer TGF-β1,2. The TGFβ receptors can also bind to TGF-β3. By "TGFβRII" or "TGFβ Receptor II" is meant a polypeptide having the wild-type human TGFβ Receptor Type 2 Isoform A sequence (e.g., the amino acid sequence of NCBI Reference Sequence (RefSeq) Accession No. NP_001020018 (SEQ ID NO: 289), or a polypeptide having the wild-type human TGFβ Receptor Type 2 Isoform B sequence (e.g., the amino acid sequence of NCBI RefSeq Accession No. NP_003233 (SEQ ID NO: 290) or having a sequence substantially identical the amino acid sequence of SEQ ID NO: 289 or of SEQ ID NO: 290. The TGFβRII may retain at least 0.1%, 0.5%, 1%, 5%, 10%, 25%, 35%, 50%, 75%, 90%, 95%, or 99% of the TGFβ-binding activity of the wild-type sequence. The polypeptide of expressed TGFβRII lacks the signal sequence.

TGF-β1 can reduce the efficacy of the MHC II in astrocytes and dendritic cells, which in turn can decrease the activation of appropriate helper T cell populations. TGF-β1 can promote tumor growth as cancer progresses and in some embodiments, does not suppress inflammatory cells responses but can promote regulatory T cell function. TGF-β1 can be produced by tumor cells, tumor-associated fibroblast cells, regulatory T cells and immature myeloid cells. TGF-β1 can inhibit T cell priming and promote an exhausted phenotype. TGF-β1 can suppress the anti-tumor activity of innate immune cell populations including natural killer cells, macrophages and dendritic cells. TGF-β receptor II can be upregulated by tumor-associated myeloid cells and can promote metastasis.

TGF-β Trap Fusion Proteins or Fragments or Variant Thereof

Provided herein is a fusion protein or a fragment or a variant thereof comprising an immune checkpoint inhibitor, such as a PD-1 inhibitor or antibody, and a cytokine trap that can neutralize the cytokine (for instance, TGF-β). In certain cases, a cytokine trap can be a TGF-β trap (also referred to as TGF-βRII or fragment or variant thereof) that comprises SEQ ID NO. 142. Examples of TGF-β trap can include, but are not limited to, extracellular domain (ECD) of the receptor (e.g., TGFβRII) or a functional variant or derivative thereof, TGF-β inhibitory peptides (for instance, SEQ ID NO. 193-227), or an anti-TGF-β antibodies. In some embodiments, the anti-TGF-β antibody comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 166, 168, 169, 171, 173, 175, or 177. In some embodiments, the anti-TGF-β antibody comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 165, 167, 170, 172, 174, 176, or 178. In certain embodiments, a TGF-β trap can specifically bind or have high affinity for TGF-β1 or TGF-β2 or TGF-β3. In other embodiments, a TGF-β trap can specifically bind or have high affinity for TGF-β1, TGF-β2 and TGF-β3. In other embodiments, a TGF-β trap can specifically bind or have high affinity for TGF-β1 and TGF-β3. In further embodiments, a TGF-β trap can have low affinity for or not bind TGF-β2.

The fusion protein or a fragment or a variant thereof provided herein (e.g., PD-1 inhibitor or antibody fused to a cytokine trap such as a TGF-β trap) can elicit a synergistic anti-tumor effect due to the simultaneous blockade of the interaction between e.g., PD-L1 on tumor cells and PD-1 on immune cells, and the neutralization of e.g., TGF-β in the tumor microenvironment. Without being bound by theory, this effect is obtained from simultaneous blocking the two major immune escape mechanisms and the targeted depletion of the TGF-β in the tumor microenvironment by a single molecular entity. This depletion can be achieved by one or more of the following: (1) anti-PD-1 targeting of tumor cells; (2) binding of the TGF-β in the tumor microenvironment by the TGF-β trap (e.g., TGFbRII); and/or (3) destruction of the bound TGF-β through the PD-L1 receptor mediated endocytosis. The fusion protein or a fragment or a variant thereof provided herein (e.g., PD-1 inhibitor or antibody fused to a cytokine trap such as a TGF-β trap) can also promote natural killer cell-mediated killing of tumor cells. (i) TGFβRII trap fusion proteins or Fragments or a variant thereof.

In some embodiments, a fusion protein or a fragment or a variant thereof also comprises a cytokine trap and a PD-1 inhibitor or anti-PD-1 antibody or a fragment or a variant thereof. In some embodiments is a fusion protein or a fragment or a variant thereof comprising the cytokine trap (for instance, TGF-β trap) fused to a PD-1 inhibitor optionally via a cleavable or non-cleavable linker. In some embodiments, the cytokine trap (e.g., TGF-β trap) is a cytokine receptor (e.g., TGFβRII). In some embodiments, the cytokine receptor sequence in a fusion protein described herein comprises an extracellular domain (ECD) of the receptor (e.g., TGFβRII) or a functional variant or derivative thereof. In some embodiments, the extracellular domain (ECD) of TGFβRII comprises a polypeptide sequence as shown in SEQ ID NO: 14. In some embodiments, the cytokine receptor sequence in a fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 14. In some embodiments, the cytokine receptor sequence in a fusion protein described herein comprises an extracellular domain (ECD) of the receptor (e.g., TGFβRII) or a functional variant or derivative thereof. In some embodiments, the extracellular domain (ECD) of TGFβRII comprises a polypeptide sequence as shown in SEQ ID NO: 141. In some embodiments, the cytokine receptor sequence in a fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 141. In some embodiments, the cytokine receptor sequence in a fusion protein described herein comprises an extracellular domain (ECD) of the receptor (e.g., TGFβRII) or a functional variant or derivative thereof. In some embodiments, the extracellular domain (ECD) of TGFβRII comprises a polypeptide sequence as shown in SEQ ID NO: 142. In some embodiments, the cytokine receptor sequence in a fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 142. In some embodiments, the cytokine receptor sequence in a fusion protein or a fragment or a variant thereof described herein binds TGF-β1 and/or TGF-β3 but does not bind TGF-β2. In certain embodiments, the cytokine receptor sequence in a fusion protein or a fragment or a variant thereof described herein only binds TGF-β1. In certain embodiments, the cytokine receptor sequence in a fusion protein or a fragment or a variant thereof described herein only binds TGF-β3. In certain embodiments, the cytokine receptor sequence in a fusion protein or a fragment or a variant thereof described herein only binds TGF-β1 and/or TGF-β3 but has low to no affinity for TGF-β2.

In some embodiments, a PD-1 antibody is fused to TGFβRII or a fragment thereof (e.g., ECD of TGFβRII). In some embodiments, a PD-1 antibody moiety is fused to TGFβRII or a fragment thereof (e.g., ECD of TGFβRII) via a linker. In some embodiments, a PD-1 antibody moiety is fused to at least one extracellular domain of TGFβRII. In some embodiments, a PD-1 antibody moiety is fused to at least one extracellular domain of TGFβRII via a linker.

In some embodiments, a PD-1 antibody fragment or variant is a Fab, $Fab_2$, $(Fab')_2$, Fv, $(Fv)_2$, scFv, scFv-$F_C$, $F_C$, diabody, triabody, or minibody of the PD-1 antibody. In some embodiments, a PD-1 antibody fragment is a single-domain antibody of the PD-1 antibody. In some embodiments, the single-domain antibody is a $V_{NAR}$ or $V_H$H fragment of the PD-1 antibody.

Figure 4A:
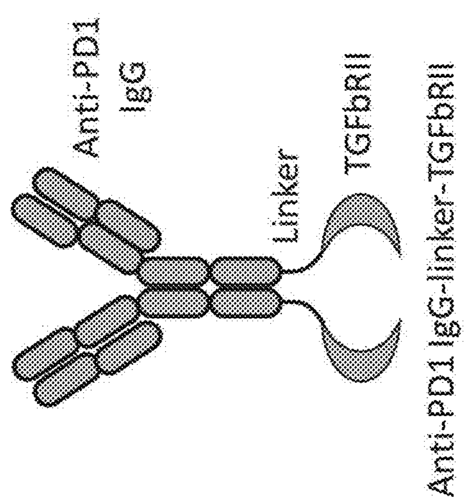
FIG. 4A, FIG. 4B, and FIG. 4C show a schematic design of anti-PD1-TGFRII fusion protein design. In other exemplary embodiments, ADA2 can be fused to anti-PD1.
Figure 4B:
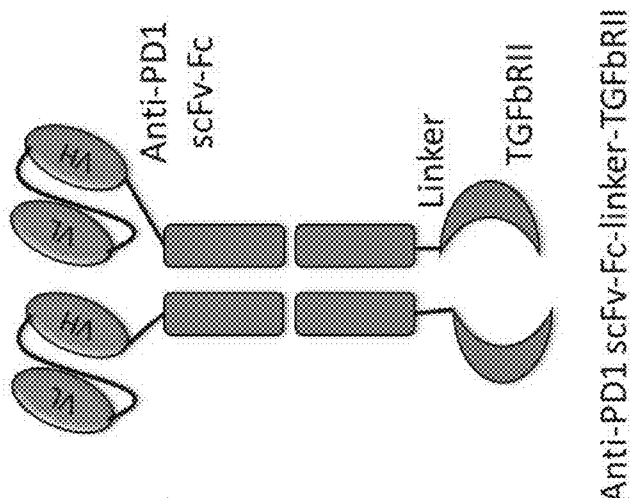
Figure 4C:
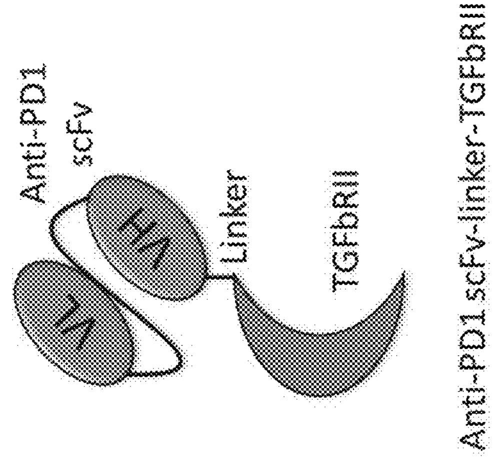

Non-limiting exemplary fusion proteins are illustrated in FIGS. 4A-4C. In some embodiments, the fusion protein comprising an anti-PD-1 antibody or a fragment or a variant thereof fused to a TGF-β trap can elicit a synergistic anti-tumor effect due to the simultaneous blockade of the interaction between PD-L1 on tumor cells and PD-1 on immune cells, and the neutralization of TGF-β in the tumor microenvironment. Without being bound by theory, this effect is obtained from simultaneous blocking the two major immune escape mechanisms and the targeted depletion of the TGF-β in the tumor microenvironment by a single molecular entity. This depletion is achieved by (1) PD-1 targeting of tumor cells; (2) binding of the TGF-β in the tumor microenvironment by the TGF-β trap (e.g., TGFβRII); and (3) destruction of the bound TGF-β through the PD-L1 receptor mediated endocytosis.

In some embodiments, the TGF-β trap (e.g., TGFβRII) is fused to a variable region of heavy chain ($V_H$) of PD-1 antibody or a fragment/variant thereof. In other embodiments, the TGF-β trap is fused to IgG of a PD-1 antibody (for example, FIG. 4A). In certain aspects, the IgG is IgG1, IgG2, IgG3, or IgG4. In an embodiment, the IgG is IgG4. In another embodiment, the IgG4 is SEQ ID NO 146 (wild type), SEQ ID NO: 291, SEQ ID NO: 292 or SEQ ID NO: 147 (S108P). In some embodiments, the TGF-β trap (e.g., TGFβRII) is fused to a variable region of heavy chain ($V_H$) of PD-1 antibody or a fragment/variant thereof via a linker. In some embodiments, the TGF-β trap (e.g., TGFβRII) is fused to a constant region of the $V_H$ of PD-1 antibody or a fragment/variant thereof via a linker. Examples of $V_H$ sequence of a PD-1 antibody or fragment or variant thereof include but are not limited to SEQ ID NOs.: 1-7 and 149-164. Examples of $V_L$ sequence of a PD-1 antibody or fragment or variant thereof include but are not limited to SEQ ID NOs.: 8-13 and 148. In some embodiments, the TGF-β trap (e.g., TGFβRII) is fused a variable region of light chain ($V_L$) of PD-1 antibody or a fragment/variant thereof. In some embodiments, the TGF-β trap (e.g., TGFβRII) is fused to a constant region of the $V_L$ of PD-1 antibody or a fragment/variant thereof via a linker. In some embodiments, the TGF-β trap (e.g., TGFβRII) is fused a variable region of light chain ($V_L$) of PD-1 antibody or a fragment/variant thereof via a linker. In one aspect, the TGF-β trap (e.g., TGFβRII) is fused to either the N- or C-terminus of the VL or VH chain or a fragment/variant thereof via a linker.

The term “anti-PD1 (VL/VH)-TGFβRII” or “anti-PD1 (VH/VL)-TGFβRII” is used interchangeably and denotes the specific VL or VH used in the fusion protein. In one embodiment, the terms "anti-PD1 (VL/VH)-TGFβRII" or "anti-PD1 (VH/VL)-TGFβRII" refers to TGF-β trap (e.g., TGFβRII) fused to constant region of the heavy chain of anti-PD1 or alternatively, refers to TGF-β trap (e.g., TGFβRII) fused to constant region of the light chain of anti-PD1.

In some embodiments, the TGF-β trap (e.g., TGFβRII) is fused to a Fab of PD-1 antibody or a fragment/variant thereof. In some embodiments, the TGF-β trap (e.g., TGFβRII) is fused to a Fab of PD-1 antibody or a fragment/variant thereof via a linker. In some embodiments, the TGF-β trap (e.g., TGFβRII) is fused to a $Fab_2$ of PD-1 antibody or a fragment/variant thereof. In some embodiments, the TGF-β trap (e.g., TGFβRII) is fused to a $Fab_2$ of PD-1 antibody or a fragment/variant thereof via a linker. In some embodiments, the TGF-β trap (e.g., TGFβRII) is fused to a $(Fab')_2$ of PD-1 antibody or a fragment/variant thereof. In some embodiments, the TGF-β trap (e.g., TGFβRII) is fused to a $(Fab')_2$ of PD-1 antibody or a fragment/variant thereof via a linker. In one aspect, the TGF-β trap (e.g., TGFβRII) is fused to either the N- or C-terminus of the Fab or $(Fab')_2$ of PD-1 antibody or a fragment/variant thereof via a linker.

In some embodiments, the TGF-β trap (e.g., TGFβRII) is fused to a Fv of PD-1 antibody or a fragment/variant thereof. In some embodiments, the TGF-β trap (e.g., TGFβRII) is fused to a Fv of PD-1 antibody or a fragment/variant thereof via a linker. In some embodiments, the TGF-β trap (e.g., TGFβRII) is fused to a $(Fv)_2$ of PD-1 antibody or a fragment/variant thereof. In some embodiments, the TGF-β trap (e.g., TGFβRII) is fused to a $(Fv)_2$ of PD-1 antibody or a fragment/variant thereof via a linker. In one aspect, the TGF-β trap (e.g., TGFβRII) is fused to either the N- or C-terminus of the Fv or $(Fv)_2$ of PD-1 antibody or a fragment/variant thereof via a linker.

In some embodiments, the TGF-β trap (e.g., TGFβRII) is fused to a scFv of PD-1 antibody or a fragment/variant thereof. In some embodiments, the TGF-β trap (e.g., TGFβRII) is fused to a scFv of PD-1 antibody or a fragment/variant thereof via a linker. In some embodiments, the TGF-β trap (e.g., TGFβRII) is fused to a scFv-$F_C$ of PD-1 antibody or a fragment/variant thereof. In some embodiments, the TGF-β trap (e.g., TGFβRII) is fused to a scFv-$F_C$ of PD-1 antibody or a fragment/variant thereof via a linker. In one aspect, the TGF-β trap (e.g., TGFβRII) is fused to either the N- or C-terminus of the scFv or scFv-Fc of PD-1 antibody or a fragment/variant thereof via a linker.

In some embodiments, the TGF-β trap (e.g., TGFβRII) is fused to a $F_C$ of PD-1 antibody or a fragment/variant thereof. In some embodiments, the TGF-β trap (e.g., TGFβRII) is fused to a $F_C$ of PD-1 antibody or a fragment/variant thereof via a linker. In some embodiments, the TGF-β trap (e.g., TGFβRII) is linked to a C-terminus $F_C$ of PD-1 antibody or a fragment/variant thereof. In some embodiments, the TGF-β trap (e.g., TGFβRII) is linked to a C-terminus $F_C$ of PD-1 antibody or a fragment/variant thereof via a linker. In some embodiments, the TGF-β trap (e.g., TGFβRII) is linked to a N-terminus $F_C$ of PD-1 antibody or a fragment/variant thereof. In some embodiments, the TGF-β trap (e.g., TGFβRII) is linked to a N-terminus $F_C$ of PD-1 antibody or a fragment/variant thereof via a linker.

In some embodiments, the TGF-β trap (e.g., TGFβRII) is fused to a diabody of PD-1 antibody or a fragment/variant thereof. In some embodiments, the TGF-β trap (e.g., TGFβRII) is fused to a diabody of PD-1 antibody or a fragment/variant thereof via a linker. In some embodiments, the TGF-β trap (e.g., TGFβRII) is fused to a triabody of PD-1 antibody or a fragment/variant thereof. In some embodiments, the TGF-β trap (e.g., TGFβRII) is fused to a triabody of PD-1 antibody or a fragment/variant thereof via a linker. In some embodiments, the TGF-β trap (e.g., TGFβRII) is fused to a minibody of PD-1 antibody or a fragment/variant thereof. In some embodiments, the TGF-β trap (e.g., TGFβRII) is fused to a minibody of PD-1 antibody or a fragment/variant thereof via a linker. In one aspect, the TGF-β trap (e.g., TGFβRII) is fused to either the N- or C-terminus of the minibody of PD-1 antibody or a fragment/variant thereof via a linker.

In some embodiments, the TGF-β trap (e.g., TGFβRII) is fused to a $V_{N}AR$ of PD-1 antibody or a fragment/variant thereof. In some embodiments, the TGF-β trap (e.g., TGFβRII) is fused to a $V_{N}AR$ of PD-1 antibody or a fragment/variant thereof via a linker. In all embodiments, as described, the TGF-β trap (e.g., TGFβRII) is fused to either the N- or C-terminus of the $V_{N}AR$ of PD-1 antibody or a fragment/variant thereof via a linker.

In some embodiments, the TGF-β trap (e.g., TGFβRII) is fused to a $V_{H}H$ of PD-1 antibody or a fragment/variant thereof. In some embodiments, the TGF-β trap (e.g., TGFβRII) is fused to a $V_{H}H$ of PD-1 antibody or a fragment/variant thereof via a linker. In all embodiments, as described, the TGF-β trap (e.g., TGFβRII) is fused to either the N- or C-terminus of the $V_{H}H$ of PD-1 antibody or a fragment/variant thereof via a linker.

In some embodiments, a PD-1 antibody moiety is fused to TGFβRII or a fragment or a variant thereof (e.g., ECD of TGFβRII). In some embodiments, a PD-1 antibody moiety is fused to TGFβRII or a fragment or a variant thereof (e.g., ECD of TGFβRII) via a linker. In some embodiments, a PD-1 antibody moiety is fused to at least one extracellular domain of TGFβRII. In some embodiments, a PD-1 antibody moiety is fused to at least one extracellular domain of TGFβRII via a linker. Non-limiting exemplary fusion proteins are illustrated in FIGS. 4A-4C.

In some embodiments, a PD-1 antibody fragment is a Fab, $Fab_2$, $(Fab')_2$, Fv, $(Fv)_2$, scFv, scFv-$F_C$, $F_C$, diabody, triabody, or minibody of the PD-1 antibody. In some embodiments, a PD-1 antibody fragment is a single-domain antibody of the PD-1 antibody. In some embodiments, the single-domain antibody is a $V_{N}AR$ or $V_{H}H$ fragment of the PD-1 antibody.

In some embodiments, the variable region of heavy chain ($V_H$) of PD-1 antibody or a fragment/variant thereof comprises one or more polypeptide sequences as shown in any one of SEQ ID NOs: 1-7. In some embodiments, the variable region of heavy chain ($V_H$) of PD-1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 1-7 and 149-164.

In some embodiments, the variable region of heavy chain ($V_L$) of PD-1 antibody or a fragment/variant thereof comprises one or more polypeptide sequences as shown in any one of SEQ ID NOs: 8-13 and 148. In some embodiments, the variable region of heavy chain ($V_L$) of PD-1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 8-13 and 148.

In some embodiments, the fusion protein comprises a variable region of heavy chain ($V_H$) comprising a polypeptide sequence as shown in SEQ ID NO: 6 and a variable region of light chain ($V_L$) comprising a polypeptide sequence as shown in SEQ ID NO: 12. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a sequence as shown in SEQ ID NO: 15 and a sequence as shown in SEQ ID NO: 16.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a sequence as shown in SEQ ID NO: 15 and a sequence as shown in SEQ ID NO: 143.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 294.

In embodiments, the fusion protein comprises a sequence as shown in SEQ ID NO: 15 and a sequence as shown in SEQ ID NO: 294.

In some embodiments, the fusion protein comprises a variable region of heavy chain ($V_H$) comprising a polypeptide sequence as shown in SEQ ID NO: 7 and a variable region of light chain ($V_L$) comprising a polypeptide sequence as shown in SEQ ID NO: 13. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145.

In some embodiments, the fusion protein comprises a sequence as shown in SEQ ID NO: 296 and a sequence as shown in SEQ ID NO: 145.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 144.

In some embodiments, the fusion protein comprises a sequence as shown in SEQ ID NO: 296 and a sequence as shown in SEQ ID NO: 144.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 295.

In some embodiments, the fusion protein comprises a sequence as shown in SEQ ID NO: 296 and a sequence as shown in SEQ ID NO: 295.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145. In some embodiments, the fusion protein comprises a sequence as shown in SEQ ID NO: 145.

In some embodiments, the fusion protein comprises a linker and a variable region of heavy chain ($V_H$) comprising a polypeptide sequence as shown in SEQ ID NO: 16 and a variable region of light chain ($V_L$) comprising a polypeptide sequence as shown in SEQ ID NO: 15. In some embodiments, the fusion protein comprises a linker and a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a variable region of heavy chain ($V_H$) comprising a polypeptide sequence as shown in SEQ ID NO: 1. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 1.

In some embodiments, the fusion protein comprises a variable region of heavy chain ($V_H$) comprising a polypeptide sequence as shown in SEQ ID NO: 2. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 2.

In some embodiments, the fusion protein comprises a variable region of heavy chain ($V_H$) comprising a polypeptide sequence as shown in SEQ ID NO: 3. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 3.

In some embodiments, the fusion protein comprises a variable region of heavy chain ($V_H$) comprising a polypeptide sequence as shown in SEQ ID NO: 4. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 4.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 6. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6.

In some embodiments, the fusion protein comprises a variable region of heavy chain ($V_H$) comprising a polypeptide sequence as shown in SEQ ID NO: 7. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7.

In some embodiments, the fusion protein comprises a variable region of heavy chain ($V_H$) comprising a polypeptide sequence as shown in SEQ ID NO: 5 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 149 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 157 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 158 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 149. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain ($V_H$) comprising a polypeptide sequence as shown in SEQ ID NO: 157. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of light chain ($V_L$) comprising a polypeptide sequence as shown in SEQ ID NO: 8. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 149. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain ($V_H$) comprising a polypeptide sequence as shown in SEQ ID NO: 150. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 150.

In some embodiments, the fusion protein comprises a variable region of heavy chain ($V_H$) comprising a polypeptide sequence as shown in SEQ ID NO: 151. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 151.

In some embodiments, the fusion protein comprises a variable region of heavy chain ($V_H$) comprising a polypeptide sequence as shown in SEQ ID NO: 152. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 152.

In some embodiments, the fusion protein comprises a variable region of heavy chain ($V_H$) comprising a polypeptide sequence as shown in SEQ ID NO: 153. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 153.

In some embodiments, the fusion protein comprises a variable region of heavy chain ($V_H$) comprising a polypeptide sequence as shown in SEQ ID NO: 154. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 154.

In some embodiments, the fusion protein comprises a variable region of heavy chain ($V_H$) comprising a polypeptide sequence as shown in SEQ ID NO: 155. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 155.

In some embodiments, the fusion protein comprises a variable region of heavy chain ($V_H$) comprising a polypeptide sequence as shown in SEQ ID NO: 156. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 156.

In some embodiments, the fusion protein comprises a variable region of heavy chain ($V_H$) comprising a polypeptide sequence as shown in SEQ ID NO: 157. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain ($V_H$) comprising a polypeptide sequence as shown in SEQ ID NO: 159. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 159.

In some embodiments, the fusion protein comprises a variable region of heavy chain ($V_H$) comprising a polypeptide sequence as shown in SEQ ID NO: 160. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 160.

In some embodiments, the fusion protein comprises a variable region of heavy chain ($V_H$) comprising a polypeptide sequence as shown in SEQ ID NO: 161. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 161.

In some embodiments, the fusion protein comprises a variable region of heavy chain ($V_H$) comprising a polypeptide sequence as shown in SEQ ID NO: 162. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 162.

In some embodiments, the fusion protein comprises a variable region of heavy chain ($V_H$) comprising a polypeptide sequence as shown in SEQ ID NO: 163. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 163.

In some embodiments, the fusion protein comprises a variable region of heavy chain ($V_H$) comprising a polypeptide sequence as shown in SEQ ID NO: 164. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 164.

In some embodiments, the fusion protein comprises a variable region of light chain ($V_L$) comprising a polypeptide sequence as shown in SEQ ID NO: 8. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of light chain ($V_L$) comprising a polypeptide sequence as shown in SEQ ID NO: 9. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 9.

In some embodiments, the fusion protein comprises a variable region of light chain ($V_L$) comprising a polypeptide sequence as shown in SEQ ID NO: 10. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 10.

In some embodiments, the fusion protein comprises a variable region of light chain ($V_L$) comprising a polypeptide sequence as shown in SEQ ID NO: 11. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 11.

In some embodiments, the fusion protein comprises a variable region of light chain ($V_L$) comprising a polypeptide sequence as shown in SEQ ID NO: 12. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a variable region of light chain ($V_L$) comprising a polypeptide sequence as shown in SEQ ID NO: 13. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a variable region of light chain ($V_L$) comprising a polypeptide sequence as shown in SEQ ID NO: 148. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 148.

In some embodiments, the fusion protein comprises a polypeptide sequence as shown in SEQ ID NO: 15. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a polypeptide sequence as shown in SEQ ID NO: 16. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a polypeptide sequence as shown in SEQ ID NO: 143. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a polypeptide sequence as shown in SEQ ID NO: 144. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 144.

In some embodiments, the fusion protein comprises a polypeptide sequence as shown in SEQ ID NO: 145. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145.

(ii) Anti-TGF β Antibodies—Fusion Proteins or Fragments or Variant Thereof

In other embodiments, the cytokine trap is an antibody, antibody fragment or an antibody variant against TGF-β. In such embodiments, such antibodies can include pan-neutralizing anti-TGFβ antibody, or an anti-receptor antibody that blocks the receptor from binding to TGFβ1, 2 and/or 3. In certain embodiments, the antibody fragment or variant is a Fab, $Fab_2$, $(Fab')_2$, Fv, $(Fv)_2$, scFv, scFv-$F_C$, $F_C$, diabody, triabody, or minibody of the TGFβ antibody. In one embodiment, the anti-TGF-β antibody or fragment or variant thereof binds to TGF-β1, TGF-β2, and TGF-β3. In certain embodiments, the anti-TGF-β antibody or fragment or variant thereof binds to TGF-β1. In certain embodiments, the anti-TGF-β antibody or fragment or variant thereof binds to TGF-β3. In certain embodiments, the anti-TGF-β antibody or fragment or variant thereof binds to TGF-β1 and TGF-β2. In certain embodiments, the anti-TGF-β antibody or fragment or variant thereof binds to TGF-β1 and TGF-β3. Examples of VH sequence of a TGF-β antibody or fragment or variant thereof include but are not limited to SEQ ID Nos. 166, 168, 169, 171, 173, 175, and 177. Examples of VL sequence of a TGF-β antibody or fragment or variant thereof include but are not limited to SEQ ID NOs: 165, 167, 170, 172, 174, 176, and 178. In some embodiments, the anti-TGF-β antibody comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 166, 168, 169, 171, 173, 175, or 177. In some embodiments, the anti-TGF-β antibody comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 165, 167, 170, 172, 174, 176, or 178.

(iii) TGF-β Antagonistic Peptides—Fusion Proteins or Fragments or Variant Thereof In certain embodiments, the cytokine trap can include TGF-β antagonistic peptides or TGF-β inhibitory peptides. Such peptides can be generated de novo using phage display. In one embodiment, such peptides can be derived from segments of TGF-β isoform(s) or TGF-β receptor(s), Examples of TGF-β antagonistic peptides can include but are not limited to SEQ ID NO. 193-227. Examples of TGF-β inhibitory peptides can include but are not limited to SEQ ID NOs: SEQ ID NO. 193-227. In one embodiment, the peptides can be fused to $V_H$ and/or $V_L$ of a PD-1 antibody or a fragment/variant thereof via a linker. In another embodiment, one peptide can be fused to a PD-1 antibody or a fragment/variant thereof. In a further embodiment, more than one peptide can be fused to a PD-1 antibody or a fragment/variant thereof. When more than one peptide is utilized, the peptide can be fused with or without a linker to form concatemers. When more than one peptide is utilized, the same peptide can be used to form concatemers. Alternatively, a combination of two or more different peptides can be used to form concatemers.

Adenosine:

Adenosine is a key immune modulator in the tumor microenvironment. Extracellular adenosine suppresses inflammatory response upon binding to the A2A adenosine receptor (A2AR) which is predominantly expressed subtype in most immune cells. Several tumors express high levels of CD39 and CD73, the ectonucleotidases responsible for converting ATP and ADP to AMP, and AMP to adenosine, respectively. Accordingly, adenosine promotes suppressive activity of regulatory T cells by inducing the expression of Foxp3, CD39 and CD73. Additionally, hypoxia induces the accumulation of extracellular adenosine in the tumor microenvironment through the induction of CD39 and CD73. In addition, high levels of extracellular adenosine in the tumor microenvironment is maintained by the hypoxia-inducible factor(HIF)-dependent inhibition of the nucleotide transporter ENT-1, and the inhibition of adenosine kinase preventing the relocation of adenosine in the intracellular space and preventing the formation of AMP, respectively. Accordingly, targeting the reduction of extracellular adenosine in the tumor microenvironment is understood to enhance immune cell function and promote tumor cell killing.

In embodiments provided herein are fusion proteins that comprise an adenosine deaminase (e.g., ADA2) to target reduction of extracellular adenosine in the tumor microenvironment.

Adenosine Deaminase

Adenosine deaminase (also known as adenosine aminohydrolase, or ADA) ADA irreversibly deaminates adenosine, converting it to the related nucleoside inosine by the substitution of the amino group for a keto group. Inosine can then be deribosylated (removed from ribose) by another enzyme called purine nucleoside phosphorylase (PNP), converting it to hypoxanthine. ADA is needed for the breakdown of adenosine from food and for the turnover of nucleic acids in tissues. Its primary function in humans is the development and maintenance of the immune system. However, ADA association has also been observed with epithelial cell differentiation, neurotransmission, and gestation maintenance. There are 2 isoforms of ADA: ADA1 and ADA2.

ADA1 is found in most body cells, particularly lymphocytes and macrophages, where it is present not only in the cytosol and nucleus but also as the ecto-form on the cell membrane attached to dipeptidyl peptidase-4 (aka, CD26). ADA1 is involved mostly in intracellular activity, and exists both in small form (monomer) and large form (dimer). The interconversion of small to large forms is regulated by a 'conversion factor' in the lung.

ADA2 was first identified in human spleen. It was subsequently found in other tissues including the macrophage where it co-exists with ADA1. The two isoforms regulate the ratio of adenosine to deoxyadenosine. ADA2 is found predominantly in the human plasma and serum, and exists mainly as a homodimer. ADA2 is the predominant form present in human blood plasma and is increased in many diseases, particularly those associated with the immune system: for example rheumatoid arthritis, psoriasis, and sarcoidosis. The plasma ADA2 isoform is also increased in most cancers. ADA2 is not ubiquitous but co-exists with ADA1 in monocytes-macrophages.

ADA2 Fusion Proteins or Fragments or Variant Thereof

Provided herein is a fusion protein or a fragment or a variant thereof comprising an immune checkpoint inhibitor, such as a PD-1 inhibitor or antibody, and an adenosine deaminase (e.g., ADA2) that can neutralize adenosine. The fusion protein or a fragment or a variant thereof provided herein (e.g., PD-1 inhibitor or antibody fused to an adenosine deaminase (e.g., ADA2) can elicit a synergistic anti-tumor effect due to the simultaneous blockade of the interaction between e.g., PD-L1 on tumor cells and PD-1 on immune cells, and the neutralization of e.g., adenosine in the tumor microenvironment. Without being bound by theory, this effect is obtained from simultaneous blocking the two major immune escape mechanisms and the targeted depletion of adenosine in the tumor microenvironment by a single molecular entity. This depletion can be achieved by one or more of the following: (1) anti-PD-1 targeting of tumor cells; (2) binding of the adenosine in the tumor microenvironment by an adenosine deaminase (e.g., ADA2); and (3) destruction of the bound adenosine through the PD-L1 receptor mediated endocytosis.

In some embodiments, the adenosine deaminase (e.g., ADA2) is a part of a fusion protein or a fragment or a variant thereof also comprising PD-1 inhibitor or antibody or a fragment or a variant thereof. In some embodiments is a fusion protein or a fragment or a variant thereof comprising the adenosine deaminase (e.g., ADA2) fused to a PD-1 inhibitor optionally via a cleavable or non-cleavable linker. In some embodiments, an adenosine deaminase is an adenosine deaminase 2 (ADA2). In some embodiments, the fusion protein described herein comprises an adenosine deaminase (e.g., ADA2) described herein or a functional variant or derivative thereof. Examples of ADA2 and variants are described in WO 2016061286, herein incorporated by reference in its entirety. In some embodiments, the TGF-β cytokine trap comprises any one of ADA2 mutant 1, ADA2 mutant 2, ADA2 mutant 3, ADA2 mutant 4, ADA2 mutant 5, ADA2 mutant 6, or ADA2 mutant 7. In some embodiments, the fusion protein or a fragment or a variant thereof provided herein comprises the PD-1 inhibitor or antibody fused to the ADA protein, or functional fragment thereof, via a linker. In some embodiments, the PD-1 inhibitor can be an antibody or a fragment or a variant of the antibody that targets PD-1.

In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 284. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 273. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 274. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 37275. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 276. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 277. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 278. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 279.

In some embodiments, the fusion protein or a fragment or a variant thereof described herein comprises an adenosine deaminase (e.g., ADA2) as described above and an antibody, a fragment or a variant of the antibody that targets immune checkpoint genes. In some embodiments, an antibody or a fragment or a variant of the antibody that target immune checkpoints, such as cytotoxic T lymphocyte associated protein-4 (CTLA-4) and programmed cell death-1 (PD-1), can be fused to an adenosine deaminase (e.g., ADA2) molecule via a linker.

In some embodiments, a PD-1 antibody moiety is fused to an adenosine deaminase (e.g., ADA2) or a fragment thereof. In some embodiments, a PD-1 antibody moiety is fused to an adenosine deaminase (e.g., ADA2) via a linker. In some embodiments, a PD-1 antibody moiety is fused to at least one domain of ADA2. In some embodiments, a PD-1 antibody moiety is fused to at least one domain of ADA2 via a linker.

In some embodiments, a PD-1 antibody fragment or variant is a Fab, $Fab_2$, $(Fab')_2$, Fv, $(Fv)_2$, scFv, scFv-$F_C$, $F_C$, diabody, triabody, or minibody of the PD-1 antibody. In some embodiments, a PD-1 antibody fragment is a single-domain antibody of the PD-1 antibody. In some embodiments, the single-domain antibody is a $V_{NAR}$ or $V_H$H fragment of the PD-1 antibody.

Figure 33A:
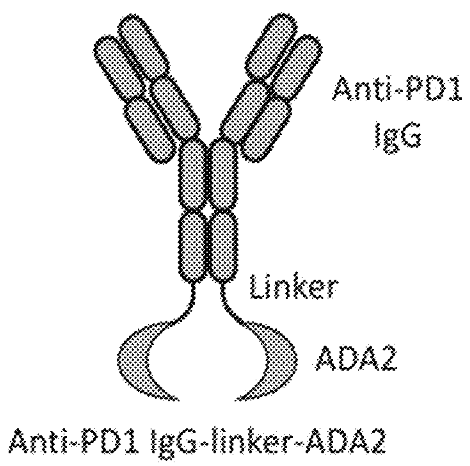
FIGS. 33A-33C show a schematic design of anti-PD1-Adenosine deaminase 2 (ADA2) design: anti-PD1-ADA2.
Figure 33B:
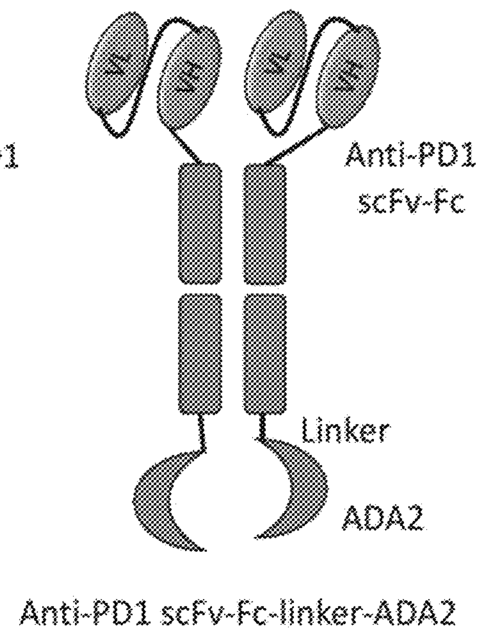
Figure 33C:
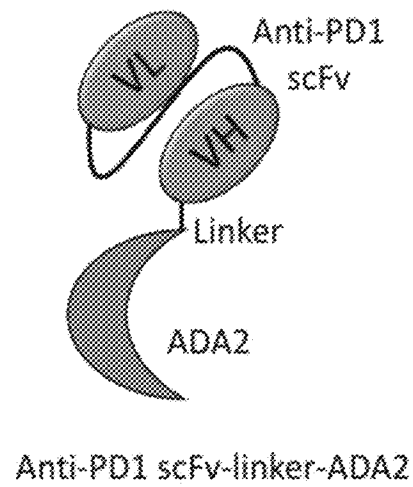

Non-limiting exemplary fusion proteins are illustrated in FIGS. 33A-33C. In some embodiments, the fusion protein comprising an anti-PD-1 antibody or a fragment or a variant thereof fused to an adenosine deaminase (e.g., ADA2) can elicit a synergistic anti-tumor effect due to the simultaneous blockade of the interaction between PD-L1 on tumor cells and PD-1 on immune cells, and targeting of the reduction of extracellular adenosine in the tumor microenvironment.

In some embodiments, the adenosine deaminase (e.g., ADA2) is fused to a variable region of heavy chain ($V_H$) of PD-1 antibody or a fragment/variant thereof. In other embodiments, the adenosine deaminase is fused to IgG of a PD-1 antibody (for example, FIG. 4*a*). In certain aspects, the IgG is IgG1, IgG2, IgG3, or IgG4. In an embodiment, the IgG is IgG4. In another embodiment, the IgG4 is SEQ ID NO 146 (wild type), SEQ ID NO: 291, SEQ ID NO: 292 or SEQ ID NO: 147 (S108P). In some embodiments, the adenosine deaminase (e.g., ADA2) is fused to a variable region of heavy chain ($V_H$) of PD-1 antibody or a fragment/variant thereof via a linker. In some embodiments, the adenosine deaminase (e.g., ADA2) is fused to a constant region of the $V_H$ of PD-1 antibody or a fragment/variant thereof via a linker. In some embodiments, the adenosine deaminase (e.g., ADA2) is fused a variable region of light chain ($V_L$) of PD-1 antibody or a fragment/variant thereof. In some embodiments, the adenosine deaminase (e.g., ADA2) is fused a variable region of light chain ($V_L$) of PD-1 antibody or a fragment/variant thereof via a linker. In some embodiments, the adenosine deaminase (e.g., ADA2) is fused to a constant region of the $V_L$ of PD-1 antibody or a fragment/variant thereof via a linker. In one aspect, the adenosine deaminase is fused to either the N- or C-terminus of the $V_H$ or $V_L$ of PD-1 antibody or a fragment/variant thereof via a linker.

In some embodiments, the adenosine deaminase (e.g., ADA2) is fused to a Fab of PD-1 antibody or a fragment/variant thereof. In some embodiments, the adenosine deaminase (e.g., ADA2) is fused to a Fab of PD-1 antibody or a fragment/variant thereof via a linker. In some embodiments, the adenosine deaminase (e.g., ADA2) is fused to a $Fab_2$ of PD-1 antibody or a fragment/variant thereof. In some embodiments, the adenosine deaminase (e.g., ADA2) is fused to a $Fab_2$ of PD-1 antibody or a fragment/variant thereof via a linker. In some embodiments, the adenosine deaminase (e.g., ADA2) is fused to a $(Fab')_2$ of PD-1 antibody or a fragment/variant thereof. In some embodiments, the adenosine deaminase (e.g., ADA2) is fused to a (Fab') 2 of PD-1 antibody or a fragment/variant thereof via a linker. In one aspect, the adenosine deaminase is fused to either the N- or C-terminus of the Fab or $Fab_2$ of PD-1 antibody or a fragment/variant thereof via a linker.

In some embodiments, the adenosine deaminase (e.g., ADA2) is fused to a Fv of PD-1 antibody or a fragment/variant thereof. In some embodiments, the adenosine deaminase (e.g., ADA2) is fused to a Fv of PD-1 antibody or a fragment/variant thereof via a linker. In some embodiments, the adenosine deaminase (e.g., ADA2) is fused to a $(Fv)_2$ of PD-1 antibody or a fragment/variant thereof. In some embodiments, the adenosine deaminase (e.g., ADA2) is fused to a $(Fv)_2$ of PD-1 antibody or a fragment/variant thereof via a linker. In one aspect, the adenosine deaminase is fused to either the N- or C-terminus of the Fv or $(Fv)_2$ of PD-1 antibody or a fragment/variant thereof via a linker.

In some embodiments, the adenosine deaminase (e.g., ADA2) is fused to a scFv of PD-1 antibody or a fragment/variant thereof. In some embodiments, the adenosine deaminase (e.g., ADA2) is fused to a scFv of PD-1 antibody or a fragment/variant thereof via a linker. In some embodiments, the adenosine deaminase (e.g., ADA2) is fused to a scFv-$F_C$ of PD-1 antibody or a fragment/variant thereof. In some embodiments, the adenosine deaminase (e.g., ADA2) is fused to a scFv-$F_C$ of PD-1 antibody or a fragment/variant thereof via a linker. In one aspect, the adenosine deaminase is fused to either the N- or C-terminus of the scFv or scFv-$F_C$ of PD-1 antibody or a fragment/variant thereof via a linker.

In some embodiments, the adenosine deaminase (e.g., ADA2) is fused to a $F_C$ of PD-1 antibody or a fragment/variant thereof. In some embodiments, the adenosine deaminase (e.g., ADA2) is fused to a $F_C$ of PD-1 antibody or a fragment/variant thereof via a linker. In some embodiments, the adenosine deaminase (e.g., ADA2) is linked to a C-terminus $F_C$ of PD-1 antibody or a fragment/variant thereof. In some embodiments, the adenosine deaminase (e.g., ADA2) is linked to a C-terminus $F_C$ of PD-1 antibody or a fragment/variant thereof via a linker. In some embodiments, the adenosine deaminase (e.g., ADA2) is linked to a N-terminus $F_C$ of PD-1 antibody or a fragment/variant thereof. In some embodiments, the adenosine deaminase (e.g., ADA2) is linked to a N-terminus $F_C$ of PD-1 antibody or a fragment/variant thereof via a linker.

In some embodiments, the adenosine deaminase (e.g., ADA2) is fused to a diabody of PD-1 antibody or a fragment/variant thereof. In some embodiments, the adenosine deaminase (e.g., ADA2) is fused to a diabody of PD-1 antibody or a fragment/variant thereof via a linker. In some embodiments, the adenosine deaminase (e.g., ADA2) is fused to a triabody of PD-1 antibody or a fragment/variant thereof. In some embodiments, the adenosine deaminase (e.g., ADA2) is fused to a triabody of PD-1 antibody or a fragment/variant thereof via a linker. In some embodiments, the adenosine deaminase (e.g., ADA2) is fused to a minibody of PD-1 antibody or a fragment/variant thereof. In some embodiments, the adenosine deaminase (e.g., ADA2) is fused to a minibody of PD-1 antibody or a fragment/variant thereof via a linker.

In some embodiments, the adenosine deaminase (e.g., ADA2) is fused to a $V_N$AR of PD-1 antibody or a fragment/variant thereof. In some embodiments, the adenosine deaminase (e.g., ADA2) is fused to a $V_N$AR of PD-1 antibody or a fragment/variant thereof via a linker. In one aspect, the adenosine deaminase is fused to either the N- or C-terminus of the $V_{NAR}$ of PD-1 antibody or a fragment/variant thereof via a linker.

In some embodiments, the adenosine deaminase (e.g., ADA2) is fused to a $V_H$H of PD-1 antibody or a fragment/variant thereof. In some embodiments, the adenosine deaminase (e.g., ADA2) is fused to a $V_H$H of PD-1 antibody or a fragment/variant thereof via a linker. In one aspect, the adenosine deaminase is fused to either the N- or C-terminus of the $V_H$H of PD-1 antibody or a fragment/variant thereof via a linker.

In some embodiments, the variable region of heavy chain ($V_H$) of PD-1 antibody or a fragment/variant thereof comprises one or more polypeptide sequences as shown in any one of SEQ ID NOs: 1-7. In some embodiments, the variable region of heavy chain ($V_H$) of PD-1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 1-7 and 149-164.

In some embodiments, the variable region of heavy chain ($V_L$) of PD-1 antibody or a fragment/variant thereof comprises one or more polypeptide sequences as shown in any one of SEQ ID NOs: 8-13 and 148. In some embodiments, the variable region of heavy chain ($V_L$) of PD-1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 8-13 and 148.

In some embodiments, the fusion protein comprises a variable region of heavy chain ($V_H$) comprising a polypeptide sequence as shown in SEQ ID NO: 6 and a variable region of light chain ($V_L$) comprising a polypeptide sequence as shown in SEQ ID NO: 12. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 280.

In some embodiments, the fusion protein comprises a sequence as shown in SEQ ID NO: 12 and a sequence as shown in SEQ ID NO: 280.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 281.

In some embodiments, the fusion protein comprises a sequence as shown in SEQ ID NO: 12 and a sequence as shown in SEQ ID NO: 281.

In some embodiments, the fusion protein comprises a variable region of heavy chain ($V_H$) comprising a polypeptide sequence as shown in SEQ ID NO: 7 and a variable region of light chain ($V_L$) comprising a polypeptide sequence as shown in SEQ ID NO: 13. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 282.

In some embodiments, the fusion protein comprises a sequence as shown in SEQ ID NO: 13 and a sequence as shown in SEQ ID NO: 282.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 283.

In some embodiments, the fusion protein comprises a sequence as shown in SEQ ID NO: 13 and a sequence as shown in SEQ ID NO: 283.

In some embodiments, the fusion protein comprises a variable region of heavy chain ($V_H$) comprising a polypeptide sequence as shown in SEQ ID NO: 1. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 1.

In some embodiments, the fusion protein comprises a variable region of heavy chain ($V_H$) comprising a polypeptide sequence as shown in SEQ ID NO: 2. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 2.

In some embodiments, the fusion protein comprises a variable region of heavy chain ($V_H$) comprising a polypeptide sequence as shown in SEQ ID NO: 3. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 3.

In some embodiments, the fusion protein comprises a variable region of heavy chain ($V_H$) comprising a polypeptide sequence as shown in SEQ ID NO: 4. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 4.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 6. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6.

In some embodiments, the fusion protein comprises a variable region of heavy chain ($V_H$) comprising a polypeptide sequence as shown in SEQ ID NO: 7. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7.

In some embodiments, the fusion protein comprises a variable region of heavy chain ($V_H$) comprising a polypeptide sequence as shown in SEQ ID NO: 149. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain ($V_H$) comprising a polypeptide sequence as shown in SEQ ID NO: 150. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 150.

In some embodiments, the fusion protein comprises a variable region of heavy chain ($V_H$) comprising a polypeptide sequence as shown in SEQ ID NO: 151. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 151.

In some embodiments, the fusion protein comprises a variable region of heavy chain ($V_H$) comprising a polypeptide sequence as shown in SEQ ID NO: 152. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 152.

In some embodiments, the fusion protein comprises a variable region of heavy chain ($V_H$) comprising a polypeptide sequence as shown in SEQ ID NO: 153. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 153.

In some embodiments, the fusion protein comprises a variable region of heavy chain ($V_H$) comprising a polypeptide sequence as shown in SEQ ID NO: 154. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 154.

In some embodiments, the fusion protein comprises a variable region of heavy chain ($V_H$) comprising a polypeptide sequence as shown in SEQ ID NO: 155. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 155.

In some embodiments, the fusion protein comprises a variable region of heavy chain ($V_H$) comprising a polypeptide sequence as shown in SEQ ID NO: 156. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 156.

In some embodiments, the fusion protein comprises a variable region of heavy chain ($V_H$) comprising a polypeptide sequence as shown in SEQ ID NO: 157. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain ($V_H$) comprising a polypeptide sequence as shown in SEQ ID NO: 159. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 159.

In some embodiments, the fusion protein comprises a variable region of heavy chain ($V_H$) comprising a polypeptide sequence as shown in SEQ ID NO: 160. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 160.

In some embodiments, the fusion protein comprises a variable region of heavy chain ($V_H$) comprising a polypeptide sequence as shown in SEQ ID NO: 161. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 161.

In some embodiments, the fusion protein comprises a variable region of heavy chain ($V_H$) comprising a polypeptide sequence as shown in SEQ ID NO: 162. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 162.

In some embodiments, the fusion protein comprises a variable region of heavy chain ($V_H$) comprising a polypeptide sequence as shown in SEQ ID NO: 163. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 163.

In some embodiments, the fusion protein comprises a variable region of heavy chain ($V_H$) comprising a polypeptide sequence as shown in SEQ ID NO: 164. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 164.

In some embodiments, the fusion protein comprises a variable region of light chain ($V_L$) comprising a polypeptide sequence as shown in SEQ ID NO: 8. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of light chain ($V_L$) comprising a polypeptide sequence as shown in SEQ ID NO: 9. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 9.

In some embodiments, the fusion protein comprises a variable region of light chain ($V_L$) comprising a polypeptide sequence as shown in SEQ ID NO: 10. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 10.

In some embodiments, the fusion protein comprises a variable region of light chain ($V_L$) comprising a polypeptide sequence as shown in SEQ ID NO: 11. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 11.

In some embodiments, the fusion protein comprises a variable region of light chain ($V_L$) comprising a polypeptide sequence as shown in SEQ ID NO: 12. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a variable region of light chain ($V_L$) comprising a polypeptide sequence as shown in SEQ ID NO: 13. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a variable region of light chain ($V_L$) comprising a polypeptide sequence as shown in SEQ ID NO: 148. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 148.

In some embodiments, the fusion protein comprises a polypeptide sequence as shown in SEQ ID NO: 15. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a polypeptide sequence as shown in SEQ ID NO: 280. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 280.

In some embodiments, the fusion protein comprises a polypeptide sequence as shown in SEQ ID NO: 281. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 281.

In some embodiments, the fusion protein comprises a polypeptide sequence as shown in SEQ ID NO: 282. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 282.

In some embodiments, the fusion protein comprises a polypeptide sequence as shown in SEQ ID NO: 283. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 283.

In some embodiments, the fusion protein comprises a variable region of heavy chain ($V_H$) comprising a polypeptide sequence as shown in SEQ ID NO: 5 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 149 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 157 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 158 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 149. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain ($V_H$) comprising a polypeptide sequence as shown in SEQ ID NO: 157. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain ($V_H$) comprising a polypeptide sequence as shown in SEQ ID NO: 158. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of light chain ($V_L$) comprising a polypeptide sequence as shown in SEQ ID NO: 8. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

Linkers

In some embodiments, the linker comprises one or more polypeptide sequences as shown in any one of SEQ ID NOs: 17-34. In some embodiments, the linker can be a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). A non-limiting example of a flexible linker can have the sequence of (Gly-Gly-Gly-Gly-Ser)n, wherein n can be 1, 2, 3, 4, 5, 6, 7, 8, 9, or 10. By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some embodiment, a flexible linker can have the sequence of (Gly)n, wherein n can be 6, 7, or 8. In some cases, flexible linkers can also be rich in small or polar amino acids such as Gly and Ser, but can contain additional amino acids such as Thr and Ala to maintain flexibility. In some cases, the linker described herein can be a rigid linker. A rigid linker can be utilized to maintain a fixed distance between domains of the fusion protein or a fragment or a variant thereof described herein. Non-limiting examples of rigid linkers can be: alpha helix-forming linkers, pro-rich sequence, (XP)n, X-Pro backbone, (EAAAK)n (n=1-6). Rigid linkers can exhibit relatively stiff structures by adopting α-helical structures or by containing multiple Pro residues in some cases. In some embodiments, the immune checkpoint inhibitor, such as a PD-1 inhibitor, and the cytokine trap (e.g., TGF-β trap) that can neutralize the cytokine (e.g., TGF-β) in a fusion protein or a fragment or a variant thereof described herein can be separated by an intervening sequence encoding an intervening linker polypeptide. In some embodiments, the immune checkpoint inhibitor, such as a PD-1 inhibitor, and the ADA2 (or mutants thereof) in a fusion protein or a fragment or a variant thereof described herein can be separated by an intervening sequence encoding an intervening linker polypeptide. In certain embodiments, the linker polypeptide comprises disclosed in the table below:

TABLE 1

Linker amino acid sequences and polynucleotide sequences

| SEQ ID NO | Linkers |
|---|---|
| 17 | DPGGGGSGGGGSNPGS |
| 18 | GGGGSGGGGSGSDPGS |
| 19 | DPGSGGGGSGGGGSGS |
| 20 | GGGGSGGGGSGGGGSDPGS |
| 21 | DPGSGGGGSGGGGSGGGGS |
| 22 | DPGSGSVPLGSGSNPGS |
| 23 | DPGSGGSVPLGSGGSNPGS |
| 24 | DPGVLEREDKPTTSKPNPGS |
| 25 | DPGVLEREDVPTTSYPNPGS |
| 26 | DPGVLEREDKVTTSKYNPGS |
| 27 | DPVLEREDKVTTSKNPGS |
| 28 | DIEGRMD |
| 29 | GEGKSSGSGSESKAS |
| 30 | GSTSGSGKPGSGEGSTKG |
| 31 | A(EAAAK)$_4$ALEA(EAAAK)$_4$A |
| 32 | (G4S)n, n = 1-10 |
| 33 | (Gly)n, n = 6-8 |
| 34 | (EAAAK)n, n = 1-6 |

In some embodiments, the linker can be a flexible linker, a rigid linker, an in vivo cleavable linker, or any combination thereof. In some cases, the linker can connect functional domains together (as in flexible and rigid linkers) or releasing free functional domain in vivo as in in vivo cleavable linkers. In some embodiments, linkers can improve biological activity, increase expression yield, and achieving desirable pharmacokinetic profiles. In some embodiments, the linker can also comprise hydrazone, peptide, disulfide, or thioesther.

In some cases, the linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (G4S)n, wherein n is 1, 2, 3, 4, 5, 6, 7, 8, 9 or 10. In some embodiment, a flexible linker can have the sequence of (Gly)n, wherein n can be 6, 7, or 8. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility. By adjusting the copy number "n", the length of these non-limiting exemplary linkers can be optimized to achieve appropriate separation of functional domains, or to maintain necessary inter-domain interactions. Besides GS linkers, other flexible linkers can be utilized for the fusion protein or a fragment or a variant thereof described herein. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein or a fragment or a variant thereof domains. In addition, although flexible linkers do not have rigid structures, they can serve as a passive linker to keep a distance between functional domains. The length of flexible linkers can be adjusted to allow for proper folding or to achieve optimal biological activity of the fusion protein or a fragment or a variant thereof.

The linker described herein can further include a rigid linker in some cases. A rigid linker can be utilized to maintain a fixed distance between domains of the fusion protein or a fragment or a variant thereof described herein. Examples of rigid linkers can be: alpha helix-forming linkers, pro-rich sequence, (XP)n, X-Pro backbone, (EAAAK)n (n=1-6), to name a few. Rigid linkers can exhibit relatively stiff structures by adopting α-helical structures or by containing multiple Pro residues in some cases.

In some embodiments, the linker described herein can be a cleavable linker. In other cases a linker is not cleavable.

Linkers that are not cleavable can covalently join functional domains of the fusion protein or a fragment or a variant thereof together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g. cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioesther. For example, a hydrazone can confer serum stability. In other cases, a hydrazone can allow for cleavage in an acidic compartment. An acidic compartment can have a pH up to 7. A linker can also include a thioether. A thioether can be nonreducible. A thioether can be designed for intracellular proteolytic degradation.

In some cases, a linker can be engineered linker. For example, a linker can be designed to comprise chemical characteristics such as hydrophobicity. In some cases, at least two different linker polypeptide sequences can encode the same polypeptide linker sequence. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker. In some cases, a polypeptide linker can also include one or more GS linker sequences, for instance, (G4S)n, (GS)n, (SG)n, (GSG)n, and (SGSG)n, wherein n can be any number from zero to fifteen.

Methods of Treating Cancer

Also provided herein is a method of treating cancer with a fusion protein comprising an immune checkpoint inhibitor, such as a PD-1 inhibitor, and a cytokine trap (e.g., TGF-β trap) that can neutralize the cytokine (e.g., TGF-β). Also provided herein is a method of treating cancer with a fusion protein comprising an immune checkpoint inhibitor, such as a PD-1 inhibitor, and adenosine deaminase protein. The development of monoclonal antibodies targeting blockade of an immune checkpoint pathway, such as PD1 and PD-L1/2 signaling pathway and CTLA-4 and CD80/86 signaling pathway, have revolutionized cancer treatment demonstrating durable clinical activity in several cancer indications including, but not limited to, melanoma, non-small cell lung cancer, renal cell carcinoma, bladder cancer, head and neck squamous cell carcinoma, MSI-high colorectal carcinoma, Merkel cell carcinoma, and Hodgkin lymphoma. Despite the durable responses, the response rate remains very low, and several patients have developed resistance leading to disease progression. Furthermore, in several indications, such as ovarian, gastroesophageal, prostate, pancreas and many other cancers, checkpoint inhibitors have failed to show any substantive clinical responses.

The failure of checkpoint blockade can be attributed to the complexity of the immunosuppressive factors present in the tumor microenvironment. These factors can include, but not limited to, suppressive cells, such as myeloid derived suppressive cells, tumor-associated macrophages (TAM); suppressive cytokine and growth factors, such as TGF-β and interleukin 10 (IL-10); and metabolic derivative, such as adenosine and indoleamine 2,3-dioxygenase (IDO) byproducts. Anti-PD1-TGFβRII fusion protein provided herein is an example of a therapy that can target two negative suppressive pathways in the tumor microenvironment. These pathways can include cell intrinsic interactions mediated by tumor cells to immune, in which PD-1/PD-L1 interaction can play a major role, and cell extrinsic interactions mediated by immunosuppressive cytokines, of which TGF-β can be a prominent member.

In some embodiments, the cancer is, but not limited to, glioblastoma, colorectal, gastric, cervical, ovarian, pancreatic, prostate, breast, and renal cancers. In addition, the fusion proteins as described herein can be amenable to indications, such as in non-small cell cancer (NSCL) and melanoma, in which response rate of checkpoint blockades is lower and TGF-β is highly expressed.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, triple negative breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, hepatocellular carcinoma (HCC), choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present disclosure is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma.

In certain embodiments, anti-PD1-TGFβRII fusion protein provided herein is an example of a therapy that can be used to treat cancers that have about 0, 5, 10, 15, 20, 25, 30, 35, 40, 45, 50, 55, 60, 65, 70, 75, 80, 85, 90 or 95% average response rate to standard therapy (including but not limited to chemotherapy, chemotherapy and current clinical trial therapies). In certain embodiments, anti-PD1-ADA2 fusion protein provided herein is an example of a therapy that can be used to treat cancers that have about 0, 5, 10, 15, 20, 25, 30, 35, 40, 45, 50, 55, 60, 65, 70, 75, 80, 85, 90 or 95% average response rate to standard therapy (including but not limited to chemotherapy, chemotherapy and current clinical trial therapies). Such cancers include but are not limited to, Hodgkin's lymphoma, melanoma, non-small cell lung cancer (NSCLC), microsatellite instability (MSI)-high or mismatch repair (MMR)-deficient solid tumors, CSCC, RCC, CRC, melanoma, Merkel cell cancer, bladder cancer, RCC, hepatocellular carcinoma (HCC), head & neck cancer (H&N), cervical cancer, gastric cancer, small cell lung cancer (SCLC), endometrial cancer, mesothelioma, ovarian cancer, triple negative breast cancer (TNBC), breast cancer, colorectal cancer (CRC), pancreatic cancer, prostate cancer.

Combination Therapy

In some embodiments, the fusion protein is administered as a combination therapy with an additional therapeutic agent. In some embodiments, an additional therapeutic agent comprises a biological molecule, such as an antibody. For example, treatment can involve the combined administration of the fusion protein with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX). In some embodiments, an additional therapeutic agent comprises an agent such as a small molecule. For example, treatment can involve the combined administration of the fusion protein or a fragment or a variant thereof provided herein with a small molecule that acts as an inhibitor against tumor-associated antigens including, but not limited to, EGFR, HER2 (ErbB2), and/or VEGF. In some embodiments, the fusion protein or a fragment or a variant thereof is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor. In another embodiment, the additional therapeutic agent is chemotherapy or other inhibitors that reduce the number of $T_{REG}$ cells. In certain embodiments, the therapeutic agent is cyclophosphamide or an anti-CTLA4 antibody. In another embodiment, the additional therapeutic reduces the presence of myeloid-derived suppressor cells. In a further embodiment, the additional therapeutic is carbotaxol. In a further embodiment, the additional therapeutic agent is ibrutinib.

In some embodiments, the method can further comprise one or more checkpoint inhibitors in combination with the fusion protein or a fragment or a variant thereof as described herein. In some embodiments, the additional checkpoint inhibitor can be an anti-CTLA-4 antibody. The anti-CTLA-4 antibody (e.g., ipilimumab) has shown durable anti-tumor activities and prolonged survival in participants with advanced melanoma, resulting in its Food and Drug Administration (FDA) approval in 2011. See Hodi et al., Improved survival with ipilimumab in patients with metastatic melanoma. N Engl J Med. (2010) Aug. 19; 363(8):711-23. In some embodiments, the one or more checkpoint inhibitors can be an anti-PD-L1 antibody. In some embodiments, the anti-PD-L1 antibody can be a full length atezolizumab (anti-PD-L1), avelumab (anti-PD-L1), durvalumab (anti-PD-L1), or a fragment or a variant thereof. In some embodiments, the one or more checkpoint inhibitors can be any one or more of CD27 inhibitor, CD28 inhibitor, CD40 inhibitor, CD122 inhibitor, CD137 inhibitor, OX40 (also known as CD134) inhibitor, GITR inhibitor, ICOS inhibitor, or any combination thereof. In some embodiments, the one or more checkpoint inhibitors can be any one or more of A2AR inhibitor, B7-H3 (also known as CD276) inhibitor, B7-H4 (also known as VTCN1) inhibitor, BTLA inhibitor, IDO inhibitor, KIR inhibitor, LAG3 inhibitor, TIM-3 inhibitor, VISTA inhibitor, or any combination thereof.

In certain embodiments, an additional therapeutic agent comprises a second immunotherapeutic agent. In some embodiments, the additional immunotherapeutic agent includes, but is not limited to, a colony stimulating factor, an interleukin, an antibody that blocks immunosuppressive functions (e.g., an anti-CTLA-4 antibody, anti-CD28 antibody, anti-CD3 antibody, anti-PD-L1 antibody, anti-TIGIT antibody), an antibody that enhances immune cell functions (e.g., an anti-GITR antibody, an anti-OX-40 antibody, an anti-CD40 antibody, or an anti-4-1BB antibody), a toll-like receptor (e.g., TLR4, TLR7, TLR9), a soluble ligand (e.g., GITRL, GITRL-Fc, OX-40L, OX-40L-Fc, CD40L, CD40L-Fc, 4-1BB ligand, or 4-1BB ligand-$F_C$), or a member of the B7 family (e.g., CD80, CD86). In some embodiments, the additional immunotherapeutic agent targets CTLA-4, CD28, CD3, PD-L1, TIGIT, GITR, OX-40, CD-40, or 4-1BB.

In some embodiments, the additional therapeutic agent is an additional immune checkpoint inhibitor. In some embodiments, the additional immune checkpoint inhibitor is an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the additional therapeutic agent is an anti-PD-L1 antibody selected from the group consisting of: BMS935559 (MDX-1105), atexolizumab (MPDL3280A), durvalumab (MEDI4736), and avelumab (MSB0010718C). In some embodiments, the additional therapeutic agent is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566. In some embodiments, the fusion protein or a fragment or a variant thereof can be administered in combination with a biologic molecule selected from the group consisting of: cytokines, adrenomedullin (AM), angiopoietin (Ang), BMPs, BDNF, EGF, erythropoietin (EPO), FGF, GDNF, granulocyte colony stimulating factor (G-CSF), granulocyte-macrophage colony stimulating factor (GM-CSF), macrophage colony stimulating factor (M-CSF), stem cell factor (SCF), GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, gamma-IFN, IL-1, IL-2, IL-3, IL-4, IL-5, IL-6, IL-7, IL-12, IL-15, and IL-18.

Cytokines

In some cases, the cytokine comprises at least one chemokine, interferon, interleukin, lymphokine, tumor necrosis factor, or variant or combination thereof. In some cases, the cytokine is an interleukin. In some cases the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and functional variants and fragments thereof. In some embodiments, the cytokines can be membrane bound or secreted. In embodiments, the cytokine is soluble IL-15, soluble IL-15/IL-15Rα complex (e.g., ALT-803). In certain cases, the interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified immune effector cell described herein. In some embodiments, the mbIL-15 comprises a full-length IL-15 (e.g., a native IL-15 polypeptide) or fragment or variant thereof, fused in frame with a full length IL-15Rα, fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," PNAS 2016. In some cases, the cytokine is expressed in the same immune effector cell as the CAR.

In some embodiments, the mbIL-15 is expressed with a cell tag such as HER1t, HER-1t-1, CD20t-1 or CD20 as described herein. The mbIL-15 can be expressed in-frame with HER1t, HER-it-1, CD20t-1 or CD20.

In some embodiments, the mbIL-15 can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties. In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In some embodiments, the fusion protein as described herein can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Gene Switch

Provided herein are gene switch polypeptides, polynucleotides encoding ligand-inducible gene switch polypeptides, and methods and systems incorporating these polypeptides and/or polynucleotides. The term "gene switch" refers to the combination of a response element associated with a promoter, and for instance, an ecdysone receptor (EcR) based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the antibody with the TGF-β cytokine trap, thereby resulting in dimerization of the DNA binding domain and the transactivation domain. Since the DNA binding and transactivation domains reside on two different molecules, the background activity in the absence of ligand is greatly reduced.

Certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter ("IP") can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/US52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); WO 2018/132494 (PCT/US2018/013196); and, U.S. Pat. No. 9,402,919; each of which is incorporated by reference in its entirety.

As used herein, the term "ligand," as applied to ligand-activated ecdysone receptor-based gene switches are small molecules of varying solubility (such as diacylhydrazine compounds) having the capability of activating a gene switch to stimulate gene expression (i.e., therein providing ligand inducible expression of polynucleotides (e.g., mRNAs, miRNAs, etc) and/or polypeptides). Examples of such ligands include, but are not limited to those described in: WO 2004/072254 (PCT/US2004/003775); WO 2004/005478 (PCT/US2003/021149); WO 2005/017126 (PCT/US2004/005149); WO 2004/078924 (PCT/US2004/005912); WO 2008/153801 (PCT/US2008/006757); WO 2009/114201 (PCT/US2009/001639); WO 2013/036758 (PCT/US2012/054141); WO 2014/144380 (PCT/US2014/028768); and, WO 2016/044390 (PCT/US2015/050375); each of which are hereby incorporated by reference herein in the entirety.

Examples of ligands also include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,258,603; 6,013,836; 5,117,057; 5,530,028; 5,378,726; 7,304,161; 7,851,220; 8,748,125; 9,272,986; 7,456,315; 7,563,928; 8,524,948; 9,102,648; 9,169,210; 9,255,273; and, 9,359,289; oxadiazolines as described in U.S. Pat. Nos. 8,669,072; and, 8,895,306; dibenzoylalkyl cyanohydrazines such as those disclosed in European Application No. 2,461,809; N-alkyl- N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Pat. Nos. 7,375,093; 8,129,355; and, 9,802,936; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxy-cholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxybenzoyl)-hydrazide), RG-115932 ((R)-3,5-Dimethyl-benzoic acid N-(1-tert-butyl-butyl)N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., WO 2008/153801 (PCT/US2008/006757); and, WO 2013/036758 (PCT/US2012/054141), both of which are incorporated herein by reference in their entireties.

For example, a ligand for the ecdysone receptor-based gene switch may be selected from any suitable ligands. Both naturally occurring ecdysone or ecdysone analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for several reasons including, for example: lower manufacturing cost, metabolic stability, absence from insects, plants, or mammals, and environmental acceptability. U.S. Pat. No. 6,379,945 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkylN'-aroyl hydrazine. (See U.S. Pat. No. 6,723,531).

In one embodiment, the ligand for an ecdysone-based gene switch system is a diacylhydrazine ligand or chiral diacylhydrazine ligand. The ligand used in the gene switch system may be compounds of Formula I Formula I

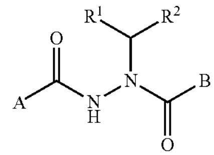

wherein A is alkoxy, arylalkyloxy or aryloxy; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; or pharmaceutically acceptable salts, hydrates, crystalline forms or amorphous forms thereof.

In another embodiment, the ligand may be enantiomerically enriched compounds of Formula II Formula II

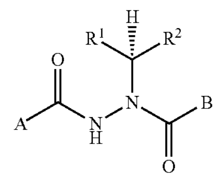

wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; with the proviso that R1 does not equal R2; wherein the absolute configuration at the asymmetric carbon atom bearing R1 and R2 is predominantly S; or pharmaceutically acceptable salts, hydrates, crystalline forms or amorphous forms thereof.

In certain embodiments, the ligand may be enantiomerically enriched compounds of Formula III Formula III

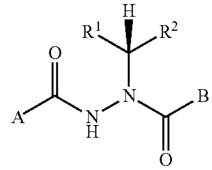

wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that R1 does not equal R2; wherein the absolute configuration at the asymmetric carbon atom bearing R1 and R2 is predominantly R; or pharmaceutically acceptable salts, hydrates, crystalline forms or amorphous forms thereof.

In one embodiment, a ligand may be (R)-3,5-dimethyl-benzoic acid N-(1-tertbutyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. Pat. Nos. 8,076,517; 8,884,060; and, 9,598,355; each of which are fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system also includes those utilizing the FK506 binding domain are FK506, Cyclosporin A, or Rapamycin. FK506, rapamycin, and their analogs are disclosed in U.S. Pat. Nos. 6,649,595; 6,187,757; 7,276,498; and, 7,273,874.

In some embodiments, a diacylhydrazine ligand for inducible gene expression is administered at unit daily dose of about 5, 10, 15, 20, 25, 30, 35, 40, 50, 60, 70, 80, 90, 100 or 120 mg. In some embodiments, the diacylhydrazine ligand is administered at a unit daily dose of about 5 mg. In some embodiments, the diacylhydrazine ligand is administered at a unit daily dose of about 10 mg. In some embodiments, the diacylhydrazine ligand is administered at a unit daily dose of about 15 mg. In some embodiments, the diacylhydrazine ligand is administered daily at a unit daily dose of about 20 mg.

In some embodiments, the combination therapy with two or more therapeutic agents can use agents that work by different mechanisms of action, although this is not required. Combination therapy using agents with different mechanisms of action can result in additive or synergetic effects. Combination therapy can allow for a lower dose of each agent than is used in monotherapy, thereby reducing toxic side effects and/or increasing the therapeutic index of the agent(s). Combination therapy can decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In certain embodiments, in addition to administering the fusion protein or a fragment or a variant thereof described herein, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that can be administered in combination with the fusion protein or a fragment or a variant thereof described herein include chemotherapeutic agents. Thus, in some embodiments, the method or treatment involves the administration of an agent described herein in combination with a chemotherapeutic agent or in combination with a cocktail of chemotherapeutic agents. In some embodiments, the methods can further comprise one or more antineoplastic agents, such as cisplatin, capecitabine, or 5-fluorouracil, in combination with the fusion protein or a fragment or a variant thereof as described herein. Treatment with an agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA.

Useful classes of chemotherapeutic agents include, for example, anti-tubulin agents, auristatins, DNA minor groove binders, DNA replication inhibitors, alkylating agents (e.g., platinum complexes such as cisplatin, mono(platinum), bis (platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, *vinca* alkaloids, or the like. In certain embodiments, the second therapeutic agent is an alkylating agent, an antimetabolite, an antimitotic, a topoisomerase inhibitor, or an angiogenesis inhibitor.

The fusion protein or a fragment or a variant thereof provided herein can be used alone or in combination with conventional therapeutic regimens such as surgery, irradiation, chemotherapy and/or bone marrow transplantation (autologous, syngeneic, allogeneic or unrelated). A set of tumor antigens can be useful, e.g., in a large fraction of cancer patients.

Fusion Proteins in Combination with Chimeric Receptors

In some embodiments, the fusion protein is administered as a combination therapy with an additional therapeutic agent. In some embodiments, an additional therapeutic agent comprises a chimeric receptor, such as chimeric antigen receptor or an engineered T-cell receptor. For example, treatment can involve the simultaneous administration of the fusion protein with a chimeric receptor. In one embodiment, the treatment can involve the co-administration of a fusion protein and a modified effector cell comprising a chimeric receptor. In one embodiment, the treatment can involve the sequential administration of a modified effector cell which comprises a chimeric receptor followed by the administration of the fusion protein. In another embodiment, the treatment can involve the sequential administration of a fusion protein followed by the administration of a modified effector cell which comprises a chimeric receptor. In one aspect, there can be a lag of at least 0.5, 1, 2, 3, 4, 5, 6, 8, 10, 12, 15, 18, 20, or 24 hours between administrations. In another aspect, there can be at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 75, 90 or more days in between administrations.

In some embodiments, modified immune effector cells are modified immune cells that comprise T cells and/or natural killer cells. T cells or T lymphocytes are a subtype of white blood cells that are involved in cell-mediated immunity. Exemplary T cells include T helper cells, cytotoxic T cells, TH17 cells, stem memory T cells (TSCM), naïve T cells, memory T cells, effector T cells, regulatory T cells, or natural killer T cells. In certain aspects, the embodiments described herein include making and/or expanding the modified immune effector cells (e.g., T-cells, Tregs, NK-cell or NK T-cells) that comprises transfecting the cells with an expression vector containing a DNA (or RNA) construct encoding the chimeric receptor.

In some embodiments, described herein includes a modified effector cell which comprises a chimeric receptor expressed on the surface of the cell. In some instances, the chimeric receptor comprises an antigen binding region that enables recognition and binding to a tumor antigen, e.g., a tumor-associated antigen or a tumor-specific antigen. In some instances, the antigen binding region comprises an antibody or binding fragment, for example, an Fab, an Fab', an $F(ab')_2$, an $F(ab')_3$, an scFv, an $sc(Fv)_2$, a dsFv, a diabody, a minibody, and a nanobody or binding fragments thereof. In some cases, the antigen binding region comprises a scFv. In some cases, the chimeric receptor comprises a scFv (e.g., a chimeric antigen receptor (CAR)). In some instances, the chimeric antigen receptor comprises a pattern-recognition receptor. In other cases, the chimeric receptor comprises an engineered T-cell receptor (TCR).

Further provided herein is an immune effector cell comprising a cell tag for use as a kill switch, selection marker, a biomarker, or a combination thereof. In some embodiments, the cell tag comprises HER1t, HER1t-1, CD20t-1 or CD20. In some cases, the cell tag comprises HER1t, and said HER1t comprises the polypeptide sequence of SEQ ID NO: 68. In some instances, the cell tag comprises HER1t-1, and said HER1t-1 comprises the polypeptide sequence of SEQ ID NO: 69.

Chimeric Antigen Receptors (CARs)

A chimeric antigen receptor (CAR) is an engineered receptor which grafts an exogenous specificity onto an immune effector cell. In some instances, a CAR comprises an extracellular domain (ectodomain) that comprises an antigen binding domain, a stalk region, a transmembrane domain and an intracellular (endodomain) domain. In some instances, the intracellular domain further comprises one or more intracellular signaling domains. In some instances, a CAR described herein comprises an antigen binding domain, a stalk region, a transmembrane domain, one or more costimulatory domains, and a signaling domain for T-cell activation.

An antigen binding domain can comprise complementary determining regions of a monoclonal antibody, variable regions of a monoclonal antibody, and/or antigen binding fragments thereof. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor can contain three CDRs (CDR1, CDR2, and CDR3). In some instances, an antigen binding domain comprises $F(ab')_2$, Fab', Fab, Fv, or scFv. In some cases, an antigen binding domain is a scFv. In some cases, an antigen binding domain is a Fab. In some cases, an antigen binding domain is a Fab'. In some cases, an antigen binding domain is F(ab')2. In some cases, an antigen binding domain is a Fv.

In some embodiments, a CAR described herein comprises an antigen binding domain that binds to an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, Mucins such as MUC-1, MUC-4 or MUC-16, MAGE-A1, h5T4, PSMA, TAG-72, EGFR, CD20, EGFRvIII, CD123 or VEGF-R2. In one embodiment, a CAR described herein comprises an antigen binding domain that binds to an epitope on MUC16. In some embodiments, a CAR described herein comprises an antigen binding domain that binds to an epitope on CD19 or CD33. In some instances, a CAR described herein comprises an antigen binding domain that binds to an epitope on CD19. In some cases, a CAR described herein comprises an antigen binding domain that binds to an epitope on CD33. In further embodiments, a CAR described herein comprises an autoantigen or an antigen binding region that binds to an epitope on HLA-A2, myelin oligodendrocyte glycoprotein (MOG), factor VIII (FVIII), MAdCAM1, SDF1, or collagen type II.

In some embodiments, the CARs and methods described herein can be used for the treatment of a hyperproliferative disease, such as a cancer, an autoimmune disease or for the treatment of an infection, such as a viral, bacterial or parasitic infection. In some aspects, the CAR targets an antigen that is elevated in cancer cells, in autoimmune cells or in cells that are infected by a virus, bacteria or parasite.

Pathogens that may be targeted include, without limitation, *Plasmodium*, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris, or autoimmune uveitis.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and Stachybotrys. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a "stalk" region, or a "spacer" or "hinge" region, is used to link the antigen-binding domain to the transmembrane domain. In some instances, a "stalk domain" or "stalk region" comprise any oligonucleotide- or polypeptide that functions to link the transmembrane domain to, either the extracellular domain or, the cytoplasmic domain in the polypeptide chain. In some embodiments, it is flexible enough to allow the antigen-binding domain to orient in different directions to facilitate antigen recognition. In some instances, the stalk region comprises the hinge region from IgG1. In alternative instances, the stalk region comprises the CH2CH3 region of immunoglobulin and optionally portions of CD3. In some cases, the stalk region comprises a CD8α hinge region, an IgG4-Fc 12 amino acid hinge region (ESKYGPPCPPCP) or IgG4 hinge regions as described in WO/2016/073755.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker.

In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof.

In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In some embodiments, a CAR described herein is administered to a subject with one or more additional therapeutic agents that include but are not limited to cytokines as described herein. In further embodiments, an immune effector cell expressing a CAR described herein expresses membrane-bound IL-15 ("mIL-15 or mbIL-15"). In aspects of the invention, the mbIL-15 comprises a fusion protein between IL-15 and IL-15Rα. In further embodiments, the mbIL-15 comprises an amino acid sequence having at least 90%, 91%, 92%, 93%, 94%, 95%, 96%, 97%, 98%, 99% or 100% identity with the amino acid sequence of SEQ ID NO: 69. In certain cases, the CAR and the cytokine is expressed in separate vectors. In specific cases, the vectors can be lentiviral vectors, retroviral vectors or Sleeping Beauty transposons.

CD19-Specific CARs

CD19 is a cell surface glycoprotein of the immunoglobulin superfamily and is found predominately in malignant B-lineage cells. In some instances, CD19 has also been detected in solid tumors such as pancreatic cancer, liver cancer, and prostate cancer.

In some embodiments, described herein include a CD19-specific CAR, in which the antigen binding domain comprises a $F(ab')_2$, Fab', Fab, Fv, or scFv. In some instances, the antigen binding domain recognizes an epitope on CD19. In some embodiments, the antigen binding domain recognizes an epitope on CD19 that is also recognized by FMC63. In some embodiments the scFv and/or VH/VL domains is derived from FMC63. FMC63 generally refers to a mouse monoclonal IgG1 antibody raised against Nalm-1 and -16 cells expressing CD19 of human origin (Ling. N. R., el al. (1987). Leucocyte typing III. 302). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, the antigen binding domain recognizes an epitope on CD19 that is also recognized by JCAR014, JCAR015, JCAR017, or 19-28z CAR (Juno Therapeutics). In some embodiments, described herein include a CD19-specific CAR-T cell, in which the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, a CD19-specific CAR-T cell described herein comprises an anti-CD19 antibody described in US20160152723. In some embodiments, a CD19-specific CAR-T cell described herein comprises an anti-CD19 antibody described in WO2015/123642. In some embodiments, a CD19-specific CAR-T cell described herein comprises an anti-CD19 scFv derived from clone FMC63 (Nicholson et al. Construction and characterisation of a functional CD19 specific single chain Fv fragment for immunotherapy of B lineage leukaemia and lymphoma. Mol. Immunol., 34:1157-1165, 1997).

In some embodiments, the antigen binding domain recognizes an epitope on CD19 that is also recognized by KTE-C19 (Kite Pharma, Inc.). In some embodiments, described herein include a CD19-specific CAR-T cell, in which the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in WO2015187528 or fragment or derivative thereof.

In some embodiments, the antigen binding domain recognizes an epitope on CD19 that is also recognized by CTL019 (Novartis). In some embodiments, described herein include a CD19-specific CAR-T cell, in which the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by UCART19 (Cellectis). In some embodiments, described herein include a CD19-specific CAR-T cell, in which the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by BPX-401 (Bellicum). In some embodiments, described herein include a CD19-specific CAR-T cell, in which the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell, in which the antigen binding domain comprises a $F(ab')_2$, Fa', Fab, Fv. or scFv. In some instances, the antigen binding domain recognizes an epitope on CD19. In some cases, the antigen binding domain recognizes an epitope on CD19 that is also recognized by blinatumomab (Amgen), coltuximabravtansine (InmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, a CD19-specific CAR-T cell described herein comprise a scFv antigen binding domain, and the antigen binding domain recognizes an epitope on CD19 that is also recognized by FMC63, blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), 134 (or DI-43) (Merck Serono), taplitumomabpaptox (National Cancer Institute), XmAb 5871 (Amgen/Xencor, Inc.), MDX-1342 (Medarex) or AFM11 (Affimed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

CD33-Specific CARs

"CD33," is a 67 kDa single pass transmembrane glycoprotein and is a member of the sialic acid-binding immunoglobulin-like lectins (Siglecs) super-family. CD33 is characterized by a V-set Ig-like domain responsible for sialic acid binding and a C2-set Ig-like domain in its extracellular domain. Alternative splicing of CD33 mRNA leads to a shorter isoform (CD33m) lacking the V-set Ig-like domain as well as the disulfide bond linking the V- and C2-set Ig-like domains. In healthy subjects, CD33 is primarily expressed as a myeloid differentiation antigen found on normal multipotent myeloid precursors, unipotent colony-forming cells, monocytes and maturing granulocytes. CD33 is expressed on more than 80% of myeloid leukemia cells but not on normal hematopoietic stem cells or mature granulocytes. (Andrews, R. et al., The L4F3 antigen is expressed by unipotent and multipotent colony-forming cells but not by their precursors, Blood, 68(5):1030-5 (1986)). CD33 has been reported to be expressed on malignant myeloid cells, activated T cells and activated NK cells and is found on at least a subset of blasts in the vast majority of AML patients (Pollard, J. et al., Correlation of CD33 expression level with disease characteristics and response to gemtuzumab ozogamicin containing chemotherapy in childhood AML, Blood, 119(16):3705-11 (2012)). In addition to broad expression on AML blasts, CD33 may be expressed on stem cells underlying AML.

In embodiments, the antigen binding moiety of a CAR described herein is specific to CD33 (CD33 CAR). The CD33-specific CAR, when expressed on the cell surface, redirects the specificity of T cells to human CD33. In embodiments, the antigen binding domain comprises a single chain antibody fragment (scFv) comprising a variable domain light chain (VL) and variable domain heavy chain (VH) of a target antigen specific monoclonal anti-CD33 antibody joined by a flexible linker, such as a glycine-serine linker or a Whitlow linker. In embodiments, the scFv are M195, m2H12, DRB2, and/or My9-6. In embodiments, the scFv is humanized, for example, hM195. In some embodiments, the antigen binding moiety may comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:35 (hM195 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:36 (hM195 VH).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:37 (M2H12 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:38 (M2H12 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:39 (DRB2 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:40 (DRB2 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:41 (My9-6 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:42 (My9-6 VL).

MUC16-Specific CARs

MUC16 is a large carbohydrate antigen, also known as CA-125. MUC16 is encoded by the MUC16 gene located on human chromosome 19. MUC16 is a highly glycosylated multi-domain type I transmembrane protein comprising 3 domains. The C-terminal domain contains multiple extracellular SEA (sea urchin sperm protein, enterokinase, and agrin) modules that have an autoproteolytic activity. SEA harbors two proteolytic sites proximal to the transmembrane (TM) domain. A large cleaved domain termed CA-125 is released into circulation at acidic pH. CA-125 is commonly used as disease biomarker for ovarian cancer. The highly conserved truncated extracellular membrane tethered protein domain called MUC16ecto domain. A MUC16 antibody was identified that specifically bound the ectodomain of MUC16 that is retained on the tumor cell surface. "Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

In embodiments, the antigen binding moiety of a CAR described herein is specific to MUC16 (MUC16 CAR). The MUC16-specific CAR, when expressed on the cell surface, redirects the specificity of T cells to human MUC16. In embodiments, the antigen binding domain comprises a single chain antibody fragment (scFv) comprising a variable domain light chain (VL) and variable domain heavy chain (VH) of a target antigen specific monoclonal anti-MUC16 antibody joined by a flexible linker, such as a glycine-serine linker or a Whitlow linker. In embodiments, the scFv are MUC16-1 scFv (SEQ ID NOs: 43-44), MUC16-2 scFv (SEQ ID NOs: 45-46), MUC16-3 scFv (SEQ ID NOs: 47-48), MUC16-4 scFv (SEQ ID NOs: 49-50), MUC16-5 scFv (SEQ ID NOs: 51-52), MUC16-6 scFv (SEQ ID NOs: 53-54) or MUC16-7 scFv (SEQ ID NOs: 55-56). In embodiments, the scFv is humanized.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:43 (MUC16-1).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:44 (MUC16-1).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:45 (MUC16-2).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:46 (MUC16-2).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:47 (MUC16-3).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:48 (MUC16-3).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:49 (MUC16-4).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:50 (MUC16-4).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:51 (MUC16-5).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:52 (MUC16-5).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:53 (MUC16-5).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:54 (MUC16-6).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:55 (MUC16-7).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:56 (MUC16-7).

In some embodiments, the antigen binding moiety can comprise VH and VL that are directionally linked, for example, from N to C terminus, VH-linker-VL or VL-linker-VH.

Engineered T-Cell Receptor (TCR)

In some embodiments, the chimeric receptor comprises an engineered T-cell receptor. The T cell receptor (TCR) is composed of two chains (αβ or γδ) that pair on the surface of the T cell to form a heterodimeric receptor. In some instances, the αβ TCR is expressed on most T cells in the body and is known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Mage A3, Titin. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook", (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR a and R variable regions respectively, Cα and Cβ are TCR a and R constant regions respectively, and L is a linker sequence. In certain embodiments single chain TCRs of the invention may have an introduced disulfide bond between residues of the respective constant domains, as described in WO 2004/033685.

The TCR described herein may be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

Therapeutic agents which may be associated with the TCRs described herein include immunomodulators, radioactive compounds, enzymes (perforin for example) or chemotherapeutic agents. To ensure that toxic effects are exercised in the desired location the toxin could be inside a liposome linked to a TCR so that the compound is released in a controlled manner. In some cases, the controlled release minimize damaging effects during the transport in the body and ensure that the toxin has maximum effect after binding of the TCR to the relevant antigen presenting cells.

In some embodiments, additional suitable therapeutic agents include for instance:

a. small molecule cytotoxic agents, e.g., compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;
b. peptide cytotoxins, i.e. proteins or fragments thereof with the ability to kill mammalian cells. For example, ricin, diphtheria toxin, *Pseudomonas* bacterial exotoxin A, DNase and RNase;
c. radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;
d. immuno-stimulants, i.e. immune effector molecules which stimulate immune response. For example, cytokines such as IL-2 and IFN-γ,
e. superantigens and mutants thereof;
f. TCR-HLA fusions;
g. chemokines such as IL-8, platelet factor 4, melanoma growth stimulatory protein, etc;
h. antibodies or fragments thereof, including anti-T cell or NK cell determinant antibodies (e.g. anti-CD3, anti-CD28 or anti-CD16);

i. alternative protein scaffolds with antibody like binding characteristics
j. complement activators; and
k. xenogeneic protein domains, allogeneic protein domains, viral/bacterial protein domains, viral/bacterial peptides.

Doses

Suitable dosages of the fusion protein and modified immune effector cells used will depend on the age and weight of the subject and the particular drug used. Dosages and therapeutic regimens of the fusion protein and modified immune effector cells can be determined by a skilled artisan.

In certain embodiments, the fusion protein is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the fusion protein is administered at a dose of about 1 mg/kg, about 3 mg/kg, about 5 mg/kg, about 10 mg/kg, about 20 mg/kg, about 30 mg/kg, or about 40 mg/kg. In some embodiments, the fusion protein is administered at a dose of about 1-3 mg/kg, or about 3-10 mg/kg. In some embodiments, the fusion protein is administered at a dose of about 0.5-2, 2-4, 2-5, 5-15, or 5-20 mg/kg. The dosing schedule can vary from e.g., once a week to once every 2, 3, or 4 weeks. In one embodiment, the fusion protein is administered at a dose from about 10 to 20 mg/kg every other week. In another embodiment, the fusion protein is administered at a dose of about 1 mg/kg once every two weeks, about 3 mg/kg once every two weeks, 10 mg/kg once every two weeks, 3 mg/kg once every four weeks, or 5 mg/kg once every four weeks.

In other embodiments, the fusion protein is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. In some embodiments, the fusion protein is administered at a dose of about 200 mg, about 250 mg, about 300 mg, about 350 mg, about 400 mg, about 450 mg, or about 500 mg. In some embodiments, the fusion protein is administered at a dose of 200 or 300 mg. In some embodiments, the fusion protein is administered at a dose of about 250-450 mg, or about 300-400 mg. In some embodiments, the fusion protein is administered at a dose of about 200-300 mg, 250-350 mg, 300-400 mg, 350-450 mg, or 400-500 mg. The dosing schedule can vary from e.g., once a week to once every 2, 3, 4, 5, or 6 weeks. In one embodiment the fusion protein is administered at a dose from about 300 mg to 400 mg once every three or once every four weeks. In one embodiment, the fusion protein is administered at a dose from about 300 mg once every three weeks. In one embodiment, the fusion protein is administered at a dose from about 400 mg once every four weeks. In one embodiment, the fusion protein is administered at a dose from about 300 mg once every four weeks. In one embodiment, the fusion protein is administered at a dose from about 400 mg once every three weeks. The fusion protein can be administered one or more times, e.g., one, two, three, four, five, six, seven or more times. In one embodiment, the fusion protein is administered six times. The fusion protein can be administered at least 5 days, e.g., about 5, 6, 7, 8, 9, 10, 11, 12, 13, 14, 20, 25, 30, 35, or 40 days, after administration of CAR-expressing cells, e.g., MUC16, CD33, CD19 or BCMA-specific CAR expressing cells. In some embodiments, the fusion protein can be administered about 8 days or about 15 days after administration of CAR-expressing cells, e.g., MUC16 specific CAR expressing cells or CD33 specific CAR expressing cells.

The fusion protein can be administered by a variety of methods known in the art, although for many therapeutic applications, the preferred route/mode of administration is intravenous injection or infusion. For example, the fusion protein can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the fusion protein can be administered by intravenous infusion at a rate of less than 10 mg/min; preferably less than or equal to 5 mg/min to reach a dose of about 1 to 100 mg/m 2, preferably about 5 to 50 mg/m2, about 7 to 25 mg/m2 and more preferably, about 10 mg/m2.

The fusion protein can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the infusion rate of about 110 to 130 mg/m2 achieves a level of about 3 mg/kg. In other embodiments, the fusion protein can be administered by intravenous infusion at a rate of less than 10 mg/min, e.g., less than or equal to 5 mg/min to reach a dose of about 1 to 100 mg/m2, e.g., about 5 to 50 mg/m2, about 7 to 25 mg/m2, or, about 10 mg/m2. In some embodiments, the antibody is infused over a period of about 30 min.

Modified Effector Cell Doses

In some embodiments, an amount of modified effector cells is administered to a subject in need thereof and the amount is determined based on the efficacy and the potential of inducing a cytokine-associated toxicity. In some cases, an amount of modified effector cells comprises about $10^5$ to about $10^9$ modified effector cells/kg. In some cases, an amount of modified effector cells comprises about $10^5$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^9$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg.

In some embodiments, the modified effector cells are modified T cells. In some instances, the modified T cells are CAR-T cells. In some cases, an amount of CAR-T cells comprises about $10^5$ to about $10^9$ CAR-T cells/kg. In some cases, an amount of CAR-T cells comprises about $10^5$ to about $10^8$ CAR-T cells/kg. In some cases, an amount of CAR-T cells comprises about $10^5$ to about $10^7$ CAR-T cells/kg. In some cases, an amount of CAR-T cells comprises about $10^6$ to about $10^9$ CAR-T cells/kg. In some cases, an amount of CAR-T cells comprises about $10^6$ to about $10^8$ CAR-T cells/kg. In some cases, an amount of CAR-T cells comprises about $10^7$ to about $10^9$ CAR-T cells/kg. In some cases, an amount of CAR-T cells comprises about $10^5$ to about $10^6$ CAR-T cells/kg. In some cases, an amount of CAR-T cells comprises about $10^6$ to about $10^7$ CAR-T cells/kg. In some cases, an amount of CAR-T cells comprises about $10^7$ to about $10^8$ CAR-T cells/kg. In some cases, an amount of CAR-T cells comprises about $10^8$ to about $10^9$ CAR-T cells/kg. In some instances, an amount of CAR-T cells comprises about $10^9$ CAR-T cells/kg. In some instances, an amount of CAR-T cells comprises about $10^8$ CAR-T cells/kg. In some instances, an amount of CAR-T cells comprises about $10^7$ CAR-T cells/kg. In some instances, an amount of CAR-T cells comprises about $10^6$ CAR-T cells/kg. In some instances, an amount of CAR-T cells comprises about $10^5$ CAR-T cells/kg.

In some embodiments, the CAR-T cells are CD19-specific CAR-T cells. In some cases, an amount of CD19-specific CAR-T cells comprises about $10^5$ to about $10^9$ CAR-T cells/kg. In some cases, an amount of CD19-specific CAR-T cells comprises about $10^5$ to about $10^8$ CAR-T cells/kg. In some cases, an amount of CD19-specific CAR-T cells comprises about $10^5$ to about $10^7$ CAR-T cells/kg. In some cases, an amount of CD19-specific CAR-T cells comprises about $10^6$ to about $10^9$ CAR-T cells/kg. In some cases, an amount of CD19-specific CAR-T cells comprises about $10^6$ to about $10^8$ CAR-T cells/kg. In some cases, an amount of CD19-specific CAR-T cells comprises about $10^7$ to about $10^9$ CAR-T cells/kg. In some cases, an amount of CD19-specific CAR-T cells comprises about $10^5$ to about $10^6$ CAR-T cells/kg. In some cases, an amount of CD19-specific CAR-T cells comprises about $10^6$ to about $10^7$ CAR-T cells/kg. In some cases, an amount of CD19-specific CAR-T cells comprises about $10^7$ to about $10^8$ CAR-T cells/kg. In some cases, an amount of CD19-specific CAR-T cells comprises about $10^8$ to about $10^9$ CAR-T cells/kg. In some instances, an amount of CD19-specific CAR-T cells comprises about $10^9$ CAR-T cells/kg. In some instances, an amount of CD19-specific CAR-T cells comprises about $10^8$ CAR-T cells/kg. In some instances, an amount of CD19-specific CAR-T cells comprises about $10^7$ CAR-T cells/kg. In some instances, an amount of CD19-specific CAR-T cells comprises about $10^6$ CAR-T cells/kg. In some instances, an amount of CD19-specific CAR-T cells comprises about $10^5$ CAR-T cells/kg.

In some embodiments, the modified T cells are engineered TCR T-cells. In some cases, an amount of engineered TCR T-cells comprises about $10^5$ to about $10^9$ TCR cells/kg. In some cases, an amount of engineered TCR cells comprises about $10^5$ to about $10^8$ TCR cells/kg. In some cases, an amount of engineered TCR cells comprises about $10^5$ to about $10^7$ TCR cells/kg. In some cases, an amount of engineered TCR cells comprises about $10^6$ to about $10^9$ TCR cells/kg. In some cases, an amount of engineered TCR cells comprises about $10^6$ to about $10^8$ TCR cells/kg. In some cases, an amount of engineered TCR cells comprises about $10^7$ to about $10^9$ TCR cells/kg. In some cases, an amount of engineered TCR cells comprises about $10^5$ to about $10^6$ TCR cells/kg. In some cases, an amount of engineered TCR cells comprises about $10^6$ to about $10^7$ TCR cells/kg. In some cases, an amount of engineered TCR cells comprises about $10^7$ to about $10^8$ TCR cells/kg. In some cases, an amount of engineered TCR cells comprises about $10^8$ to about $10^9$ TCR cells/kg. In some instances, an amount of engineered TCR cells comprises about $10^9$ TCR cells/kg. In some instances, an amount of engineered TCR cells comprises about $10^8$ TCR cells/kg. In some instances, an amount of engineered TCR cells comprises about $10^7$ TCR cells/kg. In some instances, an amount of engineered TCR cells comprises about $10^6$ TCR cells/kg. In some instances, an amount of engineered TCR cells comprises about $10^5$ TCR cells/kg.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Expression and Purification System of Fusion Proteins

The fusion protein or a fragment or a variant thereof described herein can be produced from cells by culturing a host cell transformed with the expression vector comprising one or more polynucleotides encoding the fusion protein or a fragment or a variant thereof, under conditions, and for an amount of time, sufficient to allow expression of the fusion protein, or a fragment or a variant thereof. For example, polypeptides expressed in *E. coli* can be refolded from inclusion bodies (see, e.g., Hou et al. (1998) Cytokine 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells can vary depending on a number of factors, and can be easily optimized as needed. The fusion protein or a fragment or a variant thereof described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the fusion protein or a fragment or a variant thereof can be purified or isolated. The term "purified" or "isolated" as applied to any of the fusion proteins or fragments or variants thereof described herein can refer to a polypeptide or a protein that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% by weight of the total protein in a sample.

The fusion protein or a fragment or a variant thereof described herein can be isolated or purified in a variety of ways depending on what other components are present in the sample. Standard purification methods include electrophoretic, molecular, immunological, and chromatographic techniques, including ion exchange, hydrophobic, affinity, and reverse-phase HPLC chromatography. For example, the fusion protein or a fragment or a variant thereof can be purified using a standard anti-fusion protein antibody affinity column. Ultrafiltration and diafiltration techniques, in conjunction with protein concentration, are also useful. See, e.g., Scopes (1994) "Protein Purification, 3rd edition," Springer-Verlag, New York City, N.Y. The degree of purification necessary can vary depending on the desired use. In some instances, no purification of the expressed fusion protein or a fragment or variant thereof is necessary.

Methods for determining the yield or purity of a purified fusion protein or a fragment or a variant thereof can include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain). Once expressed, purified, or after being purified following expression, a fusion protein or a fragment or a variant thereof described herein can be assayed for any one of a numbered of desired properties using in vitro or in vivo assays such as any of those described herein. For example, a fusion protein or a fragment or a variant thereof described herein can be assayed for e.g., its ability to inhibit PD-1 and trap TGF-β.

The fusion protein or a fragment or a variant thereof described herein can be produced using a variety of techniques. For example, a polynucleotide encoding a fusion protein or a fragment or a variant thereof described herein can be inserted into an expression vector that contains transcriptional and translational regulatory sequences, which can include, e.g., promoter sequences, ribosomal binding sites, transcriptional start and stop sequences, translational start and stop sequences, transcription terminator signals, polyadenylation signals, and enhancer or activator sequences. In some embodiments, the regulatory sequences can include a promoter and transcriptional start and stop sequences. In addition, the expression vector can include more than one replication system such that it can be maintained in two different organisms, for example, in mammalian or insect cells for expression and in a prokaryotic host for cloning and amplification.

Several possible vector systems are available for the expression of the fusion protein or a fragment or a variant thereof from nucleic acids in mammalian cells (e.g., host cells). For example, one class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). Another class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), polyoma virus (Deans et al. (1984) *Proc Natl Acad Sci USA* 81:1292), or SV40 virus (Lusky and Botchan (1981) *Nature* 293:79). The expression vectors can be introduced into cells (e.g., host cells) in a manner suitable for subsequent expression of the nucleic acid. The method of introduction is largely dictated by the targeted cell type, discussed below. Non-limiting exemplary methods can include $CaPO_4$ precipitation, liposome fusion, lipofectin, electroporation, viral infection, dextran-mediated transfection, polybrene-mediated transfection, protoplast fusion, and direct microinjection.

Appropriate host cells for the expression of the fusion protein or a fragment or a variant thereof can include, but not limited to, yeast, bacteria, insect, plant, and, as described above, mammalian cells. Of interest are bacteria such as *E. coli*, fungi such as *Saccharomyces cerevisiae* and *Pichia pastoris*, insect cells such as SF9, mammalian cell lines (e.g., human cell lines), as well as primary cell lines (e.g., primary mammalian cells). In some embodiments, the fusion protein or a fragment or a variant thereof can be expressed in Chinese hamster ovary (CHO) cells or in a suitable myeloma cell line such as (NSO). Suitable cell lines also include, for example, BHK-21 (baby hamster kidney) cells; 293 (human embryonic kidney) cells; HMEpC (Human Mammary Epithelial cells; 3T3 (mouse embryonic fibroblast) cells.

The methods described herein provide for the expression and purification of the fusion protein or a fragment or a variant thereof in various cell-based expression systems, such as protein production in bacterial, mammalian, insect, yeast, and chymadomonas cells. Protein expression can be constitutive or inducible with inducers such as copper sulfate, sugars such as galactose, methanol, methylamine, thiamine, tetracycline, or IPTG. After the fusion protein or a fragment or a variant thereof is expressed in the host cells, the host cells are lysed to liberate the fusion protein or a fragment or a variant thereof for purification. Methods of lysing the various host cells are featured in "Sample Preparation-Tools for Protein Research" EMD Bioscience and in the Current Protocols in Protein Sciences (CPPS). A non-limiting exemplary purification method is affinity chromatography, such as ion-metal affinity chromatograph using nickel, cobalt, or zinc affinity resins for e.g., a histidine-tagged fusion protein or fragment or variant thereof. Methods of purifying histidine-tagged proteins are described by Clontech using their Talonx cobalt resin and by Novagen in their pET system manual, 10th edition. Another non-limiting exemplary purification strategy is by immuno-affinity chromatography, for example, anti-myc antibody conjugated resin can be used to affinity purify e.g., a myc-tagged fusion protein or fragment or variant thereof. Enzymatic digestion with serine proteases, such as thrombin and enterokinase, cleave and release the fusion protein or a fragment or a variant thereof from the histidine or myc tag, releasing the fusion protein or a fragment or a variant thereof from the affinity resin while the histidine-tags and myc-tags are left attached to the affinity resin.

Methods of introducing and expressing polynucleotides encoding the fusion protein or a fragment or a variant thereof into a cell (e.g., a host cell) are known in the art. In the context of an expression vector, the vector comprising the polynucleotide encoding the fusion protein or a fragment or a variant thereof can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing polynucleotides encoding the fusion protein or a fragment or a variant thereof into a host cell can include the use of DNA and RNA vectors.

Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some embodiments, the expression vector can have the necessary 5' upstream and 3' downstream regulatory elements such as promoter sequences, ribosome recognition and binding TATA box, and 3' UTR AAUAAA transcription termination sequence for the efficient gene transcription and translation in its respective host cell. The expression vector can have additional sequence such as 6×-histidine, V5, thioredoxin, glutathione-S-transferase, c-Myc, VSV-G, HSV, FLAG, maltose binding peptide, metal-binding peptide, HA and "secretion" signals (Honeybee melittin, .alpha.-factor, PHO, Bip), which are incorporated into the expressed fusion protein or fragment or variant thereof. In addition, there can be enzyme digestion sites incorporated after these sequences to facilitate enzymatic removal of them after they are not needed. These additional sequences are useful for the detection of the fusion protein expression, for protein purification by affinity chromatography, enhanced solubility of the recombinant protein in the host cytoplasm, and/or for secreting the fusion protein out into the culture media, into the periplasm of the prokaryote bacteria, or the spheroplast of the yeast cells. The expression of the fusion protein can be constitutive in the host cells or it can be induced, e.g., with copper sulfate, sugars, such as galactose, methanol, methylamine, thiamine, tetracycline, infection with baculovirus, and (isopropyl-beta-D-thiogalactopyranoside) IPTG, a stable synthetic analog of lactose.

Non-limiting examples of expression vectors and host cells can include the pET vectors (Novagen), pGEX vectors (Amersham Pharmacia), and pMAL vectors (New England labs. Inc.) for protein expression in *E. coli* host cell such as BL21, BL21(DE3) and AD494(DE3)pLysS, Rosetta (DE3), and Origami(DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™-HT (Invitrogen) for the expression in *Spodopera frugiperda* 9 (S9) and Sf11 insect cell lines; pMT/BiP/V5-His (Invitrogen) for the expression in *Drosophila* Schneider S2 cells; *Pichia* expression vectors pPICZa, pPICZ, pFLDa and pFLD (Invitrogen) for expression in *Pichia pastoris* and vectors pMETa and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5.

Besides cell-based expression systems, cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix.

In one embodiment, a continuous cell-free translation system can be used to produce the fusion protein or a fragment or a variant thereof. A continuous cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. Large scale cell-free production is described by Chang G. el. al., Science 310:1950-3 (2005).

Other commercially available cell-free expression systems include the Expressway™ Cell-Free Expression Systems (Invitrogen), which utilize an *E. coli*-based in vitro system for efficient, coupled transcription and translation reactions to produce up to milligram quantities of active recombinant protein in a tube reaction format; the Rapid Translation System (RTS) (Roche Applied Science), which also uses an *E. coli*-based in vitro system; and the TNT Coupled Reticulocyte Lysate Systems (Promega), which uses rabbit reticulocyte-based in-vitro system.

In other exemplary production methods, the fusion protein or a fragment or a variant thereof described herein can be synthesized de novo in whole or in part, using chemical methods. For example, the component amino acid sequences of the fusion protein or a fragment or a variant thereof can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

Methods for detecting and/or measuring the amount of endotoxin present in a sample (both before and after purification) can be based on commercial kits that are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated. In some embodiments, endotoxins can be removed from the fusion protein preparations using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

In some embodiments, following expression and purification, the fusion protein or a fragment or a variant thereof described herein can be modified. The modifications can be covalent or non-covalent modifications. Such modifications can be introduced into the fusion protein or a fragment or a variant thereof by, e.g., reacting targeted amino acid residues of the fusion protein or a fragment or a variant thereof with an organic derivatizing agent that is capable of reacting with selected side chains or terminal residues. Suitable sites for modification can be chosen using any of a variety of criteria including, e.g., structural analysis or amino acid sequence analysis of the fusion protein or a fragment or a variant thereof.

In some exemplary production methods, the fusion protein or a fragment or a variant thereof as described herein can be conjugated to a heterologous moiety. In some embodiments, the heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides can include, e.g., an antigenic tag (e.g., FLAG, polyhistidine, hemagglutinin (HA), glutathione-S-transferase (GST), or maltose-binding protein (MBP)) for use in purifying antibodies or fragments or variants thereof. Heterologous polypeptides can also include polypeptides that are useful as diagnostic or detectable markers, for example, luciferase, green fluorescent protein (GFP), or chloramphenicol acetyl transferase (CAT). Where the heterologous moiety is a polypeptide, the moiety can be incorporated into the fusion protein or a fragment or a variant thereof described herein, resulting in a fusion protein comprising the heterologous moiety.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the promoter is a constitutive promoter, a tissue specific promoter, or an inducible promoter. In some embodiments, the inducible promoter is a small molecule ligand-inducible two polypeptide ecdysone receptor-based gene switch.

Additional promoter elements, e.g., enhancers, can regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it can appear that individual elements can function either cooperatively or independently to activate transcription.

Reporter

Reporter genes can be used for identifying potentially transfected cells and for evaluating the functionality of regulatory sequences. In general, a reporter gene is a gene that is not present in or expressed by the host cell and that encodes a polypeptide whose expression is manifested by some easily detectable property, e.g., enzymatic activity. Expression of the reporter gene is assayed at a suitable time after the polypeptides encoding the fusion protein or a fragment or a variant thereof has been introduced into the host cells. Suitable reporter genes can include, but not limited to, genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, a polynucleotide construct with the minimal 5' flanking region showing the highest level of expression of reporter gene is identified as the promoter. Such promoter regions can be linked to a reporter gene and used to evaluate agents for the ability to modulate promoter-driven transcription.

Variants

The term "fragment" or "variant" refers to variants and derivatives of the fusion protein described herein, containing one or more binding moieties to e.g., PD-1 and/or TGF-β. In certain embodiments, amino acid sequence variants of the fusion protein are contemplated. For example, in some embodiments, amino acid sequence variants of the fusion protein described herein are contemplated to improve the binding affinity and/or other biological properties of the fusion protein. Exemplary method for preparing amino acid variants include, but are not limited to, introducing appropriate modifications into the nucleotide sequence encoding the fusion protein, or by peptide synthesis. Such modifications include, for example, deletions from, and/or insertions into and/or substitutions of residues within the amino acid sequences of the fusion protein.

Any combination of deletion, insertion, and substitution can be made to the various domains to arrive at the final fusion protein, provided that the final fusion protein possesses the desired characteristics, e.g., PD-1 inhibition and TGF-β trap. In some embodiments, fusion protein variants having one or more amino acid substitutions are provided. In some embodiments, sites of interest for substitution mutagenesis can include the CDRs and framework regions. In some embodiments, amino acid substitutions can be introduced into the variable domains of the target-binding protein of interest and the products screened for a desired activity, e.g., retained/improved antigen binding, decreased immunogenicity, or improved antibody-dependent cell mediated cytotoxicity (ADCC) or complement dependent cytotoxicity (CDC). Both conservative and non-conservative amino acid substitutions can be contemplated for preparing the antibody variants (e.g., PD-1 antibody variants).

In another example of a substitution to create a variant fusion protein can be substituting one or more hypervariable region residues in a parent antibody. In general, variants are then selected based on improvements in desired properties compared to a parent antibody, for example, increased affinity, reduced affinity, reduced immunogenicity, increased pH dependence of binding. For example, an affinity matured variant antibody can be generated, e.g., using phage display-based affinity maturation techniques, such as those described herein and known in the field. Substitutions can be made in hypervariable regions (HVR) of a parent antibody to generate variants, and variants are then selected based on binding affinity, i.e., by affinity maturation. In some embodiments of affinity maturation, diversity can be introduced into the variable genes chosen for maturation by any of a variety of methods (e.g., error-prone PCR, chain shuffling, or oligonucleotide-directed mutagenesis). A secondary library can be then created. The library can be then screened to identify any antibody variants with the desired affinity. Another method to introduce diversity can involve HVR-directed approaches, in which several HVR residues (e.g., 4-6 residues at a time) can be randomized. HVR residues involved in antigen binding can be specifically identified, e.g., using alanine scanning mutagenesis or modeling. Substitutions can be in one, two, three, four, or more sites within a parent antibody sequence.

In some embodiments, a fragment or a variant of the fusion protein, as described herein can comprise a VL and a VH domain with amino acid sequences corresponding to the amino acid sequence of a naturally occurring VL or VH domain, respectively, but that has been "humanized", i.e., by replacing one or more amino acid residues in the amino acid sequence of the naturally occurring VL or VH domains (and in particular in the framework sequences) by one or more of the amino acid residues that occur at the corresponding position(s) in a VL or VH domain from a conventional 4-chain antibody from a human. This can be performed in a manner known in the field, which can be clear to the skilled person, for example on the basis of the further description herein. It should be noted that such humanized fusion protein or a fragment or a variant thereof are obtained in any suitable manner known per se and thus are not strictly limited to polypeptides that have been obtained using a polypeptide that comprises a naturally occurring VL and/or VH domain as a starting material.

In some embodiments, a fragment or a variant of the fusion protein, as described herein, comprises a VL and a VH domain with amino acid sequences corresponding to the amino acid sequence of a naturally occurring VL or VH domain, respectively, but that has been "camelized", i.e., by replacing one or more amino acid residues in the amino acid sequence of a naturally occurring VL or VH domain from a conventional 4-chain antibody by one or more of the amino acid residues that occur at the corresponding position(s) in a VL or a VH domain of a heavy chain antibody. Such "camelizing" can be preferably inserted at amino acid positions that form and/or are present at the VH-VL interface, and/or at the so-called Camelidae hallmark residues (see for example WO 94/04678 and Davies and Riechmann (1994 and 1996)). In some embodiments, the VH sequence that is used as a starting material or starting point for generating or designing the camelized single domain can be a VH sequence from a mammal, e.g., a human, such as a VH3 sequence. It should be noted that such camelized fusion protein or a fragment or a variant thereof, in certain embodiments, can be obtained in any suitable manner known in the field and thus are not strictly limited to polypeptides that have been obtained using a polypeptide that comprises a naturally occurring VL and/or VH domain as a starting material.

For example, both "humanization" and "camelization" can be performed by providing a nucleotide sequence that encodes a naturally occurring VL and/or VH domain, respectively, and then changing, one or more codons in the nucleotide sequence in such a way that the new polynucleotide sequence encodes a "humanized" or "camelized" fusion protein or a fragment or a variant thereof, respectively. This polynucleotide can then be expressed, so as to provide the desired binding capabilities (e.g., PD-1). Alternatively, in other embodiments, the fusion protein or a fragment or a variant thereof comprises a "humanized" or "camelized" antibody synthesized de novo using known peptide synthesis technique from the amino acid sequence of a naturally occurring antibody comprising a VL and/or VH domain. In some embodiments, the fusion protein or a fragment or a variant thereof comprises a "humanized" or "camelized" antibody synthesized de novo using known peptide synthesis technique from the amino acid sequence or nucleotide sequence of a naturally occurring antibody comprising a VL and/or VH domain, respectively, a nucleotide sequence encoding the desired humanized or camelized antibody of the disclosure, respectively, is designed and then synthesized de novo using known techniques for nucleic acid synthesis, after which the nucleic acid thus obtained is expressed in using known expression techniques, so as to provide the desired antibody.

Other suitable methods and techniques for obtaining the fusion protein or a fragment or a variant thereof, starting from naturally occurring sequences for VL or VH domains, for example, comprises combining one or more parts of one or more naturally occurring VL or VH sequences (such as one or more framework (FR) sequences and/or complementarity determining region (CDR) sequences), and/or one or more synthetic or semi-synthetic sequences, and/or a naturally occurring sequence for a CH2 domain, and a naturally occurring sequence for a CH3 domain comprising amino acid substitutions that favor formation of heterodimer over homodimer, in a suitable manner, so as to provide the fusion protein or a fragment or a variant thereof.

Antibody Engineering

In some embodiments, it can be desirable to change certain amino acids containing exposed side-chains to another amino acid residue in order to provide for greater chemical stability of a final antibody (e.g., PD-1 antibody), as follows. The deamidation of asparagine can occur on N-G or D-G sequences and result in the creation of an isoaspartic acid residue that introduces a kink into the polypeptide chain and decreases its stability (isoaspartic acid effect). In some embodiments, the antibodies of the fusion protein of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem can occur at a Asp-Gly sequence. Reissner and Aswad (2003) Cell. Mol. Life Sci. 60:1281. Isoaspartate formation can debilitate or completely abrogate binding of an antibody to its target antigen. See, Presta (2005) J. Allergy Clin. Immunol. 116:731 at 734. In one embodiment, the asparagine can be changed to glutamine (Gln). It can also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) J. Chromatog. 662:261. In addition, any methionine residues (typically solvent exposed Met) in CDRs can be changed to Lys, Leu, Ala, or Phe in order to reduce the possibility that the methionine sulfur would oxidize, which can reduce antigen binding affinity and also can contribute to molecular heterogeneity in the final antibody preparation. Id. In one embodiment, the methionine can be changed to alanine (Ala). Additionally, in order to prevent or minimize potential scissile Asn-Pro peptide bonds, it can be desirable to alter any Asn-Pro combinations found in a CDR to Gln-Pro, Ala-Pro, or Asn-Ala. Antibodies with such substitutions can be subsequently screened to ensure that the substitutions do not decrease the affinity or specificity of the antibody for human PD-L1, or other desired biological activity to unacceptable levels.

An antibody of the fusion protein disclosed herein can also be conjugated to a chemical moiety such as a radionuclide or other detectable label. Radionuclides include $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe. Fluorescent or chemilluminescent labels can include fluorophores, such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating antibody molecules to the various moieties can be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Pharmaceutical Compositions

The present disclosure provides a composition comprising the fusion protein or a fragment or a variant thereof described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the fusion protein or a fragment or a variant thereof. Any suitable carrier can be used within the context of the present disclosure, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. In some cases, the fusion protein or a fragment or a variant thereof is part of a composition formulated to protect the fusion protein or a fragment or a variant thereof from damage prior to administration. For example, the composition can be formulated to reduce loss of the fusion protein or a fragment or a variant thereof on devices used to prepare, store, or administer the fusion protein or a fragment or a variant thereof, such as glassware, syringes, or needles. The composition can be formulated to decrease the light sensitivity and/or temperature sensitivity of the fusion protein or a fragment or a variant thereof. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the fusion protein or a fragment or a variant thereof, and facilitate its administration. Formulations for fusion protein or a fragment or a variant thereof—containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the fusion protein or a fragment or a variant thereof can be present in a composition with other therapeutic or biologically-active agents. For example, factors that control inflammation, such as ibuprofen or steroids, can be part of the composition to reduce swelling and inflammation associated with in vivo administration of the fusion protein or a fragment or a variant thereof. Antibiotics, i.e., microbicides and fungicides, can be present to treat existing infection and/or reduce the risk of future infection, such as infection associated with the administration procedures.

In some instances, pharmaceutical compositions comprising the presently described fusion protein or a fragment or a variant thereof are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include the presently described fusion protein or a fragment or a variant thereof and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating can be provided around the compositions. In some embodiments, the compositions are formulated into particles (for example for administration by capsule) and some or all of the particles can be coated. In some embodiments, the compositions are formulated into particles (for example for administration by capsule) and some or all of the particles can be microencapsulated. In some embodiments, the compositions can be formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1. Fusion Protein of Anti-PD1-TGF-β Trap

Anti-PD1 VHs and VLs were synthesized and formatted in IgG, scFv-$F_C$ or scFv configurations with TGFβRII fused at C-terminal by linker (G4S)2. Anti-PD1-trap fusion proteins were transiently expressed in Expi293 cells according to manufacturer's protocol. To purify the fusion proteins, the transfected supernatants were loaded to onto a protein L column using AKTA AVANT. The column was washed with PBS, before the protein was eluted with IgG elution buffer (Pierce). The eluted protein was then buffer-exchanged into PBS using a PD-10 column (GE Healthcare).

Surface Plasmon Resonance

Surface plasma resonance (SPR) analysis was performed using Biacore3000, CM5 chip, an amine-coupling kit, 10×HBS-P running buffer and Glycine for regeneration (GE Healthcare). For anti-PD1 kinetic assay, purified PD-1 Fc fusion protein was immobilized on CM5 chip using a pre-defined ligand immobilization program. Purified anti-PD1-Trap fusion proteins were diluted in HBS-P running buffer to a range of final concentrations and injected. Dissociation was allowed to proceed followed by a pulse of 10 mM Glycine (pH 1.5) for regeneration of the chip surface.

To investigate if the anti-PD1-trap fusion protein could simultaneously binding to PD1 and TGFβRII, 100 nM of anti-PD1 trap fusion protein was injected to PD1 immobilized CM5 chip for 3 minutes, followed by 3 minutes of dissociation. Subsequently, different isoforms of TGF-β were injected to examine the binding of TGF-β to PD1 bond anti-PD1-trap fusion protein.

Figure 6:
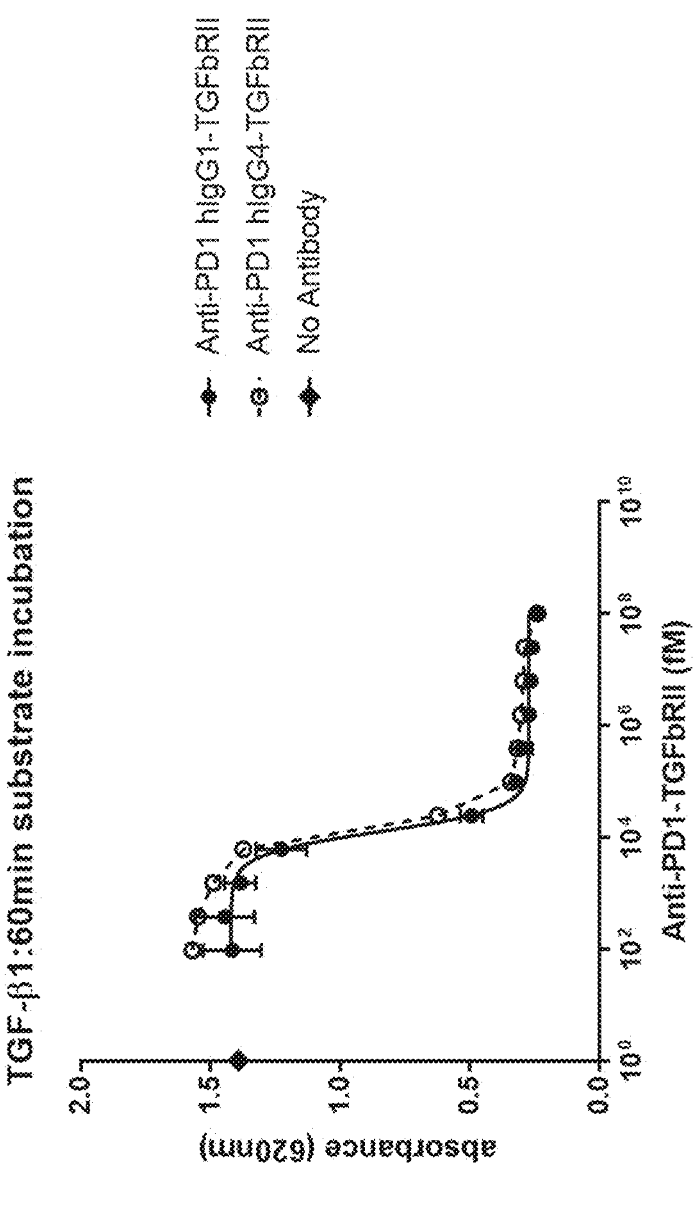
FIG. 6 is a graph showing neutralization of TGF-β1 isoform signaling by anti-PD1 (VH6-VL5) IgG1-TGFβRII and anti-PD1 (VH6-VL5) IgG4-TGFβRII.
Figure 7:
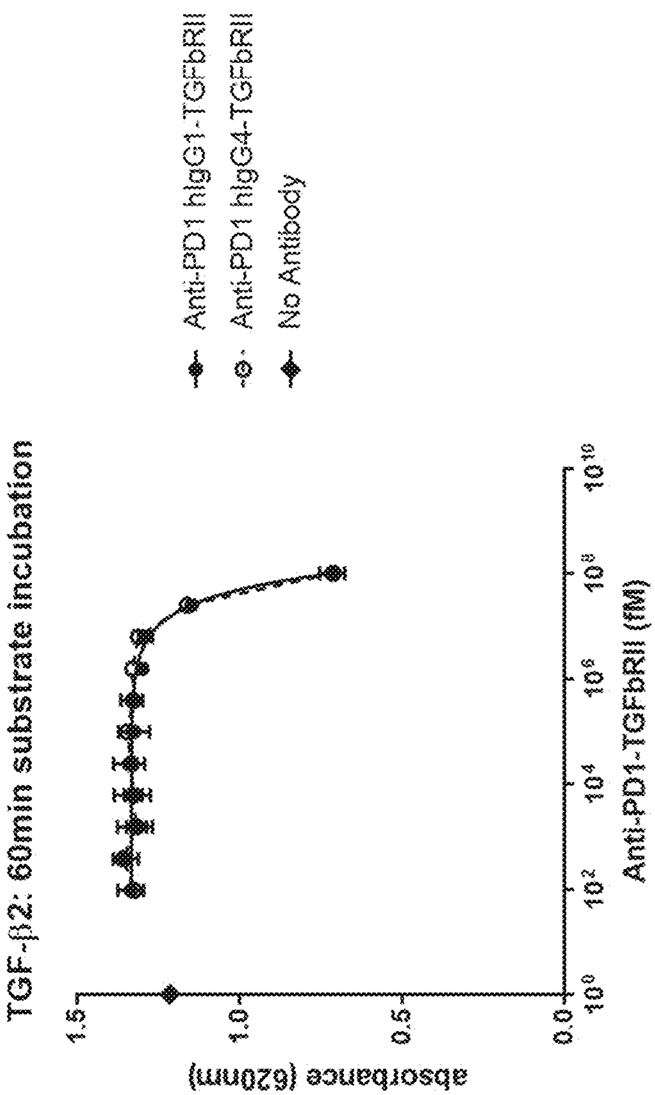
FIG. 7 is a graph showing neutralization of TGF-β2 isoform by anti-PD1(VH6-VL5) IgG1-TGFβRII and anti-PD1(VH6-VL5) IgG4-TGFβRII.
Figure 8:
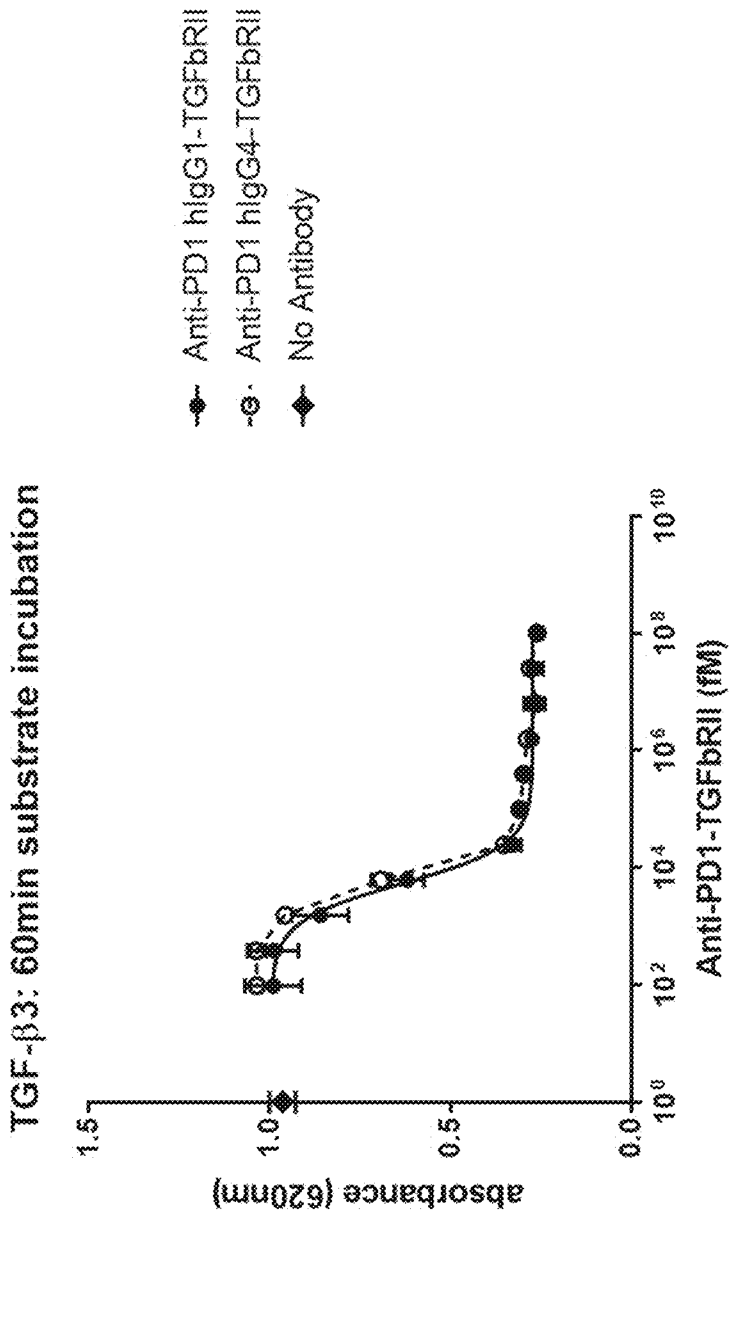
FIG. 8 is a graph showing neutralization of TGF-β3 isoform signaling by anti-PD1(VH6-VL5) IgG1-TGFβRII and anti-PD1(VH6-VL5) IgG4-TGFβRII.

To analyze the binding affinity of anti-PD1-TGFβRII to TGF-β isoforms, anti-PD1-TGFβRII were immobilized on CM5 chip and then TGF-β proteins were diluted in HBS-P running buffer to a range of final concentrations and injected to measure the binding affinity of TGF-β to immobilized anti-PD1-TGFβRII. Affinity of anti-PD1 ($V_H$6-VL5 or $V_H$7-VL6)-TGFβRII fusion protein to immobilized PD-1 is shown in Table 2 (FIGS. 6-8). Affinity of TGF-β isoforms to immobilized anti-PD-1 IgG4 antibody (VH6-VL5)-TGFβRII fusion protein is shown in Table 3. As observed, the fusion protein bound to TGF-β1 and TGF-β3 with high affinity and bound to TGF-β2 with lower affinity.

TABLE 2

Affinity of anti-PD1-TGFβRII to immobilized PD-1

| Anti-PD1-TGFβRII format | $K_D$ (M) |
|---|---|
| Anti-PD1(VH7-VL6) IgG4-TGFβRII | 3.79e−11 |
| Anti-PD1(VH6-VL5) IgG4-TGFβRII | 2.95e−11 |
| Anti-PD1(VH7-VL6) IgG1-TGFβRII | 8.11e−13 |
| Anti-PD1(VH6-VL5) IgG1-TGFβRII | 7.64e−12 |
| Anti-PD1(VH7-VL6) scFv-Fc-TGFβRII | 3.53e−10 |
| Anti-PD1(VH6-VL5) scFv-Fc-TGFβRII | 2.79e−10 |
| Anti-PD1(VH7-VL6) scFv-TGFβRII | 7.77e−9 |
| Anti-PD1(VH6-VL5) scFv-TGFβRII | 1.97e−8 |

TABLE 3

Affinity of TGF-β to immobilized anti-PD1(VH6-VL5) IgG4-TGFβRII

| Anti-PD1-TGFβRII | TGF-β isoform | $K_D$ (M) |
|---|---|---|
| Anti-PD1(VH6-VL5) | TGF-β1 | 5.22e−12 |
| IgG4-TGFPβRII | TGF-β2 | 8.59e−10 |
| | TGF-β3 | 2.19e−12 |

Binding affinity of various anti-PD-1 variants fused to TGFβRII were assessed by surface plasmon resonance (SPR) assay using Biacore 3000. PD-1 fused to human Fc region was immobilized on sensor chip CM5. Different concentrations of various fusion proteins were injected in solution phase and data was analyzed using BIAevaluation to calculate KD of the fusion proteins. Variants such as anti-PD1(VH6-VL5)-TGFβRII fusion protein and anti-PD1 (VH7-VL6)-TGFβRII fusion protein were found to have similar binding affinity to PD1 compared to respective anti-PD1 alone.

TABLE 5

Affinity of two anti-PD1-TGFβRII fusion proteins as compared to the respective anti-PD1 antibody alone

| Fusion Protein | Binding affinity to PD-1-Fc antigen ($K_D$, M) |
|---|---|
| Anti-PD1(VH6-VL5)-TGFβRII | 3.42E−13 |
| Anti-PD1(VH6-VL5) | 4.74E−13 |
| Anti-PD1(VH7-VL6)-TGFβRII | 6.69E−13 |
| Anti-PD1(VH7-VL6) | 2.44E−13 |

PD-1/PDL-1 Blockade Assay

Figure 5:
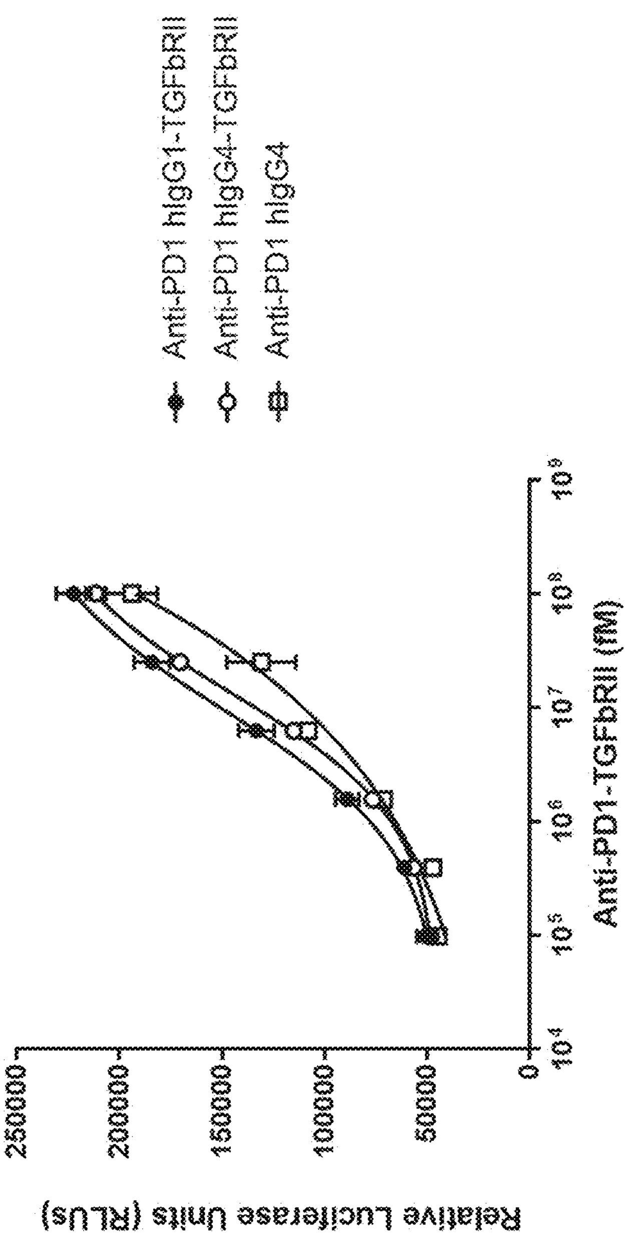
FIG. 5 is a graph showing blockade of PD-1/PD-L1 interaction by anti-PD1(VH6-VL5) IgG1-TGFβRII and anti-PD1(VH6-VL5) IgG4-TGFβRII.

To investigate if the anti-PD1-TGFβRII fusion proteins could function as anti-PD1 antibody by blocking the PD-1/PD-L1 interaction, a PD-1/PD-L1 blockade bioassay kit from Promega was employed. In brief, the PD-L1 aAPC/CHO-K1 cells were thawed one day prior to the start of the assay and allowed to recover overnight at 37° C., 5% $CO_2$ for 16 to 20 hours. To generate a dose response curve, serial dilutions of anti-PD1 TGFβRII proteins ranging from 100 nM to 0.098 nM were prepared. The plates were then removed from the incubator and cell media was discarded. Antibodies of interest were then added directly to the plate containing PD-L1 aAPC/CHO-K1 cells. Following this step, PD-1 effector cells were then thawed and added to the 96-well plate. Plates were incubated for at 37° C., 5% $CO_2$ for 6 hours. Bio-Glo™ luciferase substrate reagent (Promega) was added to each well and Relative Luciferase Units (RLUs) were measured on a Glomax 96-microplate luminometer. The $IC_{50}$ of the anti-PD1 TGFβRII proteins were determined by fitting the RLU-concentration data to a four parameter logistic equation. These values were used as a measure of PD-1/PD-L1 blocking potency (FIG. 5).

HEK-Blue TGF-β Assay

To examine the efficacy of anti-PD1 TGFβRII fusion proteins to neutralize the function of TGF-β, a stable cell line with induced reporter gene (HEK-Blue™ TGB-β reporter cell line, Invitrogen) was utilized. This stable cell line allows for the detection of bioactive TGF-β via the activation of TGF-β/SMAD pathway, leading to the production of secreted embryonic alkaline phosphatase (SEAP), which can be quantified. In brief, TGF-β1, TGF-β2, and TGF-β3 were diluted to a pre-determined $EC_{50}$ concentration and added to a flat bottom 96-well plate. To generate a dose response curve, serial dilutions of anti-PD1 TGFβRII proteins were then added to the plate containing different isoforms of TGF-β. Plates were incubated for 30 minutes at 37° C. The HEK-Blue™ TGF-β cells were then added to the plate at a final concentration of $0.7\times10^6$ cells/mL. Plates were then incubated at 37° C., 5% $CO_2$ for a total of 20 hours. Following the incubation, an aliquot of supernatant was removed and added to a plate containing the QUANTI-Blue™ substrate (Invitrogen) used to quantify secreted SEAP. Plates were incubated for one hour at 37° C. The plates were then read on a SpectraMax Plus plate reader at 620 to 655 nm. The $IC_{50}$ was determined by fitting absorbance-concentration data to a four-parameter logistic equation (GraphPad Prism). Results of the efficacy of various anti-PD1 TGFβRII fusion proteins in comparison to controls are depicted in FIGS. 5-8.

Table 6 and 7 further lists various fusion protein constructs tested and the inhibition of TGF-β1 induced reported gene activity.

TABLE 6

Summary of $IC_{50}$-inhibition of TGF-β1 induced reporter gene activity for various fusion constructs

| Fusion Protein | $IC_{50}$ (pM) |
|---|---|
| Anti-PD1 (VL5-VH6).IgG4 | 9.0 |
| Anti-PD1 (VL5-VH6).IgG4(S108P). TGFbRII | 9.7 |
| Anti-PD1 (VL5-VH6) ScFv-Fc | 4.3 |
| Anti-PD1 (VL6-VH7).IgG4.TGFbRII | 5.6 |
| Anti-PD1 (VL6-VH7).IgG4(S108P).TGFbRII | 9.3 |
| Anti-PD1 (nVL1-nVH3).IgG4-TGFbRII | 10.7 |
| Anti-PD1 (nVL1-nVH3).scFv-Fc-TGFbRII | 6.5 |
| Anti-PD1 (nVL1-nVH7).IgG4-TGFbRII | 15.1 |
| Anti-PD1 (nVL1-nVH8).IgG4-TGFbRII | 54.5 |
| Anti-RSV IgG4-TGFbRII | 8.6 |
| Anti-RSV S108P IgG4-TGFbRII | 6.9 |
| Anti-RSV scFv-Fc4 | 8.9 |

TABLE 7

Summary of TGF-β1 neutralization activity of various fusion constructs

| Fusion Protein | $IC_{50}$ (pM) |
|---|---|
| Anti-PD1 (VL5/VH6).IgG4-Linker2-TGFbRII | 1.2 |
| Anti-PD1 (VL5/VH6).IgG4-Linker12-TGFbRII | 2.7 |

TABLE 7-continued

| Summary of TGF-β1 neutralization activity of various fusion constructs | |
|---|---|
| Fusion Protein | $IC_{50}$ (pM) |
| Anti-PD1 (VL5/VH6).IgG4-Linker7-TGFbRII | 1.1 |
| Anti-PD1 (VL5/VH6).IgG4-Linker8-TGFbRII | 1.2 |
| Anti-PD1 (VL5/VH6).IgG4-Linker10-TGFbRII | 1.9 |

PD1 Binding of Various Anti-PD1 IgG4-TGFbRII Fusion Constructs

PD1-Fc antigen and reference antigen was immobilized on Biacore CM5 surface. 6-12 replicated series diluted concentrations of various anti-PD1 IgG4-TGFbRII (Table 8) were series injected on PD1-Fc antigen and reference surface. Kinetics data was evaluated for 1:1 model: Langmuir with mass transfer. As observed in Table 7, the binding affinity ($K_D$) of Anti-PD1 IgG4-TGFbRII with PD1-Fc antigen was between $10^{12}$ to $10^{10}$ range.

TABLE 8

| PD1 binding affinity analysis of PD1 IgG4-TGFbRII fusion proteins | |
|---|---|
| Fusion Protein | $K_D$ (M) |
| Anti-PD1 (nVL1-nVH3).IgG4 | 1.48E−11 |
| Anti-PD1 (nVL1-nVH3).IgG4-TGFbRII | 2.77E−11 |
| Anti-PD1 (nVL1-nVH3).IgG4 (S108P) | 1.41E−11 |
| Anti-PD1 (nVL1-nVH3).IgG4-(S108P)-TGFbRII | 8.16E−12 |
| Anti-PD1 (nVL1-nVH7).IgG4-TGFbRII | 1.47E−10 |
| Anti-PD1 (nVL1-nVH8).IgG4-TGFbRII | 3.21E−10 |

Figure 20:
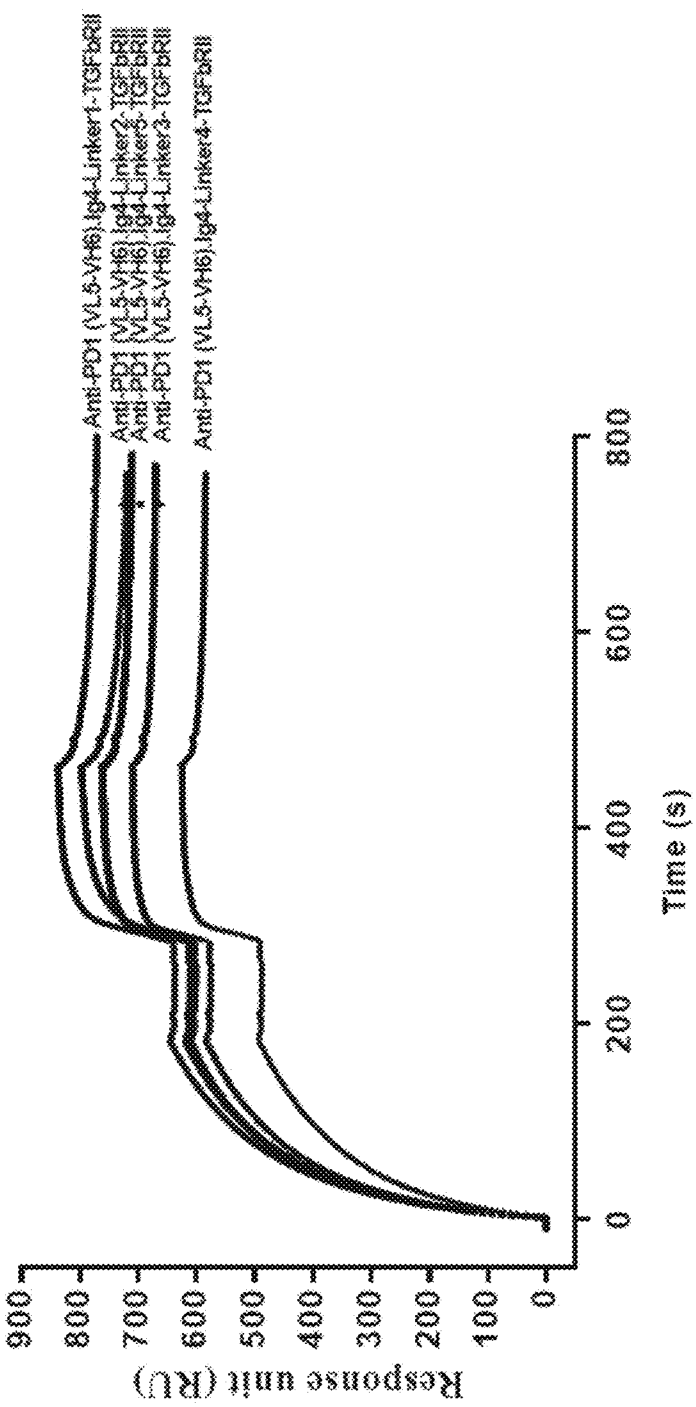
FIG. 20 is a graph depicting Biacore analysis of simultaneous binding of TGF-b1 and PD1 by anti-PD1 (VH6/VL5)-TGFRII fusion proteins using different linkers.

Simultaneous PD1 and TGF-β1 Binding of Various Anti-PD1 IgG4-TGFβRII Fusion Constructs To investigate if the anti-PD1-TGFRII fusion proteins (Table 9) with different linkers could simultaneously bind to PD1 and TGF-β31, the following constructs were made and tested in a Biacore experiment. PD1-Fc antigen was immobilized on a Biacore CM5 chip surface. Anti-PD1 (VL5-VH6).IgG4-linker-TGFbRII was injected over sensor surfaces, followed by TGFβ1 over sensor surfaces. As shown in FIG. 20, all the anti-PD1 (VL5-VH6).IgG4-linker-TGFRII constructs bound to both of PD1-Fc antigen and TGF β1 simultaneously.

TABLE 9

| anti-PD1 (VL5-VH6),IgG4-linker-TGFRII constructs with various linkers | |
|---|---|
| Fusion protein | Linker |
| Anti-PD1 (VL5-VH6). IgG4-Linker 2-TGFbRII | GGGGSGGGS (Linker 2) (SEQ ID NO. 293) |
| Anti-PD1 (VL5-VH6). IgG4-Linker12-TGFbRII | DPVLEREDKVTTSKNPGS (linker 12)(SEQ ID NO: 27) |
| Anti-PD1 (VL5-VH6). IgG4-Linker7-TGFbRII | DPGSGSVPLGSGSNPGS (llnker7) (SEQ ID NO: 22) |
| Anti-PD1 (VL5-VH6). IgG4-Linker8-TGFbRII | DPGSGGSVPLGSGGSNPGS (linker 8)(SEQ ID NO: 23) |
| Anti-PD1 (VL5-VH6). IgG4-Linker10-TGFbRII | DPGVLEREDVPTTSYPNPGS (linker10)(SEQ ID NO: 25) |

Example 2. Anti-PD1-TGF-β Trap Promotes T Cell Activation in In Vitro Culture

To assess the ability of the anti-PD1-TGF-β trap to promote T cells functions, peripheral blood mononuclear cells (PBMCs) purified using Ficoll-Hypaque from a leukapheresis product (obtained from a normal healthy donor under an Institutional Review Board (IRB) approved protocol) was used in vitro. PBMCs were labeled with the cell proliferation dye CellTrace violet and stimulated with anti-CD3 and anti-CD28. At the end of the incubation culture supernatants were collected and stored until used for IFN-γ release assay. The cells were labeled with fluorescent conjugated antibodies to assess T cell proliferation.

Figure 9A:
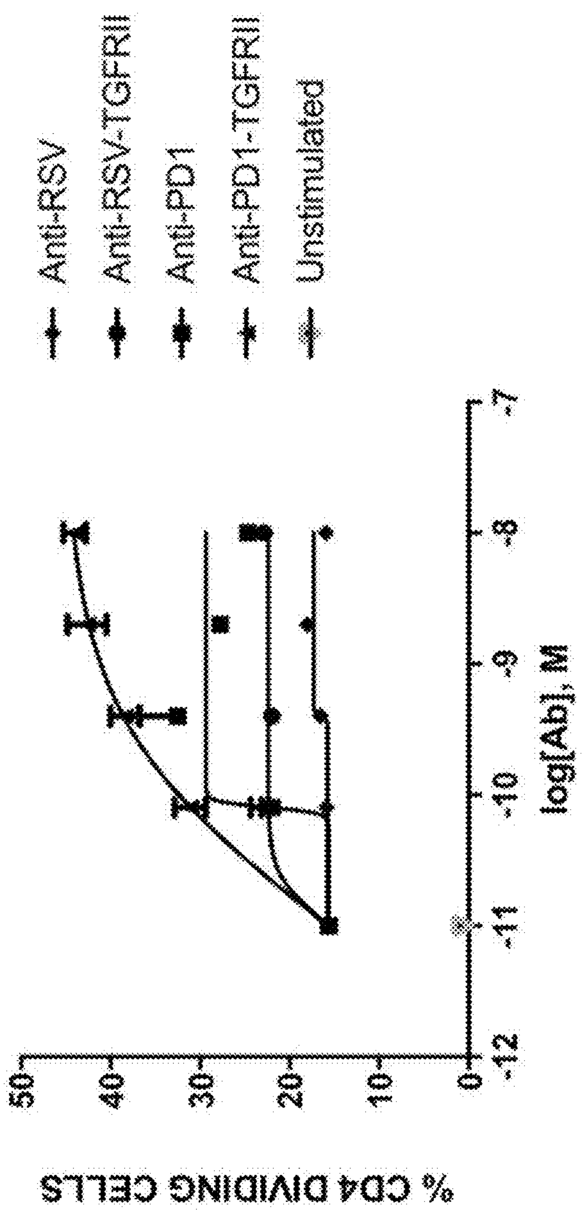
FIG. 9A, FIG. 9B, and FIG. 9C are graphs showing enhanced proliferation and IFN-7 production by stimulated PBMCs in the presence of anti-PD1-TGFRII fusion protein in a dose dependent manner compared to anti-PD1 or control antibodies.
Figure 9B:
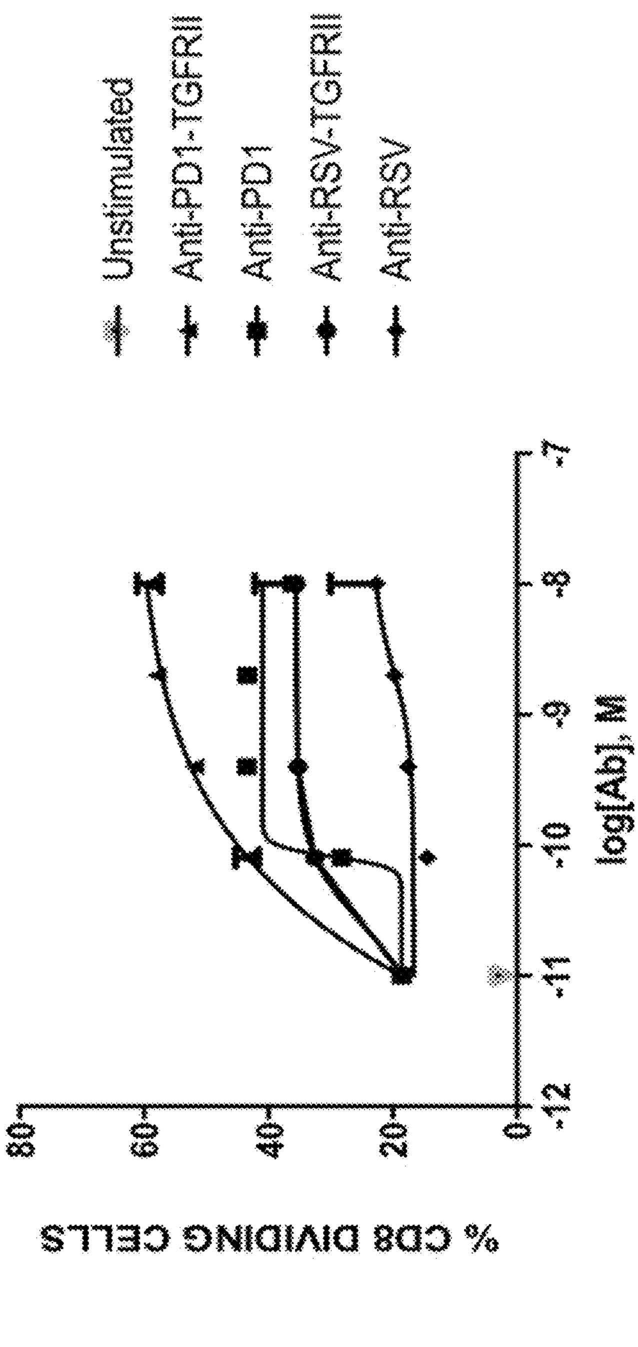
Figure 9C:
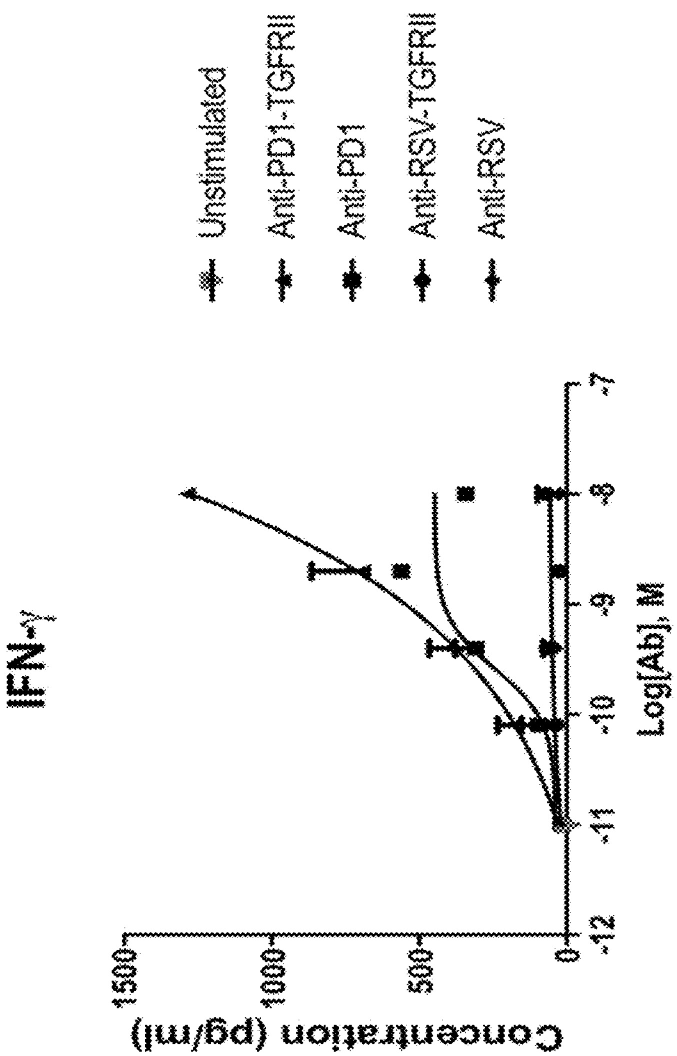

Stimulated PBMCs in the presence of anti-PD1-TGF-β trap showed enhanced proliferation and IFN-γ production in a dose dependent manner compared to anti-PD1 or anti-RSV control antibodies suggesting the ability of the fusion molecule to target both the PD-1/PD-L1 and TGF-β pathways (FIGS. 9A-9C). The data also demonstrates an additive enhanced effect of the fusion molecule compared to anti-PD1 alone.

Anti PD1-TGF-RII Exhibits Superior Anti-Tumor Response Compared to Anti PD1 Alone in an In Vitro Model of Colorectal Cancer Effectiveness of anti-PD1-TGFRII fusion protein was evaluated in an in vitro model of colorectal cancer. PBMCs purified from healthy donor were co-cultured with cancer cell line HT-29 for 5 days. The cells were stimulated with anti-CD3 in the presence of isotype control, anti-PD1 or anti-PD1-TGFRII fusion protein. The culture supernatants were collected and IFN-γ levels were quantified by MSD per manufacturer's protocol. The cells were collected and target occupancy on T cells were analyzed by flow cytometry. The levels of TGF-β1, TGF-β2 and TGF-β3 in cell culture supernatants were quantified by Luminex per manufacturer's protocol.

Figure 9D:
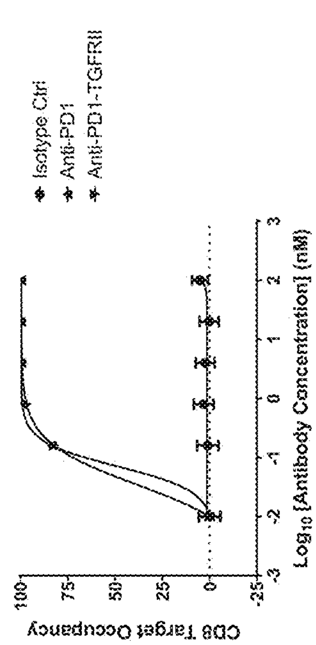
FIG. 9D and FIG. 9E are graphs showing PD1 receptor occupancy on $CD8^+$ T cells and IFN-γ production respectively when anti-PD1-TGFRII fusion protein is added to co-culture of PBMC and colorectal cancer (colorectal adenocarcinoma) cell line.
Figure 9E:
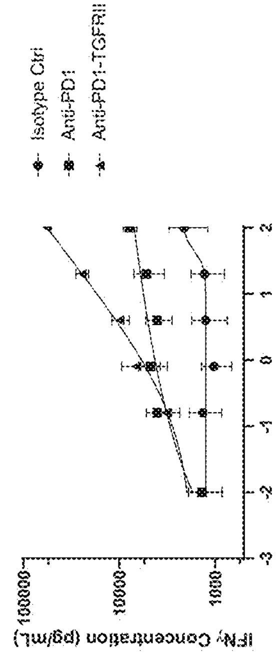

FIG. 9D, shows that anti-PD1-TGFRII binds to PD1 on CD8+ T cell surface similar to that of anti PD1. As shown in FIG. 9E anti-PD1-TGFRII fusion protein promoted higher level of IFN-γ production compared to anti-PD1 or isotype control. FIG. 9H. TGF-β1 produced in HT-29 PBMC coculture system is completely neutralized upon anti-PD1-TGFRII treatment even at the lowest dose tested. FIG. 9I. TGF-β2 produced in HT-29 PBMC coculture system is partially neutralized upon anti-PD1-TGFRII treatment. Overall, results from this in vitro model exhibit superior anti-tumor response of anti-PD1-TGFRII fusion protein compared to anti-PD1 antibody.

Anti-PD1-TGFRII Exhibits Superior Anti-Tumor Response Compared to Anti-PD1 Alone in an In Vitro Model of Head and Neck Cancer Effectiveness of anti-PD1-TGFRII fusion protein was evaluated in an in vitro model of head and neck cancer.

PBMCs purified from healthy donor were co-cultured with cancer cell line Detroit 562 for 5 days. The cells were stimulated with anti-CD3 in the presence of isotype control, anti-PD1 or anti-PD1-TGFRII fusion protein. The culture supernatants were collected and IFN-γ levels were quantified by MSD per manufacturer's protocol. The cells were collected and target occupancy on T cells were analyzed by flow cytometry. The levels of TGF-β1, TGF-β2 and TGF-β3 in cell culture supernatants were quantified by luminex per manufacturer's protocol.

Figure 9F:
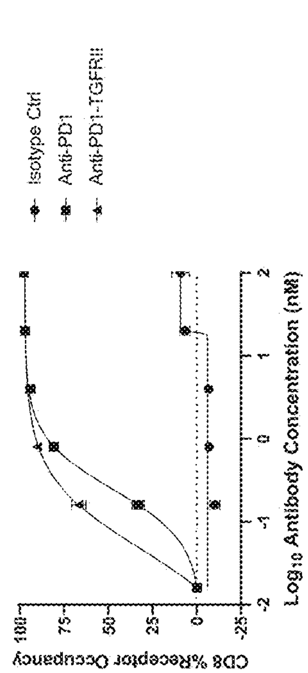
FIG. 9F and FIG. 9G are graphs showing PD1 receptor occupancy on CD8+ T cells and IFN-γ production respectively when anti-PD1-TGFRII fusion protein is added to co-culture of PBMC and head and neck cancer (pharyngeal carcinoma) cell line.
Figure 9G:
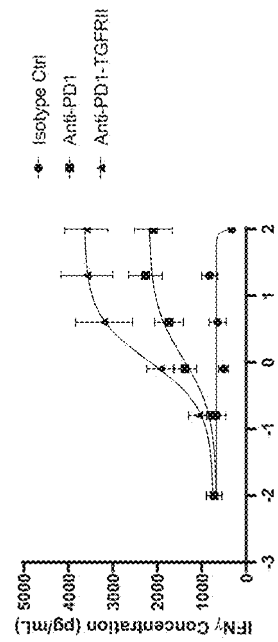
Figure 9H:
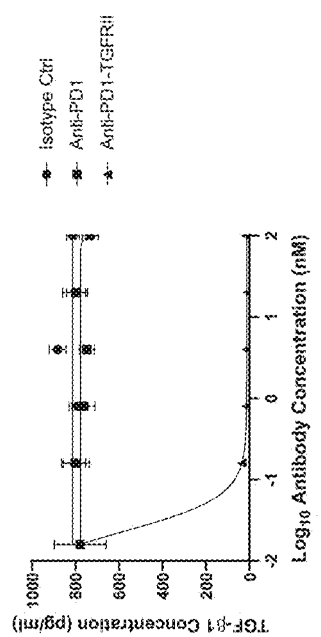
FIG. 9H and FIG. 9I are graphs depicting TGF-β1 and TGF-β2 concentration respectively in supernatant of PBMC and colorectal cancer (colorectal adenocarcinoma) cells co-culture in presence of anti-PD1-TGFRII fusion protein.
Figure 9I:
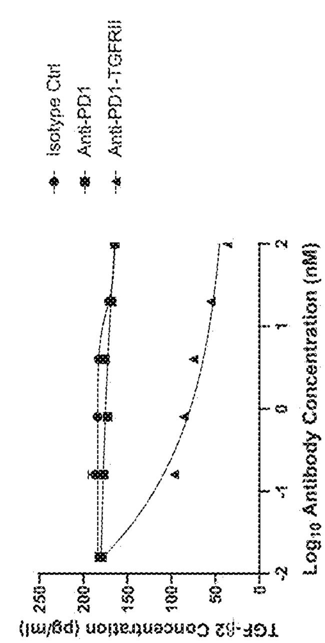
Figure 9J:
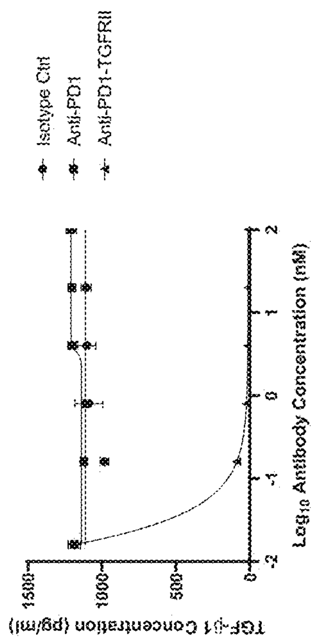
FIG. 9J and FIG. 9K are graphs depicting TGF-β1 and TGF-β2 concentration respectively in supernatant of PBCM and head and neck cancer (pharyngeal carcinoma) cells co-culture in presence of anti-PD1-TGFRII fusion protein.
Figure 9K:
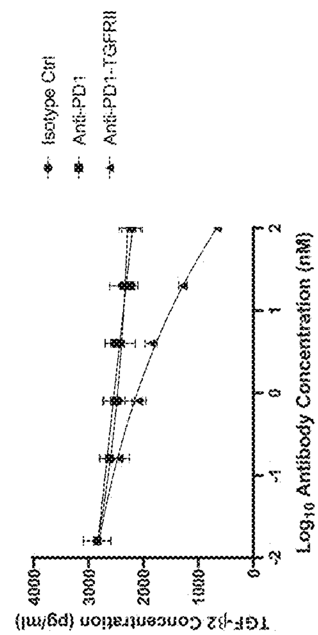

FIG. 9F, shows that anti-PD1-TGFRII binds to PD1 on CD8+ T cell surface similar to that of anti PD1. As shown in FIG. 9G, anti-PD1-TGFRII fusion protein promoted higher level of IFN-γ production compared to anti-PD1 or isotype control. FIG. 9J. TGF-β1 produced in Detroit 562 PBMC coculture system is completely neutralized upon anti-PD1-TGFRII treatment even at the lowest dose tested. FIG. 9K. TGF-β2 produced in Detroit 562 PBMC coculture system is partially neutralized upon anti-PD1-TGFRII treatment. Overall, results from this in vitro model exhibit superior anti-tumor response of anti-PD1-TGFRII fusion protein compared to anti-PD1 antibody.

Anti PD1-TGF-RII Exhibits Superior Anti-Tumor Response Compared to Anti PD1 Alone in an In Vitro 3D Tumor Spheroid Model of Colorectal Cancer Effectiveness of anti-PD1-TGFRII fusion protein was evaluated in an in vitro 3D tumor spheroid model of colorectal cancer. 3D tumor spheroids were generated by coculturing colorectal cancer cell line HT-29 and a fibroblast cell line. PBMCs purified from healthy donor were then added to spheroid culture. The cells were stimulated with anti-CD3 in the presence of isotype control, anti-PD1 or anti-PD1-TGFRII fusion protein for 5 days. The culture supernatants were collected and IFN-γ levels were quantified by MSD per manufacturer's protocol.

Figure 9M:
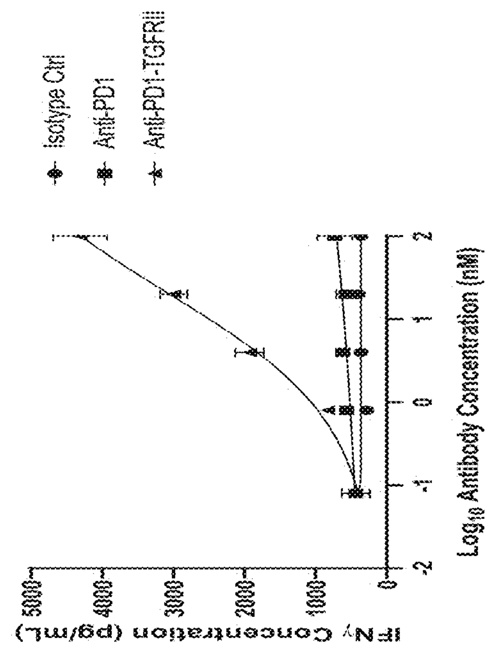
FIG. 9L and FIG. 9M are graphs depicting IFN-γ production respectively in 3D spheroid culture of colorectal cancer (colorectal adenocarcinoma) cells or head & neck cancer (pharyngeal carcinoma) cells and PBMC in presence of anti-PD1-TGFRII fusion protein as compared to anti-PD1 alone.
Figure 9L:
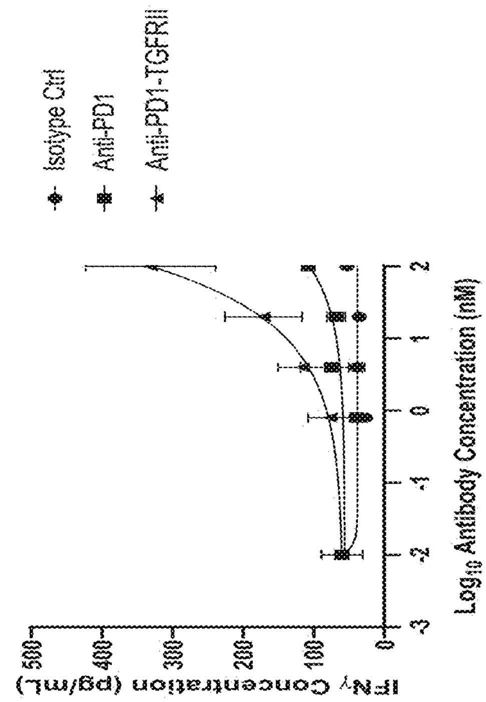
Figure 10A:
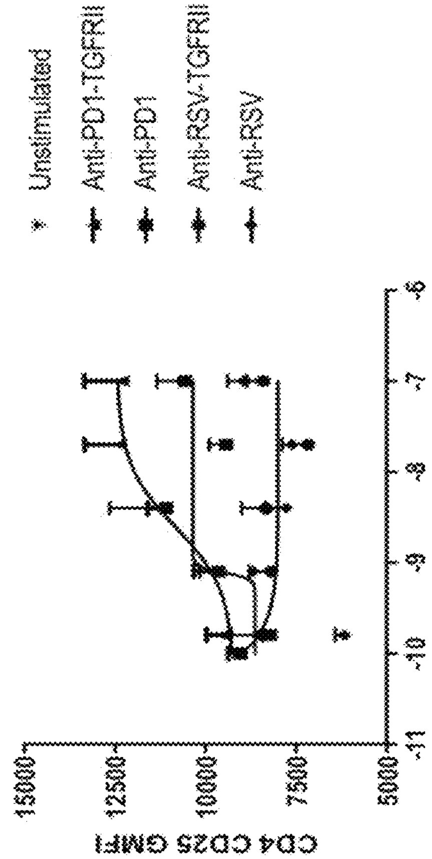
FIGS. 10A-10D show effect of anti-PD1-TGFRII fusion protein treatment on T cell proliferation and activation in the presence of recombinant TGF-β1.
Figure 10B:
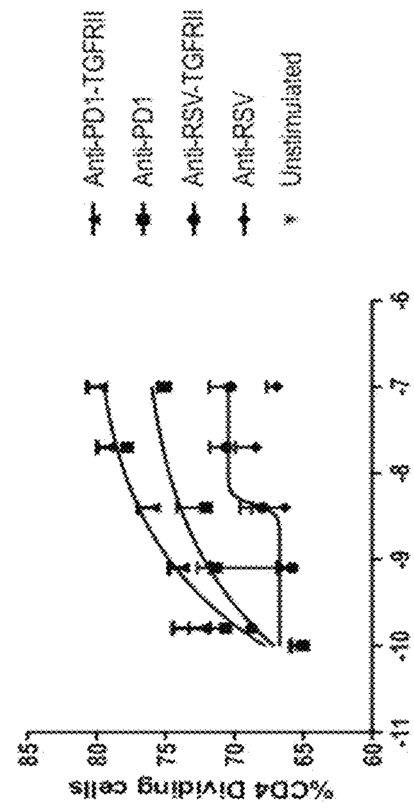
Figure 10C:
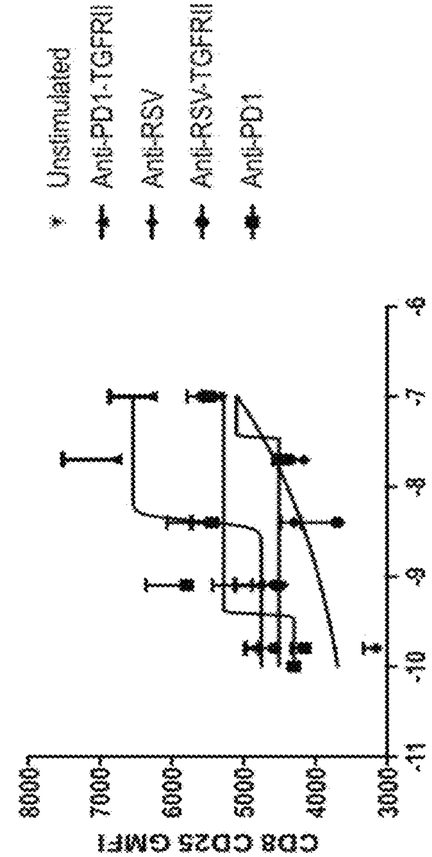
Figure 10D:
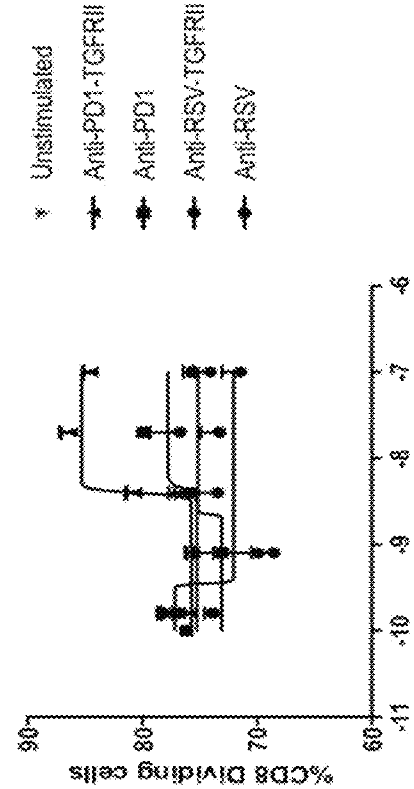
Figure 11A:
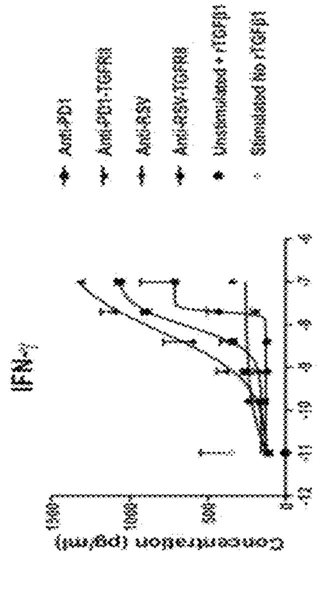
FIGS. 11A-11F show expression of various cytokines by PBMC in the presence recombinant TGF-β1 and in the presence of anti-PD1, anti-PD1-TGFRII fusion protein or control antibodies.
Figure 11B:
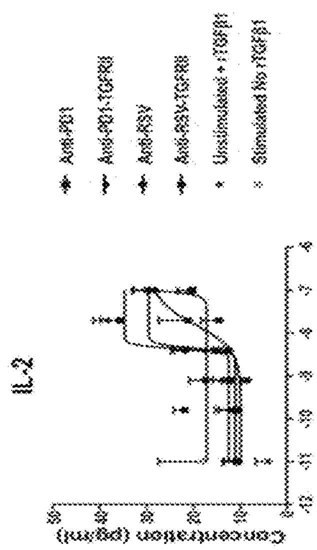
Figure 11C:
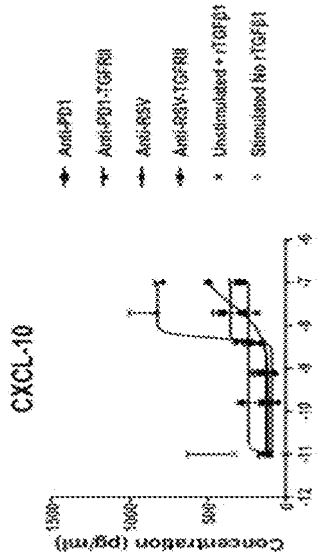
Figure 11D:
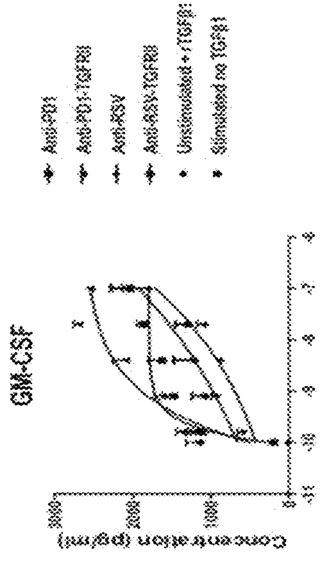
Figure 11E:
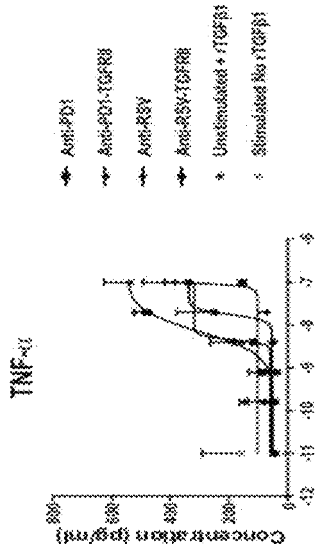
Figure 11F:
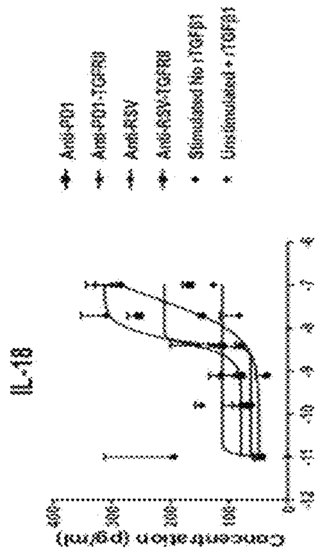

As shown in FIG. 9L, anti-PD1-TGFRII fusion protein promoted higher level of IFN-γ production compared to anti-PD1 or isotype control. Overall, result from this 3D tumor spheroid model exhibit superior anti-tumor response of anti-PD1-TGFRII fusion protein compared to anti-PD1 antibody.

Anti-PD1-TGF-RII Exhibits Superior Anti-Tumor Response Compared to Anti PD1 Alone in an In Vitro 3D Tumor Spheroid Model of Head and Neck Cancer Effectiveness of anti-PD1-TGFRII fusion protein was evaluated in an in vitro 3D tumor spheroid model of colorectal cancer. 3D tumor spheroids were generated by coculturing Detroit 562 cell line and a fibroblast cell line. PBMCs purified from healthy donor were then added to spheroid culture. The cells were stimulated with anti-CD3 in the presence of isotype control, anti-PD1 or anti-PD1-TGFRII fusion protein for 5 days. The culture supernatants were collected and IFN-γ levels were quantified by MSD per manufacturer's protocol.

As shown in FIG. 9M, anti-PD1-TGFRII fusion protein promoted higher level of IFN-γ production compared to anti-PD1 or isotype control. Overall, result from this 3D tumor spheroid model exhibit superior anti-tumor response of anti-PD1-TGFRII fusion protein compared to anti-PD1 antibody.

Example 3. Anti-PD1-TGF-β Trap has Superior Activity Compared to Anti-PD1 in the Presence of Recombinant TGF-β1 In Vitro To assess the ability of the anti-PD1-TGF-β trap to promote T cells functions, in an environment with high levels of TGF-β, PBMCs were stimulated as above in the presence of recombinant TGF-β1. At the end of the incubation, culture supernatants were collected and stored until used for cytokine analyses. The cells were labeled with fluorescent conjugated antibodies and assessed for T cell proliferation and the upregulation of IL-2 receptor alpha or CD25 as a readout for activation.

Recombinant TGF-β1 suppressed T cell activation, proliferation and cytokine and chemokine production (FIG. 10 and FIG. 11). This suppression was reversed significantly by the anti-PD1-TGF-β1 trap in a dose dependent manner compared to anti-PD1. The data suggests the ability of the fusion protein to neutralize high amount of exogenous TGF-β1 and disrupt the PD-1/PD-L1 pathway resulting in enhance T cell immune responses. Thus, the blockade of the PD-1/PD-L1 and neutralization of TGF-β by the fusion molecule can be an attractive immunotherapy for eliciting potent anti-tumor responses in cancer indications where checkpoint inhibitors treatments have failed.

Figure 12A:
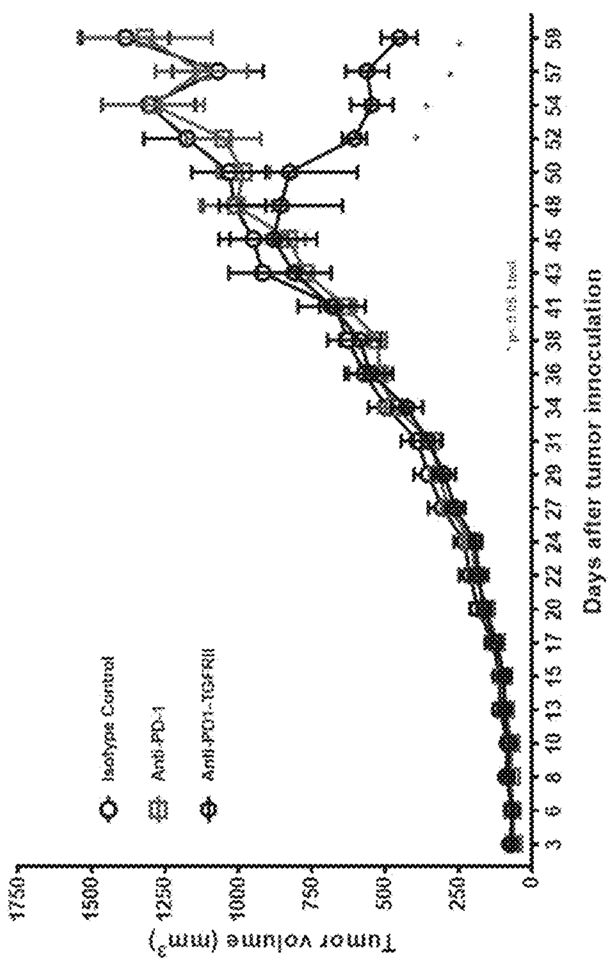
FIG. 12A shows the effect of anti-PD1-TGFRII fusion protein on tumor growth as compared to anti-PD1 alone in a humanized mouse model of colorectal cancer.
Figure 12B:
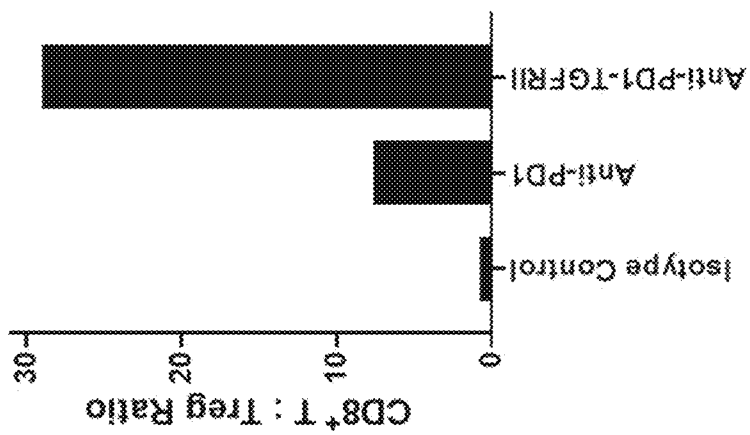
FIG. 12B shows that treatment with anti-PD1-TGFRII fusion protein significantly increases CD8+ T cell to $T_{reg}$ ratio in tumor in a humanized mouse model of colorectal cancer.
Figure 12D:
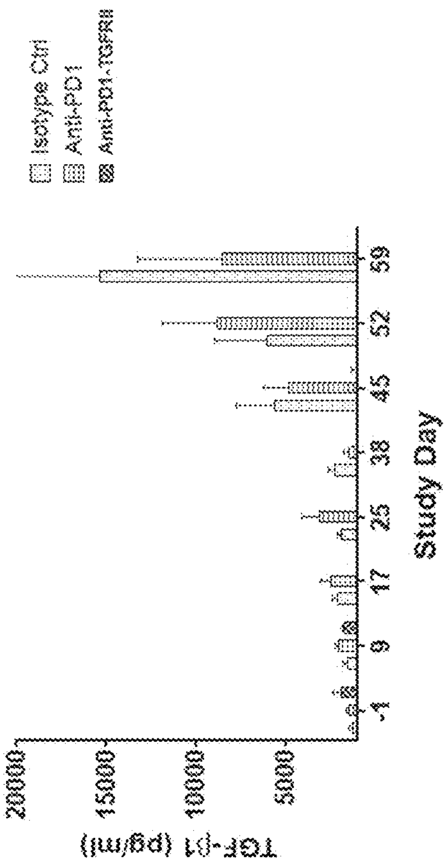
FIG. 12D and FIG. 12E shows the effect of anti-PD1-TGFRII fusion protein treatment on TGF-β1 and TGF-β2 concentrations as compared to anti-PD1 treatment respectively in a humanized mouse model of colorectal cancer.
Figure 12C:
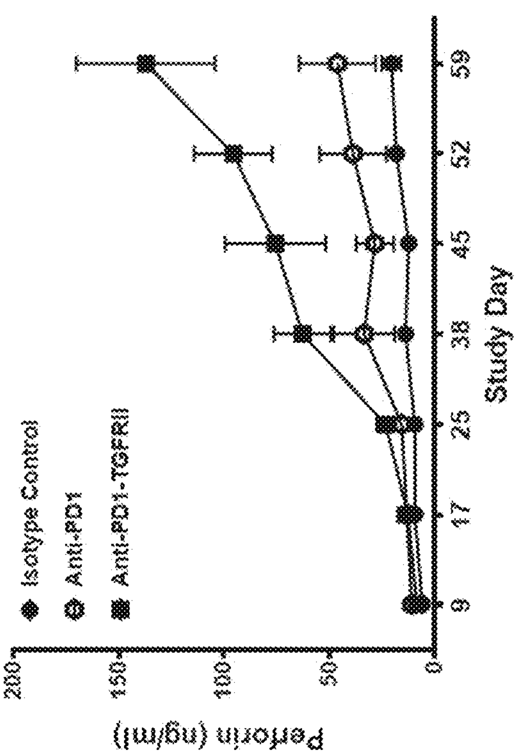
FIG. 12C shows the effect of anti-PD1-TGFRII fusion protein treatment on perforin expression levels as compared to anti-PD1 treatment in a humanized mouse model of colorectal cancer.
Figure 12E:
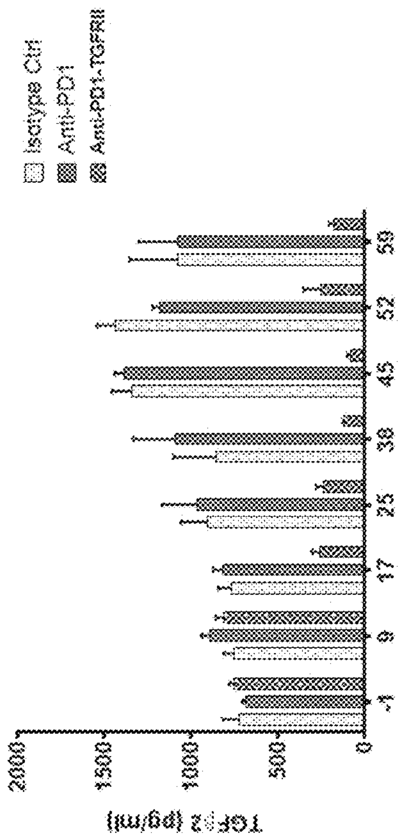

Example 4. Anti-PD1-TGF-RII Exhibits Superior Anti-Tumor Response Compared to Anti-PD1 Alone in a Humanized Mouse Model of Colorectal Cancer Ability of anti-PD1-TGFRII fusion protein to inhibit colorectal cancer tumor was evaluated in a humanized mouse model. Humanized NOG mice were administered HT-29 cancer cells. Tumor bearing mice were randomized and administered twice weekly with either anti-PD1-TGFRII fusion protein, anti-PD1 antibody alone or an isotype control. As seen in the FIG. 12A, anti-PD1-TGFRII fusion protein significantly inhibited tumor growth compared to anti-PD1 and the isotype control. Analyses of the tumors at the end of the study showed that anti-PD1-TGFRII fusion protein treated mice had higher frequency of tumor infiltrating lymphocytes (TILs). Analysis of tumors from anti-PD1-TGFRII treated mice also showed higher ratio of CD8+ T cells to regulatory T cells (Tregs).

Example 5. Anti-PD1-TGFRII Exhibits Superior Anti-Tumor Response Compared to Anti-PD1 Alone in an In Vitro Model of Head and Neck Cancer Effectiveness of anti-PD1-TGFRII fusion protein was evaluated in an in vitro model of head and neck cancer. PBMCs purified from healthy donor were co-cultured with cancer cell line Detroit 562 for 48 hours. The cells were stimulated with anti-CD3 in the presence of isotype control, anti-PD1 or anti-PD1-TGFRII fusion protein. The culture supernatants were collected and IFN-γ levels were quantified by MSD per manufacture's protocol. The cell pellets from co-culture at the end of culture period were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Figure 13A:
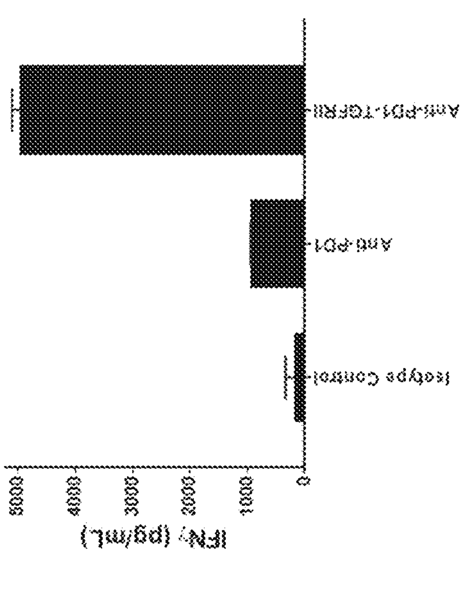
FIG. 13A shows treatment with anti-PD1-TGFRII fusion protein significantly improved IFNγ production compared to anti-PD1 treatment in an in vitro model of head and neck cancer.
Figure 13B:
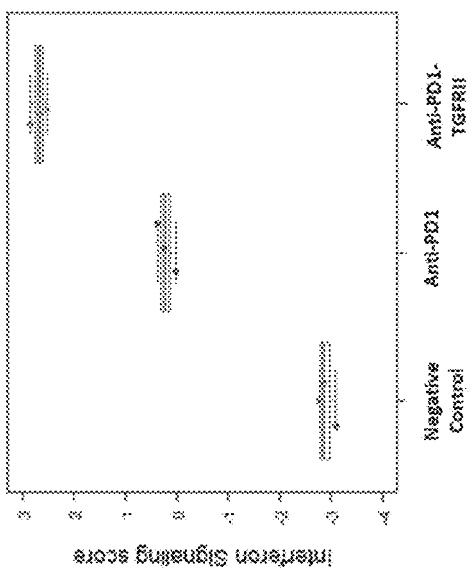
FIGS. 13B-13G show treatment with anti-PD1-TGFRII fusion protein significantly increases T-cell function as evidenced by expression analysis of various pathway genes.
Figure 13C:
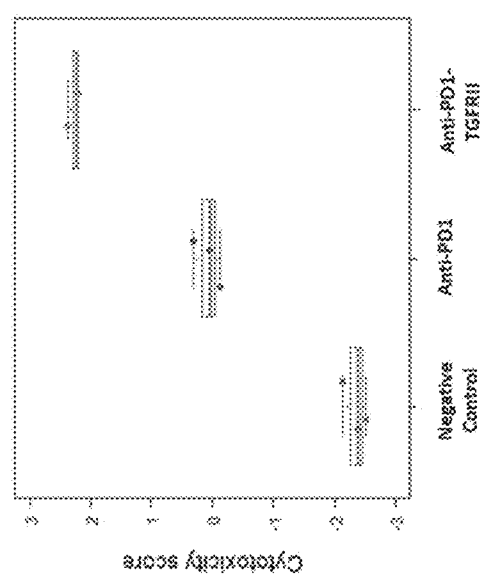
Figure 13D:
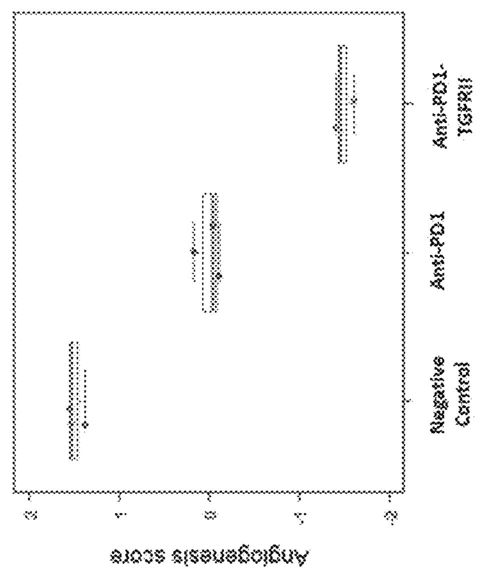
Figure 13G:
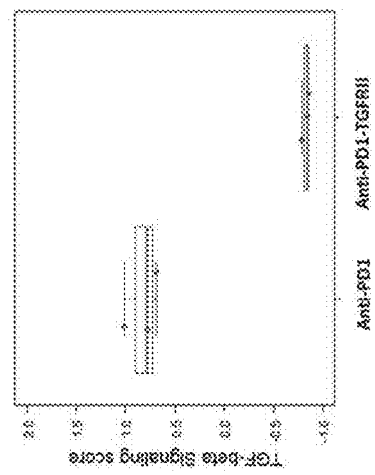
Figure 13F:
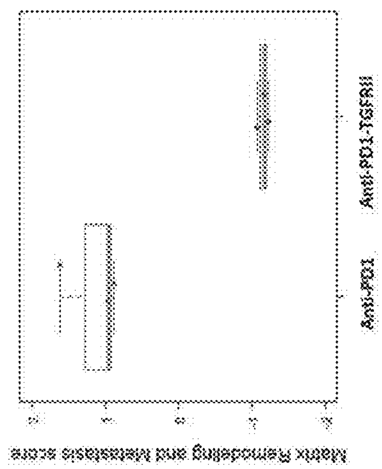
Figure 13E:
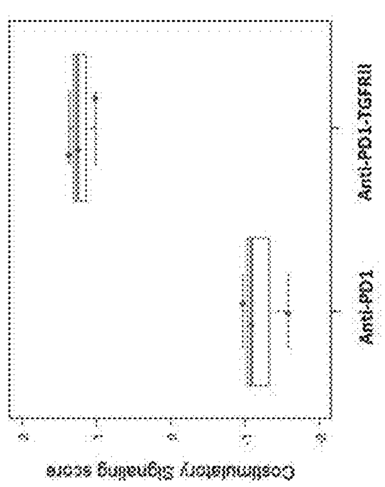

As shown in FIG. 13A, anti-PD1-TGFRII fusion protein promoted higher level of IFN-γ production compared to anti-PD1 or isotype control. Anti-PD1-TGFRII fusion protein treatment resulted in significant upregulation of interferon pathway genes (FIG. 13B) as well as cytotoxic genes (FIG. 13C) compared to anti-PD1 treatment highlighting improved cytotoxic function in presence of tumor compared to anti-PD1 antibody. Furthermore, anti-PD1-TGFRII fusion protein treatment resulted in significant downregulation of genes involved in tumor metastasis and angiogenesis pathways (FIG. 13D). Overall, results from this in vitro model exhibit superior anti-tumor response of anti-PD1-TGFRII fusion protein compared to anti-PD1 antibody.

Figure 14A:
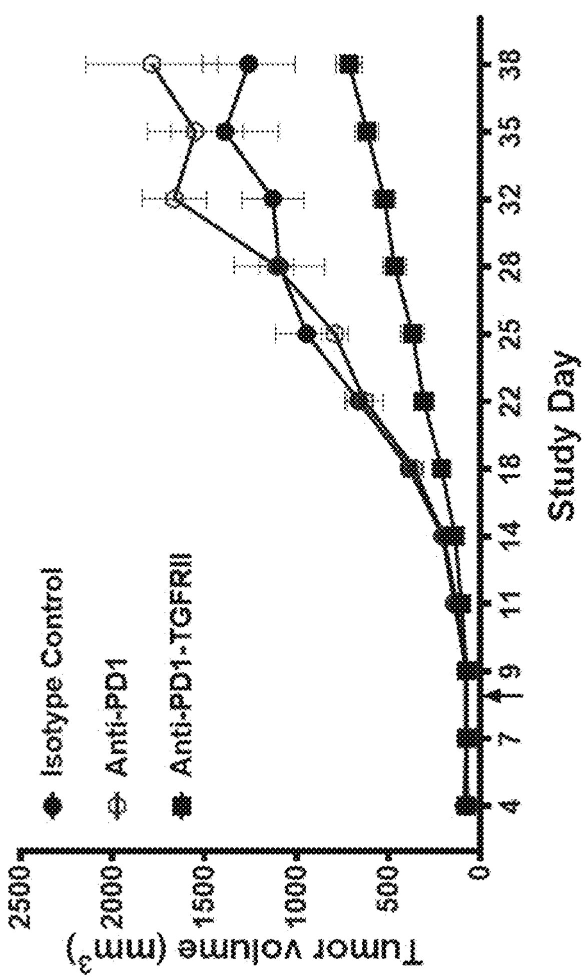
FIG. 14A shows the effect of anti-PD1-TGFRII fusion protein on tumor growth as compared to anti-PD1 alone in a humanized mouse model of head and neck cancer.
Figure 14C:
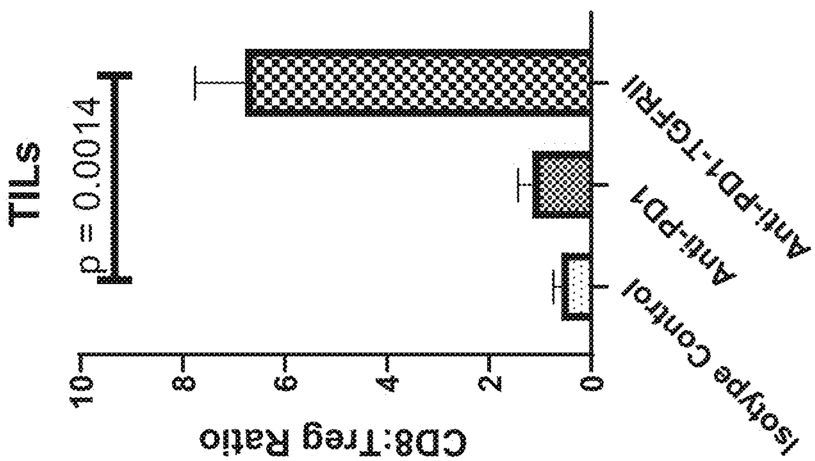
FIG. 14C shows ratio of CD8+ T cells to regulatory T cells in tumors of mice treated with anti-PD1-TGFRII fusion protein in a humanized mouse model of head and neck cancer.
Figure 14B:
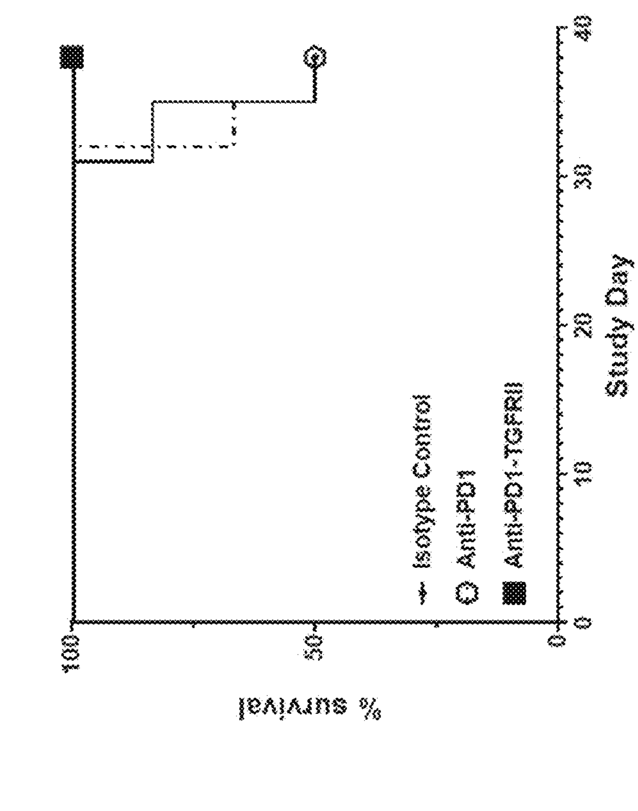
FIG. 14B shows survival of tumor bearing mice in humanized mouse model of head and neck cancer when treated with anti-PD1-TGFRII fusion protein vs. anti-PD1 alone or isotype control.
Figure 14E:
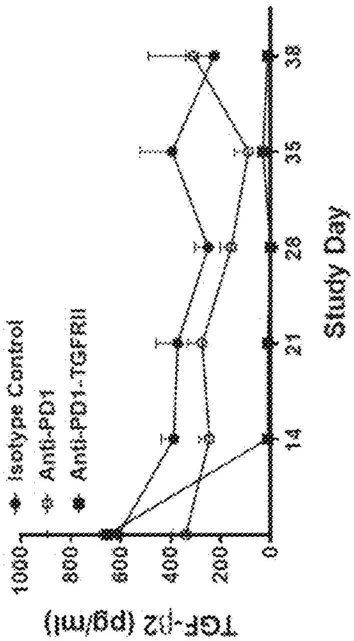
FIG. 14D and FIG. 14E shows the effect of anti-PD1-TGFRII fusion protein on TGF-β1 and TGF-β2 concentrations as compared to anti-PD1 alone in a humanized mouse model of head and neck cancer.
Figure 14D:
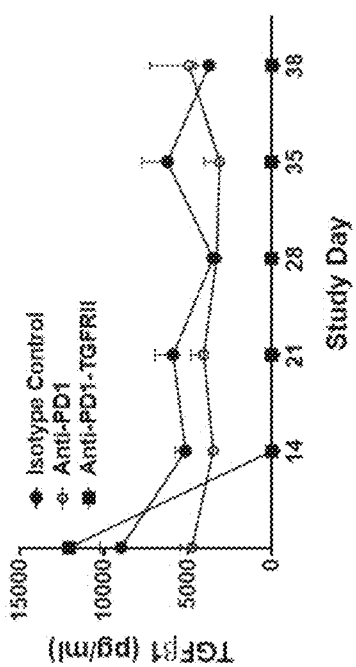
Figure 14F:
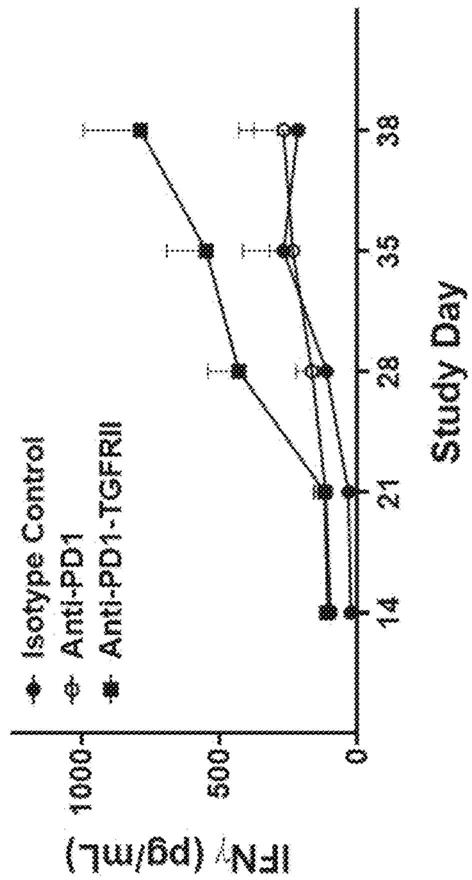
FIG. 14F shows the effect of anti-PD1-TGFRII fusion protein on IFN-γ production in a humanized mouse model of head and neck cancer.

Example 6. Anti-PD1-TGFRII Exhibits Superior Anti-Tumor Response Compared to Anti-PD1 Alone in a Humanized Mouse Model of Head and Neck Cancer Ability of anti-PD1-TGFRII fusion protein to inhibit head and neck cancer was evaluated in a humanized mouse model. Humanized NSG mice were administered D562 cell line. Tumor bearing mice were randomized in and administered twice weekly with anti-PD1-TGFRII fusion protein, anti-PD1 antibody alone or an isotype control. As seen in FIG. 14, Anti-PD1-TGFRII fusion protein significantly inhibited tumor growth (FIG. 14A), improved survival of tumor bearing mice (FIG. 14B) and increase in IFNγ levels (FIG. 14F) compared to anti-PD1 and the isotype control. Treatment with anti-PD1-TGFRII fusion protein significantly improved CD8+ T cells to Treg ratio in tumors (FIG. 14C).

Example 7. Anti-PD1-TGFRII Exhibits Superior Anti-Tumor Response Compared to Anti-PD1 Alone in Primary Colorectal Cancer (CRC) Patient Samples Effectiveness of anti-PD1-TGFRII fusion protein was evaluated in primary colorectal cancer patient samples. PBMCs from CRC patients were co-cultured with dissociated tumor cells. The cells were stimulated in the presence of isotype control, anti-PD1 or anti-PD1-TGFRII fusion protein. The culture supernatants were collected and IFN-γ levels were quantified by MSD per manufacturer's protocol. TGF-β levels were assessed by Luminex per manufacturer's protocol. The cell pellets from co-culture at the end of culture period were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Figure 15B:
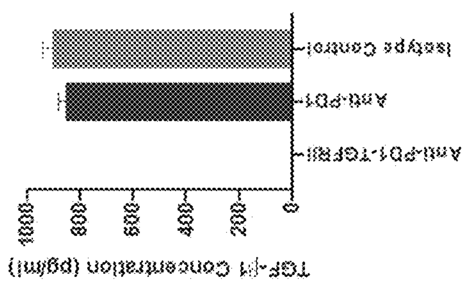
FIGS. 15A-15B shows the effect of anti-PD1(VH7/VL6)-TGFRII fusion protein on IFN-γ production and TGF-β1 concentration in primary colorectal cancer patient samples.
Figure 15A:
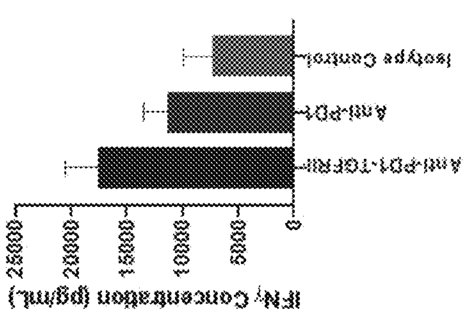
Figure 15C:
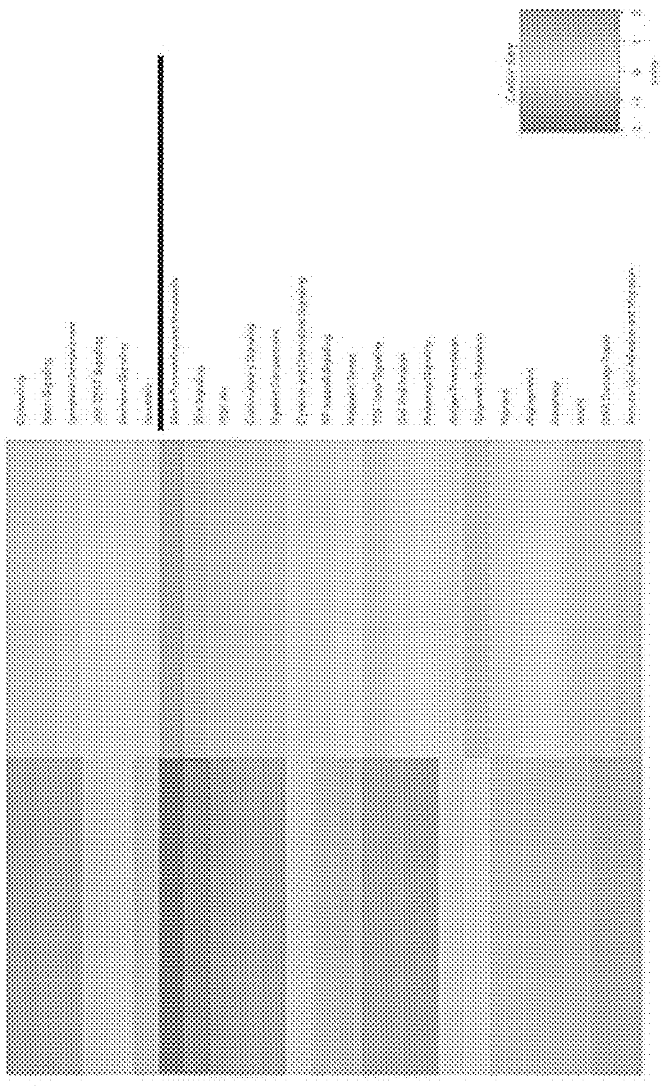
FIG. 15C shows the gene expression analysis of primary colorectal cancer patient samples co-cultured with anti-PD1 (VH7/VL6)-TGFRII fusion protein.

As shown in FIG. 15A, anti-PD1-TGFRII fusion protein promoted higher level of IFN-γ production compared to anti-PD1 or isotype control. Anti-PD-TGFRII fusion protein completely neutralized TGF-31 produced by patient PBMC and dissociated tumor cells (FIG. 15B). Anti-PD1-TGFRII fusion protein treatment resulted in significant upregulation of cytotoxic genes (FIG. 15C) compared to anti-PD1 treatment highlighting improved cytotoxic function in presence of tumor compared to anti-PD1 antibody. Furthermore, anti-PD1-TGFRII fusion protein treatment resulted in significant downregulation of genes involved in tumor metastasis and angiogenesis pathways (FIG. 15C). As expected TGF-β signaling pathway is significantly downregulated in anti-PD1-TGFRII fusion protein treatment group. Overall, results from this patient derived samples exhibit superior anti-tumor response of anti-PD1-TGFRII fusion protein compared to anti-PD1 antibody.

Example 8. Anti-PD1-TGFRII Exhibits Increased Cytotoxicity Compared to Anti-PD-L1-TGFRII in an In Vitro Model of Ovarian Cancer Effectiveness of Anti-PD1-TGFRII was compared with Anti-PD-L1-TGFRII in an in vitro model of ovarian cancer. PBMCs purified from healthy donors were co-cultured with cancer cell line SK-OV-3. The immune cells were stimulated in the presence of isotype control, anti-PD1-TGFRII fusion protein or anti-PD-L1-TGFRII fusion protein. The killing of tumor cells was assessed across culture period using Incucyte live cell analysis system.

Figure 16:
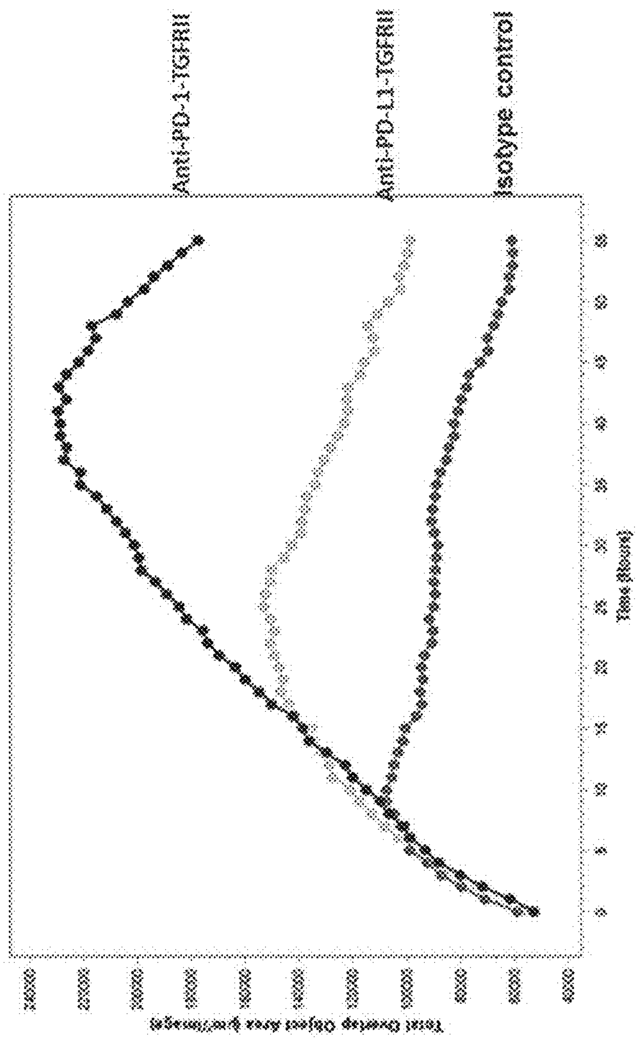
FIG. 16 shows a graph depicting the results of a cytotoxicity assay of anti-PD1 (VH7/VL6)-TGFRII fusion protein compared to anti-PD-L1-TGFRII fusion protein.

As shown in FIG. 16, the presence of anti-PD1-TGFRII fusion protein exhibited increased killing of tumor cells when compared to anti-PD-L1-TGFRII fusion protein. Overall, anti-PD1-TGFRII exhibits improved cytotoxicity when compared to anti-PD-L1-TGFRII.

Example 9. Combination of Anti-PD1-TGF-RII with CAR-T Significantly Enhanced 3D Tumor Spheroid Killing when Compared to Combination with Anti-PD1 or CAR-T Alone Combination of anti-PD1-TGFRII fusion protein with CAR-T cells was evaluated in an in vitro 3D tumor spheroid model of ovarian cancer. Note that in this example, CAR-T cells refer to T cells engineered to express MUC16 CAR. 3D tumor spheroids were generated by coculturing ovarian cancer cell line SK-OV-3 and a fibroblast cell line. CAR-T cells were then added to the 3D tumor spheroid culture in the presence of anti-PD1-TGFRII fusion protein or anti-PD1. The target specific killing of 3D tumor spheroid was assessed across time using Incucyte live cell analysis system.

Figure 17:
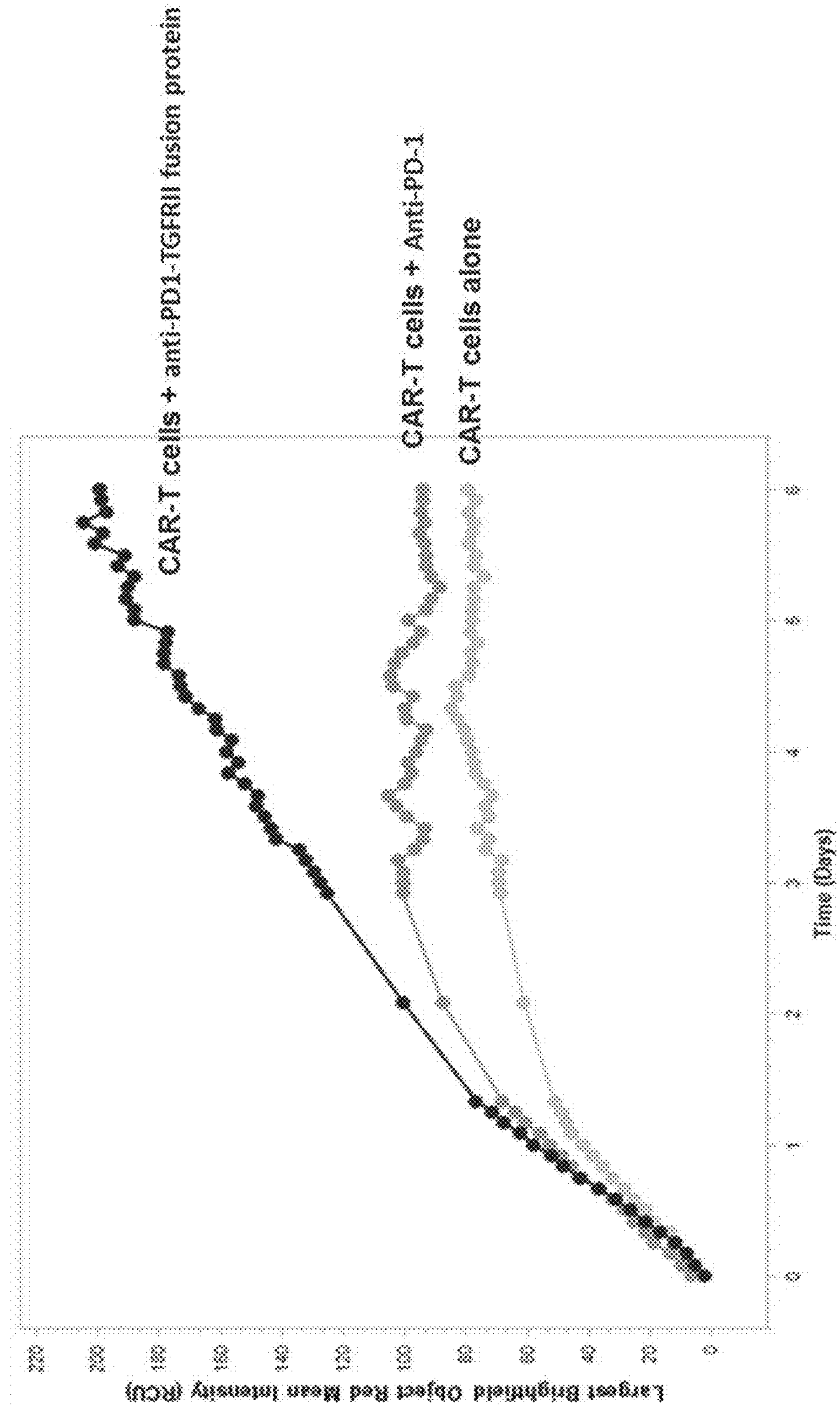
FIG. 17 is a graph depicting the results of a cytotoxicity assay of anti-PD1(VH7/VL6)-TGFRII fusion protein in combination with a chimeric receptor antigen (CAR) T cells vs. anti-PD1 in combination with a CAR T cells vs. CAR T cells alone.

As shown in FIG. 17, the combination of anti-PD1-TGFRII fusion protein with CAR-T cells showed increased killing of 3-D tumor spheroids when compared to the combination of anti-PD1 and CAR-T cells or CAR-T cells alone. Overall, result from this kill assay suggest that addition of anti-PD-1-TGF-RII to CAR-T cells enhances the anti-tumor response of CAR-T cells.

Example 10 Combination of Anti-PD1-TGF-RII with CD33 Specific CAR-T Cells

CD33 CAR-T cells were co-cultured with MOLM-13 AML tumor cell line in a cytotoxicity assay in and the cultures were incubated in the IncuCyte S3 live cell analysis instrument. Anti PD1 or anti-PD1-TGFRII was added to the indicated cultures at a equimolar concentration. Sytox Green was directly added at the start of the culture to allow for the identification and enumeration of dying cells in the culture. Analysis was performed using the IncuCyte S3 Software. The data presented in the graph shown is the mean±SD from triplicate wells, with 5 scans/well taken. As shown in FIG. 18A, the combination of anti-PD1 (VH6/VL5)-TGFRII fusion protein with the CD33 CAR T cells showed increased killing compared to CAR T cells and anti-PD1(VH6/VL5) combination or CAR T cells alone.

Figure 18B:
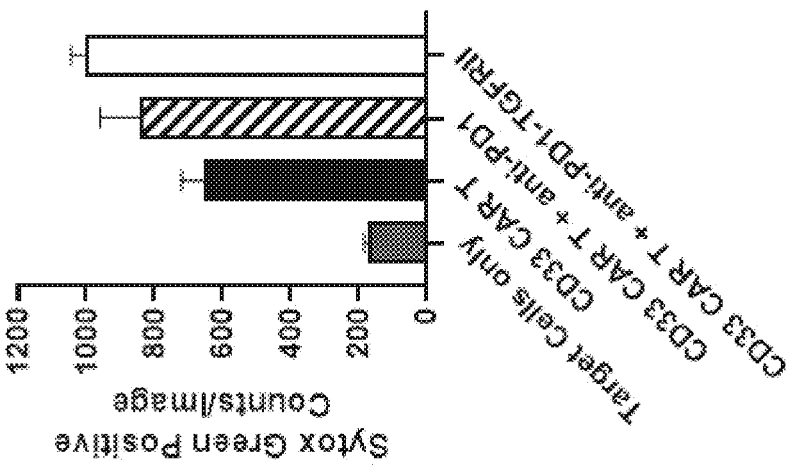
FIG. 18A and FIG. 18B are graphs depicting the results of a cytotoxicity assay of anti-PD1 (VH6/VL5)-TGFRII fusion protein in combination with CD33 CAR-T and a cytotoxicity assay of anti-PD1 (VH7/VL6)-TGFRII fusion protein in combination with CD33 CAR-T respectively.
Figure 18A:
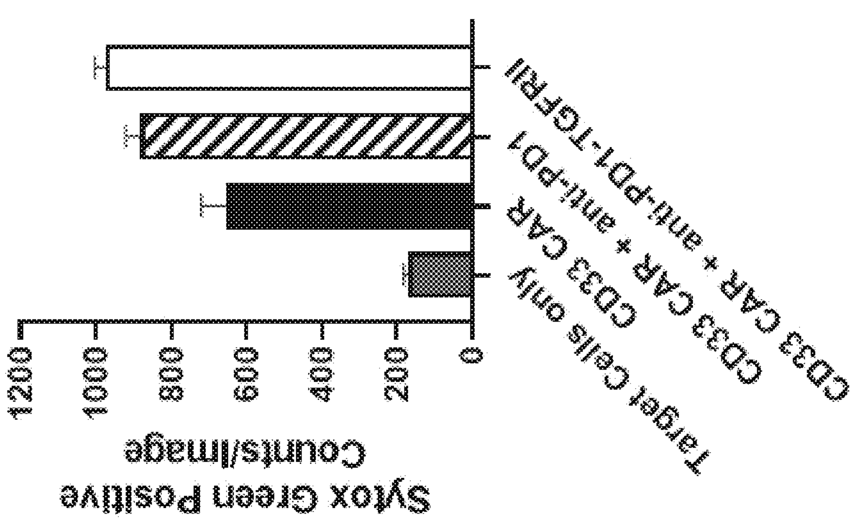

As shown in FIG. 18B, the combination of anti-PD1 (VH7/VL6)-TGFRII fusion protein with the CD33 CAR-T cells showed increased killing compared to CAR-T cells and anti-PD1 combination or CAR-T cells alone. Overall, the result for these cytotoxicity assays demonstrate that anti-PD1 (VH6/VL5)-TGFRII fusion protein and anti-PD1(VH7/VL6)-TGFRII fusion protein enhance the anti-tumor immune responses of CAR-T cells.

Example 11. Combination of Anti-PD1-TGF-RII with CD19 CAR-T Cells Enhances Tumor Cell Killing CD19 CAR-T cells are co-cultured with tumor cells expressing CD19 antigen on cell surface in presence of anti-PD1-TGFRII fusion protein or anti-PD1. The combination of anti-PD1-TGFRII fusion protein with CD19 CAR-T cells shows increase in killing of tumor cells when compared to the combination of anti-PD1 and CAR-T cells or CAR-T cells alone.

Example 12. Combination of Anti-PD1-TGF-RII with BCMA Specific CAR-T Improves Cytotoxic Potential of CAR-T Cells BCMA specific CAR-T cells are co-cultured with tumor cell line expressing BCMA antigen in presence or absence of anti-PD1-TGFRII fusion protein or anti-PD1. The combination of anti-PD1-TGFRII fusion protein with CAR-T cells improves cytotoxic potential of CAR-T cells compared to the combination of anti-PD1 and CAR-T cells or CAR-T cells alone.

Example 13. Combination of Anti-PD1-TGF-RII with PSMA Specific CAR-T Enhances Tumor Cell Killing by CAR-T Cells PSMA specific CAR-T cells are co-cultured with tumor cell line expressing PSMA antigen in presence or absence of anti-PD1-TGFRII fusion protein or anti-PD1. The combination of anti-PD1-TGFRII fusion protein with CAR-T cells improves cytotoxicity of CAR-T cells when compared to the combination of anti-PD1 and CAR-T cells or CAR-T cells alone.

Example 14. NK Cell Target Cell Lysis was Improved by Anti-PD1-TGFRII

Figure 19A:
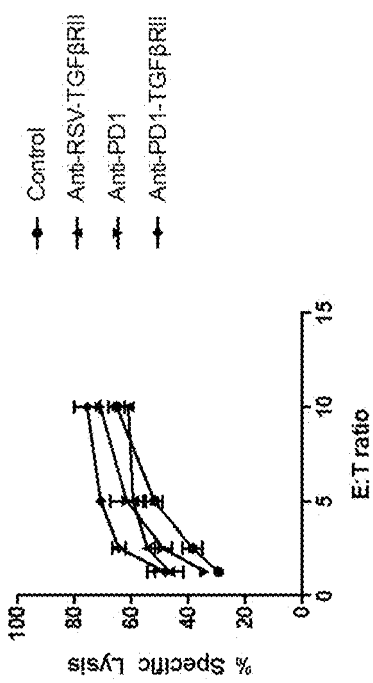
FIG. 19A and FIG. 19B are graphs depicting tumor cell lysis using anti-PD1 (VH6/VL5)-TGFRII fusion protein and anti-PD1 (VH7/VL6)-TGFRII fusion protein respectively when co-cultured with NK cells.
Figure 19B:
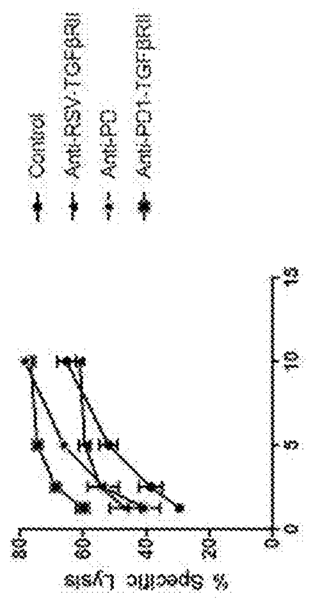

The ability of anti-PD1 (VH7/VL6)-TGFRII and anti-PD1 (VH6/VL5)-TGFRII to promote natural killer cell-mediated killing of tumor cells was assessed in an in vitro model of ovarian cancer. Effector NK cells were purified from healthy donor and co-cultured with SK-OV-3 target cell line overnight at different E:T cell ratios in the presence of anti-RSV-TFGBRII (control), anti-PD1 (VH6/VL5) and anti-PD1 (VH7/VL6), anti-PD1 (VH7/VL6)-TGFRII and anti-PD1 (VH6/VL5)-TGFRII. Propidium iodine was added to the culture to identify dead cells and cell death was assayed using the Nexcelom Celigo. As observed in FIG. 19A and FIG. 19B, anti-PD1-TGFBRII fusion proteins promoted higher tumor cell killing compared to anti-PD1 or the TGFBRII alone (Anti-RSV-TGFBRII).

Example 15: Fusion Protein of Anti-PD1-ADA2

Anti-PD1 VHs and VLs were synthesized and formatted in IgG, scFv-Fc or scFv configurations with adenosine deaminase 2 (ADA2) fused at C-terminal by linker (G4S)2. Anti-PD1-adenosine deaminase fusion proteins were transiently expressed in Expi293 cells according to manufacturer's protocol and purified using AKTA AVANT system.

Surface Plasmon Resonance

Surface plasma resonance (SPR) analysis was performed using Biacore3000, CM5 chip, an amine-coupling kit, 10×HBS-P running buffer and Glycine for. For anti-PD1 kinetic assay, recombinant PD-1 Fc protein was immobilized on chip using a pre-defined ligand immobilization program. Purified anti-PD1-adenosine deaminase fusion proteins were diluted in running buffer to a range of final concentrations and injected. Dissociation was allowed to proceed followed by regeneration of the chip surface.

TABLE 10

Affinity of anti-PD1-ADA2 to immobilized PD1

| Fusion protein | $K_D$ (M) |
|---|---|
| Anti-PD1 (VH7-VL6) IgG4-ADA2 | 6.63e−14 |
| Anti-PD1 (VH6-VL5) IgG4-ADA2 | 6.16e−14 |
| Anti-PD1 (VH7-VL6) IgG1-ADA2 | 5.09e−13 |
| Anti-PD1 (VH6-VL5) IgG1-ADA2 | 3.09e−13 |
| Anti-PD1 (VH7-VL6) scFv-Fc-ADA2 | 5.63e−10 |
| Anti-PD1 (VH6-VL5) scFv-Fc-ADA2 | 1.84e−12 |
| Anti-PD1 (VH7-VL6) scFv-ADA2 | 1.3e−10 |
| Anti-PD1 (VH6-VL5) scFv-ADA2 | 3.46e−9 |

PD-1/PDL-1 Blockade Assay

Figure 21:
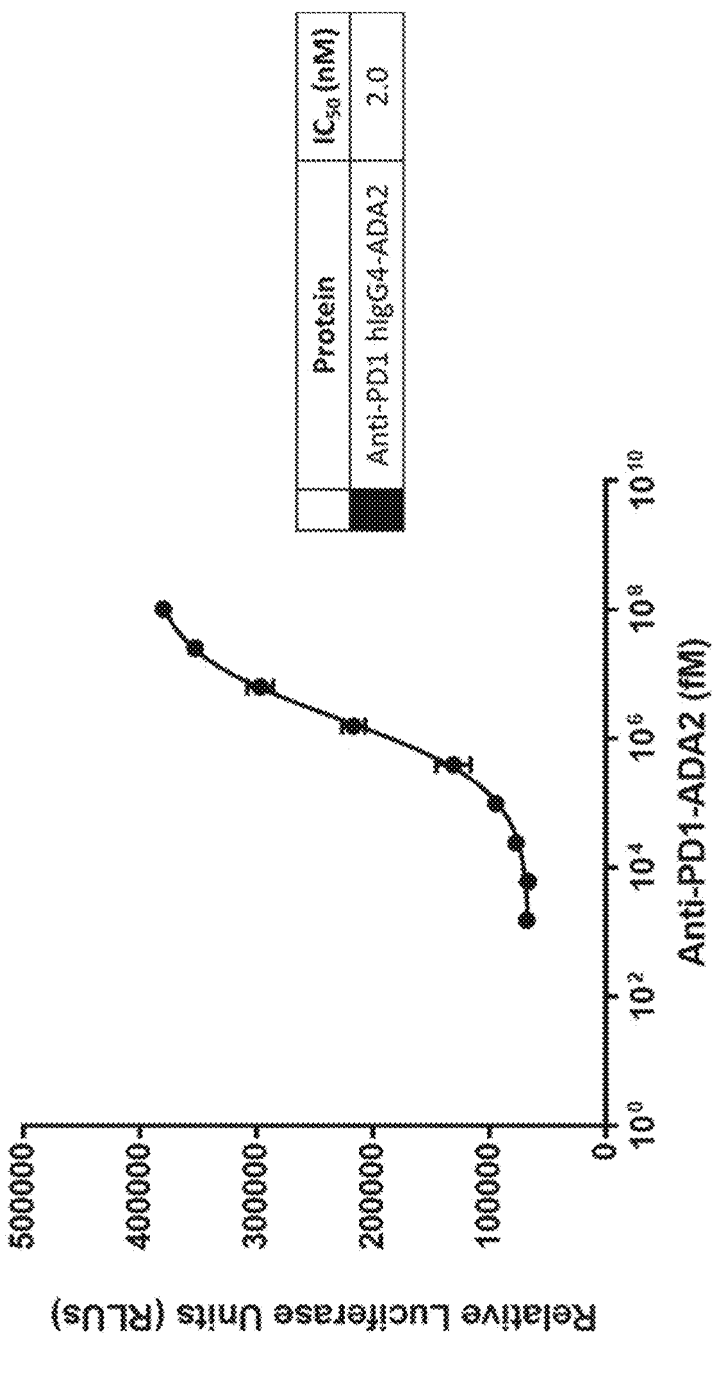
FIG. 21 is a graph showing blockade of PD-1/PD-L1 interaction by anti-PD1 IgG4-ADA2.

To investigate if the anti-PD1-ADA2 fusion proteins could function as anti-PD1 antibody by blocking the PD-1/PD-L1 interaction, a PD-1/PD-L1 blockade bioassay kit from Promega used as depicted in Example 1. These values was used as a measure of PD-1/PD-L1 blocking potency (FIG. 21).

ADA Enzymatic Activity Assay

Figure 22:
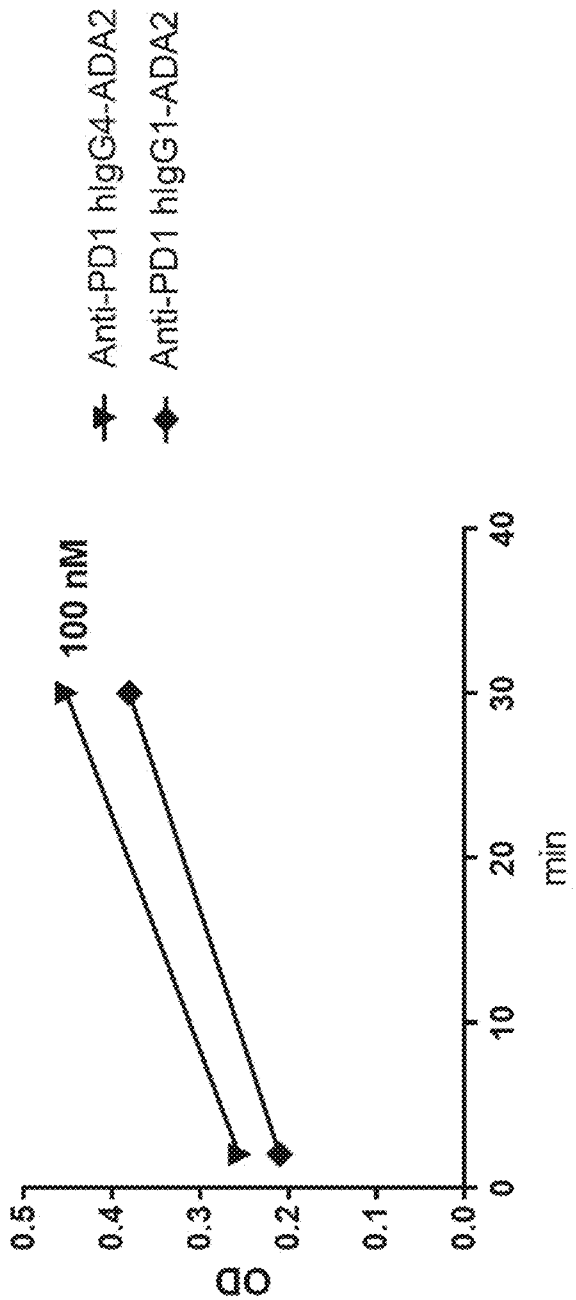
FIG. 22 is a graph showing ADA2 enzymatic activity measured for anti-PD1 hIgG1-ADA2 and anti-PD1 hIgG4-ADA2.

To determine the anti-PD1 ADA2 fusion protein enzymatic activity, the colorimetric Adenosine Deaminase (ADA) Activity Kit (Abcam) was utilized according to the manufacturers' recommendations. 2 minutes and 30 minutes timepoints were selected to calculate the ADA enzymatic activity over time. As shown in FIG. 22, anti-PD1-ADA2 fusion proteins exhibited enzymatic activity over time.

Example 16: PD1 Binding Affinity Analysis of Anti-PD1 IgG4 S108P-wtADA2 and -mutADA2

PD1-Fc antigen and reference was immobilized on Biacore CM5 surface, then 6-12 replicated series diluted concentrations of Anti-PD1 IgG4 S108P-wtADA2 and -mutADA2 were series injected on PD1-Fc antigen and reference surface. Kinetics data was evaluated for 1:1 model: Langmuir with mass transfer. Results are as depicted in Table 11.

TABLE 11

Binding affinity of Anti-PD1 (VH6/VL5) and (VH7/VL6) IgG4 S108P and the Anti-PD1-wtADA2 and-mutADA2

| Analyte | $K_D$ (M) |
|---|---|
| Anti-PD1 (VH6/VL5) IgG4 S108P | 3.34e−13 |
| Anti-PD1 (VH6/VL5) IgG4 S108P-ADA2 | 7.53e−13 |
| Anti-PD1 (VH6/VL5) IgG4 S108P-mutADA2 | 2.18e−13 |
| Anti-PD1 (VH7/VL6) IgG4 S108P | 3.92e−13 |
| Anti-PD1 (VH7/VL6) IgG4 S108P-ADA2 | 4.13e−13 |
| Anti-PD1 (VH7/VL6) IgG4 S108P-mutADA2 | 3.38e−13 |

Example 17: Anti-PD1-ADA2 Fusion Proteins Effectively Blocked PD-L1/PD1 Signaling Ability of anti-PD1-ADA2 fusion proteins to block PD1/PD-L1 interaction was evaluated using a reporter bioassay as mentioned in Example 12.

Figure 23A:
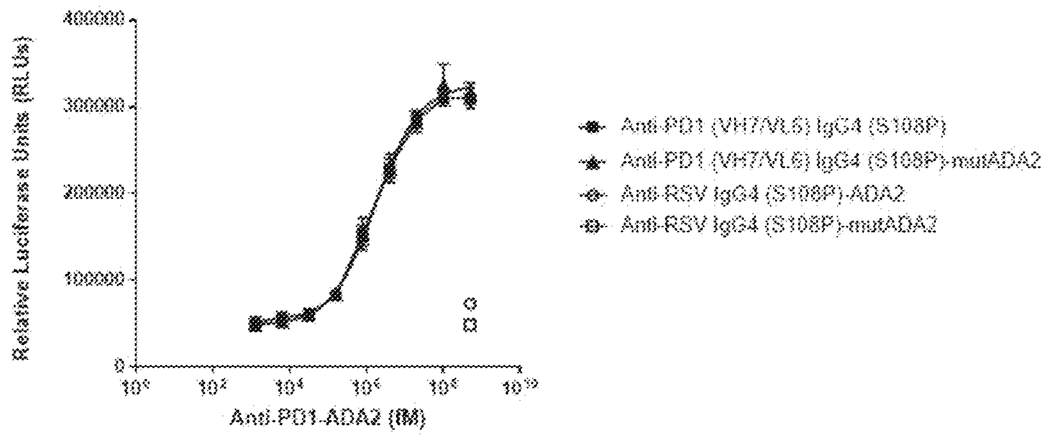
FIGS. 23A-23C are graphs showing the effect of various variants of Anti-PD1 and Anti-PD1-ADA2 fusion proteins on PD-L1/PD-1 interaction.
Figure 23B:
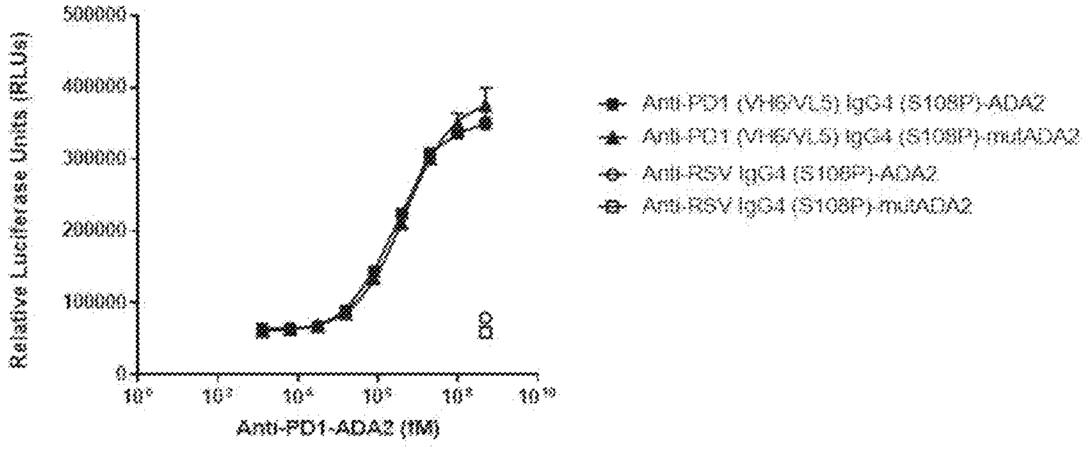
Figure 23C:
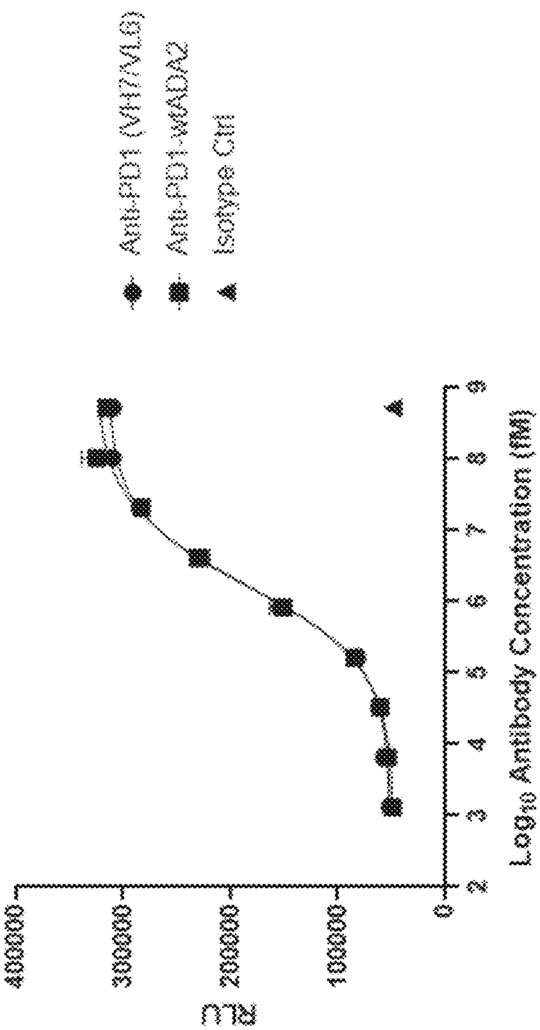
Figure 24A:
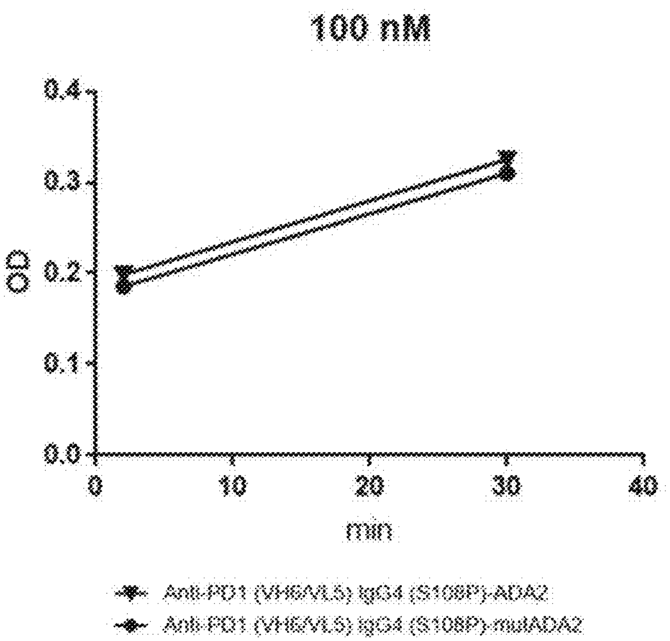
FIGS. 24A-24F are graphs showing the enzymatic activity of various variants of Anti-PD1-ADA2 fusion proteins as measured by ADA enzymatic activity.
Figure 24B:
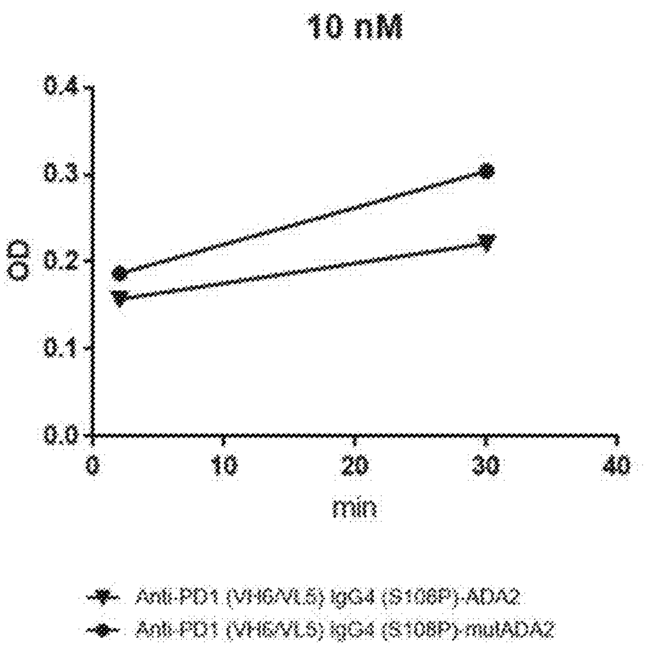
Figure 24C:
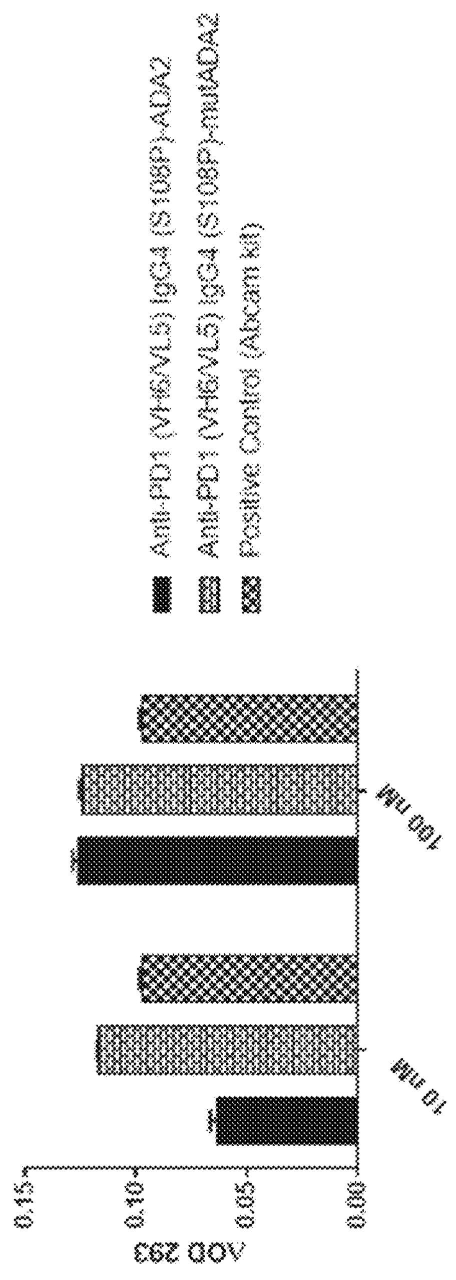
Figure 24E:
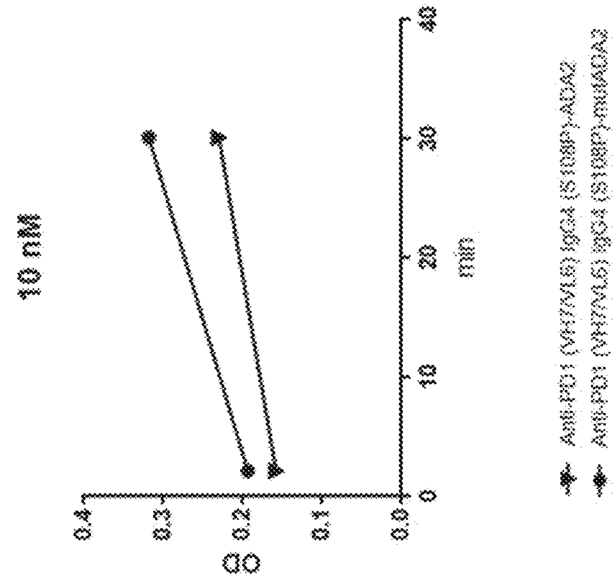
Figure 24D:
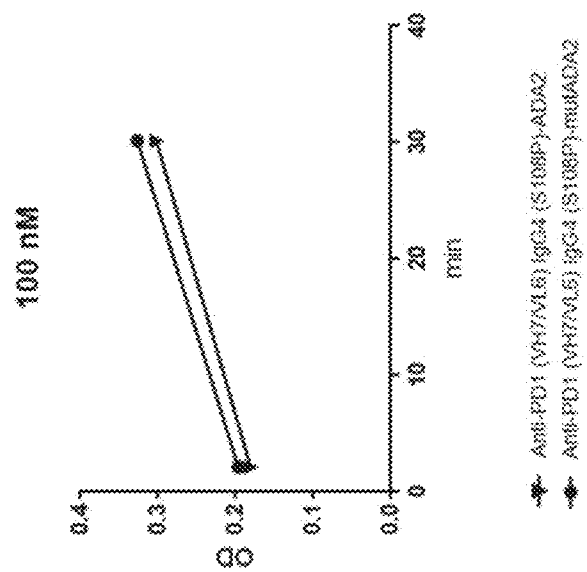
Figure 24F:
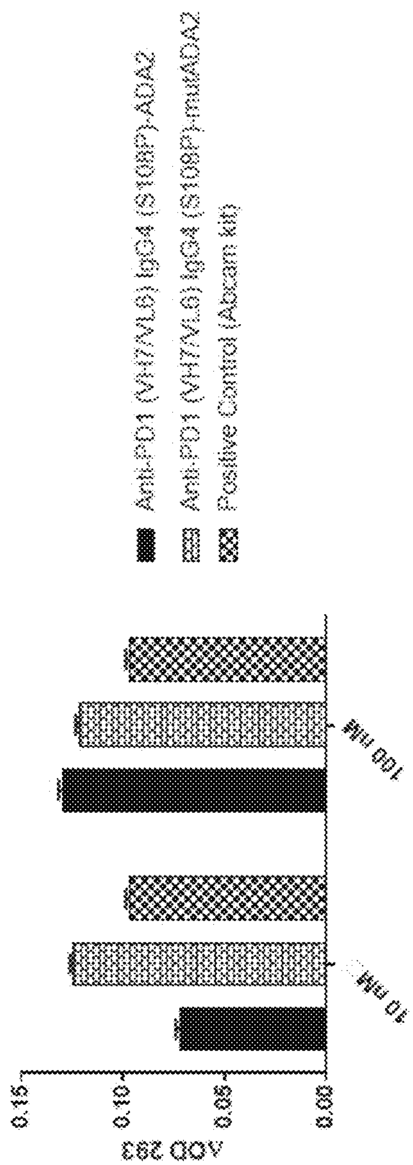

As shown in FIG. 23A-23B, anti-PD1 (VH7/VL6)-wtADA2 and -mut7ADA2, anti-PD1 (VH6/VL5)-wtADA2 and -mut7ADA2 blocked PD1/PD-L1 interaction with similar potency.

Example 18: ADA2 Enzymatic Activity

Ability of anti-PD1-ADA2 fusion proteins to enzymatically degrade adenosine was evaluated in an in vitro ADA enzymatic activity assay as mentioned in Example 12.

As shown in FIG. 24A-24F, at lower concentration of Adenosine, mut7ADA2 has higher enzymatic activity compare to the wtADA2.

Example 19: Anti-PD1-Mut7-ADA2 has a Higher Enzymatic Activity than Anti-PD1-wtADA2

Figure 25:
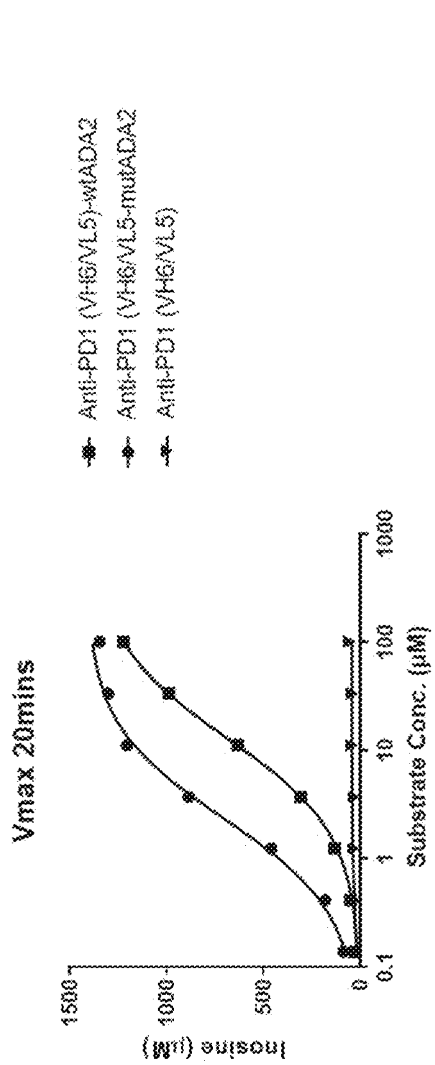
FIG. 25 is a graph showing the enzymatic activity of Anti-PD1-mutADA2 vs. anti-PD1-wtADA2 as measured by ADA enzymatic activity.

The Michaelis Menten constants (Km) of anti-PD1(VH6/VL5)-wtADA2 and anti-PD1(VH6/VL5)-mut7ADA2 were measured using the fluorometric ADA2 enzyme assay kit. As observed in FIG. 25, anti-PD1-mut7ADA2 has a higher Km compared to anti-PD1-wtADA2.

Figure 26A:
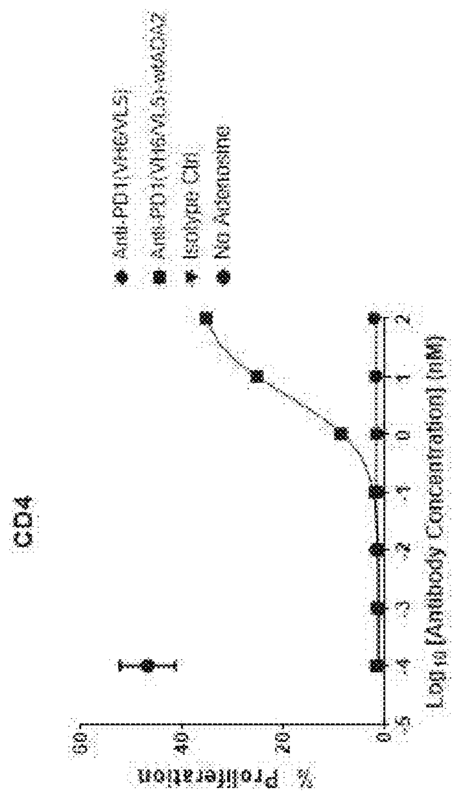
FIG. 26A-26D are graphs depicting the effect of variants of anti-PD1-wtADA2 on T cell proliferation.
Figure 26B:
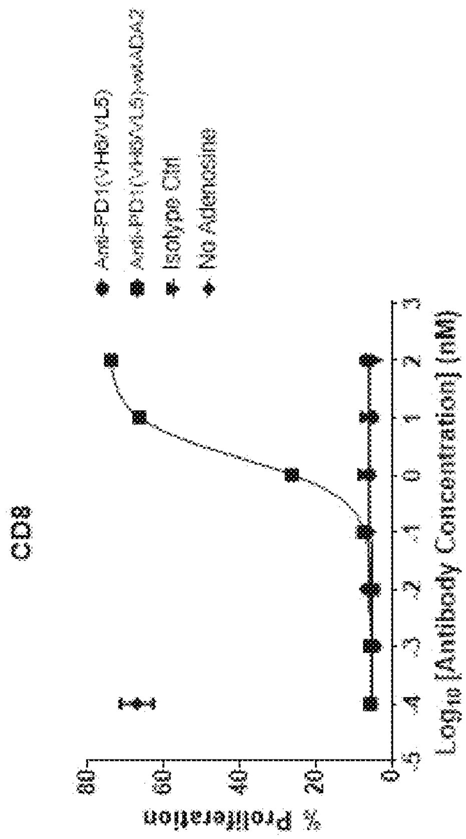
Figure 26C:
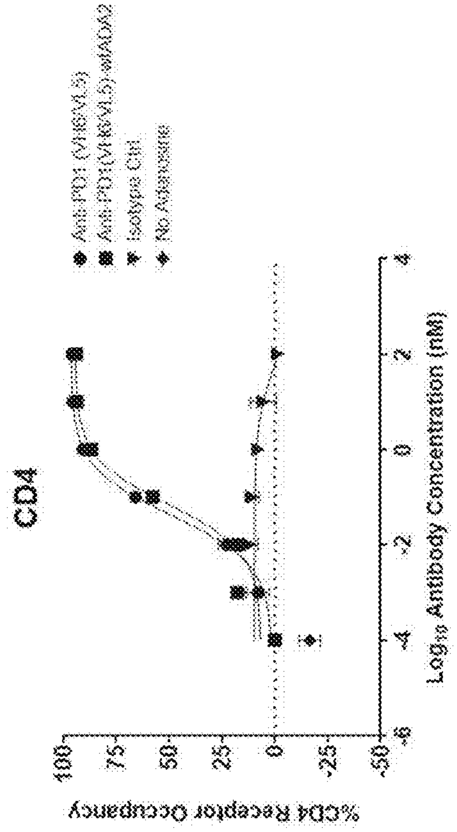
Figure 26D:
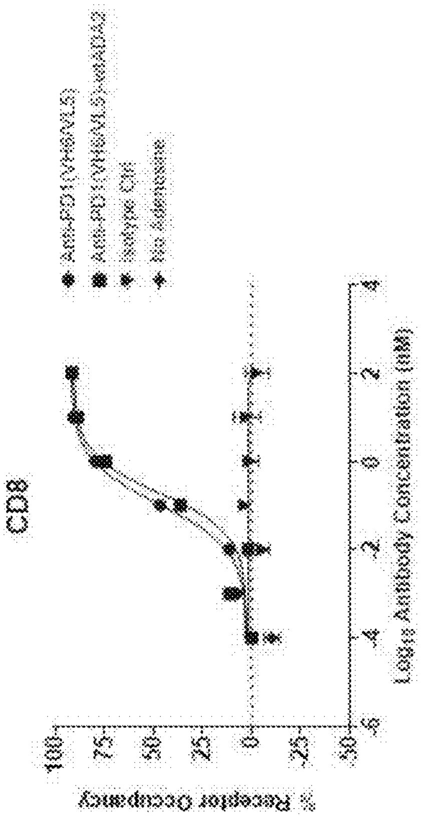

Example 20: Anti-PD1-wtADA2 Reverses Adenosine-Mediated Suppression of T Cell Proliferation The ability of anti-PD1-wtADA2 to promote T cell proliferation was assessed in vitro using normal donor PBMCs. CellTrace Violet-labeled PBMCs cocultured in media containing 1 mM adenosine were stimulated in the presence of increasing concentrations of anti-PD1(VH6/VL5)-wtADA2, and anti-PD1(VH6/VL5). The supernatants were collected for cytokine analysis. The cells were assayed for T cell proliferation by flow cytometry. The data showed that Anti-PD1 (VH6/VL5)-wtADA2 significantly reversed the adenosine-mediated suppression of CD4+(FIG. 26A) and CD8+ T cells (FIG. 26B) compared to Anti-PD1 (VH6/VL5) or isotype control. As observed in FIGS. 26C and D, both anti-PD1 and anti-PD1-wtADA2 similarly occupied PD1 receptor on CD4+(FIG. 26C) and CD8+ T cells (FIG. 26D).

Figure 26E:
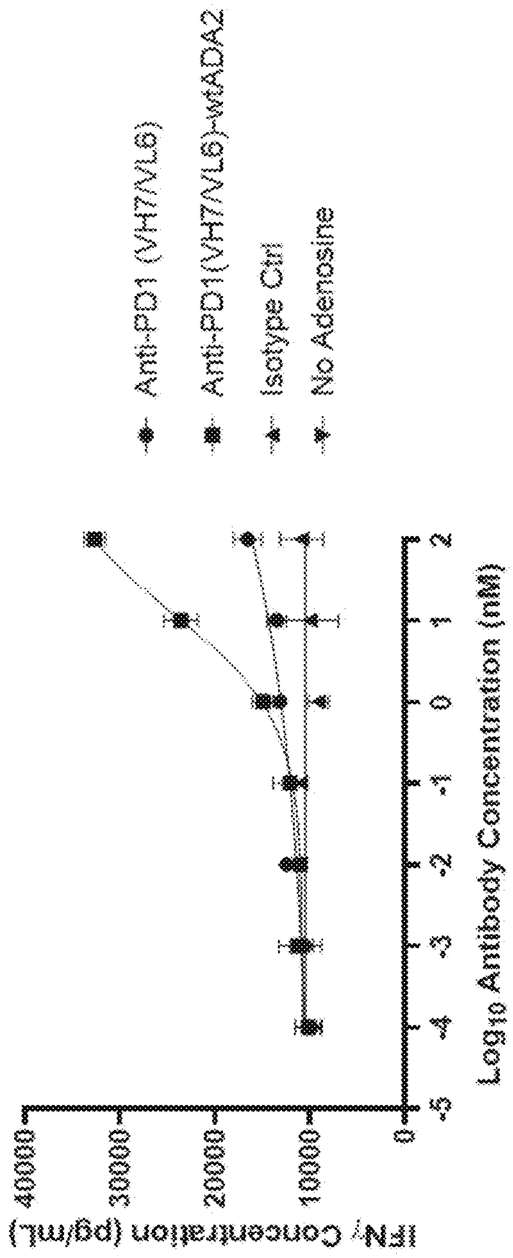
FIG. 26E is a graph depicting IFNγ production by anti-PD1-wtADA2 as compared to anti-PD1 or isotype control.

The ability of anti-PD1(VH7/VL6)-wtADA2 to promote T cells function was further assessed by stimulating PBMCs in media containing adenosine in the presence of increasing concentrations of anti-PD1 (VH7/VL6), anti-PD1(VH7/VL6)-wtADA2 or isotype controls. The culture supernatants were collected and assayed for production of IFNγ. FIG. 26E shows that anti-PD1(VH7/VL6)-wtADA2 treatment induced significantly more IFN-γ compared to anti-PD1 or isotype control.

Figure 27A:
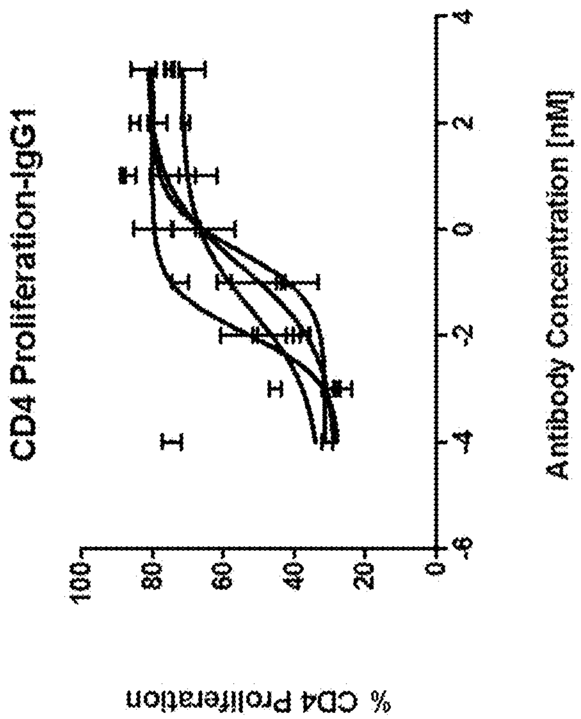
FIGS. 27A-27B are graphs depicting the effectiveness of wtADA2 and mutADA2 to reverse adenosine-mediated suppression of T cell proliferation.
Figure 27B:
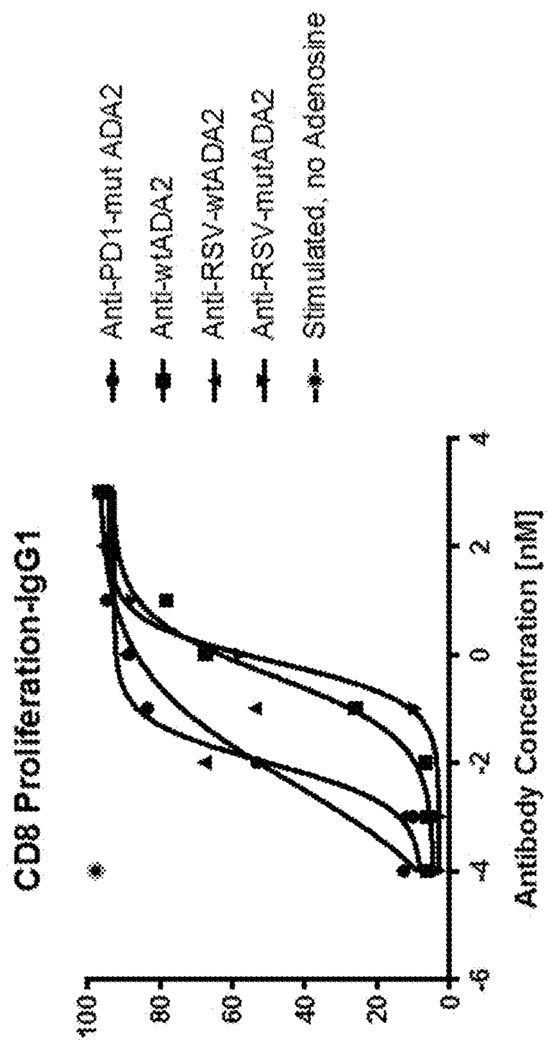

Example 21: WtADA2 and mutADA2 Showed Comparable Reversal of Adenosine-Mediated Suppression of T Cell Proliferation The effectiveness of wtADA2 and mutADA2 to reverse adenosine-mediated suppression of T cell proliferation was assessed by stimulating-labeled PBMCs in a media containing adenosine in the presence of increasing concentration of anti-PD1-wtADA2, anti-PD1-mutADA2, anti-RSV-wtADA2 and anti-RSV-mutADA2. The cells were stained, then analyzed for proliferation by flow cytometry. Both the wtADA2 and mutADA fusion proteins were equally effective at reversing the adenosine-mediated suppression of CD4 T cells (FIG. 27A) and CD8 T cells (FIG. 27B).

Example 22: Blockade of PD1-PDL1 Interaction by Anti-PD1(VH6/VL5)-ADA2

Ability of various forms of anti-PD1-ADA2 fusion proteins to block PD1/PD-L1 interaction was evaluated using a reporter bioassay as mentioned in Example 12.

Figure 28:
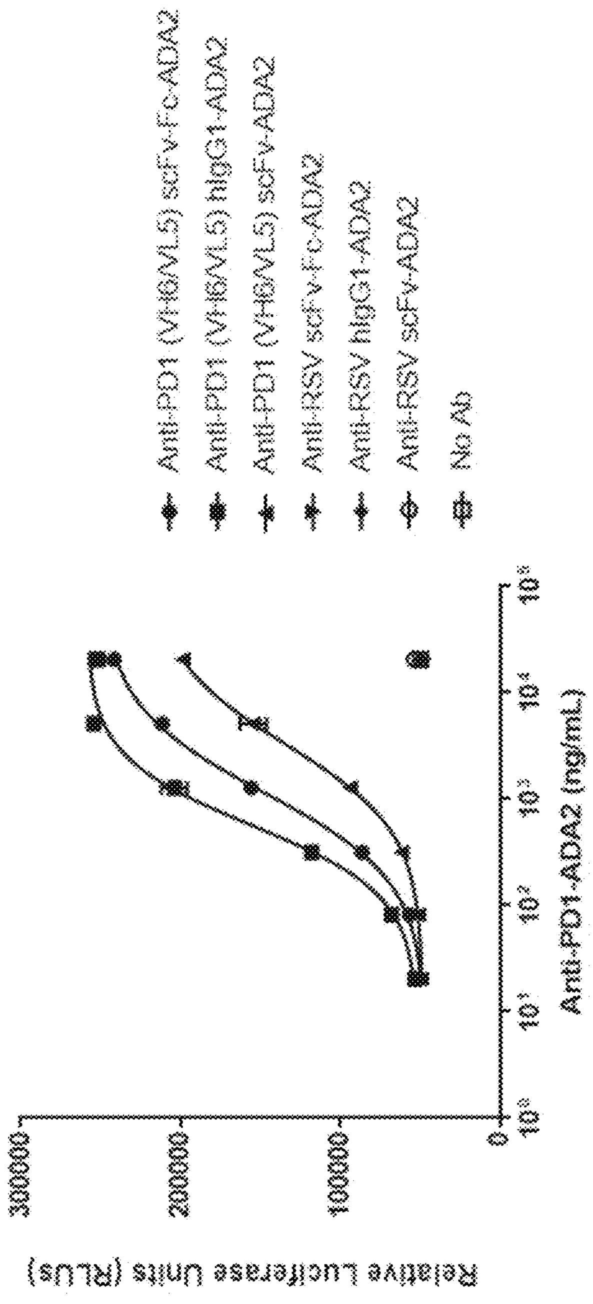
FIG. 28 is a graph depicting the effect of variants of anti-PD1-ADA2 fusion proteins on the blockade of PD1-PDL1 interaction.

As shown in FIG. 28, anti-PD1 (VH6/VL5) scFv-Fc-ADA2, hIgG1-ADA2 and scFv-ADA2 all showed functional activity as measured by the PD1/PD-L1 Blockade Bioassay.

Example 23: ADA Enzymatic Activity of Anti-PD1-ADA2-scFv-Fc

Ability of various forms of anti-PD1-ADA2 fusion proteins to to enzymatically degrade adenosine was evaluated in an in vitro ADA enzymatic activity assay as mentioned in Example 12.

Figure 29:
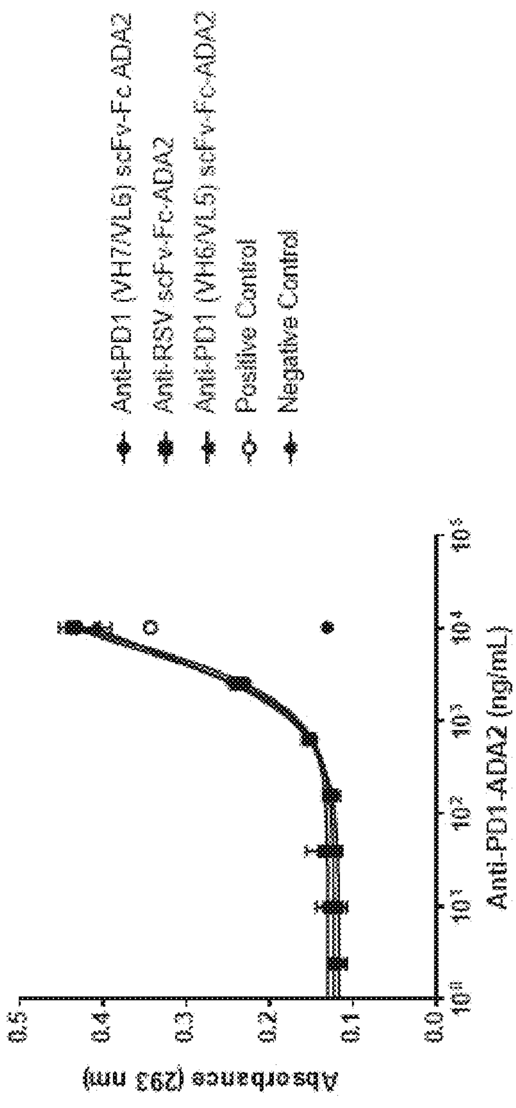
FIG. 29 a graph showing the enzymatic activity of Anti-PD1-ADA2-scFv-Fc as measured by ADA enzymatic activity.

As shown in FIG. 29, Anti-PD1 (VH7/VL6) scFv-Fc-ADA2 and (VH6/VL5) scFv-Fc-ADA2 have similar ADA2 enzymatic activity comparable to the control.

Figure 30:
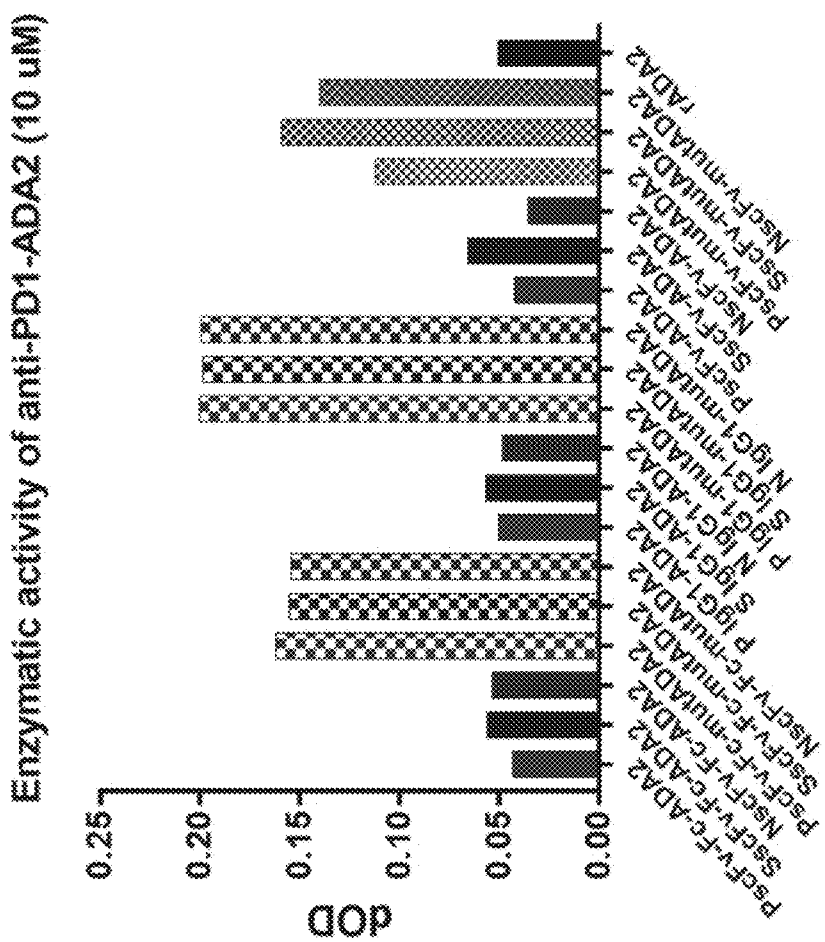
FIG. 30 is a bar graph showing the enzymatic activity of variants of anti-PD1-ADA2 as measured by ADA enzymatic activity.

Example 24: ADA Enzymatic Activity of Various Anti-PD1-ADA2 and Anti-PD1-mutADA2 Constructs The ADA enzymatic activity assay was conducted as described above. As shown in FIG. 30, at 10 nM of Adenosine mutADA2 has higher enzymatic activity compared to the wtADA2.

Example 25: Anti-PD1-ADA2 Promoted IFN-γ Production and Proliferation of Tumor-Infiltrating Lymphocytes (TILs) in Primary CRC Patient Tumor PBMCs purified from CRC patients were co-cultured with matched dissociated tumor cells. CellTrace Violet-labeled cells were stimulated with anti-CD3 and anti-CD28 in the presence of isotype control, anti-PD1 (VH6/VL5) or anti-PD1 (VH6/VL5)-wtADA2 fusion protein. The culture supernatants were collected and IFN-γ levels were quantified by MSD per manufacturer's protocol and cells assessed for T cell proliferation. For gene expression analysis, the cells pellets were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Figure 31B:
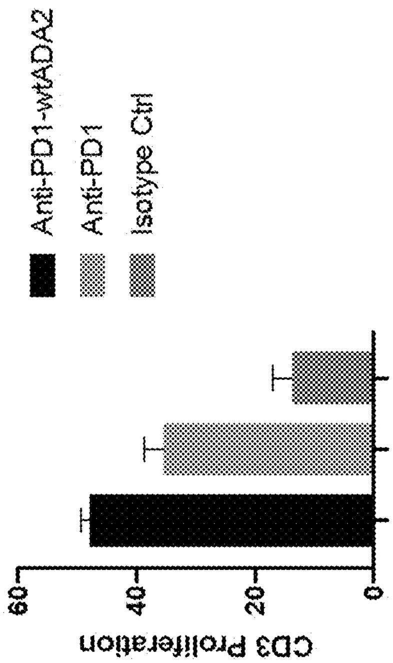
FIGS. 31A-31B are graphs depicting the effect of anti-PD1-wtADA2 on IFN-γ Production and Proliferation of Tumor-infiltrating Lymphocytes (TILs) in Primary CRC Patient Tumor.
Figure 31A:
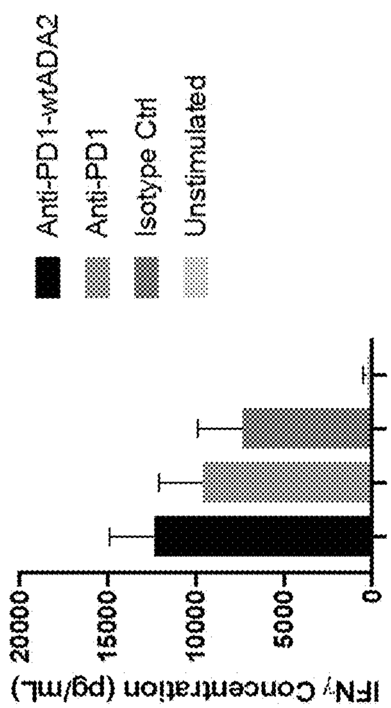

As shown in FIG. 31A, anti-PD1-wtADA2 fusion protein promoted higher level of IFN-γ production and T cell proliferation (FIG. 31B) compared to anti-PD1 or isotype control. anti-PD1-wtADA2 fusion protein treatment resulted in significant upregulation of IFN-γ signaling and chemokine signaling genes and cytotoxic genes (FIG. 31C) compared to anti-PD1 treatment highlighting improved cytotoxic function of T cells in the presence of tumor compared to anti-PD1 antibody.

Figure 32:
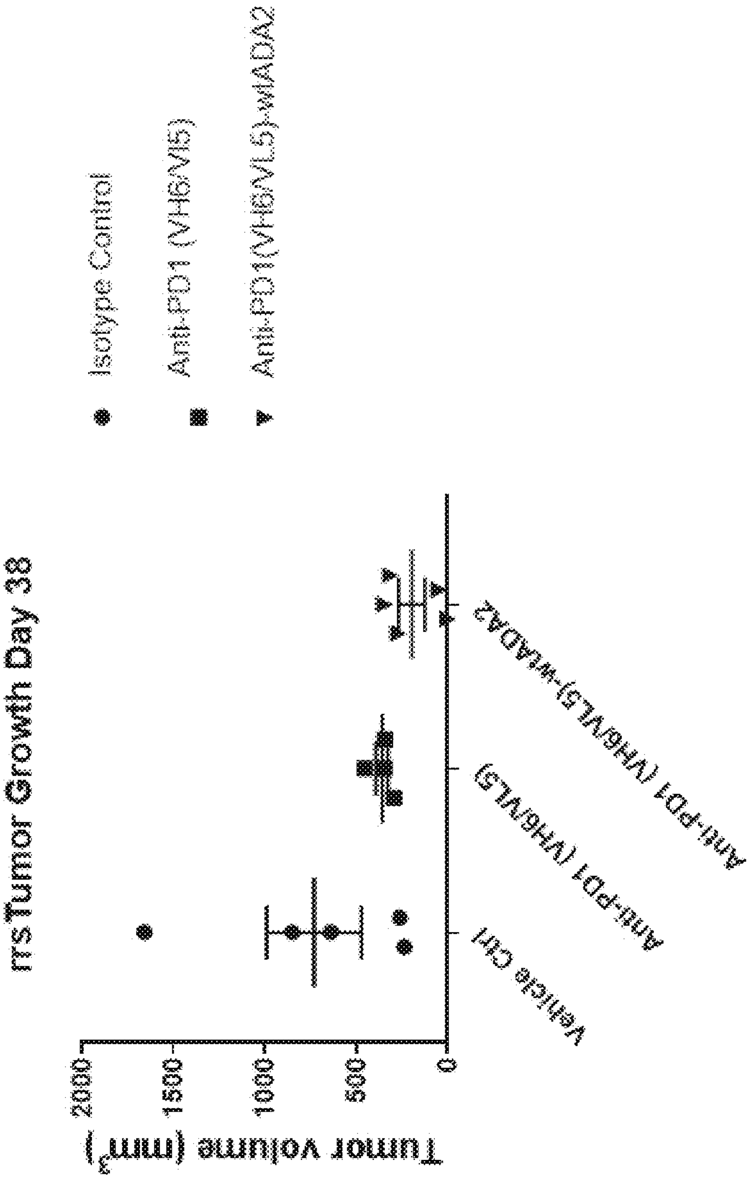
FIG. 32 is a graph depicting the effect of anti-PD1 vs. anti-PD1-wtADA2 on tumor volume of a humanized mouse model of lung cancer.

Example 26: Effect of Anti-PD1-wtADA2 Fusion Protein in a Humanized Mouse Model of Lung Cancer NSG mice humanized with peripheral blood mononuclear cells were inoculated intra-prancreatically (ortotopic injection) with the pancreatic cancer cell line Panc.08.fLuc.eGFP. Mice body weight were measured weekly and tumor weights were measured at the endoof the study on day 38. Mice were randomized into treatment groups and treated twice weekly with HBSS (vehicle control), anti-PD1 (VH6/VL5) and anti-PD1(VH6/VL5)-wtADA2. As can be seen in FIG. 32, mice treated with anti-PD-wtADA2 had significantly smaller tumors compared to mice treated with anti-PD1 or isotype control.

As can be seen in FIG. 32, mice treated with anti-PD-wtADA2 had significantly smaller tumors compared to mice treated with anti-PD1 or isotype control.

Example 27: Treatment of Anti-PD1(VH6/VL5)-wtADA2 Downregulated the Adenosine Pathway, Angiogenesis and Upregulated Cytotoxicity and Cytokine Genes PBMCs purified from CRC patients were co-cultured with matched dissociated tumor cells. CellTrace Violet-labeled cells were stimulated with anti-CD3 and anti-CD28 in the presence of isotype control, anti-PD1 (VH6/VL5) or anti-PD1 (VH6/VL5)-wtADA2 fusion protein. The culture supernatants were collected and IFN-γ levels were quantified by MSD per manufacturer's protocol and cells assess for T cell proliferation. For gene expression analysis, the cultules were duplicated and the cells pellets were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Anti-PD1-wtADA2 fusion protein promoted higher level of IFN-γ production and T cell proliferation compared to anti-PD1 or isotype control. Anti-PD1-wtADA2 fusion protein treatment also resulted in significant upregulation of IFN-γ signaling and chemokine signaling genes and cytotoxic genes (data not shown) compared to anti-PD1 treatment highlighting improved cytotoxic function of T cells in the presence of tumor compared to anti-PD1 antibody.

SEQUENCES

Provided herein is a representative list of certain sequences included in embodiments provided herein.

TABLE 4

Non-limiting exemplary polypeptide and nucleotide sequences

| Name | SEQ ID NO | Amino Acid Sequence | SEQ ID NO | Nucleotide Sequence |
|---|---|---|---|---|
| Anti-PD1<br>VH1 | 1 | QVQLVESGGGVVQPGR<br>SLRLSCAASGFTFRSYG<br>MHWVRQAPGKGLEWV<br>AIIFYDGSNKYYADSVK<br>GRFTISRDNSKNTLYLQ<br>MNSLRAEDTAVYYCAR<br>DDDYWGQGALVTVSS | | |
| Anti-PD1<br>VH2 | 2 | EVQLVQSGGGVVQPGR<br>SLRLSCAASGFTFSSYG<br>MHWVRQAPGKGLEWV<br>AVIWYDGSNKYYADSV<br>KGRFTISRDNSKNTLYL<br>QMNSLRAEDTAVYYC<br>AGEGFDYWGQGTLVT<br>VSS | | |
| Anti-PD1<br>VH3 | 3 | QVQLVQSGAEVKKPGA<br>SVKVSCKASGYTFTGY<br>YMHWVRQAPGQGLEW<br>MGAINPNSGGTNYAQK<br>FQGRVTMTRDTSISTAY<br>MELSRLRSDDTAVYYC<br>ARRPDRANWHFDYWG<br>QGTLVTVSS | | |
| Anti-PD1<br>VH4 | 4 | QVQLVQSGAEVKKPG<br>ASVKVSCKASGYTFTG<br>YYMHWVRQAPGQGL<br>EWMGAINPNSGGTNY<br>AQKLQGRVTMTTDTS<br>TSTAYMELRSLRSDDT<br>AVYYCARHGLKGDGY<br>FDYWGQGTLVTVSS | | |
| Anti-PD1<br>VH5 | 5 | QVQLVESGGGVVQPG<br>RSLRLDCKASGITFSNS<br>GMHWVRQAPGKGLE<br>WVAVIWYDGSKRYY<br>ADSVKGRFTISRDNSK<br>NTLFLQMNSLRAEDTA<br>VYYCATNNDYWGQG<br>TLVTVSS | | |
| Anti-PD1<br>VH6 | 6 | QVQLVESGGGVVQPGR<br>SLRLDCKASGITFSNSG | 109 | caggtgcagctggtcgaaagcggaggaggagtggtccagccaggacga<br>tccctgagactggattgtaaggcctctggaatcacattctctaacagtggaat |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | MHWVRQAPGKGLEWV<br>AVIWYDGSKRYYADSV<br>KGRFTISRDNSKNTLFL<br>QMNSLRAEDTAVYYC<br>ATNDDYWGQGTLVTV<br>SS | | gcactgggtgcgccaggcaccaggaaaaggactggagtgggtggccgt<br>catctggtacgacgggtcaaagcgatactatgcagatagcgtgaaaggaa<br>ggttcacaatttcacgcgacaacagcaagaatactctgtttctgcagatgaa<br>ctctctgagagcagaggatactgccgtgtactattgtgctaccaatgacgatt<br>attgggggcagggaactctggtgaccgtcagttca |
| Anti-PD1<br>VH7 | 7 | QVQLVQSGVEVKKPGA<br>SVKVSCKASGYTFTNY<br>YMYWVRQAPGQGLEW<br>MGGINPSNGGTNFNEK<br>FKNRVTLTTDSSTTTAY<br>MELKSLQFDDTAVYYC<br>ARRDYRFDMGFDYWG<br>QGTTVTVSS | 110 | caggtgcagctggtccagagcggcgtggaagtcaagaaacccggggcct<br>cagtgaaggtcagctgtaaagcttccggctacaccttcacaaactactatat<br>gtattgggtgagacaggcaccaggacagggactggagtggatgggcgg<br>gattaaccctagtaatggaggcactaacttcaacgaaaagtttaaaaacagg<br>gtgaccctgaccacagattcaagcactaccacagcttacatggagctgaag<br>tccctgcagtttgacgatacagccgtgtactattgtgctcggagagactaca<br>ggttcgatatgggctttgactattggggccaggggactaccgtgaccgtctc<br>ctct |
| Anti-PD1<br>VL1 | 8 | EIVMTQSPATLSLSPGE<br>RATLSCRASQSVSSYLA<br>WYQQKPGQAPRLLIYD<br>ASNRATGIPARFSGSGS<br>GTDFTLTISSLEPEDFAV<br>YYCQQYNNWPRTFGQ<br>GTKVEIK | | |
| Anti-PD1<br>VL2 | 9 | EIVLTQSPATLSLSPGER<br>ATLSCRASQSVSSYLA<br>WYQQKPGQAPRLLIYD<br>ASNRATGIPARFSGSGS<br>GTDFTLTISSLEPEDFAV<br>YYCQQRSNWPKTFGQG<br>TKVEIK | | |
| Anti-PD1<br>VL3 | 10 | RNVLTQSPLSLPVTPGE<br>PASISCRSSQSLSSSGYT<br>YLDWYLQKPGQSPQLL<br>IYLASWRDSGVPDRFSG<br>SGSGTDFTLKISRVEAE<br>DVGVYYCMQAEQTPG<br>PGNTFGQGTKLEIK | | |
| Anti-PD1<br>VL4 | 11 | DVVMTQSPLSLPVTPGE<br>PASISCRSSQSLLHTNG<br>YNYLHWYLQKPGQSPQ<br>LLIYLGSWQDSGVPDRF<br>SGSGSGTDFTLKISRVE<br>AEDVGVYYCMQAEQT<br>PRTFGQGTRLEVK | | |
| Anti-PD1<br>VL5 | 12 | EIVLTQSPATLSLSPGER<br>ATLSCRASQSVSSYLA<br>WYQQKPGQAPRLLIYD<br>ASNRATGIPARFSGSGS<br>GTDFTLTISSLEPEDFAV<br>YYCQQSSNWPRTFGQG<br>TKVEIK | 111 | gagatcgtcctgacacagagtccagcaactctgagcctgtcccccggcga<br>acgagctactctgtcctgccgggcatctcagagtgtgtctagttacctggcct<br>ggtatcagcagaagcccggccaggctcctaggctgctgatctacgacgcc<br>agcaacagagctaccgggattcctgccaggactcaggcagcgggtccgg<br>aacagactttaccctgacaatctcaagcctggagcccgaagatttcgctgtg<br>tactattgccagcagtcctctaattggcctcgcacctttggccaggggacaa<br>aggtcgagatcaag |
| Anti-PD1<br>VL6 | 13 | EIVLTQSPATLSLSPGER<br>ATLSCRASKGVSTSGYS<br>YLHWYQQKPGQAPRLL<br>IYLASYLESGVPARFSG<br>SGSGTDFTLTISSLEPED<br>FAVYYCQHSRDLPLTF<br>GGGTKVEIK | 112 | gagatcgtcctgactcagtccccagcaaccctgagtctgtcaccaggagaa<br>agggcaaccctgagctgccgagcatccaagggggtgagcacatccggat<br>actcttatctgcactggtaccagcagaaacccggacaggctcctcgactgc<br>tgatctacctggcatcttatctggagagtggcgtgcctgctcggactctggg<br>agtggatcaggcaccgattttacactgactatttctagtctggagccagaag<br>atttcgcagtgtactattgccagcattctcgagacctgcccctgacatttggc<br>gggggaactaaggtcgagatcaaa |
| TGFβRII<br>ECD | 14 | IPPHVQKSVNNDMIVTD<br>NNGAVKFPQLCKFCDV<br>RFSTCDNQKSCMSNCSI<br>TSICEKPQEVCVAVWR<br>KNDENITLETVCHDPKL<br>PYHDFILEDAASPKCIM<br>KEKKKPGETFFMCSCSS<br>DECNDNIIFSEEYNTSNP<br>D | | |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| TGFβRII2 ECD | 141 | IPPHVQKSDVEMEAQK DEIICPSCNRTAHPLRHI NNDMIVTDNNGAVKFP QLCKFCDVRFSTCDNQ KSCMSNCSITSICEKPQE VCVAVWRKNDENITLE TVCHDPKLPYHDFILED AASPKCIMKEKKKPGE TFFMCSCSSDECNDNIIF SEEYNTSNPD | | |
| TGFβRII min ECD | 142 | PQLCKFCDVRFSTCDN QKSCMSNCSITSICEKP QEVCVAVWRKNDENIT LETVCHDPKLPYHDFIL EDAASPKCIMKEKKKP GETFFMCSCSSDECND NIIFSEEYNTSNPD | | |
| TGFβRII | 289 | MGRGLLRGLWPLHIVL WTRIASTIPPHVQKSDV EMEAQKDEIICPSCNRT AHPLRHINNDMIVTDN NGAVKFPQLCKFCDVR FSTCDNQKSCMSNCSIT SICEKPQEVCVAVWRK NDENITLETVCHDPKLP YHDFILEDAASPKCIMK EKKKPGETFFMCSCSSD ECNDNIIFSEEYNTSNPD LLLVIFQVTGISLLPPLG VAISVIIIFYCYRVNRQQ KLSSTWETGKTRKLME FSEHCAIILEDDRSDISS TCANNINHNIELLPIEL DTLVGKGRFAEVYKAK LKQNTSEQFETVAVKIF PYEEYASWKTEKDIFSD INLKHENILQFLTAEER KIELGKQYWLITAFHA KGNLQEYLTRHVISWE DLRKLGSSLARGIAHLH SDHTPCGRPKMPIVHR DLKSSNILVKNDLTCCL CDFGLSLRLDPTLSVDD LANSGQVGTARYMAPE VLESRMNLENVESFKQ TDVYSMALVLWEMTS RCNAVGEVKDYEPPFG SKVREHPCVESMKDNV LRDRGRPEIPSFWLNHQ GIQMVCETLTECWDHD PEARLTAQCVAERFSEL EHLDRLSGRSCSEEKIP EDGSLNTTK | | |
| TGFβRII Isoform B | 290 | MGRGLLRGLWPLHIVL WTRIASTIPPHVQKSVN NDMIVTDNNGAVKFPQ LCKFCDVRFSTCDNQK SCMSNCSITSICEKPQEV CVAVWRKNDENITLET VCHDPKLPYHDFILEDA ASPKCIMKEKKKPGETF FMCSCSSDECNDNIIFSE EYNTSNPDLLLVIFQVT GISLLPPLGVAISVIIIFY CYRVNRQQKLSSTWET GKTRKLMEFSEHCAIIL EDDRSDISSTCANNINH NIELLPIELDTLVGKGR FAEVYKAKLKQNTSEQ FETVAVKIFPYEEYASW KIEKDIFSDINLKHENIL | | |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | QFLTAEERKTELGKQY WLITAFHAKGNLQEYL TRHVISWEDLRKLGSSL ARGIAHLHSDHTPCGRP KMPIVHRDLKSSNILVK NDLTCCLCDFGLSLRLD PTLSVDDLANSGQVGT ARYMAPEVLESRMNLE NVESFKQTDVYSMALV LWEMTSRCNAVGEVK DYEPPFGSKVREHPCVE SMKDNVLRDRGRPEIPS FWLNHQGIQMVCETLT ECWDHDPEARLTAQCV AERFSELEHLDRLSGRS CSEEKIPEDGSLNTTK | | |
| Anti-PD1 (VL5) IgG4-(light chain) | 15 | EIVLTQSPATLSLSPGERAT LSCRASQSVSSYLAWYQQKP GQAPRLLIYD ASNRATGIPARFSGSGSGTD FTLTISSLEPEDFAVYYCQQ SSNWPRTFGQ GTKVEIKRTVAAPSVFIFPP SDEQLKSGTASVVCLLNNFY PREAKVQWKV DNALQSGNSQESVTEQDSKD STYSLSSTLTLSKADYEKHK VYACEVTHQG LSSPVTKSFNRGEC | 299 | GAGATCGTCCTGACACAGAGTCCAGCAACTCTGAGCCTG TCCCCGGCGAACGAGCTACTCTGTCCTGCCGGGCATCT CAGAGTGTGTCTAGTTACCTGGCCTGGTATCAGCAGAAG CCCGGCCAGGCTCCTAGGCTGCTGATCTACGACGCCAGC AACAGAGCTACCGGGATTCCTGCCAGGTTCTCAGGCAGC GGGTCCGGAACAGACTTTACCCTGACAATCTCAAGCCTG GAGCCCGAAGATTTCGCTGTGTACTATTGCCAGCAGTCC TCTAATTGGCCTCGCACCTTTGGCCAGGGGACAAAGGTC GAGATCAAGCGTACGGTGGCTGCACCATCTGTCTTCATC TTCCCGCCATCTGATGAGCAGTTGAAATCTGGAACTGCC TCTGTTGTGTGCCTGCTGAATAACTTCTATCCCAGAGAG GCCAAAGTACAGTGGAAGGTGGATAACGCCCTCCAATCG GGTAACTCCCAGGAGAGTGTCACAGAGCAGGACAGCAAG GACAGCACCTACAGCCTCAGCAGCACCCTGACGCTGAGC AAAGCAGACTACGAGAAACACAAAGTCTACGCCTGCGAA GTCACCCATCAGGGCCTGAGCTCGCCCGTCACAAAGAGC TTCAACAGGGGAGAGTGT |
| Anti-PD1 (VL6) IgG4-(light chain) | 296 | EIVLTQSPATLSLSPGERAT LSCRASKGVSTSGYSYLHWY QQKPGQAPRL LIYLASYLESGVPARFSGSG SGTDFTLTISSLEPEDFAVY YCQHSRDLPL TFGGGTKVEIKRTVAAPSVF IFPPSDEQLKSGTASVVCLL NNFYPREAKV QWKVDNALQSGNSQESVTEQ DSKDSTYSLSSTLTLSKADY EKHKVYACEV THQGLSSPVTKSFNRGEC | 300 | GAGATCGTCCTGACTCAGTCCCCAGCAACCCTGAGTCTG TCACCAGGAGAGAAAGGGCAACCCTGAGCTGCCGAGCATCC AAGGGGGTGAGCACATCCGGATACTCTTATCTGCACTGG TACCAGCAGAAACCCGGACAGGCTCCTCGACTGCTGATC TACCTGGCATCTTATCTGGAGAGTGGCGTGCCTGCTCGG TTCTCTGGGAGTGGATCAGGCACCGATTTTACACTGACT ATTTCTAGTCTGGAGCCAGAAGATTTCGCAGTGTACTAT TGCCAGCATTCTCGAGACCTGCCCCTGACATTTGGCGGG GGAACTAAGGTCGAGATCAAACGTACGGTGGCTGCACCA TCTGTCTTCATCTTCCCGCCATCTGATGAGCAGTTGAAA TCTGGAACTGCCTCTGTTGTGTGCCTGCTGAATAACTTC TATCCCAGAGAGGCCAAAGTACAGTGGAAGGTGGATAAC GCCCTCCAATCGGGTAACTCCCAGGAGAGTGTCACAGAG CAGGACAGCAAGGACAGCACCTACAGCCTCAGCAGCACC CTGACGCTGAGCAAAGCAGACTACGAGAAACACAAAGTC TACGCCTGCGAAGTCACCCATCAGGGCCTGAGCTCGCCC GTCACAAAGAGCTTCAACAGGGGAGAGTGT |
| Anti-PD1 (VH6) IgG4-linker-TGFβRII | 16 | QVQLVESGGGVVQPGR SLRLDCKASGITFSNSG MHWVRQAPGKGLEWV AVIWYDGSKRYYADSV KGRFTISRDNSKNTLFL QMNSLRAEDTAVYYC ATNDDYWGQGTLVTV SSASTKGPSVFPLAPCS RSTSESTAALGCLVKD YFPEPVTVSWNSGALTS GVHTFPAVLQSSGLYSL SSVVTVPSSSLGTKTYT CNVDHKPSNTKVDKRV ESKYGPPCPSCPAPEFL GGPSVFLFPPKPKDTLM ISRTPEVTCVVVDVSQE DPEVQFNWYVDGVEV HNAKTKPREEQFNSTY RVVSVLTVLHQDWLN GKEYKCKVSNKGLPSSI EKTISKAKGQPREPQVY | 113 | CAGGTGCAGCTGGTCGAAAGCGGAGGAGGAG TGGTCCAGCCAGGACGATCCCTGAGACTGGA TTGTAAGGCCTCTGGAATCACATTCTCTAACA GTGGAATGCACTGGGTGCGCCAGGCACCAGG AAAAGGACTGGAGTGGGTGGCCGTCATCTGG TACGACGGGTCAAAGCGATACTATGCAGATA GCGTGAAAGGAAGGTTCACAATTTCACGCGA CAACAGCAAGAATACTCTGTTTCTGCAGATGA ACTCTCTGAGAGCAGAGGATACTGCCGTGTA CTATTGTGCTACCAATGACGATTATTGGGGGC AGGGAACTCTGGTGACCGTCAGTTCAGCTAG CACCAAGGGCCCATCGGTCTTCCCCCTGGCGC CCTGCTCCAGGAGCACCTCCGAGAGCACAGC CGCCCTGGGCTGCCTGGTCAAGGACTACTTCC CCGAACCGGTGACGGTGTCGTGGAACTCAGG CGCCCTGACCAGCGGCGTGCACACCTTCCCGG CTGTCCTACAGTCCTCAGGACTCTACTCCCTC AGCAGCGTGGTGACCGTGCCCTCCAGCAGCTT GGGCACGAAGACCTACACCTGCAACGTAGAT CACAAGCCCAGCAACACCAAGGTGGACAAGA GAGTTGAGTCCAAATATGGTCCCCCATGCCCA |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| | | TLPPSQEEMTKNQVSLT<br>CLVKGFYPSDIAVEWES<br>NGQPENNYKTTPPVLD<br>SDGSFFLYSRLTVDKSR<br>WQEGNVFSCSVMHEAL<br>HNHYTQKSLSLSPGKG<br>GGGSGGGGSIPPHVQKS<br>VNNDMIVTDNNGAVKF<br>PQLCKFCDVRFSTCDN<br>QKSCMSNCSITSICEKP<br>QEVCVAVWRKNDENIT<br>LETVCHDPKLPYHDFIL<br>EDAASPKCIMKEKKKP<br>GETFFMCSCSSDECND<br>NIIFSEEYNTSNPD | | TCATGCCCAGCACCTGAGTTCCTGGGGGGACC<br>ATCAGTCTTCCTGTTCCCCCCAAAACCCAAGG<br>ACACTCTCATGATCTCCCGGACCCCTGAGGTC<br>ACGTGCGTGGTGGTGGACGTGAGCCAGGAAG<br>ACCCCGAGGTCCAGTTCAACTGGTACGTGGAT<br>GGCGTGGAGGTGCATAATGCCAAGACAAAGC<br>CGCGGGAGGAGCAGTTCAACAGCACGTACCG<br>TGTGGTCAGCGTCCTCACCGTCCTGCACCAGG<br>ACTGGCTGAACGGCAAGGAGTACAAGTGCAA<br>GGTCTCCAACAAAGGCCTCCCGTCCTCCATCG<br>AGAAAACCATCTCCAAAGCCAAAGGGCAGCC<br>CCGAGAGCCACAGGTGTACACCCTGCCCCCA<br>TCCCAGGAGGAGATGACCAAGAACCAGGTCA<br>GCCTGACCTGCCTGGTCAAAGGCTTCTACCCC<br>AGCGACATCGCCGTGGAGTGGGAGAGCAATG<br>GGCAGCCGGAGAACAACTACAAGACCACGCC<br>TCCCGTGCTGGACTCCGACGGCTCCTTCTTCC<br>TCTACAGCAGGCTCACCGTGGACAAGAGCAG<br>GTGGCAGGAGGGGAATGTCTTCTCATGCTCCG<br>TGATGCATGAGGCTCTGCACAACCACTACAC<br>ACAGAAGAGCCTCTCCCTGTCTCCGGGTAAA<br>GGTGGAGGTGGTTCTGGAGGTGGAGGTAGTA<br>TCCCTCCTCACGTACAGAAGTCCGTGAACAAT<br>GACATGATTGTCACTGACAATAACGGAGCCG<br>TCAAGTTTCCTCAGCTATGTAAGTTCTGCGAT<br>GTTCGGTTCTCCACATGCGATAATCAGAAAAG<br>CTGTATGTCTAATTGCAGTATCACTAGTATAT<br>GCGAAAAACCTCAAGAAGTTTGCGTCGCCGT<br>GTGGCGGAAAAATGATGAAAATATCACGCTT<br>GAGACTGTCTGCCATGATCCAAAGTTACCCTA<br>CCACGACTTCATCTTAGAAGACGCCGCATCAC<br>CCAAGTGCATTATGAAAGAGAAAAAGAAGCC<br>AGGAGAAACATTCTTTATGTGCTCATGCTCCT<br>CTGACGAATGCAACGACAACATTATCTTCTCT<br>GAGGAGTATAACACCTCAAATCCAGAC |
| Anti-PD1 (VH6) IgG4-(S108P). linker-TGFβRII | 143 | QVQLVESGGGVVQPGR<br>SLRLDCKASGITFSNSG<br>MHWVRQAPGKGLEWV<br>AV<br>IWYDGSKRYYADSVKG<br>RFTISRDNSKNTLFLQM<br>NSLRAEDTAVYYCATN<br>D<br>DYWGQGTLVTVSSAST<br>KGPSVFPLAPCSRSTSES<br>TAALGCLVKDYFPEPV<br>TVSWNSGALTSGVHTF<br>PAVLQSSGLYSLSSVVT<br>VPSSSLGTKTYTCNVD<br>H<br>KPSNTKVDKRVESKYG<br>PPCPPCPAPEFLGGPSVF<br>LFPPKPKDTLMISRTP<br>EVTCVVVDVSQEDPEV<br>QFNWYVDGVEVHNAK<br>TKPREEQFNSTYRVVSV<br>LT<br>VLHQDWLNGKEYKCK<br>VSNKGLPSSIEKTISKAK<br>GQPREPQVYTLPPSQEE<br>MTKNQVSLTCLVKGFY<br>PSDIAVEWESNGQPEN<br>NYKTTPPVLDSDGSFFL<br>Y<br>SRLTVDKSRWQEGNVF<br>SCSVMHEALHNHYTQK<br>SLSLSPGKGGGGSGGG<br>GS<br>IPPHVQKSVNNDMIVTD<br>NNGAVKFPQLCKFCDV<br>RFSTCDNQKSCMSNCSI<br>TSICEKPQEVCVAVWR<br>KNDENITLETVCHDPKL | 114 | CAGGTGCAGCTGGTCGAAAGCGGAGGAGGAG<br>TGGTCCAGCCAGGACGATCCCTGAGACTGGA<br>TTGTAAGGCCTCTGGAATCACATTCTCTAACA<br>GTGGAATGCACTGGGTGCGCCAGGCACCAGG<br>AAAAGGACTGGAGTGGGTGGCCGTCATCTGG<br>TACGACGGGTCAAAGCGATACTATGCAGATA<br>GCGTGAAAGGAAGGTTCACAATTTCACGCGA<br>CAACAGCAAGAATACTCTGTTTCTGCAGATGA<br>ACTCTCTGAGAGCAGAGGATACTGCCGTGTA<br>CTATTGTGCTACCAATGACGATTATTGGGGGC<br>AGGGAACTCTGGTGACCGTCAGTTCAGCTAG<br>CACCAAGGGCCCATCGGTCTTCCCCCTGGCGC<br>CCTGCTCCAGGAGCACCTCCGAGAGCACAGC<br>CGCCCTGGGCTGCCTGGTCAAGGACTACTTCC<br>CCGAACCGGTGACGGTGTCGTGGAACTCAGG<br>CGCCCTGACCAGCGGCGTGCACACCTTCCCGG<br>CTGTCCTACAGTCCTCAGGACTCTACTCCCTC<br>AGCAGCGTGGTGACCGTGCCCTCCAGCAGCTT<br>GGGCACGAAGACCTACACCTGCAACGTAGAT<br>CACAAGCCCAGCAACACCAAGGTGGACAAGA<br>GAGTTGAGTCCAAATATGGTCCCCCATGCCCA<br>CCATGCCCAGCACCTGAGTTCCTGGGGGGAC<br>CATCAGTCTTCCTGTTCCCCCCAAAACCCAAG<br>GACACTCTCATGATCTCCCGGACCCCTGAGGT<br>CACGTGCGTGGTGGTGGACGTGAGCCAGGAA<br>GACCCCGAGGTCCAGTTCAACTGGTACGTGG<br>ATGGCGTGGAGGTGCATAATGCCAAGACAAA<br>GCCGCGGGAGGAGCAGTTCAACAGCACGTAC<br>CGTGTGGTCAGCGTCCTCACCGTCCTGCACCA<br>GGACTGGCTGAACGGCAAGGAGTACAAGTGC<br>AAGGTCTCCAACAAAGGCCTCCCGTCCTCCAT<br>CGAGAAAACCATCTCCAAAGCCAAAGGGCAG<br>CCCCGAGAGCCACAGGTGTACACCCTGCCCC<br>CATCCCAGGAGGAGATGACCAAGAACCAGGT<br>CAGCCTGACCTGCCTGGTCAAAGGCTTCTACC<br>CCAGCGACATCGCCGTGGAGTGGGAGAGCAA<br>TGGGCAGCCGGAGAACAACTACAAGACCACG<br>CCTCCCGTGCTGGACTCCGACGGCTCCTTCTT |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| | | PYHDFILEDAASPKCIM<br>KEKKKPGETFFMCSCSS<br>DECNDNIIFSEEYNTSNP<br>D | | CCTCTACAGCAGGCTCACCGTGGACAAGAGC<br>AGGTGGCAGGAGGGGAATGTCTTCTCATGCT<br>CCGTGATGCATGAGGCTCTGCACAACCACTAC<br>ACACAGAAGAGCCTCTCCCTGTCTCCGGGTAA<br>AGGTGGAGGTGGTTCTGGAGGTGGAGGTAGT<br>ATCCCTCCTCACGTACAGAAGTCCGTGAACAA<br>TGACATGATTGTCACTGACAATAACGGAGCC<br>GTCAAGTTTCCTCAGCTATGTAAGTTCTGCGA<br>TGTTCGGTTCTCCACATGCGATAATCAGAAAA<br>GCTGTATGTCTAATTGCAGTATCACTAGTATA<br>TGCGAAAAACCTCAAGAAGTTTGCGTCGCCG<br>TGTGGCGGAAAAATGATGAAAATATCACGCT<br>TGAGACTGTCTGCCATGATCCAAAGTTACCCT<br>ACCACGACTTCATCTTAGAAGACGCCGCATCA<br>CCCAAGTGCATTATGAAAGAGAAAAAGAAGC<br>CAGGAGAAACATTCTTTATGTGCTCATGCTCC<br>TCTGACGAATGCAACGACAACATTATCTTCTC<br>TGAGGAGTATAACACCTCAAATCCAGAC |
| Anti-PD1<br>VH7 IgG4<br>(S108P)<br>linker-<br>TGFβRII | 144 | QVQLVQSGVEVKKPGA<br>SVKVSCKASGYTFTNY<br>YMYWVRQAPGQGLEW<br>MGG<br>INPSNGGTNFNEKFKNR<br>VTLTTDSSTTTAYMEL<br>KSLQFDDTAVYYCARR<br>D<br>YRFDMGFDYWGQGTT<br>VTVSSASTKGPSVFPLA<br>PCSRSTSESTAALGCLV<br>K<br>DYFPEPVTVSWNSGAL<br>TSGVHTFPAVLQSSGLY<br>SLSSVVTVPSSSLGTKT<br>YTCNVDHKPSNTKVDK<br>RVESKYGPPCPPCPAPE<br>FLGGPSVFLFPPKPKDT<br>LMISRTPEVTCVVVDVS<br>QEDPEVQFNWYVDGV<br>EVHNAKTKPREEQFNS<br>TY<br>RVVSVLTVLHQDWLN<br>GKEYKCKVSNKGLPSSI<br>EKTISKAKGQPREPQVY<br>T<br>LPPSQEEMTKNQVSLTC<br>LVKGFYPSDIAVEWES<br>NGQPENNYKTTPPVLD<br>S<br>DGSFFLYSRLTVDKSR<br>WQEGNVFSCSVMHEAL<br>HNHYTQKSLSLSPGKG<br>GG<br>GSGGGGSIPPHVQKSVN<br>NDMIVTDNNGAVKFPQ<br>LCKFCDVRFSTCDNQK<br>S<br>CMSNCSITSICEKPQEV<br>CVAVWRKNDENITLET<br>VCHDPKLPYHDFILEDA<br>ASPKCIMKEKKKPGETF<br>FMCSCSSDECNDNIIFSE<br>EYNTSNPD* | 115 | CAGGTGCAGCTGGTCCAGAGCGGCGTGGAAG<br>TCAAGAAACCCGGGGCCTCAGTGAAGGTCAG<br>CTGTAAAGCTTCCGGCTACACCTTCACAAACT<br>ACTATATGTATTGGGTGAGACAGGCACCAGG<br>ACAGGGACTGGAGTGGATGGGCGGGATTAAC<br>CCTAGTAATGGAGGCACTAACTTCAACGAAA<br>AGTTTAAAAACAGGGTGACCCTGACCACAGA<br>TTCAAGCACTACCACAGCTTACATGGAGCTGA<br>AGTCCCTGCAGTTTGACGATACAGCCGTGTAC<br>TATTGTGCTCGGAGAGACTACAGGTTCGATAT<br>GGGCTTTGACTATTGGGGCCAGGGGACTACC<br>GTGACCGTCTCCTCTGCTAGCACCAAGGGCCC<br>ATCGGTCTTCCCCCTGGCGCCCTGCTCCAGGA<br>GCACCTCCGAGAGCACAGCCGCCCTGGGCTG<br>CCTGGTCAAGGACTACTTCCCCGAACCGGTGA<br>CGGTGTCGTGGAACTCAGGCGCCCTGACCAG<br>CGGCGTGCACACCTTCCCGGCTGTCCTACAGT<br>CCTCAGGACTCTACTCCCTCAGCAGCGTGGTG<br>ACCGTGCCCTCCAGCAGCTTGGGCACGAAGA<br>CCTACACCTGCAACGTAGATCACAAGCCCAG<br>CAACACCAAGGTGGACAAGAGAGTTGAGTCC<br>AAATATGGTCCCCCATGCCCACCATGCCCAGC<br>ACCTGAGTTCCTGGGGGGACCATCAGTCTTCC<br>TGTTCCCCCCAAAACCCAAGGACACTCTCATG<br>ATCTCCCGGACCCCTGAGGTCACGTGCGTGGT<br>GGTGGACGTGAGCCAGGAAGACCCCGAGGTC<br>CAGTTCAACTGGTACGTGGATGGCGTGGAGG<br>TGCATAATGCCAAGACAAAGCCGCGGGAGGA<br>GCAGTTCAACAGCACGTACCGTGTGGTCAGC<br>GTCCTCACCGTCCTGCACCAGGACTGGCTGAA<br>CGGCAAGGAGTACAAGTGCAAGGTCTCCAAC<br>AAAGGCCTCCCGTCCTCCATCGAGAAAACCA<br>TCTCCAAAGCCAAAGGGCAGCCCCGAGAGCC<br>ACAGGTGTACACCCTGCCCCCATCCCAGGAG<br>GAGATGACCAAGAACCAGGTCAGCCTGACCT<br>GCCTGGTCAAAGGCTTCTACCCCAGCGACATC<br>GCCGTGGAGTGGGAGAGCAATGGGCAGCCGG<br>AGAACAACTACAAGACCACGCCTCCCGTGCT<br>GGACTCCGACGGCTCCTTCTTCCTCTACAGCA<br>GGCTCACCGTGGACAAGAGCAGGTGGCAGGA<br>GGGGAATGTCTTCTCATGCTCCGTGATGCATG<br>AGGCTCTGCACAACCACTACACACAGAAGAG<br>CCTCTCCCTGTCTCCGGGTAAAGGTGGAGGTG<br>GTTCTGGAGGTGGAGGTAGTATCCCTCCTCAC<br>GTACAGAAGTCCGTGAACAATGACATGATTG<br>TCACTGACAATAACGGAGCCGTCAAGTTTCCT<br>CAGCTATGTAAGTTCTGCGATGTTCGGTTCTC<br>CACATGCGATAATCAGAAAAGCTGTATGTCT<br>AATTGCAGTATCACTAGTATATGCGAAAAAC<br>CTCAAGAAGTTTGCGTCGCCGTGTGGCGGAA<br>AAATGATGAAAATATCACGCTTGAGACTGTCT<br>GCCATGATCCAAAGTTACCCTACCACGACTTC<br>ATCTTAGAAGACGCCGCATCACCCAAGTGCA<br>TTATGAAAGAGAAAAAGAAGCCAGGAGAAA<br>CATTCTTTATGTGCTCATGCTCCTCTGACGAA |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| | | | | TGCAACGACAACATTATCTTCTCTGAGGAGTA<br>TAACACCTCAAATCCAGAC |
| Anti-PD1 VH7 IgG4 (linker-TGFβRII | 145 | QVQLVQSGVEVKKPGA<br>SVKVSCKASGYTFTNY<br>YMYWVRQAPGQGLEW<br>MGG<br>INPSNGGTNFNEKFKNR<br>VTLTTDSSTTTAYMEL<br>KSLQFDDTAVYYCARR<br>D<br>YRFDMGFDYWGQGTT<br>VTVSSASTKGPSVFPLA<br>PCSRSTSESTAALGCLV<br>K<br>DYFPEPVTVSWNSGAL<br>TSGVHTFPAVLQSSGLY<br>SLSSVVTVPSSSLGTKT<br>YTCNVDHKPSNTKVDK<br>RVESKYGPPCPSCPAPE<br>FLGGPSVFLFPPKPKDT<br>LMISRTPEVTCVVVDVS<br>QEDPEVQFNWYVDGV<br>EVHNAKTKPREEQFNS<br>TY<br>RVVSVLTVLHQDWLN<br>GKEYKCKVSNKGLPSSI<br>EKTISKAKGQPREPQVY<br>T<br>LPPSQEEMTKNQVSLTC<br>LVKGFYPSDIAVEWES<br>NGQPENNYKTTPPVLD<br>S<br>DGSFFLYSRLTVDKSR<br>WQEGNVFSCSVMHEAL<br>HNHYTQKSLSLSPGKG<br>GG<br>GSGGGGSIPPHVQKSVN<br>NDMIVTDNNGAVKFPQ<br>LCKFCDVRFSTCDNQK<br>S<br>CMSNCSITSICEKPQEV<br>CVAVWRKNDENITLET<br>VCHDPKLPYHDFILEDA<br>ASPKCIMKEKKKPGETF<br>FMCSCSSDECNDNIIFSE<br>EYNTSNPD | 116 | CAGGTGCAGCTGGTCCAGAGCGGCGTGGAAG<br>TCAAGAAACCCGGGGCCTCAGTGAAGGTCAG<br>CTGTAAAGCTTCCGGCTACACCTTCACAAACT<br>ACTATATGTATTGGGTGAGACAGGCACCAGG<br>ACAGGGACTGGAGTGGATGGGCGGGATTAAC<br>CCTAGTAATGGAGGCACTAACTTCAACGAAA<br>AGTTTAAAAACAGGGTGACCCTGACCACAGA<br>TTCAAGCACTACCACAGCTTACATGGAGCTGA<br>AGTCCCTGCAGTTTGACGATACAGCCGTGTAC<br>TATTGTGCTCGGAGAGACTACAGGTTCGATAT<br>GGGCTTTGACTATTGGGGCCAGGGGACTACC<br>GTGACCGTCTCCTCTGCTAGCACCAAGGGCCC<br>ATCGGTCTTCCCCCTGGCGCCCTGCTCCAGGA<br>GCACCTCCGAGAGCACAGCCGCCCTGGGCTG<br>CCTGGTCAAGGACTACTTCCCCGAACCGGTGA<br>CGGTGTCGTGGAACTCAGGCGCCCTGACCAG<br>CGGCGTGCACACCTTCCCGGCTGTCCTACAGT<br>CCTCAGGACTCTACTCCCTCAGCAGCGTGGTG<br>ACCGTGCCCTCCAGCAGCTTGGGCACGAAGA<br>CCTACACCTGCAACGTAGATCACAAGCCCAG<br>CAACACCAAGGTGGACAAGAGAGTTGAGTCC<br>AAATATGGTCCCCCATGCCCATCATGCCCAGC<br>ACCTGAGTTCCTGGGGGGACCATCAGTCTTCC<br>TGTTCCCCCCAAAACCCAAGGACACTCTCATG<br>ATCTCCCGGACCCCTGAGGTCACGTGCGTGGT<br>GGTGGACGTGAGCCAGGAAGACCCCGAGGTC<br>CAGTTCAACTGGTACGTGGATGGCGTGGAGG<br>TGCATAATGCCAAGACAAAGCCGCGGGAGGA<br>GCAGTTCAACAGCACGTACCGTGTGGTCAGC<br>GTCCTCACCGTCCTGCACCAGGACTGGCTGAA<br>CGGCAAGGAGTACAAGTGCAAGGTCTCCAAC<br>AAAGGCCTCCCGTCCTCCATCGAGAAAACCA<br>TCTCCAAAGCCAAAGGGCAGCCCCGAGAGCC<br>ACAGGTGTACACCCTGCCCCCATCCCAGGAG<br>GAGATGACCAAGAACCAGGTCAGCCTGACCT<br>GCCTGGTCAAAGGCTTCTACCCCAGCGACATC<br>GCCGTGGAGTGGGAGAGCAATGGGCAGCCGG<br>AGAACAACTACAAGACCACGCCTCCCGTGCT<br>GGACTCCGACGGCTCCTTCTTCCTCTACAGCA<br>GGCTCACCGTGGACAAGAGCAGGTGGCAGGA<br>GGGGAATGTCTTCTCATGCTCCGTGATGCATG<br>AGGCTCTGCACAACCACTACACACAGAAGAG<br>CCTCTCCCTGTCTCCGGGTAAAGGTGGAGGTG<br>GTTCTGGAGGTGGAGGTAGTATCCCTCCTCAC<br>GTACAGAAGTCCGTGAACAATGACATGATTG<br>TCACTGACAATAACGGAGCCGTCAAGTTTCCT<br>CAGCTATGTAAGTTCTGCGATGTTCGGTTCTC<br>CACATGCGATAATCAGAAAAGCTGTATGTCT<br>AATTGCAGTATCACTAGTATATGCGAAAAAC<br>CTCAAGAAGTTTGCGTCGCCGTGTGGCGGAA<br>AAATGATGAAAATATCACGCTTGAGACTGTCT<br>GCCATGATCCAAAGTTACCCTACCACGACTTC<br>ATCTTAGAAGACGCCGCATCACCCAAGTGCA<br>TTATGAAAGAGAAAAAGAAGCCAGGAGAAA<br>CATTCTTTATGTGCTCATGCTCCTCTGACGAA<br>TGCAACGACAACATTATCTTCTCTGAGGAGTA<br>TAACACCTCAAATCCAGAC |
| VH6-IgG4 (mut)-linker-ECD | 294 | QVQLVESGGGVVQPGR<br>SLRLDCKASGITFSNSG<br>MHWVRQAPGKGLEWV<br>AV<br>IWYDGSKRYYADSVKG<br>RFTISRDNSKNTLFLQM<br>NSLRAEDTAVYYCATN<br>D<br>DYWGQGTLVTVSSAST<br>KGPSVFPLAPCSRSTSES<br>TAALGCLVKDYFPEPV<br>TVSWNSGALTSGVHTF<br>PAVLQSSGLYSLSSVVT | 297 | CAGGTGCAGCTGGTCGAAAGCGGAGGAGGAG<br>TGGTCCAGCCAGGACGATCCCTGAGACTGGA<br>TTGTAAGGCCTCTGGAATCACATTCTCTAACA<br>GTGGAATGCACTGGGTGCGCCAGGCACCAGG<br>AAAAGGACTGGAGTGGGTGGCCGTCATCTGG<br>TACGACGGGTCAAAGCGATACTATGCAGATA<br>GCGTGAAAGGAAGGTTCACAATTTCACGCGA<br>CAACAGCAAGAATACTCTGTTTCTGCAGATGA<br>ACTCTCTGAGAGCAGAGGATACTGCCGTGTA<br>CTATTGTGCTACCAATGACGATTATTGGGGGC<br>AGGGAACTCTGGTGACCGTCAGTTCAGCTAG<br>CACCAAGGGCCCATCGGTCTTCCCCCTGGCGC<br>CCTGCTCCAGGAGCACCTCCGAGAGCACAGC |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| | | VPSSSLGTKTYTCNVD H KPSNTKVDKRVESKYG PPCPPCPAPEFLGGPSVF LFPPKPKDTLMISRTP EVTCVVVDVSQEDPEV QFNWYVDGVEVHNAK TKPREEQFNSTYRVVSV LT VLHQDWLNGKEYKCK VSNKGLPSSIEKTISKAK GQPREPQVYTLPPSQEE MTKNQVSLTCLVKGFY PSDIAVEWESNGQPEN NYKTTPPVLDSDGSFFL Y SRLTVDKSRWQEGNVF SCSVMHEALHNHYTQK SLSLSLGKGGGGSGGG GS IPPHVQKSVNNDMIVTD NNGAVKFPQLCKFCDV RFSTCDNQKSCMSNCSI TSICEKPQEVCVAVWR KNDENITLETVCHDPKL PYHDFILEDAASPKCIM KEKKKPGETFFMCSCSS DECNDNIIFSEEYNTSNP D* | | CGCCCTGGGCTGCCTGGTCAAGGACTACTTCC CCGAACCGGTGACGGTGTCGTGGAACTCAGG CGCCCTGACCAGCGGCGTGCACACCTTCCCGG CTGTCCTACAGTCCTCAGGACTCTACTCCCTC AGCAGCGTGGTGACCGTGCCCTCCAGCAGCTT GGGCACGAAGACCTACACCTGCAACGTAGAT CACAAGCCCAGCAACACCAAGGTGGACAAGA GAGTTGAGTCCAAATATGGTCCCCCATGCCCA CCATGCCCAGCACCTGAGTTCCTGGGGGGAC CATCAGTCTTCCTGTTCCCCCCAAAACCCAAG GACACTCTCATGATCTCCCGGACCCCTGAGGT CACGTGCGTGGTGGTGGACGTGAGCCAGGAA GACCCCGAGGTCCAGTTCAACTGGTACGTGG ATGGCGTGGAGGTGCATAATGCCAAGACAAA GCCGCGGGAGGAGCAGTTCAACAGCACGTAC CGTGTGGTCAGCGTCCTCACCGTCCTGCACCA GGACTGGCTGAACGGCAAGGAGTACAAGTGC AAGGTCTCCAACAAAGGCCTCCCGTCCTCCAT CGAGAAAACCATCTCCAAAGCCAAAGGGCAG CCCCGAGAGCCACAGGTGTACACCCTGCCCC CATCCCAGGAGGAGATGACCAAGAACCAGGT CAGCCTGACCTGCCTGGTCAAAGGCTTCTACC CCAGCGACATCGCCGTGGAGTGGGAGAGCAA TGGGCAGCCGGAGAACAACTACAAGACCACG CCTCCCGTGCTGGACTCCGACGGCTCCTTCTT CCTCTACAGCAGGCTCACCGTGGACAAGAGC AGGTGGCAGGAGGGGAATGTCTTCTCATGCT CCGTGATGCATGAGGCTCTGCACAACCACTAC ACACAGAAGAGCCTCTCCCTGTCTCTGGGTAA AGGTGGAGGTGGTTCTGGAGGTGGAGGTAGT ATCCCTCCTCACGTACAGAAGTCCGTGAACAA TGACATGATTGTCACTGACAATAACGGAGCC GTCAAGTTTCCTCAGCTATGTAAGTTCTGCGA TGTTCGGTTCTCCACATGCGATAATCAGAAAA GCTGTATGTCTAATTGCAGTATCACTAGTATA TGCGAAAAACCTCAAGAAGTTTGCGTCGCCG TGTGGCGGAAAAATGATGAAAATATCACGCT TGAGACTGTCTGCCATGATCCAAAGTTACCCT ACCACGACTTCATCTTAGAAGACGCCGCATCA CCCAAGTGCATTATGAAAGAGAAAAAGAAGC CAGGAGAAACATTCTTTATGTGCTCATGCTCC TCTGACGAATGCAACGACAACATTATCTTCTC TGAGGAGTATAACACCTCAAATCCAGAC |
| VH7-IgG4 (mut)-linker-ECD | 295 | QVQLVQSGVEVKKPGA SVKVSCKASGYTFTNY YMYWVRQAPGQGLEW MGG INPSNGGTNFNEKFKNR VTLTTDSSTTTAYMEL KSLQFDDTAVYYCARR D YRFDMGFDYWGQGTT VTVSSASTKGPSVFPLA PCSRSTSESTAALGCLV K DYFPEPVTVSWNSGAL TSGVHTFPAVLQSSGLY SLSSVVTVPSSSLGTKT YTCNVDHKPSNTKVDK RVESKYGPPCPPCPAPE FLGGPSVFLFPPKPKDT LMISRTPEVTCVVVDVS QEDPEVQFNWYVDGV EVHNAKTKPREEQFNS TY RVVSVLTVLHQDWLN GKEYKCKVSNKGLPSSI EKTISKAKGQPREPQVY T LPPSQEEMTKNQVSLTC LVKGFYPSDIAVEWES NGQPENNYKTTPPVLD S | 298 | CAGGTGCAGCTGGTCCAGAGCGGCGTGGAAG TCAAGAAACCCGGGGCCTCAGTGAAGGTCAG CTGTAAAGCTTCCGGCTACACCTTCACAAACT ACTATATGTATTGGGTGAGACAGGCACCAGG ACAGGGACTGGAGTGGATGGGCGGGATTAAC CCTAGTAATGGAGGCACTAACTTCAACGAAA AGTTTAAAAACAGGGTGACCCTGACCACAGA TTCAAGCACTACCACAGCTTACATGGAGCTGA AGTCCCTGCAGTTTGACGATACAGCCGTGTAC TATTGTGCTCGGAGAGACTACAGGTTCGATAT GGGCTTTGACTATTGGGGCCAGGGGACTACC GTGACCGTCTCCTCTGCTAGCACCAAGGGCCC ATCGGTCTTCCCCCTGGCGCCCTGCTCCAGGA GCACCTCCGAGAGCACAGCCGCCCTGGGCTG CCTGGTCAAGGACTACTTCCCCGAACCGGTGA CGGTGTCGTGGAACTCAGGCGCCCTGACCAG CGGCGTGCACACCTTCCCGGCTGTCCTACAGT CCTCAGGACTCTACTCCCTCAGCAGCGTGGTG ACCGTGCCCTCCAGCAGCTTGGGCACGAAGA CCTACACCTGCAACGTAGATCACAAGCCCAG CAACACCAAGGTGGACAAGAGAGTTGAGTCC AAATATGGTCCCCCATGCCCACCATGCCCAGC ACCTGAGTTCCTGGGGGGACCATCAGTCTTCC TGTTCCCCCCAAAACCCAAGGACACTCTCATG ATCTCCCGGACCCCTGAGGTCACGTGCGTGGT GGTGGACGTGAGCCAGGAAGACCCCGAGGTC CAGTTCAACTGGTACGTGGATGGCGTGGAGG TGCATAATGCCAAGACAAAGCCGCGGGAGGA GCAGTTCAACAGCACGTACCGTGTGGTCAGC GTCCTCACCGTCCTGCACCAGGACTGGCTGAA |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | DGSFFLYSRLTVDKSR WQEGNVFSCSVMHEAL HNHYTQKSLSLSLGKG GG GSGGGGSIPPHVQKSVN NDMIVTDNNGAVKFPQ LCKFCDVRFSTCDNQK S CMSNCSITSICEKPQEV CVAVWRKNDENITLET VCHDPKLPYHDFILEDA ASPKCIMKEKKKPGETF FMCSCSSDECNDNIIFSE EYNTSNPD* | | CGGCAAGGAGTACAAGTGCAAGGTCTCCAAC AAAGGCCTCCCGTCCTCCATCGAGAAAACCA TCTCCAAAGCCAAAGGGCAGCCCCGAGAGCC ACAGGTGTACACCCTGCCCCCATCCCAGGAG GAGATGACCAAGAACCAGGTCAGCCTGACCT GCCTGGTCAAAGGCTTCTACCCCAGCGACATC GCCGTGGAGTGGGAGAGCAATGGGCAGCCGG AGAACAACTACAAGACCACGCCTCCCGTGCT GGACTCCGACGGCTCCTTCTTCCTCTACAGCA GGCTCACCGTGGACAAGAGCAGGTGGCAGGA GGGGAATGTCTTCTCATGCTCCGTGATGCATG AGGCTCTGCACAACCACTACACACAGAAGAG CCTCTCCCTGTCTCTGGGTAAAGGTGGAGGTG GTTCTGGAGGTGGAGGTAGTATCCCTCCTCAC GTACAGAAGTCCGTGAACAATGACATGATTG TCACTGACAATAACGGAGCCGTCAAGTTTCCT CAGCTATGTAAGTTCTGCGATGTTCGGTTCTC CACATGCGATAATCAGAAAAGCTGTATGTCT AATTGCAGTATCACTAGTATATGCGAAAAAC CTCAAGAAGTTTGCGTCGCCGTGTGGCGGAA AAATGATGAAAATATCACGCTTGAGACTGTCT GCCATGATCCAAAGTTACCCTACCACGACTTC ATCTTAGAAGACGCCGCATCACCCAAGTGCA TTATGAAAGAGAAAAAGAAGCCAGGAGAAA CATTCTTTATGTGCTCATGCTCCTCTGACGAA TGCAACGACAACATTATCTTCTCTGAGGAGTA TAACACCTCAAATCCAGAC |
| Linker | 17 | DPGGGGSGGGGSNPGS | | |
| Linker | 18 | GGGGSGGGGSGSDPGS | | |
| Linker | 19 | DPGSGGGGSGGGGSGS | | |
| Linker | 20 | GGGGSGGGGSGGGGSD PGS | | |
| Linker | 21 | DPGSGGGGSGGGGSGG GGS | | |
| Linker 7 | 22 | DPGSGSVPLGSGSNPGS | | |
| Linker 8 | 23 | DPGSGGSVPLGSGGSNP GS | | |
| Linker | 24 | DPGVLEREDKPTTSKPN PGS | | |
| Linker 10 | 25 | DPGVLEREDVPTTSYPN PGS | | |
| Linker | 26 | DPGVLEREDKVTTSKY NPGS | | |
| Linker 12 | 27 | DPVLEREDKVTTSKNP GS | | |
| Linker | 28 | DIEGRMD | | |
| Linker | 29 | GEGKSSGSGSESKAS | | |
| Linker | 30 | GSTSGSGKPGSGEGSTK G | | |
| Linker | 31 | A(EAAAK)$_4$ALEA(EAAA K)$_4$A | | |
| Linker | 32 | (G4S)n, n = 1-10 | | |
| Linker | 33 | (Gly)n, n = 6-8 | | |
| Linker | 34 | (EAAAK)n, n = 1-6 | | |
| hM195 | 35 | DIQMTQSPSSLSASVGD | 72 | gacattcagatgacccagtctccgagctctctgtccgcatcagtaggagac |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| VL | | RVTITCRASESVDNYGI SFMNWFQQKPGKAPKL LIYAASNQGSGVPSRFS GSGSGTDFTLTISSLQPD DFATYYCQQSKEVPWT FGQGTKVEIK | | agggtcaccatcacatgcagagccagcgaaagtgtcgacaattatggcatt agctttatgaactggttccaacagaaacccgggaaggctcctaagcttctga tttacgctgcatccaaccaaggctccggggtaccctctcgcttctcaggcag tggatctgggacagacttcactctcaccatttcatctctgcagcctgatgactt cgcaacctattactgtcagcaaagtaaggaggttccgtggacgttcggtca agggaccaaggtggagatcaaa |
| hM195 VH | 36 | QVQLVQSGAEVKKPGS SVKVSCKASGYTFTDY NMHWVRQAPGQGLEW IGYIYPYNGGTGYNQKF KSKATITADESTNTAY MELSSLRSEDTAVYYC ARGRPAMDYWGQGTL VTVSS | 73 | caggttcagctggtgcagtctggagctgaggtgaagaagcctgggagctc agtgaaggtttcctgcaaagcttctggctacaccttcactgactacaacatgc actgggtgaggcaggctcctggccaaggcctggaatggattggatatattt atccttacaatggtggtaccggctacaaccagaagttcaagagcaaggcca caattacagcagacgagagtactaacacagcctacatggaactctccagcc tgaggtctgaggacactgcagtctattactgcgcaagagggcgccccgct atggactactggggccaagggactctggtcactgtctcttca |
| M2H12 VH | 37 | QVQLQQSGPELVRPGT FVKISCKASGYTFTNYD INWVNQRPGQGLEWIG WIYPGDGSTKYNEKF KAKATLTADKSSSTAY LQLNNLTSENSAVYFC ASGYEDAMDYWGQGT SVTVSS | | |
| M2H12 VL | 38 | DIKMTQSPSSMYASLGE RVIINCKASQDINSYLS WFQQKPGKSPKTLIYR ANRLVDGVPSRFSGSG SGQDYSLTISSLEYEDM GIYYCLQYDEFPLTFGA GTKLELKR | | |
| DRB2 VH | 39 | EVKLQESGPELVKPGAS VKMSCKASGYKFTDYV VHWLKQKPGQGLEWI GYINPYNDGTKYNEKF KGKATLTSDKSSSTAY MEVSSLTSEDSAVYYC ARDYRYEVYGMDYWG QGTSVTVSS | | |
| DRB2 VL | 40 | DIVLTQSPTIMSASPGER VTMTCTASSSVNYIH WYQQKSGDSPLRWIFD TSKVASGVPARFSGSG SGTSYSLTISTMEAEDA ATYYCQQWRSYPLTFG DGTRLELKRADAAPTV S | | |
| My9-6 VH | 41 | QVQLQQPGAEVVKPGA SVKMSCKASGYTFTS YYIHWIKQTPGQGLEW VGVIYPGNDDISYNQK FKGKATLTADKSSTTA YMQLSSLTSEDSAVYY CAREVRLRYFDVWGA GTTVTVSS | | |
| My9-6 VL | 42 | NIMLTQSPSSLAVSAGE KVTMSCKSSQSVFFSS SQKNYLAWYQQIPGQS PKLLIYVVASTRESGVP DRFTGSGSGTDFTLTISS VQSEDLAIYYCHQYLS SRTFGGGTKLEIKR | | |
| MUC16-1 VL | 43 | DIELTQSPSSLAVSAGE KVTMSCKSSQSLLNSRT RKNQLAWYQQKPGQS PELLIYWASTRQSGVPD RFTGSGSGTDFTLTISSV QAEDLAVYYCQQSYNL | 74 | GACATCGAGCTGACACAGAGCCCATCTAGCC TGGCTGTGTCTGCCGGCGAGAAAGTGACCAT GAGCTGCAAGAGCAGCCAGAGCCTGCTGAAC AGCCGGACCAGAAAGAATCAGCTGGCCTGGT ATCAGCAGAAGCCCGGCCAATCTCCTGAGCT GCTGATCTACTGGGCCAGCACAAGACAGAGC |

TABLE 4-continued

| Name | SEQ ID NO | Amino Acid Sequence | SEQ ID NO | Nucleotide Sequence |
|---|---|---|---|---|
| Non-limiting exemplary polypeptide and nucleotide sequences | | | | |
| | | LTFGPGTKLEVKR | | GGCGTGCCCGATAGATTCACAGGATCTGGCA GCGGCACCGACTTCACCCTGACAATCAGTTCT GTGCAGGCCGAGGACCTGGCCGTGTACTACT GTCAGCAGAGCTACAACCTGCTGACCTTCGG ACCCGGCACCAAGCTGGAAGTGAAGAGA |
| MUC16-1 VH | 44 | VKLQESGGGFVKPGGS LKVSCAASGFTFSSYA MSWVRLSPEMRLEWV ATISSAGGYIFYSDSVQ GRFTISRDNAKNTLHLQ MGSLRSGDTAMYYCA RQGFGNYGDYYAMDY WGQGTTVTVSS | 75 | GTGAAGCTGCAAGAGTCCGGCGGAGGCTTTG TGAAGCCTGGCGGCTCTCTGAAAGTGTCCTGT GCCGCCAGCGGCTTCACCTTTAGCAGCTACGC CATGAGCTGGGTCCGACTGAGCCCTGAGATG AGACTGGAATGGGTCGCCACCATCAGTAGCG CAGGCGGCTACATCTTCTACAGCGACTCTGTG CAGGGCAGATTCACCATCAGCCGGGACAACG CCAAGAACACCCTGCACCTCCAGATGGGCAG TCTGAGAAGCGGCGATACCGCCATGTACTACT GCGCCAGACAAGGCTTCGGCAACTACGGCGA CTACTATGCCATGGATTACTGGGGCCAGGGC ACCACCGTGACAGTCTCTTCT |
| MUC16-2 VL | 45 | DIELTQSPSSLAVSAGE KVTMSCKSSQSLLNSRT RKNQLAWYQQKTGQS PELLIYWASTRQSGVPD RFTGSGSGTDFTLTISSV QAEDLAVYYCQQSYNL LTFGPGTKLEIKR | 76 | GACATCGAGCTGACACAGAGCCCATCTAGCC TGGCTGTGTCTGCCGGCGAGAAAGTGACCAT GAGCTGCAAGAGCAGCCAGAGCCTGCTGAAC AGCCGGACCAGAAAGAATCAGCTGGCCTGGT ATCAGCAGAAAACCGGACAGAGCCCCGAGCT GCTGATCTACTGGGCCAGCACAAGACAGAGC GGCGTGCCCGATAGATTCACAGGATCTGGCA GCGGCACCGACTTCACCCTGACAATCAGTTCT GTGCAGGCCGAGGACCTGGCCGTGTACTACT GTCAGCAGAGCTACAACCTGCTGACCTTCGG ACCCGGCACCAAGCTGGAAATCAAGAGA |
| MUC16-2 VH | 46 | VKLEESGGGFVKPGGS LKISCAASGFTFRNYAM SWVRLSPEMRLEWVAT ISSAGGYIFYSDSVQGR FTISRDNAKNTHLQMG SLRSGDTAMYYCARQG FGNYGDYYAMDYWGQ GTTVTVSS | 77 | GTGAAGCTGGAAGAGTCCGGCGGAGGCTTTG TGAAGCCTGGCGGAAGCCTGAAGATCAGCTG TGCCGCCAGCGGCTTCACCTTCAGAAACTACG CCATGAGCTGGGTCCGACTGAGCCCCGAGAT GAGACTGGAATGGGTCGCCACAATCAGCAGC GCAGGCGGCTACATCTTCTACAGCGATAGCGT GCAGGGCAGATTCACCATCAGCCGGGACAAC GCCAAGAACACCCTGCACCTCCAGATGGGCA GTCTGAGATCTGGCGACACCGCCATGTACTAC TGCGCCAGACAAGGCTTCGGCAACTACGGCG ACTACTATGCCATGGATTACTGGGGCCAGGG CACCACCGTGACAGTCTCTTCT |
| MUC16-3 VL | 47 | DIKMAQSPSSVNASLGE RVTITCKASRDINNFLS WFHQKPGKSPKTLIYR ANRLVDGVPSRFSGSGS GQDYSFTISSLEYEDVG IYYCLQYGDLYTFGGG TKLEIK | 78 | GACATCAAGATGGCTCAGTCCCCTTCTAGCGT GAATGCTTCGCTAGGGGAGCGTGTGACCATC ACATGTAAAGCATCACGCGACATAAATAATT TCCTTTCCTGGTTTCATCAGAAACCGGGCAAG TCGCCTAAGACGCTGATTTACAGAGCAAATC GGTTGGTAGATGGAGTGCCAAGCAGATTCAG CGGGAGCGGAAGTGGACAGGATTATAGCTTC ACTATTTCATCCCTGGAATACGAGGACGTAGG TATCTATTATTGCCTCCAGTATGGCGATCTTT ACACATTTGGTGGGGGGACTAAGCTGGAGAT TAAG |
| MUC16-3 VH | 48 | DVQLLESGPGLVRPSQS LSLTCSVTGYSIVSHYY WNWIRQFPGNKLEWM GYISSDGSNEYNPSLKN RISISLDTSKNQFFLKFD FVTTADTATYFCVRGV DYWGQGTTLTVSS | 79 | GACGTGCAACTTCTGGAGAGCGGGCCAGGGC TAGTCAGGCCCTCCCAGTCGCTTTCACTGACT TGCAGTGTGACCGGTTACTCTATTGTGAGTCA CTACTATTGGAACTGGATTCGGCAGTTCCCAG GCAACAAACTGGAATGGATGGGGTACATATC TTCCGATGGCTCGAATGAATATAACCCATCAT TGAAAAATCGTATTTCCATCAGTCTGGATACG AGTAAAAACCAGTTTTTCCTCAAATTCGATTT CGTGACTACAGCAGATACTGCCACATACTTCT GTGTACGAGGTGTCGATTATTGGGGACAGGG CACAACGCTGACCGTAAGTTCT |
| MUC16-4 VL | 49 | DIQMTQSSSFLSVSLGG RVTITCKASDLIHNWLA WYQQKPGNAPRLLISG ATSLETGVPSRFSGSGS GNDYTLSIASLQTEDAA TYYCQQYWTTPFTFGS | 80 | GACATCCAGATGACCCAGAGCAGCAGCTTCC TGAGCGTGTCCCTTGGCGGCAGAGTGACCATC ACCTGTAAAGCCAGCGACCTGATCCACAACT GGCTGGCCTGGTATCAGCAGAAGCCTGGCAA CGCTCCCAGACTGCTGATTAGCGGCGCCACCT CTCTGGAAACAGGCGTGCCAAGCAGATTTTCC |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | GTKLEIK | | GGCAGCGGCTCCGGCAACGACTACACACTGT CTATTGCCAGCCTGCAGACCGAGGATGCCGC CACCTATTACTGCCAGCAGTACTGGACCACAC CTTTCACCTTTGGCAGCGGCACCAAGCTGGAA ATCAAG |
| MUC16-4 VH | 50 | DVQLQESGPGLVNPSQ SLSLTCTVTGYSITNDY AWNWIRQFPGNKLEW MGYINYSGYTTYNPSL KSRISITRDTSKNQFFLH LNSVTTEDTATYYCAR WDGGLTYWGQGTLVT VSA | 81 | GACGTTCAGCTGCAAGAGTCTGGCCCTGGCCT GGTCAATCCTAGCCAGAGCCTGAGCCTGACA TGTACCGTGACCGGCTACAGCATCACCAACG ACTACGCCTGGAACTGGATCAGACAGTTCCCC GGCAACAAGCTGGAATGGATGGGCTACATCA ACTACAGCGGCTACACCACCTACAATCCCAG CCTGAAGTCCCGGATCTCCATCACCAGAGAC ACCAGCAAGAACCAGTTCTTCCTGCACCTGAA CAGCGTGACCACCGAGGATACCGCCACCTAC TACTGCGCTAGATGGGATGGCGGCCTGACAT ATTGGGGCCAGGGAACACTGGTCACCGTGTC TGCT |
| MUC16-5 VL | 51 | DIQMTQSPSSLSASVGD RVTITCKASDLIHNWLA WYQQKPGKAPKLLISG ATSLETGVPSRFSGSGS GTDFTLTISSLQPEDFAT YYCQQYWTTPFTFGQG TKVEIKR | 82 | GACATCCAGATGACCCAGAGCCCCAGCAGCC TGAGCGCCAGCGTGGGCGACAGGGTGACCAT CACCTGCAAGGCCAGCGACCTGATCCACAAC TGGCTGGCCTGGTACCAGCAGAAGCCCGGCA AGGCCCCCAAGCTGCTGATCAGCGGCGCCAC CAGCCTGGAGACCGGCGTGCCCAGCAGGTTC AGCGGCAGCGGCAGCGGCACCGACTTCACCC TGACCATCAGCAGCCTGCAGCCCGAGGACTT CGCCACCTACTACTGCCAGCAGTACTGGACCA CCCCCTTCACCTTCGGCCAGGGCACCAAGGTG GAGATCAAGAGG |
| MUC16-5 VH-L | 52 | EVQLVESGGGLVQPGG SLRLSCAASGYSITNDY AWNWVRQAPGKGLEW VGYINYSGYTTYNPSLK SRFTISRDNSKNTLYLQ MNSLRAEDTAVYYCAR WDGGLTYWGQGTLVT VSS | 83 | GAGGTGCAGCTGGTGGAGAGCGGCGGCGGCC TGGTGCAGCCCGGCGGCAGCCTGAGGCTGAG CTGCGCCGCCAGCGGCTACAGCATCACCAAC GACTACGCCTGGAACTGGGTGAGGCAGGCCC CCGGCAAGGGCCTGGAGTGGGTGGGCTACAT CAACTACAGCGGCTACACCACCTACAACCCC AGCCTGAAGAGCAGGTTCACCATCAGCAGGG ACAACAGCAAGAACACCCTGTACCTGCAGAT GAACAGCCTGAGGGCCGAGGACACCGCCGTG TACTACTGCGCCAGGTGGGACGGCGGCCTGA CCTACTGGGGCCAGGGCACCCTGGTGACCGT GAGCAGC |
| MUC16-5 VH-F | 53 | EVQLVESGGGLVQPGG SLRLSCAASGYSITNDY AWNWVRQAPGKGLEW VGYINYSGYTTYNPSLK SRFTISRDNSKNTFYLQ MNSLRAEDTAVYYCAR WDGGLTYWGQGTLVT VSS | 84 | GAGGTGCAGCTGGTGGAGAGCGGCGGCGGCC TGGTGCAGCCCGGCGGCAGCCTGAGGCTGAG CTGCGCCGCCAGCGGCTACAGCATCACCAAC GACTACGCCTGGAACTGGGTGAGGCAGGCCC CCGGCAAGGGCCTGGAGTGGGTGGGCTACAT CAACTACAGCGGCTACACCACCTACAACCCC AGCCTGAAGAGCAGGTTCACCATCAGCAGGG ACAACAGCAAGAACACCTTCTACCTGCAGAT GAACAGCCTGAGGGCCGAGGACACCGCCGTG TACTACTGCGCCAGGTGGGACGGCGGCCTGA CCTACTGGGGCCAGGGCACCCTGGTGACCGT GAGCAGC |
| MUC16-6 VL | 54 | DIVLTQSPAIMSASLGE RVTMTCTASSSVSSSYL HWYQQKPGSSPKLWIY STSNLASGVPGRFSGSG SGTSYSLTISSMEAEDA ATYYCHQYHRSPYTFG GGTKVEIKR | 85 | GACATCGTGCTGACACAGAGCCCTGCCATCAT GTCTGCCAGCCTCGGCGAGCGAGTGACCATG ACATGTACAGCCAGCAGCAGCGTGTCCAGCA GCTACCTGCATTGGTATCAGCAGAAGCCCGG CAGCAGCCCCAAGCTGTGGATCTACAGCACA AGCAATCTGGCCAGCGGCGTGCCAGGCAGAT TTTCTGGTTCTGGCAGCGGCACCAGCTACAGC CTGACAATCAGCAGCATGGAAGCCGAGGATG CCGCCACCTACTACTGCCACCAGTACCACAGA AGCCCCTACACCTTTGGCGGAGGCACCAAGG TGGAAATCAAGCGG |
| MUC16-7 VL | 55 | DIQMTQSPSSLSASVGD RVTITCTASSSVSSSYLH WYQQKPGKAPKLLIYS TSNLASGVPSRFSGSGS GTDFTLTISSLQPEDFAT | 86 | GACATCCAGATGACACAGAGCCCTAGCAGCC TGTCTGCCAGCGTGGGAGACAGAGTGACCAT CACCTGTACAGCCAGCAGCAGCGTGTCCAGC AGCTACCTGCATTGGTATCAGCAGAAGCCCG GCAAGGCCCCTAAGCTGCTGATCTACAGCAC |

TABLE 4-continued

| Name | SEQ ID NO | Amino Acid Sequence | SEQ ID NO | Nucleotide Sequence |
|---|---|---|---|---|
| Non-limiting exemplary polypeptide and nucleotide sequences | | | | |
| | | YYCHQYHRSPYTFGQG TKVEIKR | | CAGCAATCTGGCCAGCGGCGTGCCAAGCAGA TTTTCTGGCTCTGGCAGCGGCACCGACTTCAC CCTGACCATATCTAGCCTGCAGCCTGAGGACT TCGCCACCTACTACTGCCACCAGTACCACAGA AGCCCCTACACCTTTGGCCAGGGCACCAAGG TGGAAATCAAGCGG |
| MUC16-7 VH | 56 | EVQLVESGGGLVQPGG SLRLSCAASGFNIKDTY MHWVRQAPGKGLEWV GRVDPANGNTKYDPKF QGRFTISADTSKNTAYL QMNSLRAEDTAVYYC VRDYYGHTYGFAFWG QGTLVTVSS | 87 | GAGGTGCAGCTGGTTGAATCTGGCGGAGGAC TGGTTCAGCCTGGCGGATCTCTGAGACTGTCT TGTGCCGCCAGCGGCTTCAACATCAAGGACA CCTACATGCACTGGGTCCGACAGGCCCCTGGC AAAGGACTTGAGTGGGTTGGAAGAGTGGACC CCGCCAACGGCAACACCAAATACGACCCCAA GTTCCAGGGCAGATTCACCATCAGCGCCGAC ACCAGCAAGAACACCGCCTACCTGCAGATGA ACAGCCTGAGAGCCGAGGACACCGCCGTGTA CTATTGCGTGCGGGATTACTACGGCCATACCT ACGGCTTCGCCTTTTGGGGCCAGGGCACACTG GTTACCGTTAGCTCT |
| CD8alpha hinge | 57 | KPTTTPAPRPPTPAPTIA SQPLSLRPEACRPAAGG AVHTRGLDFACD | 88 | AAGCCCACCACCACCCCTGCCCCTAGACCTCC AACCCCAGCCCCTACAATCGCCAGCCAGCCC CTGAGCCTGAGGCCCGAAGCCTGTAGACCTG CCGCTGGCGGAGCCGTGCACACCAGAGGCCT GGATTTCGCCTGCGAC |
| CD8alpha 2x | 58 | KPTTTPAPRPPTPAPTIA SQPLSLRPEASRPAAGG AVHTRGLDFASDKPTT TPAPRPPTPAPTIASQPL SLRPEACRPAAGGAVH TRGLDFACD | 89 | AAACCTACTACAACTCCTGCCCCCCGGCCTCC TACACCAGCTCCTACTATCGCCTCCCAGCCAC TCAGTCTCAGACCCGAGGCTTCTAGGCCAGCG GCCGGAGGCGCGGTCCACACCCGCGGGCTGG ACTTTGCATCCGATAAGCCCACCACCACCCCT GCCCCTAGACCTCCAACCCCAGCCCCTACAAT CGCCAGCCAGCCCCTGAGCCTGAGGCCCGAA GCCTGTAGACCTGCCGCTGGCGGAGCCGTGC ACACCAGAGGCCTGGATTTCGCCTGCGAC |
| CD8alpha 3x | 59 | KPTTTPAPRPPTPAPTIA SQPLSLRPEASRPAAGG AVHTRGLDFASDKPTT TPAPRPPTPAPTIASQPL SLRPEASRPAAGGAVH TRGLDFASDKPTTTPAP RPPTPAPTIASQPLSLRP EACRPAAGGAVHTRGL DFACD | 90 | AAGCCTACCACCACCCCCGCACCTCGTCCTCC AACCCCTGCACCTACGATTGCCAGTCAGCCTC TTTCACTGCGGCCTGAGGCCAGCAGACCAGCT GCCGGCGGTGCCGTCCATACAAGAGGACTGG ACTTCGCGTCCGATAAACCTACTACCACTCCA GCCCCAAGGCCCCCAACCCCAGCACCGACTA TCGCATCACAGCCTTTGTCACTGCGTCCTGAA GCCAGCCGGCCAGCTGCAGGGGGGGCCGTCC ACACAAGGGGACTCGACTTTGCGAGTGATAA GCCCACCACCACCCCTGCCCCTAGACCTCCAA CCCCAGCCCCTACAATCGCCAGCCAGCCCCTG AGCCTGAGGCCCGAAGCCTGTAGACCTGCCG CTGGCGGAGCCGTGCACACCAGAGGCCTGGA TTTCGCCTGCGAC |
| CD8alpha 4x | 60 | TTPAPRPPTPAPTIASQP LSLRPEASRPAAGGAV HTRGLDFASDKPTTTPA PRPPTPAPTIASQPLSLR PEASRPAAGGAVHTRG LDFASDKPTTTPAPRPP TPAPTIASQPLSLRPEAS RPAAGGAVHTRGLDFA SDKPTTTPAPRPPTPAPT IASQPLSLRPEACRPAA GGAVHTRGLDFACD | 91 | AAGCCTACCACCACCCCCGCACCTCGTCCTCC AACCCCTGCACCTACGATTGCCAGTCAGCCTC TTTCACTGCGGCCTGAGGCCAGCAGACCAGCT GCCGGCGGTGCCGTCCATACAAGAGGACTGG ACTTCGCGTCCGATAAACCTACTACCACTCCA GCCCCAAGGCCCCCAACCCCAGCACCGACTA TCGCATCACAGCCTTTGTCACTGCGTCCTGAA GCCAGCCGGCCAGCTGCAGGGGGGGCCGTCC ACACAAGGGGACTCGACTTTGCGAGTGATAA ACCTACTACAACTCCTGCCCCCCGGCCTCCTA CACCAGCTCCTACTATCGCCTCCCAGCCACTC AGTCTCAGACCCGAGGCTTCTAGGCCAGCGG CCGGAGGCGCGGTCCACACCCGCGGGCTGGA CTTTGCATCCGATAAGCCCACCACCACCCCTG CCCCTAGACCTCCAACCCCAGCCCCTACAATC GCCAGCCAGCCCCTGAGCCTGAGGCCCGAAG CCTGTAGACCTGCCGCTGGCGGAGCCGTGCA CACCAGAGGCCTGGATTTCGCCTGCGAC |
| CD8alpha TM | 61 | IYIWAPLAGTCGVLLLS LVITLYCNHRN | 92 | ATCTACATCTGGGCCCCTCTGGCCGGCACCTG TGGCGTGCTGCTGCTGAGCCTGGTCATCACCC TGTACTGCAACCACCGGAAT |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| CD28 TM | 62 | FWVLVVVGGVLACYSL LVTVAFIIFWV | 93 | TTTTGGGTGCTGGTGGTGGTTGGTGGAGTCCT GGCTTGCTATAGCTTGCTAGTAACAGTGGCCT TTATTATTTTCTGGGTG |
| 4-1BB signaling domain | 63 | KRGRKKLLYIFKQPFM RPVQTTQEEDGCSCRFP EEEEGGCEL | 94 | AAGAGAGGCCGGAAGAAACTGCTGTACATCT TCAAGCAGCCCTTCATGCGGCCCGTGCAGACC ACCCAGGAAGAGGACGGCTGCAGCTGCCGGT TCCCCGAGGAAGAGGAAGGCGGCTGCGAACT G |
| CD28 signaling domain | 64 | RSKRSRGGHSDYMNM TPRRPGPTRKHYQPYAP PRDFAAYRS | 95 | AGGAGCAAGCGGAGCAGAGGCGGCCACAGC GACTACATGAACATGACCCCCCGGAGGCCTG GCCCCACCCGGAAGCACTACCAGCCCTACGC CCCTCCCAGGGACTTCGCCGCCTACCGGAGC |
| DNAX-activation protein 10 (DAP 10) Signaling Domain | 65 | LCARPRRSPAQEDGKV YINMPGRG | 96 | CTGTGCGCACGCCCACGCCGCAGCCCCGCCC AAGAAGATGGCAAAGTCTACATCAACATGCC AGGCAGGGGC |
| DNAX-activation protein 12 (DAP12) Signaling Domain | 66 | YFLGRLVPRGRGAAEA ATRKQRITETESPYQEL QGQRSDVYSDLNTQRP YYK | 97 | TACTTCCTGGGCCGGCTGGTCCCTCGGGGGCG AGGGGCTGCGGAGGCAGCGACCCGGAAACAG CGTATCACTGAGACCGAGTCGCCTTATCAGGA GCTCCAGGGTCAGAGGTCGGATGTCTACAGC GACCTCAACACACAGAGGCCGTATTACAAA |
| CD3ζ signaling domain | 67 | RVKFSRSADAPAYQQG QNQLYNELNLGRREEY DVLDKRRGRDPEMGG KPRRKNPQEGLYNELQ KDKMAEAYSEIGMKGE RRRGKGHDGLYQGLST ATKDTYDALHMQALPP R | 98 | CGGGTGAAGTTCAGCCGGAGCGCCGACGCCC CTGCCTACCAGCAGGGCCAGAACCAGCTGTA CAACGAGCTGAACCTGGGCCGGAGGGAGGAG TACGACGTGCTGGACAAGCGGAGAGGCCGGG ACCCTGAGATGGGCGGCAAGCCCCGGAGAAA GAACCCTCAGGAGGGCCTGTATAACGAACTG CAGAAAGACAAGATGGCCGAGGCCTACAGCG AGATCGGCATGAAGGGCGAGCGGCGGAGGG GCAAGGGCCACGACGGCCTGTACCAGGGCCT GAGCACCGCCACCAAGGATACCTACGACGCC CTGCACATGCAGGCCCTGCCCCCCAGA |
| HER1t | 68 | RKVCNGIGIGEFKDSLSI NATNIKHFKNCTSISGD LHILPVAFRGDSFTHTP PLDPQELDILKTVKEIT GFLLIQAWPENRTDLH AFENLEIIRGRTKQHGQ FSLAVVSLNITSLGLRSL KEISDGDVIISGNKNLC YANTINWKKLFGTSGQ KTKIISNRGENSCKATG QVCHALCSPEGCWGPE PRDCVSCRNVSRGREC VDKCNLLEGEPREFVE NSECIQCHPECLPQAMN ITCTGRGPDNCIQCAHY IDGPHCVKTCPAGVMG ENNTLVWKYADAGHV CHLCHPNCTYGCTGPG LEGCPTNGPKIPSIATG MVGALLLLLVVALGIG LFM | 99 | CGCAAAGTGTGTAACGGAATAGGTATTGGTG AATTTAAAGACTCACTCTCCATAAATGCTACG AATATTAAACACTTCAAAAACTGCACCTCCAT CAGTGGCGATCTCCACATCCTGCCGGTGGCAT TTAGGGGTGACTCCTTCACACATACTCCTCCT CTGGATCCACAGGAACTGGATATTCTGAAAA CCGTAAAGGAAATCACAGGGTTTTTGCTGATT CAGGCTTGGCCTGAAAACAGGACGGACCTCC ATGCCTTTGAGAACCTAGAAATCATACGCGG CAGGACCAAGCAACATGGTCAGTTTTCTCTTG CAGTCGTCAGCCTGAACATAACATCCTTGGGA TTACGCTCCCTCAAGGAGATAAGTGATGGAG ATGTGATAATTTCAGGAAACAAAAATTTGTGC TATGCAAATACAATAAACTGGAAAAAACTGT TTGGGACCTCCGGTCAGAAAACCAAAATTAT AAGCAACAGAGGTGAAAACAGCTGCAAGGCC ACAGGCCAGGTCTGCCATGCCTTGTGCTCCCC CGAGGGCTGCTGGGGCCCGGAGCCCAGGGAC TGCGTCTCTTGCCGGAATGTCAGCCGAGGCAG GGAATGCGTGGACAAGTGCAACCTTCTGGAG GGTGAGCCAAGGGAGTTTGTGGAGAACTCTG AGTGCATACAGTGCCACCCAGAGTGCCTGCCT CAGGCCATGAACATCACCTGCACAGGACGGG GACCAGACAACTGTATCCAGTGTGCCCACTAC ATTGACGGCCCCCACTGCGTCAAGACCTGCCC GGCAGGAGTCATGGGAGAAAACAACACCCTG GTCTGGAAGTACGCAGACGCCGGCCATGTGT GCCACCTGTGCCATCCAAACTGCACCTACGGA TGCACTGGGCCAGGTCTTGAAGGCTGTCCAAC GAATGGGCCTAAGATCCCGTCCATCGCCACTG GGATGGTGGGGGCCCTCCTCTTGCTGCTGGTG GTGGCCCTGGGGATCGGCCTCTTCATG |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| HER1t-1 | 69 | RKVCNGIGIGEFKDSLSI<br>NATNIKHFKNCTSISGD<br>LHILPVAFRGDSFTHTP<br>PLDPQELDILKTVKEIT<br>GFLLIQAWPENRTDLH<br>AFENLEIIRGRTKQHGQ<br>FSLAVVSLNITSLGLRSL<br>KEISDGDVIISGNKNLC<br>YANTINWKKLFGTSGQ<br>KTKIISNRGENSCKATG<br>QVCHALCSPEGCWGPE<br>PRDCVSGGGGSGGGSG<br>GGGSGGGGSFWVLVV<br>VGGVLACYSLLVTVAFI<br>IFWVRSKRS | 100 | CGCAAAGTGTGTAACGGAATAGGTATTGGTG<br>AATTTAAAGACTCACTCTCCATAAATGCTACG<br>AATATTAAACACTTCAAAAACTGCACCTCCAT<br>CAGTGGCGATCTCCACATCCTGCCGGTGGCAT<br>TTAGGGGTGACTCCTTCACACATACTCCTCCT<br>CTGGATCCACAGGAACTGGATATTCTGAAAA<br>CCGTAAAGGAAATCACAGGGTTTTTGCTGATT<br>CAGGCTTGGCCTGAAAACAGGACGGACCTCC<br>ATGCCTTTGAGAACCTAGAAATCATACGCGG<br>CAGGACCAAGCAACATGGTCAGTTTTCTCTTG<br>CAGTCGTCAGCCTGAACATAACATCCTTGGGA<br>TTACGCTCCCTCAAGGAGATAAGTGATGGAG<br>ATGTGATAATTTCAGGAAACAAAAATTTGTGC<br>TATGCAAATACAATAAACTGGAAAAAACTGT<br>TTGGGACCTCCGGTCAGAAAACCAAAATTAT<br>AAGCAACAGAGGTGAAAACAGCTGCAAGGCC<br>ACAGGCCAGGTCTGCCATGCCTTGTGCTCCCC<br>CGAGGGCTGCTGGGGCCCGGAGCCCAGGGAC<br>TGCGTCTCTGGTGGCGGTGGCTCGGGCGGTGG<br>TGGGTCGGGTGGCGGCGGATCTGGTGGCGGT<br>GGCTCGTTTTGGGTGCTGGTGGTGGTTGGTGG<br>AGTCCTGGCTTGCTATAGCTTGCTAGTAACAG<br>TGGCCTTTATTATTTTCTGGGTGAGGAGTAAG<br>AGGAGC |
| FL CD20 | 70 | MTTPRNSVNGTFPAEP<br>MKGPIAMQSGPKPLFR<br>RMSSLVGPTQSFFMRES<br>KTLGAVQIMNGLFHIAL<br>GGLLMIPAGIYAPICVT<br>VWYPLWGGIMYIISGSL<br>LAATEKNSRKCLVKGK<br>MIMNSLSLFAAISGMIL<br>SIMDILNIKISHFLKMES<br>LNFIRAHTPYINIYNCEP<br>ANPSEKNSPSTQYCYSI<br>QSLFLGILSVMLIFAFFQ<br>ELVIAGIVENEWKRTCS<br>RPKSNIVLLSAEEKKEQ<br>TIEIKEEVVGLTETSSQP<br>KNEEDIEIIPIQEEEEEET<br>ETNFPEPPQDQESSPIEN<br>DSSP | 101 | ATGACAACACCCAGAAATTCAGTAAATGGGA<br>CTTTCCCGGCAGAGCCAATGAAAGGCCCTATT<br>GCTATGCAATCTGGTCCAAAACCACTCTTCAG<br>GAGGATGTCTTCACTGGTGGGCCCCACGCAA<br>AGCTTCTTCATGAGGGAATCTAAGACTTTGGG<br>GGCTGTCCAGATTATGAATGGGCTCTTCCACA<br>TTGCCCTGGGGGGTCTTCTGATGATCCCAGCA<br>GGGATCTATGCACCCATCTGTGTGACTGTGTG<br>GTACCCTCTCTGGGGAGGCATTATGTATATTA<br>TTTCCGGATCACTCCTGGCAGCAACGGAGAA<br>AAACTCCAGGAAGTGTTTGGTCAAAGGAAAA<br>ATGATAATGAATTCATTGAGCCTCTTTGCTGC<br>CATTTCTGGAATGATTCTTTCAATCATGGACA<br>TACTTAATATTAAAATTTCCCATTTTTTAAAA<br>ATGGAGAGTCTGAATTTTATTAGAGCTCACAC<br>ACCATATATTAACATATACAACTGTGAACCAG<br>CTAATCCCTCTGAGAAAAACTCCCCATCTACC<br>CAATACTGTTACAGCATACAATCTCTGTTCTT<br>GGGCATTTTGTCAGTGATGCTGATCTTTGCCT<br>TCTTCCAGGAACTTGTAATAGCTGGCATCGTT<br>GAGAATGAATGGAAAAGAACGTGCTCCAGAC<br>CCAAATCTAACATAGTTCTCCTGTCAGCAGAA<br>GAAAAAAAAGAACAGACTATTGAAATAAAAG<br>AAGAAGTGGTTGGGCTAACTGAAACATCTTC<br>CCAACCAAAGAATGAAGAAGACATTGAAATT<br>ATTCCAATCCAAGAAGAGGAAGAAGAAGAAA<br>CAGAGACGAACTTTCCAGAACCTCCCCAAGA<br>TCAGGAATCCTCACCAATAGAAAATGACAGC<br>TCTCCT |
| CD20t-1 | 71 | MTTPRNSVNGTFPAEP<br>MKGPIAMQSGPKPLFR<br>RMSSLVGPTQSFFMRES<br>KTLGAVQIMNGLFHIAL<br>GGLLMIPAGIYAPICVT<br>VWYPLWGGIMYIISGSL<br>LAATEKNSRKCLVKGK<br>MIMNSLSLFAAISGMIL<br>SIMDILNIKISHFLKMES<br>LNFIRAHTPYINIYNCEP<br>ANPSEKNSPSTQYCYSI<br>QSLFLGILSVMLIFAFFQ<br>ELVIAGIVENEWKRTCS<br>RPKSNIVLLSAEEKKEQ<br>TIEIKEEVVGLTETSSQP<br>KNEEDIE | 102 | ATGACCACACCACGGAACTCTGTGAATGGCA<br>CCTTCCCAGCAGAGCCAATGAAGGGACCAAT<br>CGCAATGCAGAGCGGACCCAAGCCTCTGTTTC<br>GGAGAATGAGCTCCCTGGTGGGCCCAACCCA<br>GTCCTTCTTTATGAGAGAGTCTAAGACACTGG<br>GCGCCGTGCAGATCATGAACGGACTGTTCCA<br>CATCGCCCTGGGAGGACTGCTGATGATCCCA<br>GCCGGCATCTACGCCCCTATCTGCGTGACCGT<br>GTGGTACCCTCTGTGGGGCGGCATCATGTATA<br>TCATCTCCGGCTCTCTGCTGGCCGCCACAGAG<br>AAGAACAGCAGGAAGTGTCTGGTGAAGGGCA<br>AGATGATCATGAATAGCCTGTCCCTGTTTGCC<br>GCCATCTCTGGCATGATCCTGAGCATCATGGA<br>CATCCTGAACATCAAGATCAGCCACTTCCTGA<br>AGATGGAGAGCCTGAACTTCATCAGAGCCCA<br>CACCCCTTACATCAACATCTATAATTGCGAGC<br>CTGCCAACCCATCCGAGAAGAATTCTCCAAG<br>CACACAGTACTGTTATTCCATCCAGTCTCTGT<br>TCCTGGGCATCCTGTCTGTGATGCTGATCTTT |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | | | GCCTTCTTTCAGGAGCTGGTCATCGCCGGCAT<br>CGTGGAGAACGAGTGGAAGAGGACCTGCAGC<br>CGCCCCAAGTCCAATATCGTGCTGCTGTCCGC<br>CGAGGAGAAGAAGGAGCAGACAATCGAGAT<br>CAAGGAGGAGGTGGTGGGCCTGACCGAGACA<br>TCTAGCCAGCCTAAGAATGAGGAGGATATCG<br>AG |
| mbIL15 | 103 | MDWTWILFLVAAATR<br>VHSNWVNVISDLKKIE<br>DLIQSMHIDATLYTESD<br>VHPSCKVTAMKCFLLE<br>LQVISLESGDASIHDTV<br>ENLIILANNSLSSNGNV<br>TESGCKECEELEEKNIK<br>EFLQSFVHIVQMFINTSS<br>GGGSGGGGSGGGGSGG<br>GGSGGGSLQITCPPPMS<br>VEHADIWVKSYSLYSR<br>ERYICNSGFKRKAGTSS<br>LTECVLNKATNVAHWT<br>TPSLKCIRDPALVHQRP<br>APPSTVTTAGVTPQPES<br>LSPSGKEPAASSPSSNN<br>TAATTAAIVPGSQLMPS<br>KSPSTGTTEISSHESSHG<br>TPSQTTAKNWELTASA<br>SHQPPGVYPQGHSDTT<br>VAISTSTVLLCGLSAVS<br>LLACYLKSRQTPPLASV<br>EMEAMEALPVTWGTSS<br>RDEDLENCSHHL | 106 | ATGGATTGGACCTGGATTCTGTTTCTGGTGGC<br>CGCTGCCACAAGAGTGCACAGCAACTGGGTG<br>AATGTGATCAGCGACCTGAAGAAGATCGAGG<br>ATCTGATCCAGAGCATGCACATTGATGCCACC<br>CTGTACACAGAATCTGATGTGCACCCTAGCTG<br>TAAAGTGACCGCCATGAAGTGTTTTCTGCTGG<br>AGCTGCAGGTGATTTCTCTGGAAAGCGGAGA<br>TGCCTCTATCCACGACACAGTGGAGAATCTGA<br>TCATCCTGGCCAACAATAGCCTGAGCAGCAA<br>TGGCAATGTGACAGAGTCTGGCTGTAAGGAG<br>TGTGAGGAGCTGGAGGAGAAGAACATCAAGG<br>AGTTTCTGCAGAGCTTTGTGCACATCGTGCAG<br>ATGTTCATCAATACAAGCTCTGGCGGAGGATC<br>TGGAGGAGGCGGATCTGGAGGAGGAGGCAGT<br>GGAGGCGGAGGATCTGGCGGAGGATCTCTGC<br>AGATTACATGCCCTCCTCCAATGTCTGTGGAG<br>CACGCCGATATTTGGGTGAAGTCCTACAGCCT<br>GTACAGCAGAGAGAGATACATCTGCAACAGC<br>GGCTTTAAGAGAAAGGCCGGCACCTCTTCTCT<br>GACAGAGTGCGTGCTGAATAAGGCCACAAAT<br>GTGGCCCACTGGACAACACCTAGCCTGAAGT<br>GCATTAGAGATCCTGCCCTGGTCCACCAGAG<br>GCCTGCCCCTCCATCTACAGTGACAACAGCCG<br>GAGTGACACCTCAGCCTGAATCTCTGAGCCCT<br>TCTGGAAAAGAACCTGCCGCCAGCTCTCCTAG<br>CTCTAATAATACCGCCGCCACAACAGCCGCC<br>ATTGTGCCTGGATCTCAGCTGATGCCTAGCAA<br>GTCTCCTAGCACAGGCACAACAGAGATCAGC<br>AGCCACGAATCTTCTCACGGAACACCTTCTCA<br>GACCACCGCCAAGAATTGGGAGCTGACAGCC<br>TCTGCCTCTCACCAGCCTCCAGGAGTGTATCC<br>TCAGGGCCACTCTGATACAACAGTGGCCATC<br>AGCACATCTACAGTGCTGCTGTGTGGACTGTC<br>TGCCGTGTCTCTGCTGGCCTGTTACCTGAAGT<br>CTAGACAGACACCTCCTCTGGCCTCTGTGGAG<br>ATGGAGGCCATGGAAGCCCTGCCTGTGACAT<br>GGGGAACAAGCAGCAGAGATGAGGACCTGG<br>AGAATTGTTCTCACCACCTG |
| IL-15 | 104 | NWVNVISDLKKIEDLIQ<br>SMHIDATLYTESDVHPS<br>CKVTAMKCFLLELQVIS<br>LESGDASIHDTVENLIIL<br>ANNSLSSNGNVTESGC<br>KECEELEEKNIKEFLQS<br>FVHIVQMFINTS | 107 | AACTGGGTGAATGTGATCAGCGACCTGAAGA<br>AGATCGAGGATCTGATCCAGAGCATGCACAT<br>TGATGCCACCCTGTACACAGAATCTGATGTGC<br>ACCCTAGCTGTAAAGTGACCGCCATGAAGTG<br>TTTTCTGCTGGAGCTGCAGGTGATTTCTCTGG<br>AAAGCGGAGATGCCTCTATCCACGACACAGT<br>GGAGAATCTGATCATCCTGGCCAACAATAGC<br>CTGAGCAGCAATGGCAATGTGACAGAGTCTG<br>GCTGTAAGGAGTGTGAGGAGCTGGAGGAGAA<br>GAACATCAAGGAGTTTCTGCAGAGCTTTGTGC<br>ACATCGTGCAGATGTTCATCAATACAAGC |
| IL-15Rα | 105 | ITCPPPMSVEHADIWVK<br>SYSLYSRERYICNSGFK<br>RKAGTSSLTECVLNKA<br>TNVAHWTTPSLKCIRDP<br>ALVHQRPAPPSTVTTA<br>GVTPQPESLSPSGKEPA<br>ASSPSSNNTAATTAAIV<br>PGSQLMPSKSPSTGTTEI<br>SSHESSHGTPSQTTAKN<br>WELTASASHQPPGVYP<br>QGHSDTTVAISTSTVLL<br>CGLSAVSLLACYLKSR<br>QTPPLASVEMEAMEAL<br>PVTWGTSSRDEDLENC<br>SHHL | 108 | ATTACATGCCCTCCTCCAATGTCTGTGGAGCA<br>CGCCGATATTTGGGTGAAGTCCTACAGCCTGT<br>ACAGCAGAGAGAGATACATCTGCAACAGCGG<br>CTTTAAGAGAAAGGCCGGCACCTCTTCTCTGA<br>CAGAGTGCGTGCTGAATAAGGCCACAAATGT<br>GGCCCACTGGACAACACCTAGCCTGAAGTGC<br>ATTAGAGATCCTGCCCTGGTCCACCAGAGGCC<br>TGCCCCTCCATCTACAGTGACAACAGCCGGA<br>GTGACACCTCAGCCTGAATCTCTGAGCCCTTC<br>TGGAAAAGAACCTGCCGCCAGCTCTCCTAGCT<br>CTAATAATACCGCCGCCACAACAGCCGCCATT<br>GTGCCTGGATCTCAGCTGATGCCTAGCAAGTC<br>TCCTAGCACAGGCACAACAGAGATCAGCAGC<br>CACGAATCTTCTCACGGAACACCTTCTCAGAC<br>CACCGCCAAGAATTGGGAGCTGACAGCCTCT |

TABLE 4-continued

| Name | SEQ ID NO | Amino Acid Sequence | SEQ ID NO | Nucleotide Sequence |
|---|---|---|---|---|
| Non-limiting exemplary polypeptide and nucleotide sequences | | | | |
| | | | | GCCTCTCACCAGCCTCCAGGAGTGTATCCTCA GGGCCACTCTGATACAACAGTGGCCATCAGC ACATCTACAGTGCTGCTGTGTGGACTGTCTGC CGTGTCTCTGCTGGCCTGTTACCTGAAGTCTA GACAGACACCTCCTCTGGCCTCTGTGGAGATG GAGGCCATGGAAGCCCTGCCTGTGACATGGG GAACAAGCAGCAGAGATGAGGACCTGGAGA ATTGTTCTCACCACCTG |
| HUMAN Immunoglobulin heavy constant gamma 4 (IgG4 CH) | 146 | ASTKGPSVFPLAPCSRS TSESTAALGCLVKDYFP EPVTVSWNSGALTSGV HTFPAVLQSS GLYSLSSVVTVPSSSLG TKTYTCNVDHKPSNTK VDKRVESKYGPPCPSCP APEFLGGPSV FLFPPKPKDTLMISRTPE VTCVVVDVSQEDPEVQ FNWYVDGVEVHNAKT KPREEQFNSTY RVVSVLTVLHQDWLN GKEYKCKVSNKGLPSSI EKTISKAKGQPREPQVY TLPPSQEEMTK NQVSLTCLVKGFYPSDI AVEWESNGQPENNYKT TPPVLDSDGSFFLYSRL TVDKSRWQEG NVFSCSVMHEALHNHY TQKSLSLSLGK | | |
| IgG4 CH (S108P, L325P) | 147 | ASTKGPSVFPLAPCSRS TSESTAALGCLVKDYFP EPVTVSWNSGALTSGV HTFPAVLQSSGLYSLSS VVTVPSSSLGTKTYTCN VDHKPSNTKVDKRVES KYGPPCPPCPAPEFLGG PSVFLFPPKPKDTLMISR TPEVTCVVVDVSQEDP EVQFNWYVDGVEVHN AKTKPREEQFNSTYRV VSVLTVLHQDWLNGKE YKCKVSNKGLPSSIEKT ISKAKGQPREPQVYTLP PSQEEMTKNQVSLTCL VKGFYPSDIAVEWESN GQPENNYKTTPPVLDS DGSFFLYSRLTVDKSR WQEGNVFSCSVMHEAL HNHYTQKSLSLSPGK | 117 | GCTAGCACCAAGGGCCCATCGGTCTTCCCCCT GGCGCCCTGCTCCAGGAGCACCTCCGAGAGC ACAGCCGCCCTGGGCTGCCTGGTCAAGGACT ACTTCCCCGAACCGGTGACGGTGTCGTGGAA CTCAGGCGCCCTGACCAGCGGCGTGCACACC TTCCCGGCTGTCCTACAGTCCTCAGGACTCTA CTCCCTCAGCAGCGTGGTGACCGTGCCCTCCA GCAGCTTGGGCACGAAGACCTACACCTGCAA CGTAGATCACAAGCCCAGCAACACCAAGGTG GACAAGAGAGTTGAGTCCAAATATGGTCCCC CATGCCCACCATGCCCAGCACCTGAGTTCCTG GGGGGACCATCAGTCTTCCTGTTCCCCCCAAA ACCCAAGGACACTCTCATGATCTCCCGGACCC CTGAGGTCACGTGCGTGGTGGTGGACGTGAG CCAGGAAGACCCCGAGGTCCAGTTCAACTGG TACGTGGATGGCGTGGAGGTGCATAATGCCA AGACAAAGCCGCGGGAGGAGCAGTTCAACAG CACGTACCGTGTGGTCAGCGTCCTCACCGTCC TGCACCAGGACTGGCTGAACGGCAAGGAGTA CAAGTGCAAGGTCTCCAACAAAGGCCTCCCG TCCTCCATCGAGAAAACCATCTCCAAAGCCA AAGGGCAGCCCCGAGAGCCACAGGTGTACAC CCTGCCCCCATCCCAGGAGGAGATGACCAAG AACCAGGTCAGCCTGACCTGCCTGGTCAAAG GCTTCTACCCCAGCGACATCGCCGTGGAGTGG GAGAGCAATGGGCAGCCGGAGAACAACTACA AGACCACGCCTCCCGTGCTGGACTCCGACGG CTCCTTCTTCCTCTACAGCAGGCTCACCGTGG ACAAGAGCAGGTGGCAGGAGGGGAATGTCTT CTCATGCTCCGTGATGCATGAGGCTCTGCACA ACCACTACACACAGAAGAGCCTCTCCCTGTCT CCGGGTAAA |
| IgG4 CH (S108P) | 291 | ASTKGPSVFPLAPCSRS TSESTAALGCLVKDYFP EPVTVSWNSGALTSGV HTFPAVLQSSGLYSLSS VVTVPSSSLGTKTYTCN VDHKPSNTKVDKRVES KYGPPCPPCPAPEFLGG PSVFLFPPKPKDTLMISR TPEVTCVVVDVSQEDP | | |

TABLE 4-continued

Non-limiting exemplary polypeptide and nucleotide sequences

| Name | SEQ ID NO | Amino Acid Sequence | SEQ ID NO | Nucleotide Sequence |
|---|---|---|---|---|
| | | EVQFNWYVDGVEVHN<br>AKTKPREEQFNSTYRV<br>VSVLTVLHQDWLNGKE<br>YKCKVSNKGLPSSIEKT<br>ISKAKGQPREPQVYTLP<br>PSQEEMTKNQVSLTCL<br>VKGFYPSDIAVEWESN<br>GQPENNYKTTPPVLDS<br>DGSFFLYSRLTVDKSR<br>WQEGNVFSCSVMHEAL<br>HNHYTQKSLSLSLGK | | |
| IgG4 CH<br>(L325P) | 292 | ASTKGPSVFPLAPCSRS<br>TSESTAALGCLVKDYFP<br>EPVTVSWNSGALTSGV<br>HTFPAVLQSS<br>GLYSLSSVVTVPSSSLG<br>TKTYTCNVDHKPSNTK<br>VDKRVESKYGPPCPSCP<br>APEFLGGPSV<br>FLFPPKPKDTLMISRTPE<br>VTCVVVDVSQEDPEVQ<br>FNWYVDGVEVHNAKT<br>KPREEQFNSTY<br>RVVSVLTVLHQDWLN<br>GKEYKCKVSNKGLPSSI<br>EKTISKAKGQPREPQVY<br>TLPPSQEEMTK<br>NQVSLTCLVKGFYPSDI<br>AVEWESNGQPENNYKT<br>TPPVLDSDGSFFLYSRL<br>TVDKSRWQEG<br>NVFSCSVMHEALHNHY<br>TQKSLSLSPGK | | |
| Anti-PD1<br>(nVL1) | | | 118 | gagatagttatgactcaaagccccgctacattatccctgtctccgggtgaac<br>gggccaccctgtcatgccgggcttcacagtcagtgtcaagctatctggcat<br>ggtatcagcagaagcctggacaggccccaaggctactgatttatgacgcc<br>agcaaccgcgctacaggtattcctgctaggttctcagggtcaggctctgga<br>accgactttactctgactatctcctctcttgaacccgaggatttcgcggtgtac<br>tactgtcagcagtataataactggccacgcacattcggccagggcactaaa<br>gtcgaaattaag |
| Anti-PD1<br>(nVL2) | | | 119 | gagatcgtactgactcagtctccagccacattgtccctgtccccaggggag<br>cgcgccaccctgagctgtagagcttcacagtccgtcagttcttacctcgcgt<br>ggtatcagcaaaaacctggacaagctccgaggttgcttatctatgacgcctc<br>caaccgcgccactggcataccagcaaggttcagcggatctgggtccggc<br>acagattttaccctcactatttctagccttgagccggaagatttcgctgtttact<br>actgccagcagcgatccaactggcccaagacattcggccagggaactaa<br>agtggaaatcaaa |
| Anti-PD1<br>(nVL3) | 148 | EIVLTQSPATLSLSPGERAT<br>LSC RASQSVSSYLAWYQQKP<br>GQAPRLLIYDASNRANGIPA<br>RFSGSGSGTDFTLTISSLEP<br>EDFAVYYCQQSSNWPRTFGQ<br>GTKVEIKR | 120 | gaaattgtgttgacacagtctccagccaccctgtctttgtctccaggggaaa<br>gagccaccctctcctgcagggccagtcagagtgttagtagttacttagcctg<br>gtaccaacagaaacctggccaggctcccaggctcctcatctatgatgcatc<br>caacagggccaacggcatcccagccaggttcagtggcagtgggtctggg<br>acagacttcactctcaccatcagcagcctagagcctgaagatttcgcagttt<br>attactgtcagcagagtagcaactggcctcggacgttcggccaagggacc<br>aaggtggaaatcaaaaga |
| Anti-PD1<br>(pVL1) | | | 121 | cggaacgtgctgacccagtccccccttagcctccccgtc<br>acgcccggagagcccgcaagtatcagctgccgcagttca<br>caaagtctgagttcttctggatacacctatttggactgg<br>tatttgcagaagccagggcaatccccacagctcctgata<br>tacctcgcaagctggagagatagcggagtacctgatcgc<br>ttttctggtagcggatctggtacggatttcactctgaag<br>atttctagggtggaggcggaggacgtgggagtgtactac<br>tgtatgcaagccgagcagactcccggcccaggtaacacg<br>ttcggacaggggaccaaactggagattaag |
| Anti-PD1<br>(pVL2) | | | 122 | gatgtggtaatgacccagtcacctctttcactgcctgtc<br>actcccggagagccagcttcaatctcctgccgtagctct<br>caatcattgttgcacaccaatggatacaactacctccac<br>tggtatctccagaagcccggacaaagcccgcagctgctg<br>atctacctgggcagctggcaggactccggggtgcccgac |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | | | cgatttagcggcagtgggagcggcacggactttacactg aagatcagccgagtagaggcggaggacgtgggcgtttac tactgtatgcaggcagagcagacccccagaaccttcggc cagggcacccggctggaggtgaaa |
| Anti-PD1 (nVH1) | | | 123 | caggtgcagttggttgaaagcggaggaggcgtggttcaa cccggtagaagcctacggctgtcatgtgcggcctccggc ttcacatttcgatcttacggaatgcactgggtcaggcag gcacccggcaagggtctggagtgggtcgccataattttc tatgacggcagcaacaagtattacgccgacagtgttaag gggcggtttaccatcagcagagacaactctaaaaacact ctttatctgcaaatgaactctctgcgggcagaggatacc gctgtttactattgcgccagagatgacgactactggggg cagggtgccttggtgactgtgagcagc |
| Anti-PD1 (nVH2) | | | 124 | gaggtccagttagtccaaagcggcggaggcgtagtgcaa cctggcagaagcctgcggttatcgtgcgccgcaagcggc ttcacctttagctcttatggtatgcactgggtcagacag gcccctgggaagggcctggagtgggtggccgtgatctgg tatgacgggagcaacaagtattacgcggattccgtcaag ggacggttcaccatatcccgcgataacagcaagaatact ctttacttacagatgaacagcctgagggccgaggacacc gcagtatattattgcgctggcgaaggctttgactattgg ggtcagggcactctggtgactgtgagcagc |
| Anti-PD1 (nVH3) | 149 | QVQLVESGGGVVQPGRSLRL DCKASGITFSNSGMHWVRQA PGKGLEWVAVIWYDGSKRYY ADSVKGRFTISRDNSKNTLF LQMNSLRAEDTAVYYCATNN DYWGQGTLVTVSS | 125 | Caggtgcagctggtggagtctgggggaggcgtggtccag cctgggaggtccctgagactcgactgtaaagcgtctgga atcaccttcagtaactctggcatgcactgggtccgccag gctccaggcaaggggctggagtgggtggcagttatttgg tatgatggaagtaaaagatactatgcagactccgtgaag ggccgattcaccatctccagagacaattccaagaacacg ctgtttctgcaaatgaacagcctgagagccgaggacacg gctgtgtattactgtgcgacaaacaacgactactggggc cagggaaccctggtcaccgtctcctca |
| Anti-PD1 (nVH4) | 150 | QVQLVESGGGVVQPGRSLRL DCKASGITFSNSGMHWVRQA PGKGLEWVAVIWYDGSKRYY ADSVKGRFTISRDNSKNTLF LQMNSLRAEDTAVYYCARND DYWGQGTLVTVSS | 126 | caggtgcagctggtggagtctgggggaggcgtggtccag cctgggaggtccctgagactcgactgtaaagcgtctgga atcaccttcagtaactctggcatgcactgggtccgccag gctccaggcaaggggctggagtgggtggcagttatttgg tatgatggaagtaaaagatactatgcagactccgtgaag ggccgattcaccatctccagagacaattccaagaacacg ctgtttctgcaaatgaacagcctgagagccgaggacacg gctgtgtattactgtgcgagaaacgacgactactggggc cagggaaccctggtcaccgtctcctca |
| Anti-PD1 (pVH1) | 151 | QVQLVQSGAEVKKPGASVKV SCKASGYTFTGYYMHWVRQA PGQGLEWMGAINPNSGGTNY AQKFQGRVTMTRDTSISTAY MELSRLRSDDTAVYYCARRP DRANWHFDYWGQGTLVTVSS | 127 | Caggtacagctggtgcagagcggcgcagaggtgaagaag ccaggcgcttctgtaaaggtatcctgcaaggcatccggg tatactttcaccggctattacatgcactgggttcgtcag gcacccggccagggactagaatggatgggggccatcaac cctaatagtggcggtactaactacgcacaaaagtttcag gggcgagtgaccatgactcgggatacctccatctccacg gcatacatggagctgagtcgcttgcggtcagatgacact gcggtgtactactgcgctcgcaggcccgaccgagctaat tggcactttgactactggggacagggtacactggtgacc gtgtcatca |
| Anti-PD1 (pVH2) | 152 | QVQLVQSGAEVKKPGASVKV SCKASGYTFTGYYMHWVRQA PGQGLEWMGAINPNSGGTNY AQKLQGRVTMTTDTSTSTAY MELRSLRSDDTAVYYCARHG LKGDGYFDYWGQGTLVTVSS | 128 | Caggtgcagctggtccagagcggcgcggaagtgaaaaag cccggcgcttccgtgaaggtttcttgcaaagcctctgga tacacattcactggctattatatgcactgggtcagacag gcccccggccagggattggagtggatgggtgcaatcaac cccaattctggtgggaccaattacgcacagaaactccag ggccgagtgacaatgaccaccgacacttctaccagcact gcctacatggagctgcggtctctgcgatcagacgacacc gctgtgtactattgtgcaagacacgggctgaagggcgac ggctattttgactactggggacagggcacgctggttacc gtgagttcc |
| Anti-PD1 (pVH3) | 153 | QVQLVQSGVEVKKPGASVKV SCKASGYTFTNYYMYWVRQA PGQGLEWMGGINPSNGGTNF NEKFKNRVTLTTDSSTTTAY MELKSLQFDDTAVYYCARRD YRFYMGFDYWGQGTTVTVSS | 129 | caggtccagctcgtgcaaagcggagtggaagtgaaaaag cctggcgcttccgtcaaggtcagctgtaaggccagcgga tacacattcacaaactattacatgtactgggtgaggcag gctcccggacagggactggaatggatgggcggaatcaat ccctccaacggaggcacaaactttaacgaaaagtttaag aatagagtcaccctcaccacagactccagcacaaccaca gcctatatggaactgaaaagcctccagtttgacgatacc |

TABLE 4-continued

| Name | SEQ ID NO | Amino Acid Sequence | SEQ ID NO | Nucleotide Sequence |
|---|---|---|---|---|
| Non-limiting exemplary polypeptide and nucleotide sequences | | | | |
| | | | | gctgtgtattactgtgccaggagagattacaggttctac<br>atgggattcgattactggggccaaggcacaaccgtcacc<br>gtcagctcc |
| Anti-PD1<br>(pVH4) | 154 | PQVQLVQSGVEVKKPGASVKV<br>SCKASGYTFTNYYMYWVRQA<br>PGQGLEWMGGINPSNGGTNF<br>NEKFKNRVTLTTDSSTTTAY<br>MELKSLQFDDTAVYYCARRD<br>YRFNMGFDYWGQGTTVTVSS | 130 | caggtccagctcgtgcaaagcggagtggaagtgaaaaag<br>cctggcgcttccgtcaaggtcagctgtaaggccagcgga<br>tacacattcacaaactattacatgtactgggtgaggcag<br>gctcccggacagggactggaatggatgggcggaatcaat<br>ccctccaacggaggcacaaactttaacgaaaagtttaag<br>aatagagtcaccctcaccacagactccagcacaaccaca<br>gcctatatggaactgaaaagcctccagtttgacgatacc<br>gctgtgtattactgtgccaggagagattacaggttcaac<br>atgggattcgattactggggccaaggcacaaccgtcacc<br>gtcagctcc |
| Anti-PD1<br>(pVH5) | 155 | QVQLVQSGVEVKKPGASVKV<br>SCKASGYTFTNYYMYWVRQA<br>PGQGLEWMGGIQPSNGGTNF<br>NEKFKNRVTLTTDSSTTTAY<br>MELKSLQFDDTAVYYCARRD<br>YRFYMGFDYWGQGTTVTVSS | 131 | Caggtccagctcgtgcaaagcggagtggaagtgaaaaag<br>cctggcgcttccgtcaaggtcagctgtaaggccagcgga<br>tacacattcacaaactattacatgtactgggtgaggcag<br>gctcccggacagggactggaatggatgggcggaatccag<br>ccctccaacggaggcacaaactttaacgaaaagtttaag<br>aatagagtcaccctcaccacagactccagcacaaccaca<br>gcctatatggaactgaaaagcctccagtttgacgatacc<br>gctgtgtattactgtgccaggagagattacaggttctac<br>atgggattcgattactggggccaaggcacaaccgtcacc<br>gtcagctcc |
| Anti-PD1<br>(pVH6) | 156 | QVQLVQSGVEVKKPGASVKV<br>SCKASGYTFTNYYMYWVRQA<br>PGQGLEWMGGIDPSNGGTNF<br>NEKFKNRVTLTTDSSTTTAY<br>MELKSLQFDDTAVYYCARYD<br>YRFDMGFDYWGQGTTVTVSS | 132 | Caggtccagctcgtgcaaagcggagtggaagtgaaaaag<br>cctggcgcttccgtcaaggtcagctgtaaggccagcgga<br>tacacattcacaaactattacatgtactgggtgaggcag<br>gctcccggacagggactggaatggatgggcggaatcgac<br>ccctccaacggaggcacaaactttaacgaaaagtttaag<br>aatagagtcaccctcaccacagactccagcacaaccaca<br>gcctatatggaactgaaaagcctccagtttgacgatacc<br>gctgtgtattactgtgccaggtacgattacaggttcgat<br>atgggattcgattactggggccaaggcacaaccgtcacc<br>gtcagctcc |
| Ant PD1<br>(nVH7) | 157 | QVQLVESGGGVVQPGRSLRL<br>DCKASGFTFSNSGMHWVRQA<br>PGKGLEWVAVIWYDGSKRYY<br>ADSVKGRFTISRDNSKNTLF<br>LQMNSLRAEDTAVYYCATNN<br>DYWGQGTLVTVSS | 133 | caggtgcagctggtggagtctgggggaggcgtggtccag<br>cctgggaggtccctgagactcgactgtaaagcgtctgga<br>ttcaccttcagtaactctggcatgcactgggtccgccag<br>gctccaggcaaggggctggagtgggtggcagttatttgg<br>tatgatggaagtaaaagatactatgcagactccgtgaag<br>ggccgattcaccatctccagagacaattccaagaacacg<br>ctgtttctgcaaatgaacagcctgagagccgaggacacg<br>gctgtgtattactgtgcgacaaacaacgactactggggc<br>cagggaaccctggtcaccgtctcctca |
| Anti-PD1<br>(nVH8) | 158 | EVQLVQSGGGVVQPGRSLRL<br>SCAASGFTFSSYGMHWVRQA<br>PGKGLEWVAVIWYDGSNKYY<br>ADSVKGRFTISRDNSKNTLY<br>LQMNSLRAEDTAVYYCATNN<br>DYWGQGTLVTVSS | 134 | gaggtccagttagtccaaagcggcggaggcgtagtgcaa<br>cctggcagaagcctgcggttatcgtgcgccgcaagcggc<br>ttcacctttagctcttatggtatgcactgggtcagacag<br>gcccctgggaagggcctggagtgggtggccgtgatctgg<br>tatgacgggagcaacaagtattacgcggattccgtcaag<br>ggacggttcaccatatcccgcgataacagcaagaatact<br>ctttacttacagatgaacagcctgagggccgaggacacc<br>gcagtatattattgcgctaccaataatgactattggggt<br>cagggcactctggtgactgtgagcagc |
| Anti-PD1<br>(nVH9) | 159 | EVQLVQSGGGVVQPGRSLRL<br>SCAASGITFSNSMHWVRQAP<br>GKGLEWVAVI<br>WYDGSKRYYADSVKGRFTIS<br>RDNSKNTLYLQMNSLRAEDT<br>AVYYCATNND<br>YWGQGTLVTVSS | 135 | gaggtgcaactggttcagtccggcgggggcgtcgtccag<br>ccggggcgcagtctgcgcttgagctgtgctgcctctggg<br>attacctttagcaactccatgcattgggtgcggcaggca<br>cccgggaagggactggaatgggtcgcagtgatctggtac<br>gatggatcaaagcggtattacgccgactccgtcaaaggc<br>cggttcacaatcagccgcgacaacagcaaaaatacttta<br>tatcttcagatgaattcccttagggcagaggatactgct<br>gtgtattactgcgctactaacaacgattattgggggcag<br>gggacactagtcactgtttctagt |
| Anti-PD1<br>(nVH10) | 160 | EVQLVQSGGGVVQPGRSLRL<br>SCAASGFTFSNSGMHWVRQA<br>PGKGLEWVAVIWYDGSNKYY<br>ADSVKGRFTISRDNSKNTLY<br>LQMNSLRAEDTAVYYCATNN<br>DYWGQGTLVTVSS | 136 | gaggtccagttagtccaaagcggcggaggcgtagtgcaa<br>cctggcagaagcctgcggttatcgtgcgccgcaagcggc<br>ttcacctttagcaattctggtatgcactgggtcagacag<br>gcccctgggaagggcctggagtgggtggccgtgatctgg<br>tatgacgggagcaacaagtattacgcggattccgtcaag<br>ggacggttcaccatatcccgcgataacagcaagaatact<br>ctttacttacagatgaacagcctgagggccgaggacacc |

TABLE 4-continued

| Non-limiting exemplary polypeptide and nucleotide sequences | | | | |
|---|---|---|---|---|
| Name | SEQ ID NO | Amino Acid Sequence | SEQ ID NO | Nucleotide Sequence |
| | | | | gcagtatattattgcgctaccaataatgactattggggt cagggcactctggtgactgtgagcagc |
| Anti-PD1 (nVH11) | 161 | EVQLVQSGGGVVQPGRSLRL SCAASGFTFSSYGMHWVRQA PGKGLEWVAVIWYDGSKYYA DSVKGRFTISRDNSKNTLYL QMNSLRAEDTAVYYCATNND YWGQGTLVTVSS | 137 | gaggtccagttagtccaaagcggcggaggcgtagtgcaa cctggcagaagcctgcggttatcgtgcgccgcaagcggc ttcacctttagctcttatggtatgcactgggtcagacag gcccctgggaagggcctggagtgggtggccgtgatctgg tatgacgggagcaagtattacgcggattccgtcaaggga cggttcaccatatcccgcgataacagcaagaatactctt tacttacagatgaacagcctgagggccgaggacaccgca gtatattattgcgctaccaataatgactattggggtcag ggcactctggtgactgtgagcagc |
| Anti-PD1 (nVH12) | 162 | QVQLVESGGGVVQPGRSLRL DCKASGITFSNSGMHWVRQA PGKGLEWVAVIWYDGSNKRY YADSVKGRFTISRDNSKNTL FLQMNSLRAEDTAVYYCATN NDYWGQGTLVTVSS | 138 | caggtgcagctggtggagtctggggggaggcgtggtccag cctgggaggtccctgagactcgactgtaaagcgtctgga atcaccttcagtaactctggcatgcactgggtccgccag gctccaggcaaggggctggagtgggtggcagttatttgg tatgatggaagtaacaaaagatactatgcagactccgtg aagggccgattcaccatctccagagacaattccaagaac acgctgtttctgcaaatgaacagcctgagagccgaggac acggctgtgtattactgtgcgacaaacaacgactactgg ggccagggaaccctggtcaccgtctcctca |
| Anti-PD1 (nVH12) | 163 | QVQLVESGGGVVQPGRSLRL DCKASGFTFSNSGMHWVRQA PGKGL | 139 | caggtgcagctggtggagtctggggggaggcgtggtccag cctgggaggtccctgagactcgactgtaaagcgtctgga ttcaccttcagtaactctggcatgcactgggtccgccag gctccaggcaaggggctggagtgggtggcagttatttgg tatgatggaagtaacaaaagatactatgcagactccgtg aagggccgattcaccatctccagagacaattccaagaac acgctgtttctgcaaatgaacagcctgagagccgaggac acggctgtgtattactgtgcgacaaacaacgactactgg ggccagggaaccctggtcaccgtctcctca |
| Anti-PD1 (nVH14) | 164 | EVQLVQSGGGVVQPGRSLRL SCAASGITFSNSGMHWVRQA PGKGLEWVAVIWYDGSKYYA DSVKGRFTISRDNSKNTLYL QMNSLRAEDTAVYYCATNND YWGQGTLVTVSS | 140 | gaggtgcaacttgtgcaaagcggcggcggagtcgtgcag cccggtcgatctcttcgcctgagttgtgctgccagcggc attacctttagcaattctggtatgcactgggtacgtcag gccccccggtaaggggctagaatgggtggctgtgatttgg tacgatggttctaagtactacgccgacagcgttaaaggc cgattcaccatcagtagagacaacagtaagaacaccctc tacctccagatgaacagtctgcgagctgaagacactgct gtgtactactgtgccaccaacaacgactactggggacag ggaaccctggtcaccgtgagtagt |

TABLE 12

Exemplary anti-TGFβ VH and VL Sequences

Table 12 provides exemplary TGFβ receptor sequences for use in anti-PD1 fusion proteins described herein. In any embodiments exemplifying a fusion protein with, e.g., a TGFβII ECD, an anti-TGFβ antibody (e.g., scFv, Fab), may be employed instead.

| Name | SEQ ID NO | Amino Acid Sequence | SEQ ID NO | Nucleotide Sequence |
|---|---|---|---|---|
| Anti-TGFb clone 1 VL | 165 | DIMMTQSPSS LAVSAGEKVT MSCKSSQSVL YSSNQKNYLA WYQQKPGCSP KLLIYWASTR ESGVPDRFTG SGSGTDFTLT ISSVQAEDLA VYYCHQYLSS DTFGGGTKLE IKRTVA | 179 | gat ata atg atg aca cag agc ccc agc tct cta gct gtg agt gct ggc gag aag gtg acc atg agc tgt aag agc agt caa agc gtg ctg tac agt tcc aat cag aaa aat tac ctc gca tgg tat cag cag aag cca ggt caa agc cct aag ctc ctt atc tac tgg gcc tca acc cgt gaa agt gga gtg cct gac aga ttt act ggt tca ggg agc ggc acc gat ttc act ctg act att agc tct gtg cag gca gaa gac ctt gcc gtg tat tac tgt cac cag tat ctg tct tca gac acg ttt gga ggt ggg acc aaa cta gaa atc aaa cgt act gtc gca |
| Anti-TGFb clone 1 VH | 166 | QVXLXQSGAE LVRPGTSVKV SCKASGYAFT NYLIEWVKQR | 180 | caggtgnnnctgnnncagagcggcgccgagctggtgagg cccggcaccagcgtgaaggtg agctgcaaggccagcggctacgccttcaccaactacctg atcgagtgggtgaagcagagg |

TABLE 12-continued

Exemplary anti-TGFβ VH and VL Sequences
Table 12 provides exemplary TGFβ receptor sequences for use in anti-PD1 fusion proteins described herein. In any embodiments exemplifying a fusion protein with, e.g., a TGFβII ECD, an anti-TGFβ antibody (e.g., scFv, Fab), may be employed instead.

| Name | SEQ ID NO | Amino Acid Sequence | SEQ ID NO | Nucleotide Sequence |
|---|---|---|---|---|
| | | PGQGLEWIGV NNPGSGGSNY NEKFKGKATL TADKSSSTAY MQLSSLTSDD SAVYFCARSG GFYFDYWGQG TTQSPSPQPK RRAH | | cccggccagggcctggagtggatcggcgtgaacaacccc ggcagcggcggcagcaactac aacgagaagttcaagggcaaggccaccctgaccgccgac aagagcagcagcaccgcctac atgcagctgagcagcctgaccagcgacgacagcgccgtg tacttctgcgccaggagcggc ggcttctacttcgactactggggccagggcaccacccag agccccagcccccagcccaag aggagggcccac |
| Anti-TGFb clone 2 VL | 167 | DIQMTQSPSS LSASVGDRVT ITCRASQSVL YSSNQKNYLA WYQQKPGKAP KLLIYWASTR ESGVPSRFSG SGSGTDFTLT ISSLQPEDFA TYYCHQYLSS DTFGQGTKVE IKRTVA | 181 | gacatccagatgacccagagccccagcagcctgagcgcc agcgtgggcgacagggtgacc atcacctgcagggccagccagagcgtgctgtacagcagc aaccagaagaactacctggcc tggtaccagcagaagcccggcaaggcccccaagctgctg atctactgggccagcaccagg gagagcggcgtgcccagcaggttcagcggcagcggcagc ggcaccgacttcaccctgacc atcagcagcctgcagcccgaggacttcgccacctactac tgccaccagtacctgagcagc gacaccttcggccagggcaccaaggtggagatcaagagg accgtggcc |
| Anti-TGFb clone 2 VH | 168 | EVQLVESGGG LVQPGGSLRL SCAASGYAFT NYLIEWVRQA PGKGLEWVGV NNPGSGGSNY NEKFKGRATI SADNSKNTLY LQMNSLRAED TAVYYCARSG GFYFDYWGQG TLVTVSSAST KGPS | 182 | gaggtgcagctggtggagagcggcggcggcctggtgcag cccggcggcagcctgaggctg agctgcgccgccagcggctacgccttcaccaactacctg atcgagtgggtgaggcaggcc cccggcaagggcctggagtgggtgggcgtgaacaacccc ggcagcggcggcagcaactac aacgagaagttcaagggcagggccaccatcagcgccgac aacagcaagaacaccctgtac ctgcagatgaacagcctgagggccgaggacaccgccgtg tactactgcgccaggagcggc ggcttctacttcgactactggggccagggcaccctggtg accgtgagcagcgccagcacc aagggccccagc |
| Anti-TGFb clone 3 VH | 169 | LARPGASVKM SCKTSGYTFT NYWMHWVRQR PGQGLEWIGT IYPGNSDTNY NQKFKDKAKL TAVTSATTAY MELSSLTNED SAVYFCTRED SRSLYYNGWD YFDYWGQGTT LTVSS | 183 | ctggccaggcccggcgccagcgtgaagatgagctgcaag accagcggctacaccttcacc aactactggatgcactgggtgaggcagaggcccggccag ggcctggagtggatcggcacc atctaccccggcaacagcgacaccaactacaaccagaag ttcaaggacaaggccaagctg accgccgtgaccagcgccaccaccgcctacatggagctg agcagcctgaccaacgaggac agcgccgtgtacttctgcaccagggaggacagcaggagc ctgtactacaacggctgggac tacttcgactactggggccagggcaccaccctgaccgtg agcagc |
| Anti-TGFb clone 3 VL | 170 | LTQSPASLAV SLGQRATISC RASESVDNYG ISFLNWFQQK PGQPPKLLIY AASNQGSGVP ARFSGSGSGT DFSLNIHPME EDDTGMYFCQ QSKEVPRTFG GGTKLEII | 184 | ctgacccagagccccgccagcctggccgtgagcctgggc cagagggccaccatcagctgc agggccagcgagagcgtggacaactacggcatcagcttc ctgaactggttccagcagaag cccggccagccccccaagctgctgatctacgccgccagc aaccagggcagcggcgtgccc gccaggttcagcggcagcggcagcggcaccgacttcagc ctgaacatccaccccatggag gaggacgacaccggcatgtacttctgccagcagagcaag gaggtgcccaggaccttcggc ggcggcaccaagctggagatcatc |
| Anti-TGFb clone 4 VH | 171 | QVQLVQSGAEVKKPGSSVKV SCKASGGTFSSYAISWVRQA PGQGLEWMGGIIPIFGTAN YAQKFQGRVTITADESTSTA YMELSSLRSEDTAVYYCARG LWEVRALPSVYWGQGTLVTV SS | 185 | caggtgcagctggtgcagagcggcgccgaggtgaagaag cccggcagcagcgtgaaggtg agctgcaaggccagcggcggcaccttcagcagctacgcc atcagctgggtgaggcaggcc cccggccagggcctggagtggatgggcggcatcatcccc atcttcggcaccgccaactac gcccagaagttccagggcagggtgaccatcaccgccgac gagagcaccagcaccgcctac atggagctgagcagcctgaggagcgaggacaccgccgtg |

TABLE 12-continued

Exemplary anti-TGFβ VH and VL Sequences
Table 12 provides exemplary TGFβ receptor sequences for use in anti-PD1 fusion proteins described herein. In any embodiments exemplifying a fusion protein with, e.g., a TGFβII ECD, an anti-TGFβ antibody (e.g., scFv, Fab), may be employed instead.

| Name | SEQ ID NO | Amino Acid Sequence | SEQ ID NO | Nucleotide Sequence |
|---|---|---|---|---|
| | | | | tactactgcgccaggggcctg tgggaggtgagggccctgcccagcgtgtactggggccag ggcaccctggtgaccgtgagc agc |
| Anti-TGFb clone 4 VL | 172 | SYELTQPPSVSVAPGQTARI TCGANDIGSKSVHWYQQKAG QAPVLVVSEDIIRPSGIPER I SGSNSGNTATLTISRVEAGD EADYYCQVWDRDSDQYVFGT GTKVTVLG | 186 | agctacgagctgacccagcccccagcgtgagcgtggcc cccggccagaccgccaggatc acctgcggcgccaacgacatcggcagcaagagcgtgcac tggtaccagcagaaggccggc caggcccccgtgctggtggtgagcgaggacatcatcagg cccagcggcatccccgagagg atcagcggcagcaacagcggcaacaccgccaccctgacc atcagcagggtggaggccggc gacgaggccgactactactgccaggtgtgggacagggac agcgaccagtacgtgttcggc accggcaccaaggtgaccgtgctgggc |
| Anti-TGFb clone 5 VH | 173 | QVQLVQSGAE VKKPGSSVKV SCKASGYTFS SNVISWVRQA PGQGLEWMGG VIPIVDIANY AQRFKGRVTI TADESTSTTY MELSSLRSED TAVYYCASTL GLVLDAMDYW GQGTLVTVSS | 187 | caggtgcagctggtgcagagcggcgccgaggtgaagaag cccggcagcagcgtgaaggtg agctgcaaggccagcggctacaccttcagcagcaacgtg atcagctgggtgaggcaggcc cccggccagggcctggagtggatgggcggcgtgatcccc atcgtggacatcgccaactac gcccagaggttcaagggcagggtgaccatcaccgccgac gagagcaccagcaccacctac atggagctgagcagcctgaggagcgaggacaccgccgtg tactactgcgccagcaccctg ggcctggtgctggacgccatggactactggggccagggc accctggtgaccgtgagcagc |
| Anti-TGFb clone 5 VL | 174 | ETVLTQSPGT LSLSPGERAT LSCRASQSLG SSYLAWYQQK PGQAPRLLIY GASSRAPGIP DRFSGSGSGT DFTLTISRLE PEDFAVYYCQ QYADSPITFG QGTRLEIK | 188 | gagaccgtgctgacccagagccccggcaccctgagcctg agccccggcgagagggccacc ctgagctgcagggccagccagagcctgggcagcagctac ctggcctggtaccagcagaag cccggccaggcccccaggctgctgatctacggcgccagc agcagggcccccggcatcccc gacaggttcagcggcagcggcagcggcaccgacttcacc ctgaccatcagcaggctggag cccgaggacttcgccgtgtactactgccagcagtacgcc gacagccccatcaccttcggc cagggcaccaggctggagatcaag |
| Anti-TGFb clone 6 VH | 175 | QVQLVQSGAE VKKPGSSVKV SCKASGYTFS SNVISWVRQA PGQGLEWMGG VIPIVDIANY AQRFKGRVTI TADESTSTTY MELSSLRSED TAVYYCALPR AFVLDAMDYW GQGTLVTVSS | 189 | caggtgcagctggtgcagagcggcgccgaggtgaagaag cccggcagcagcgtgaaggtg agctgcaaggccagcggctacaccttcagcagcaacgtg atcagctgggtgaggcaggcc cccggccagggcctggagtggatgggcggcgtgatcccc atcgtggacatcgccaactac gcccagaggttcaagggcagggtgaccatcaccgccgac gagagcaccagcaccacctac atggagctgagcagcctgaggagcgaggacaccgccgtg tactactgcgccctgcccagg gccttcgtgctggacgccatggactactggggccagggc accctggtgaccgtgagcagc |
| Anti-TGFb clone 6 VL | 176 | ETVLTQSPGT LSLSPGERAT LSCRASQSLG SSYLAWYQQK PGQAPRLLIY GASSRAPGIP DRFSGSGSGT DFTLTISRLE PEDFAVYYCQ QYADSPITFG QGTRLEIK | 190 | gagaccgtgctgacccagagccccggcaccctgagcctg agccccggcgagagggccacc ctgagctgcagggccagccagagcctgggcagcagctac ctggcctggtaccagcagaag cccggccaggcccccaggctgctgatctacggcgccagc agcagggcccccggcatcccc gacaggttcagcggcagcggcagcggcaccgacttcacc ctgaccatcagcaggctggag cccgaggacttcgccgtgtactactgccagcagtacgcc gacagccccatcaccttcggc cagggcaccaggctggagatcaag |
| Anti-TGFb clone 7 VH | 177 | QVQLVQSGAE VKKPGSSVKV SCKASGGTFS TSFINWVRQA | 191 | caggtgcagctggtgcagagcggcgccgaggtgaagaag cccggcagcagcgtgaaggtg agctgcaaggccagcggcggcaccttcagcaccagcttc atcaactgggtgaggcaggcc |

TABLE 12-continued

Exemplary anti-TGFβ VH and VL Sequences
Table 12 provides exemplary TGFβ receptor sequences for use in anti-PD1 fusion proteins described herein. In any embodiments exemplifying a fusion protein with, e.g., a TGFβII ECD, an anti-TGFβ antibody (e.g., scFv, Fab), may be employed instead.

| Name | SEQ ID NO | Amino Acid Sequence | SEQ ID NO | Nucleotide Sequence |
|---|---|---|---|---|
| | | PGQGLEWMGG IIPIFDITNY AQKFQSRVTI TADKSTSTAY MELSSLRSED TAVYYCARGN GNYALDAMDY WGQGTLVTVS S | | cccggccagggcctggagtggatgggcggcatcatcccc atcttcgacatcaccaactac gcccagaagttccagagcagggtgaccatcaccgccgac aagagcaccagcaccgcctac atggagctgagcagcctgaggagcgaggacaccgccgtg tactactgcgccaggggcaac ggcaactacgccctggacgccatggactactggggccag ggcaccctggtgaccgtgagc agc |
| Anti-TGFb clone 7 VL | 178 | EIVLTQSPGT LSLSPGERAT LSCRASQSVS SSYFAWYQQK PGQAPRLLIY GASSRATGIP DRFSGSGSGT DFTLTISRLE PEDFAVYYCQ QYYDSPITFG QGTRLEIK | 192 | gagatcgtgctgacccagagccccggcaccctgagcctg agccccggcgagagggccacc ctgagctgcagggccagccagagcgtgagcagcagctac ttcgcctggtaccagcagaag cccggccaggcccccaggctgctgatctacggcgccagc agcagggccaccggcatcccc gacaggttcagcggcagcggcagcggcaccgacttcacc ctgaccatcagcaggctggag cccgaggacttcgccgtgtactactgccagcagtactac gacagccccatcaccttcggc cagggcaccaggctggagatcaag |

TABLE 13

Exemplary TGFβ1 Inhibitory Peptide and Nucleotide Sequences
Table 13 provides exemplary TGFβ1 inhibitory peptides for use in anti-PD1 fusion proteins described herein. In any embodiments exemplifying a fusion protein with, e.g., a TGFβRII ECD, a TGFβ1 inhibitory peptides may be employed instead.

| Name | SEQ ID NO | Amino acid sequence | SEQ ID NO | Nucleotide sequence |
|---|---|---|---|---|
| TGFb1-136 | 263 | HANFCLGPCPYI WSLA | 268 | CACGCCAACTTCTGCCTGGGCCCCTGCCCCTACATCT GGAGCCTGGCC |
| TGFb1-137 | 264 | FCLGPCPYIWSL DTA | 269 | TTCTGCCTGGGCCCCTGCCCCTACATCTGGAGCCTGG ACACCGCC |
| TGFb1-138 | 265 | SNPYSAFQVDII VDIA | 270 | AGCAACCCCTACAGCGCCTTCCAGGTGGACATCATC GTGGACATCGCC |
| TGFb1-139 | 266 | TSLDATMIWTM MA | 271 | ACCAGCCTGGACGCCACCATGATCTGGACCATGATG GCC |
| TGFb1-140 | 267 | TSLDASIWAMM QNA | 272 | ACCAGCCTGGACGCCAGCATCTGGGCCATGATGCAG AACGCC |

TABLE 14

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| ADA2 mutant 1 | 273 | IDETRAHLLLKEKMMRLGGR LVLNTKEELANERLMTLKIA EMKEAMRTLIFPPSMHFFQA KHLIERSQVFNILRMMPKGA ALHLHDIGIVTMDWLVRNVT | | |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | YRPHGIALPGDSLLRNFTLV TQHPEVIYTNQNVVLSKFET IFFTISGLIHYAPVFRDYVF RSMQEFYEDNVLYMEIRASL LPVYELSGEHHDEEWSVKTY QEVAQDFVETHPEFIGIKII YSDHRSKDVAVIAESIRMAM GLRIKFPTVVAGFDLVGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 2 | 274 | IDETRAHLLLKEKMMRLGGR LVLNTKEELANERLMTLKIA EMKEAMRTLIFPPSMHFFQA KHLIERSQVFNILRMMPKGA ALHLHDIGIVTMDWLVRNVT YRPHGIALPGDSLLRNFTLV TQHPEVIYTNQNVVWSKFET IVFTISGLIHYAPVFRDYVF RSMQEFYEDNVLYMEIRARL LPVYELSGEHHDEEWSVKTY QEVAQDFVETHPEFIGIKII YSDHRSKDVAVIAESIRMAM GLRIKFPTVVAGFDLAGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 3 | 275 | EMKEAMRTLIFPPSMHFFQA KHLIERSQVFNILRMMPKGA ALHLHDIGIVTMDWLVRNVT YRPHGIALPGDSLLRNFTLV TQHPEVIYTNQNVVLSKFET IVFTISGLIHYAPVFRDYVF RSMQEFYEDNVLYMEIRARL LPVYELSGEHHDEEWSVKTY QEVAQDFVETHPEFIGIKII YSDHRSKDVAVIAESIRMAM GLRIKFPTVVAGFDLVGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 4 | 276 | IDETRAHLLLKEKMMRLGGR LVLNTKEELANERLMTLKIA EMKEAMRTLIFPPSMHFFQA KHLIERSQVFNILRMMPKGA ALHLHDIGIVTMDWLGGGGS GGGGSVTEFDDSLLRNFTLV | | |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | TQHPEVIYTNQNVVWSKFET IFFTISGLIHYAPVFRDYVF RSMQEFYEDNVLYMEIRARL LPVYELSGEHHDEEWSVKTY QEVAQEFVETHPEFIGIKII YSDHRSRDVAVIAESIRMAM GLRIKFPTVVAGFDLSGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 5 | 277 | IDETRAHLLLKEKMMRLGGR LVLNTKEELANERLMTLKIA EMKEAMRTLIFPPSMHFFQA KHLIERSQVFNILRMMPKGA ALHLHNIGIVTMDWLGGGGS GGGGSVTEFDDSLLRNFTLV TQHPEVIYTNQNVVWSKFET IFFTISGLIHYAPVFRDYVF RSMQEEYEDNVLYMEIRARL LPVYELSGEHHDEEWSVKTY QEVAQDFVETHPEFIGIKII YSDHRSYDVAVIAESIRMAM GLRIKFPTVVAGFDLVGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 6 | 278 | IDETRAHLLLKEKMMRLGGR LVLNTKEELANERLMTLKIA EMKEAMRTLIFPPSMHFFQA KHLIERSQVFNILRMMPKGA ALHLHDIGIVTMDWLVRNVT YRPHCHICFTPRGIMQFRFA HPTPRPSEKCSKWILLEDYR KRVQNVTEFDDSLLRNFTLV TQHPEVIYTNQNVVWSKFET IFFTISGLIHYAPVFRDYVF RSMQEFYEDNVLYMEIRARL LPVYELSGEHHDEEWSVKTY QEVAQKFVETHPEFIGIKII YSDHRSKDVAVIAESIRMAM GLRIKFPTVVAGFDLVGHED TGHSLHDYKEALMIPAKDGV KLPYFFHAGETDWQGTSIDR NILDALMLNTTRIGHGFALS KHPAVRTYSWKKDIPIEVCP ISNQVLKLVSDLRNHPVATL MATGHPMVISSDDPAMFGAK GLSYDFYEVFMGIGGMKADL RTLKQLAMNSIKYSTLLESE KNTFMEIWKKRWDKFIADVA TK | | |
| ADA2 mutant 7 | 279 | IDETRAHLLLKEKMMRLGGR LVLNTKEELANERLMTLKIA EMKEAMRTLIFPPSMHFFQA | | |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | KHLIERSQVFNILRMMPKGA<br>ALHLHDIGIVTMDWLVRNVT<br>YRPHCHICFTPRGIMQFRFA<br>HPTPRPSEKCSKWILLEDYR<br>KRVQNVTEFDDSLLRNFTLV<br>TQHPEVIYTNQNVVWSKFET<br>IFFTISGLIHYAPVFRDYVF<br>RSMQEFYEDNVLYMEIRAQL<br>LPVYELSGEHHDEEWSVKTY<br>QEVAQKFVETHPEFIGIKII<br>YNDHRSKDVAVIAESIRMAM<br>GLRIKFPTVVAGFDLVGHED<br>TGHSLHDYKEALMIPAKDGV<br>KLPYFFHAGETDWQGTSIDR<br>NILDALMLNTTRIGHGFALS<br>KHPAVRTYSWDKDIPIEVCP<br>ISNQVLKLVSDLRNHPVATL<br>MATGHPMVISSDDPAMFGAK<br>GLSYDFYEVFMGIGGMKADL<br>RTLKQLAMNSIKYSTLLESE<br>KNTFMEIWKKRWDKFIADVA<br>TK | | |
| VH6<br>ADA2 | 280 | QVQLVESGGGVVQPGRSLRL<br>DCKASGITFSNSGMHWVRQA<br>PGKGLEWVAV<br>IWYDGSKRYYADSVKGRFTI<br>SRDNSKNTLFLQMNSLRAED<br>TAVYYCATND<br>DYWGQGTLVTVSSASTKGPS<br>VFPLAPCSRSTSESTAALGC<br>LVKDYFPEPV<br>TVSWNSGALTSGVHTFPAVL<br>QSSGLYSLSSVVTVPSSSLG<br>TKTYTCNVDH<br>KPSNTKVDKRVESKYGPPCP<br>PCPAPEFLGGPSVFLFPPKP<br>KDTLMISRTP<br>EVTCVVVDVSQEDPEVQFNW<br>YVDGVEVHNAKTKPREEQFN<br>STYRVVSVLT<br>VLHQDWLNGKEYKCKVSNKG<br>LPSSIEKTISKAKGQPREPQ<br>VYTLPPSQEE<br>MTKNQVSLTCLVKGFYPSDI<br>AVEWESNGQPENNYKTTPPV<br>LDSDGSFFLY<br>SRLTVDKSRWQEGNVFSCSV<br>MHEALHNHYTQKSLSLSPGK<br>GGGGSGGGGS<br>IDETRAHLLLKEKMMRLGGR<br>LVLNTKEELANERLMTLKIA<br>EMKEAMRTLI<br>FPPSMHFFQAKHLIERSQVF<br>NILRMMPKGAALHLHDIGIV<br>TMDWLVRNVT<br>YRPHCHICFTPRGIMQFRFA<br>HPTPRPSEKCSKWILLEDYR<br>KRVQNVTEFD<br>DSLLRNFTLVTQHPEVIYTN<br>QNVVWSKFETIFFTISGLIH<br>YAPVFRDYVF<br>RSMQEEYEDNVLYMEIRARL<br>LPVYELSGEHHDEEWSVKTY<br>QEVAQKFVET<br>HPEFIGIKIIYSDHRSKDVA<br>VIAESIRMAMGLRIKFPTVV<br>AGFDLVGHED<br>TGHSLHDYKEALMIPAKDGV<br>KLPYFFHAGETDWQGTSIDR<br>NILDALMLNT | 285 | CAGGTGCAGCTGGTCGAAAGCGGAGGAGGAGTGGTCCAG<br>CCAGGACGATCCCTGAGACTGGATTGTAAGGCCTCTGGA<br>ATCACATTCTCTAACAGTGGAATGCACTGGGTGCGCCAG<br>GCACCAGGAAAAGGACTGGAGTGGGTGGCCGTCATCTGG<br>TACGACGGGTCAAAGCGATACTATGCAGATAGCGTGAAA<br>GGAAGGTTCACAATTTCACGCGACAACAGCAAGAATACT<br>CTGTTTCTGCAGATGAACTCTCTGAGAGCAGAGGATACT<br>GCCGTGTACTATTGTGCTACCAATGACGATTATTGGGGG<br>CAGGGAACTCTGGTGACCGTCAGTTCAGCTAGCACCAAG<br>GGCCCATCGGTCTTCCCCCTGGCGCCCTGCTCCAGGAGC<br>ACCTCCGAGAGCACAGCCGCCCTGGGCTGCCTGGTCAAG<br>GACTACTTCCCCGAACCGGTGACGGTGTCGTGGAACTCA<br>GGCGCCCTGACCAGCGGCGTGCACACCTTCCCGGCTGTC<br>CTACAGTCCTCAGGACTCTACTCCCTCAGCAGCGTGGTG<br>ACCGTGCCCTCCAGCAGCTTGGGCACGAAGACCTACACC<br>TGCAACGTAGATCACAAGCCCAGCAACACCAAGGTGGAC<br>AAGAGAGTTGAGTCCAAATATGGTCCCCCATGCCCACCA<br>TGCCCAGCACCTGAGTTCCTGGGGGGACCATCAGTCTTC<br>CTGTTCCCCCCAAAACCCAAGGACACTCTCATGATCTCC<br>CGGACCCCTGAGGTCACGTGCGTGGTGGTGGACGTGAGC<br>CAGGAAGACCCCGAGGTCCAGTTCAACTGGTACGTGGAT<br>GGCGTGGAGGTGCATAATGCCAAGACAAAGCCGCGGGAG<br>GAGCAGTTCAACAGCACGTACCGTGTGGTCAGCGTCCTC<br>ACCGTCCTGCACCAGGACTGGCTGAACGGCAAGGAGTAC<br>AAGTGCAAGGTCTCCAACAAAGGCCTCCCGTCCTCCATC<br>GAGAAAACCATCTCCAAAGCCAAAGGGCAGCCCCGAGAG<br>CCACAGGTGTACACCCTGCCCCCATCCCAGGAGGAGATG<br>ACCAAGAACCAGGTCAGCCTGACCTGCCTGGTCAAAGGC<br>TTCTACCCCAGCGACATCGCCGTGGAGTGGGAGAGCAAT<br>GGGCAGCCGGAGAACAACTACAAGACCACGCCTCCCGTG<br>CTGGACTCCGACGGCTCCTTCTTCCTCTACAGCAGGCTC<br>ACCGTGGACAAGAGCAGGTGGCAGGAGGGGAATGTCTTC<br>TCATGCTCCGTGATGCATGAGGCTCTGCACAACCACTAC<br>ACACAGAAGAGCCTCTCCCTGTCTCCGGGTAAAGGTGGA<br>GGTGGTTCTGGAGGTGGAGGTAGTATCGACGAAACCAGA<br>GCACACTTACTGCTGAAAGAGAAAATGATGCGCCTGGGC<br>GGGAGATTGGTGTTAAATACTAAGGAAGAGCTGGCAAAT<br>GAAAGACTCATGACACTGAAGATTGCTGAAATGAAGGAG<br>GCGATGAGGACGCTGATCTTTCCGCCTTCCATGCACTTC<br>TTCCAAGCTAAACACCTGATCGAAAGATCCCAAGTGTTT<br>AACATCCTGAGGATGATGCCTAAGGGGGCCGCTCTGCAC<br>CTTCACGATATTGGGATTGTAACAATGGACTGGCTGGTA<br>AGGAACGTGACATACAGACCTCATTGCCATATTTGTTTT<br>ACTCCCCGAGGAATCATGCAATTCAGGTTTGCCCACCCA<br>ACTCCTCGGCCAAGCGAGAAGTGTAGTAAGTGGATTTTG<br>CTGGAAGATTACCGTAAGCGCGTGCAGAATGTGACAGAG<br>TTTGATGACTCCCTGCTCCGCAATTTTACCCTGGTGACC<br>CAGCACCCCGAAGTTATATACACTAACCAAAATGTCGTG |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | TRIGHGFALSKHPAVRTYSW KKDIPIEVCPISNQVLKLVS DLRNHPVATL MATGHPMVISSDDPAMFGAK GLSYDFYEVFMGIGGMKADL RTLKQLAMNS IKYSTLLESEKNTFMEIWKK RWDKFIADVATK | | TGGTCCAAGTTTGAGACGATCTTCTTCACGATTTCAGGC TTGATCCACTACGCCCCGGTCTTTCGGGATTATGTGTTT AGGAGTATGCAGGAGTTTTATGAGGATAATGTTCTGTAC ATGGAGATCCGAGCCCGGCTGCTTCCAGTCTACGAACTA TCCGGCGAACACCATGACGAGGAATGGAGCGTCAAGACC TATCAAGAGGTGGCCCAGAAGTTCGTAGAAACGCATCCA GAGTTCATCGGTATTAAGATTATCTACTCTGATCACCGC TCAAAGGATGTGGCTGTCATCGCCGAGTCTATACGGATG GCCATGGGCCTGCGGATTAAGTTCCCTACCGTCGTCGCC GGATTCGACCTCGTTGGGCATGAGGATACTGGCCATAGT CTCCATGACTATAAAGAAGCCCTTATGATCCCAGCAAAG GACGGAGTGAAGCTGCCCTACTTCTTCCACGCAGGGGAG ACCGACTGGCAGGGAACGAGCATCGACCGGAACATACTT GATGCACTCATGCTTAATACCACACGAATCGGCCACGGC TTCGCTCTCTCCAAGCACCCAGCCGTGAGAACCTACAGC TGGAAGAAGGATATCCCCATCGAGGTTTGTCCCATCAGC AATCAGGTGCTGAAATTGGTGAGTGACCTGAGAAACCAC CCAGTCGCAACATTAATGGCCACTGGCCACCCTATGGTG ATTTCAAGCGATGATCCAGCCATGTTCGGAGCAAAAGGA CTCAGTTACGACTTCTATGAGGTATTCATGGGTATTGGT GGTATGAAGGCAGACCTGCGGACTCTTAAGCAGTTGGCA ATGAACTCAATTAAGTACTCTACCTTATTGGAGTCTGAA AAGAACACATTTATGGAGATCTGGAAAAAGCGCTGGGAC AAATTCATCGCAGATGTTGCCACAAAA |
| VH6 ADA2 mut 7 | 281 | QVQLVESGGGVVQPGRSLRL DCKASGITFSNSGMHWVRQA PGKGLEWVAV IWYDGSKRYYADSVKGRFTI SRDNSKNTLFLQMNSLRAED TAVYYCATND DYWGQGTLVTVSSASTKGPS VFPLAPCSRSTSESTAALGC LVKDYFPEPV TVSWNSGALTSGVHTFPAVL QSSGLYSLSSVVTVPSSSLG TKTYTCNVDH KPSNTKVDKRVESKYGPPCP PCPAPEFLGGPSVFLFPPKP KDTLMISRTP EVTCVVVDVSQEDPEVQFNW YVDGVEVHNAKTKPREEQFN STYRVVSVLT VLHQDWLNGKEYKCKVSNKG LPSSIEKTISKAKGQPREPQ VYTLPPSQEE MTKNQVSLTCLVKGFYPSDI AVEWESNGQPENNYKTTPPV LDSDGSFFLY SRLTVDKSRWQEGNVFSCSV MHEALHNHYTQKSLSLSPGK GGGGSGGGGS IDETRAHLLLKEKMMRLGGR LVLNTKEELANERLMTLKIA EMKEAMRTLI FPPSMHFFQAKHLIERSQVF NILRMMPKGAALHLHDIGIV TMDWLVRNVT YRPHCHICFTPRGIMQFRFA HPTPRPSEKCSKWILLEDYR KRVQNVTEFD DSLLRNFTLVTQHPEVIYTN QNVVWSKFETIFFTISGLIH YAPVFRDYVF RSMQEFYEDNVLYMEIRAQL LPVYELSGEHHDEEWSVKTY QEVAQKFVET HPEFIGIKIIYNDHRSKDVA VIAESIRMAMGLRIKFPTVV AGFDLVGHED TGHSLHDYKEALMIPAKDGV | 286 | CAGGTGCAGCTGGTCGAAAGCGGAGGAGGAGTGGTCCAG CCAGGACGATCCCTGAGACTGGATTGTAAGGCCTCTGGA ATCACATTCTCTAACAGTGGAATGCACTGGGTGCGCCAG GCACCAGGAAAAGGACTGGAGTGGGTGGCCGTCATCTGG TACGACGGGTCAAAGCGATACTATGCAGATAGCGTGAAA GGAAGGTTCACAATTTCACGCGACAACAGCAAGAATACT CTGTTTCTGCAGATGAACTCTCTGAGAGCAGAGGATACT GCCGTGTACTATTGTGCTACCAATGACGATTATTGGGGG CAGGGAACTCTGGTGACCGTCAGTTCAGCTAGCACCAAG GGCCCATCGGTCTTCCCCCTGGCGCCCTGCTCCAGGAGC ACCTCCGAGAGCACAGCCGCCCTGGGCTGCCTGGTCAAG GACTACTTCCCCGAACCGGTGACGGTGTCGTGGAACTCA GGCGCCCTGACCAGCGGCGTGCACACCTTCCCGGCTGTC CTACAGTCCTCAGGACTCTACTCCCTCAGCAGCGTGGTG ACCGTGCCCTCCAGCAGCTTGGGCACGAAGACCTACACC TGCAACGTAGATCACAAGCCCAGCAACACCAAGGTGGAC AAGAGAGTTGAGTCCAAATATGGTCCCCCATGCCCACCA TGCCCAGCACCTGAGTTCCTGGGGGGACCATCAGTCTTC CTGTTCCCCCCAAAACCCAAGGACACTCTCATGATCTCC CGGACCCCTGAGGTCACGTGCGTGGTGGTGGACGTGAGC CAGGAAGACCCCGAGGTCCAGTTCAACTGGTACGTGGAT GGCGTGGAGGTGCATAATGCCAAGACAAAGCCGCGGGAG GAGCAGTTCAACAGCACGTACCGTGTGGTCAGCGTCCTC ACCGTCCTGCACCAGGACTGGCTGAACGGCAAGGAGTAC AAGTGCAAGGTCTCCAACAAAGGCCTCCCGTCCTCCATC GAGAAAACCATCTCCAAAGCCAAAGGGCAGCCCCGAGAG CCACAGGTGTACACCCTGCCCCCATCCCAGGAGGAGATG ACCAAGAACCAGGTCAGCCTGACCTGCCTGGTCAAAGGC TTCTACCCCAGCGACATCGCCGTGGAGTGGGAGAGCAAT GGGCAGCCGGAGAACAACTACAAGACCACGCCTCCCGTG CTGGACTCCGACGGCTCCTTCTTCCTCTACAGCAGGCTC ACCGTGGACAAGAGCAGGTGGCAGGAGGGGAATGTCTTC TCATGCTCCGTGATGCATGAGGCTCTGCACAACCACTAC ACACAGAAGAGCCTCTCCCTGTCTCCGGGTAAAGGTGGA GGTGGTTCTGGAGGTGGAGGTAGTATCGACGAAACCAGA GCACACTTACTGCTGAAAGAGAAAATGATGCGCCTGGGC GGGAGATTGGTGTTAAATACTAAGGAAGAGCTGGCAAAT GAAAGACTCATGACACTGAAGATTGCTGAAATGAAGGAG GCGATGAGGACGCTGATCTTTCCGCCTTCCATGCACTTC TTCCAAGCTAAACACCTGATCGAAAGATCCCAAGTGTTT AACATCCTGAGGATGATGCCTAAGGGGGCCGCTCTGCAC CTTCACGATATTGGGATTGTAACAATGGACTGGCTGGTA AGGAACGTGACATACAGACCTCATTGCCATATTTGTTTT ACTCCCCGAGGAATCATGCAATTCAGGTTTGCCCACCCA ACTCCTCGGCCAAGCGAGAAGTGTAGTAAGTGGATTTTG CTGGAAGATTACCGTAAGCGCGTGCAGAATGTGACAGAG |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | KLPYFFHAGETDWQGTSIDR<br>NILDALMLNT<br>TRIGHGFALSKHPAVRTYSW<br>DKDIPIEVCPISNQVLKLVS<br>DLRNHPVATL<br>MATGHPMVISSDDPAMFGAK<br>GLSYDFYEVFMGIGGMKADL<br>RTLKQLAMNS<br>IKYSTLLESEKNTFMEIWKK<br>RWDKFIADVATK | | TTTGATGACTCCCTGCTCCGCAATTTTACCCTGGTGACC<br>CAGCACCCCGAAGTTATATACACTAACCAAAATGTCGTG<br>TGGTCCAAGTTTGAGACGATCTTCTTCACGATTTCAGGC<br>TTGATCCACTACGCCCCGGTCTTTCGGGATTATGTGTTT<br>AGGAGTATGCAGGAGTTTTATGAGGATAATGTTCTGTAC<br>ATGGAGATCCGAGCCCAGCTGCTTCCAGTCTACGAACTA<br>TCCGGCGAACACCATGACGAGGAATGGAGCGTCAAGACC<br>TATCAAGAGGTGGCCCAGAAGTTCGTAGAAACGCATCCA<br>GAGTTCATCGGTATTAAGATTATCTACAATGATCACCGC<br>TCAAAGGATGTGGCTGTCATCGCCGAGTCTATACGGATG<br>GCCATGGGCCTGCGGATTAAGTTCCCTACCGTCGTCGCC<br>GGATTCGACCTCGTTGGGCATGAGGATACTGGCCATAGT<br>CTCCATGACTATAAAGAAGCCCTTATGATCCCAGCAAAG<br>GACGGAGTGAAGCTGCCCTACTTCTTCCACGCAGGGGAG<br>ACCGACTGGCAGGGAACGAGCATCGACCGGAACATACTT<br>GATGCACTCATGCTTAATACCACACGAATCGGCCACGGC<br>TTCGCTCTCTCCAAGCACCCAGCCGTGAGAACCTACAGC<br>TGGGATAAGGATATCCCCATCGAGGTTTGTCCCATCAGC<br>AATCAGGTGCTGAAATTGGTGAGTGACCTGAGAAACCAC<br>CCAGTCGCAACATTAATGGCCACTGGCCACCCTATGGTG<br>ATTTCAAGCGATGATCCAGCCATGTTCGGAGCAAAAGGA<br>CTCAGTTACGACTTCTATGAGGTATTCATGGGTATTGGT<br>GGTATGAAGGCAGACCTGCGGACTCTTAAGCAGTTGGCA<br>ATGAACTCAATTAAGTACTCTACCTTATTGGAGTCTGAA<br>AAGAACACATTTATGGAGATCTGGAAAAAGCGCTGGGAC<br>AAATTCATCGCAGATGTTGCCACAAAA |
| VH7<br>ADA2 | 282 | QVQLVQSGVEVKKPGASVKV<br>SCKASGYTFTNYYMYWVRQA<br>PGQGLEWMGG<br>INPSNGGTNFNEKFKNRVTL<br>TTDSSTTTAYMELKSLQFDD<br>TAVYYCARRD<br>YRFDMGFDYWGQGTTVTVSS<br>ASTKGPSVFPLAPCSRSTSE<br>STAALGCLVK<br>DYFPEPVTVSWNSGALTSGV<br>HTFPAVLQSSGLYSLSSVVT<br>VPSSSLGTKT<br>YTCNVDHKPSNTKVDKRVES<br>KYGPPCPPCPAPEFLGGPSV<br>FLFPPKPKDT<br>LMISRTPEVTCVVVDVSQED<br>PEVQFNWYVDGVEVHNAKTK<br>PREEQFNSTY<br>RVVSVLTVLHQDWLNGKEYK<br>CKVSNKGLPSSIEKTISKAK<br>GQPREPQVYT<br>LPPSQEEMTKNQVSLTCLVK<br>GFYPSDIAVEWESNGQPENN<br>YKTTPPVLDS<br>DGSFFLYSRLTVDKSRWQEG<br>NVFSCSVMHEALHNHYTQKS<br>LSLSPGKGGG<br>GSGGGGSIDETRAHLLLKEK<br>MMRLGGRLVLNTKEELANER<br>LMTLKIAEMK<br>EAMRTLIFPPSMHFFQAKHL<br>IERSQVFNILRMMPKGAALH<br>LHDIGIVTMD<br>WLVRNVTYRPHCHICFTPRG<br>IMQFRFAHPTPRPSEKCSKW<br>ILLEDYRKRV<br>QNVTEFDDSLLRNFTLVTQH<br>PEVIYTNQNVVWSKFETIFF<br>TISGLIHYAP<br>VFRDYVFRSMQEFYEDNVLY<br>MEIRARLLPVYELSGEHHDE<br>EWSVKTYQEV<br>AQKFVETHPEFIGIKIIYSD<br>HRSKDVAVIAESIRMAMGLR | 287 | CAGGTGCAGCTGGTCCAGAGCGGCGTGGAAGTCAAGAAA<br>CCCGGGGCCTCAGTGAAGGTCAGCTGTAAAGCTTCCGGC<br>TACACCTTCACAAACTACTATATGTATTGGGTGAGACAG<br>GCACCAGGACAGGGACTGGAGTGGATGGGCGGGATTAAC<br>CCTAGTAATGGAGGCACTAACTTCAACGAAAAGTTTAAA<br>AACAGGGTGACCCTGACCACAGATTCAAGCACTACCACA<br>GCTTACATGGAGCTGAAGTCCCTGCAGTTTGACGATACA<br>GCCGTGTACTATTGTGCTCGGAGAGACTACAGGTTCGAT<br>ATGGGCTTTGACTATTGGGGCCAGGGGACTACCGTGACC<br>GTCTCCTCTGCTAGCACCAAGGGCCCATCGGTCTTCCCC<br>CTGGCGCCCTGCTCCAGGAGCACCTCCGAGAGCACAGCC<br>GCCCTGGGCTGCCTGGTCAAGGACTACTTCCCCGAACCG<br>GTGACGGTGTCGTGGAACTCAGGCGCCCTGACCAGCGGC<br>GTGCACACCTTCCCGGCTGTCCTACAGTCCTCAGGACTC<br>TACTCCCTCAGCAGCGTGGTGACCGTGCCCTCCAGCAGC<br>TTGGGCACGAAGACCTACACCTGCAACGTAGATCACAAG<br>CCCAGCAACACCAAGGTGGACAAGAGAGTTGAGTCCAAA<br>TATGGTCCCCCATGCCCACCATGCCCAGCACCTGAGTTC<br>CTGGGGGGACCATCAGTCTTCCTGTTCCCCCCAAAACCC<br>AAGGACACTCTCATGATCTCCCGGACCCCTGAGGTCACG<br>TGCGTGGTGGTGGACGTGAGCCAGGAAGACCCCGAGGTC<br>CAGTTCAACTGGTACGTGGATGGCGTGGAGGTGCATAAT<br>GCCAAGACAAAGCCGCGGGAGGAGCAGTTCAACAGCACG<br>TACCGTGTGGTCAGCGTCCTCACCGTCCTGCACCAGGAC<br>TGGCTGAACGGCAAGGAGTACAAGTGCAAGGTCTCCAAC<br>AAAGGCCTCCCGTCCTCCATCGAGAAAACCATCTCCAAA<br>GCCAAAGGGCAGCCCCGAGAGCCACAGGTGTACACCCTG<br>CCCCCATCCCAGGAGGAGATGACCAAGAACCAGGTCAGC<br>CTGACCTGCCTGGTCAAAGGCTTCTACCCCAGCGACATC<br>GCCGTGGAGTGGGAGAGCAATGGGCAGCCGGAGAACAAC<br>TACAAGACCACGCCTCCCGTGCTGGACTCCGACGGCTCC<br>TTCTTCCTCTACAGCAGGCTCACCGTGGACAAGAGCAGG<br>TGGCAGGAGGGGAATGTCTTCTCATGCTCCGTGATGCAT<br>GAGGCTCTGCACAACCACTACACACAGAAGAGCCTCTCC<br>CTGTCTCCGGGTAAAGGTGGAGGTGGTTCTGGAGGTGGA<br>GGTAGTATCGACGAAACCAGAGCACACTTACTGCTGAAA<br>GAGAAAATGATGCGCCTGGGCGGGAGATTGGTGTTAAAT<br>ACTAAGGAAGAGCTGGCAAATGAAAGACTCATGACACTG<br>AAGATTGCTGAAATGAAGGAGGCGATGAGGACGCTGATC<br>TTTCCGCCTTCCATGCACTTCTTCCAAGCTAAACACCTG<br>ATCGAAAGATCCCAAGTGTTTAACATCCTGAGGATGATG<br>CCTAAGGGGGCCGCTCTGCACCTTCACGATATTGGGATT<br>GTAACAATGGACTGGCTGGTAAGGAACGTGACATACAGA<br>CCTCATTGCCATATTTGTTTTACTCCCCGAGGAATCATG |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | IKFPTVVAGF<br>DLVGHEDTGHSLHDYKEALM<br>IPAKDGVKLPYFFHAGETDW<br>QGTSIDRNIL<br>DALMLNTTRIGHGFALSKHP<br>AVRTYSWKKDIPIEVCPISN<br>QVLKLVSDLR<br>NHPVATLMATGHPMVISSDD<br>PAMFGAKGLSYDFYEVFMGI<br>GGMKADLRTL<br>KQLAMNSIKYSTLLESEKNT<br>FMEIWKKRWDKFIADVATK | | CAATTCAGGTTTGCCCACCCAACTCCTCGGCCAAGCGAG<br>AAGTGTAGTAAGTGGATTTTGCTGGAAGATTACCGTAAG<br>CGCGTGCAGAATGTGACAGAGTTTGATGACTCCCTGCTC<br>CGCAATTTTACCCTGGTGACCCAGCACCCCGAAGTTATA<br>TACACTAACCAAAATGTCGTGTGGTCCAAGTTTGAGACG<br>ATCTTCTTCACGATTTCAGGCTTGATCCACTACGCCCCG<br>GTCTTTCGGGATTATGTGTTTAGGAGTATGCAGGAGTTT<br>TATGAGGATAATGTTCTGTACATGGAGATCCGAGCCCGG<br>CTGCTTCCAGTCTACGAACTATCCGGCGAACACCATGAC<br>GAGGAATGGAGCGTCAAGACCTATCAAGAGGTGGCCCAG<br>AAGTTCGTAGAAACGCATCCAGAGTTCATCGGTATTAAG<br>ATTATCTACTCTGATCACCGCTCAAAGGATGTGGCTGTC<br>ATCGCCGAGTCTATACGGATGGCCATGGGCCTGCGGATT<br>AAGTTCCCTACCGTCGTCGCCGGATTCGACCTCGTTGGG<br>CATGAGGATACTGGCCATAGTCTCCATGACTATAAAGAA<br>GCCCTTATGATCCCAGCAAAGGACGGAGTGAAGCTGCCC<br>TACTTCTTCCACGCAGGGGAGACCGACTGGCAGGGAACG<br>AGCATCGACCGGAACATACTTGATGCACTCATGCTTAAT<br>ACCACACGAATCGGCCACGGCTTCGCTCTCTCCAAGCAC<br>CCAGCCGTGAGAACCTACAGCTGGAAGAAGGATATCCCC<br>ATCGAGGTTTGTCCCATCAGCAATCAGGTGCTGAAATTG<br>GTGAGTGACCTGAGAAACCACCCAGTCGCAACATTAATG<br>GCCACTGGCCACCCTATGGTGATTTCAAGCGATGATCCA<br>GCCATGTTCGGAGCAAAAGGACTCAGTTACGACTTCTAT<br>GAGGTATTCATGGGTATTGGTGGTATGAAGGCAGACCTG<br>CGGACTCTTAAGCAGTTGGCAATGAACTCAATTAAGTAC<br>TCTACCTTATTGGAGTCTGAAAAGAACACATTTATGGAG<br>ATCTGGAAAAAGCGCTGGGACAAATTCATCGCAGATGTT<br>GCCACAAAA |
| VH7<br>ADA2<br>mut7 | 283 | QVQLVQSGVEVKKPGASVKV<br>SCKASGYTFTNYYMYWVRQA<br>PGQGLEWMGG<br>INPSNGGTNFNEKFKNRVTL<br>TTDSSTTTAYMELKSLQFDD<br>TAVYYCARRD<br>YRFDMGFDYWGQGTTVTVSS<br>ASTKGPSVFPLAPCSRSTSE<br>STAALGCLVK<br>DYEPEPVTVSWNSGALTSGV<br>HTFPAVLQSSGLYSLSSVVT<br>VPSSSLGTKT<br>YTCNVDHKPSNTKVDKRVES<br>KYGPPCPPCPAPEFLGGPSV<br>FLFPPKPKDT<br>LMISRTPEVTCVVVDVSQED<br>PEVQFNWYVDGVEVHNAKTK<br>PREEQFNSTY<br>RVVSVLTVLHQDWLNGKEYK<br>CKVSNKGLPSSIEKTISKAK<br>GQPREPQVYT<br>LPPSQEEMTKNQVSLTCLVK<br>GFYPSDIAVEWESNGQPENN<br>YKTTPPVLDS<br>DGSFFLYSRLTVDKSRWQEG<br>NVFSCSVMHEALHNHYTQKS<br>LSLSPGKGGG<br>GSGGGGSIDETRAHLLLKEK<br>MMRLGGRLVLNTKEELANER<br>LMTLKIAEMK<br>EAMRTLIFPPSMHFFQAKHL<br>IERSQVFNILRMMPKGAALH<br>LHDIGIVTMD<br>WLVRNVTYRPHCHICFTPRG<br>IMQFRFAHPTPRPSEKCSKW<br>ILLEDYRKRV<br>QNVTEFDDSLLRNFTLVTQH<br>PEVIYTNQNVVWSKFETIFF<br>TISGLIHYAP<br>VFRDYVFRSMQEEYEDNVLY<br>MEIRAQLLPVYELSGEHHDE | 288 | CAGGTGCAGCTGGTCCAGAGCGGCGTGGAAGTCAAGAAA<br>CCCGGGGCCTCAGTGAAGGTCAGCTGTAAAGCTTCCGGC<br>TACACCTTCACAAACTACTATATGTATTGGGTGAGACAG<br>GCACCAGGACAGGGACTGGAGTGGATGGGCGGGATTAAC<br>CCTAGTAATGGAGGCACTAACTTCAACGAAAAGTTTAAA<br>AACAGGGTGACCCTGACCACAGATTCAAGCACTACCACA<br>GCTTACATGGAGCTGAAGTCCCTGCAGTTTGACGATACA<br>GCCGTGTACTATTGTGCTCGGAGAGACTACAGGTTCGAT<br>ATGGGCTTTGACTATTGGGGCCAGGGGACTACCGTGACC<br>GTCTCCTCTGCTAGCACCAAGGGCCCATCGGTCTTCCCC<br>CTGGCGCCCTGCTCCAGGAGCACCTCCGAGAGCACAGCC<br>GCCCTGGGCTGCCTGGTCAAGGACTACTTCCCCGAACCG<br>GTGACGGTGTCGTGGAACTCAGGCGCCCTGACCAGCGGC<br>GTGCACACCTTCCCGGCTGTCCTACAGTCCTCAGGACTC<br>TACTCCCTCAGCAGCGTGGTGACCGTGCCCTCCAGCAGC<br>TTGGGCACGAAGACCTACACCTGCAACGTAGATCACAAG<br>CCCAGCAACACCAAGGTGGACAAGAGAGTTGAGTCCAAA<br>TATGGTCCCCCATGCCCACCATGCCCAGCACCTGAGTTC<br>CTGGGGGGACCATCAGTCTTCCTGTTCCCCCCAAAACCC<br>AAGGACACTCTCATGATCTCCCGGACCCCTGAGGTCACG<br>TGCGTGGTGGTGGACGTGAGCCAGGAAGACCCCGAGGTC<br>CAGTTCAACTGGTACGTGGATGGCGTGGAGGTGCATAAT<br>GCCAAGACAAAGCCGCGGGAGGAGCAGTTCAACAGCACG<br>TACCGTGTGGTCAGCGTCCTCACCGTCCTGCACCAGGAC<br>TGGCTGAACGGCAAGGAGTACAAGTGCAAGGTCTCCAAC<br>AAAGGCCTCCCGTCCTCCATCGAGAAAACCATCTCCAAA<br>GCCAAAGGGCAGCCCCGAGAGCCACAGGTGTACACCCTG<br>CCCCCATCCCAGGAGGAGATGACCAAGAACCAGGTCAGC<br>CTGACCTGCCTGGTCAAAGGCTTCTACCCCAGCGACATC<br>GCCGTGGAGTGGGAGAGCAATGGGCAGCCGGAGAACAAC<br>TACAAGACCACGCCTCCCGTGCTGGACTCCGACGGCTCC<br>TTCTTCCTCTACAGCAGGCTCACCGTGGACAAGAGCAGG<br>TGGCAGGAGGGGAATGTCTTCTCATGCTCCGTGATGCAT<br>GAGGCTCTGCACAACCACTACACACAGAAGAGCCTCTCC<br>CTGTCTCCGGGTAAAGGTGGAGGTGGTTCTGGAGGTGGA<br>GGTAGTATCGACGAAACCAGAGCACACTTACTGCTGAAA<br>GAGAAAATGATGCGCCTGGGCGGGAGATTGGTGTTAAAT<br>ACTAAGGAAGAGCTGGCAAATGAAAGACTCATGACACTG<br>AAGATTGCTGAAATGAAGGAGGCGATGAGGACGCTGATC<br>TTTCCGCCTTCCATGCACTTCTTCCAAGCTAAACACCTG<br>ATCGAAAGATCCCAAGTGTTTAACATCCTGAGGATGATG |

TABLE 14-continued

Exemplary ADA2 Sequences
Table 14 provides exemplary ADA2 sequences for use in anti-PD1 fusion proteins described herein. In any embodiments exemplifying a fusion protein with, e.g., a TGFβRII ECD, an ADA2 sequence may be employed instead.

| Name | SEQ ID NO | Amino Acid Sequence | SEQ ID NO | Nucleotide Sequence |
|---|---|---|---|---|
| | | EWSVKTYQEV AQKFVETHPEFIGIKIIYND HRSKDVAVIAESIRMAMGLR IKFPTVVAGF DLVGHEDTGHSLHDYKEALM IPAKDGVKLPYFFHAGETDW QGTSIDRNIL DALMLNTTRIGHGFALSKHP AVRTYSWDKDIPIEVCPISN QVLKLVSDLR NHPVATLMATGHPMVISSDD PAMFGAKGLSYDFYEVFMGI GGMKADLRTL KQLAMNSIKYSTLLESEKNT FMEIWKKRWDKFIADVATK | | CCTAAGGGGGCCGCTCTGCACCTTCACGATATTGGGATT GTAACAATGGACTGGCTGGTAAGGAACGTGACATACAGA CCTCATTGCCATATTTGTTTTACTCCCCGAGGAATCATG CAATTCAGGTTTGCCCACCCAACTCCTCGGCCAAGCGAG AAGTGTAGTAAGTGGATTTTGCTGGAAGATTACCGTAAG CGCGTGCAGAATGTGACAGAGTTTGATGACTCCCTGCTC CGCAATTTTACCCTGGTGACCCAGCACCCCGAAGTTATA TACACTAACCAAAATGTCGTGTGGTCCAAGTTTGAGACG ATCTTCTTCACGATTTCAGGCTTGATCCACTACGCCCCG GTCTTTCGGGATTATGTGTTTAGGAGTATGCAGGAGTTT TATGAGGATAATGTTCTGTACATGGAGATCCGAGCCCAG CTGCTTCCAGTCTACGAACTATCCGGCGAACACCATGAC GAGGAATGGAGCGTCAAGACCTATCAAGAGGTGGCCCAG AAGTTCGTAGAAACGCATCCAGAGTTCATCGGTATTAAG ATTATCTACAATGATCACCGCTCAAAGGATGTGGCTGTC ATCGCCGAGTCTATACGGATGGCCATGGGCCTGCGGATT AAGTTCCCTACCGTCGTCGCCGGATTCGACCTCGTTGGG CATGAGGATACTGGCCATAGTCTCCATGACTATAAAGAA GCCCTTATGATCCCAGCAAAGGACGGAGTGAAGCTGCCC TACTTCTTCCACGCAGGGGAGACCGACTGGCAGGGAACG AGCATCGACCGGAACATACTTGATGCACTCATGCTTAAT ACCACACGAATCGGCCACGGCTTCGCTCTCTCCAAGCAC CCAGCCGTGAGAACCTACAGCTGGGATAAGGATATCCCC ATCGAGGTTTGTCCCATCAGCAATCAGGTGCTGAAATTG GTGAGTGACCTGAGAAACCACCCAGTCGCAACATTAATG GCCACTGGCCACCCTATGGTGATTTCAAGCGATGATCCA GCCATGTTCGGAGCAAAAGGACTCAGTTACGACTTCTAT GAGGTATTCATGGGTATTGGTGGTATGAAGGCAGACCTG CGGACTCTTAAGCAGTTGGCAATGAACTCAATTAAGTAC TCTACCTTATTGGAGTCTGAAAAGAACACATTTATGGAG ATCTGGAAAAAGCGCTGGGACAAATTCATCGCAGATGTT GCCACAAAA |
| Human ADA2 | 284 | SIDETRAHLLLKEKMM RLGGRLVLNTKEELAN ERLMTLKIAEMKEAMR TLIFPPSMHFFQAKHLIE RSQVFNILRMMPKGAA LHLHDIGIVTMDWLVR NVTYRPHCHICFTPRGI MQFRFAHPTPRPSEKCS KWILLEDYRKRVQNVT EFDDSLLRNFTLVTQHP EVIYTNQNVVWSKFETI FFTISGLIHYAPVFRDY VFRSMQEFYEDNVLYM EIRARLLPVYELSGEHH DEEWSVKTYQEVAQKF VETHPEFIGIKIIYSDHR SKDVAVIAESIRMAMG LRIKFPTVVAGFDLVGH EDTGHSLHDYKEALMI PAKDGVKLPYFFHAGE TDWQGTSIDRNILDAL MLNTTRIGHGFALSKHP AVRTYSWKKDIPIEVCP ISNQVLKLVSDLRNHPV ATLMATGHPMVISSDD PAMFGAKGLSYDFYEV FMGIGGMKADLRTLKQ LAMNSIKYSTLLESEKN TFMEIWKKRWDKFIAD VATK | | |

TABLE 15

Exemplary anti-PD1 VH/VL Pairs
Table 15 provides exemplary anti-PD1 VH/VL pairs for use in the fusion proteins described herein

| Exemplary anti-PD1 VL | Exemplary anti-PD1 VH |
|---|---|
| Anti-PD1 VL5 (SEQ ID NO:12) | Anti-PD1 VH6 (SEQ ID NO: 6) |
| Anti-PD1 VL6 (SEQ ID NO: 13 | Anti-PD1 VH7 (SEQ ID NO: 7) |
| Anti-PD1 VL1 (SEQ ID NO: 8) | Anti-PD1 VH5 (SEQ ID NO: 5) |
| Anti-PD1 nVL1 (SEQ ID NO: 8) | Anti-PD1 nVH3 (SEQ ID NO: 149) |
| Anti-PD1 nVL1 (SEQ ID NO: 8) | Anti-PD1 nVH7 (SEQ ID NO: 157) |
| Anti PD1 nVL1 (SEQ ID NO: 8) | Anti-PD1 nVH8 (SEQ ID NO: 158) |

TABLE 16

Exemplary anti-PD1-TGFbRII ECD Fusion Protein Sequences
Table 16 provides exemplary anti-PD1-TGFbRII ECD fusion protein sequences. The anti-PD1 fusion proteins comprise a sequence encoding an anti-PD1 variable region of light chain and a sequence encoding an anti-PD1 variable region of heavy chain. ECD stands for extracellular domain. "wt" refers to wild type sequence and "mut" refers to mutant sequence.

| Exemplary VL | Exemplary VH-IgG4-ECD |
|---|---|
| VL5 (SEQ ID NO: 15) | VH6-IgG4(wt)-linker-ECD (SEQ NO: 16) |
| VL5 (SEQ ID NO: 15) | VH6-IgG4(mut)-linker-ECD (SEQ NO: 143) |
| VL5 (SEQ ID NO: 15) | VH6-IgG4(mut)-linker-ECD (SEQ NO: 294) |
| VL6 (SEQ ID NO: 296 | VH7-IgG4(wt)-linker-ECD (SEQ NO: 145) |
| VL6 (SEQ ID NO: 296) | VH7-IgG4(mut)-linker-ECD (SEQ NO: 144) |
| VL6 (SEQ ID NO: 296) | VH7-IgG4(mut)-linker-ECD (SEQ NO: 295) |

TABLE 17

Exemplary anti-PD1-ADA2 Fusion Protein Sequences
Table 17 provides exemplary anti-PD1-ADA2 fusion protein sequences. The anti-PD1 fusion proteins comprise a sequence encoding an anti-PD1 variable region of light chain and a sequence encoding an anti-PD1 variable region of heavy chain."wt" refers to wild type sequence and "mut" refers to mutant sequence

| Exemplary VL | Exemplary VH-IgG4-ADA2 |
|---|---|
| VL5 (SEQ ID NO: 12) | VH6-IgG4(mut)-linker-ADA2 (wt) (SEQ NO. 280) |
| VL5 (SEQ ID NO: 12) | VH6-IgG4(mut)-linker-ADA2 (mut 7) (SEQ NO. 281) |
| VL6 (SEQ ID NO: 13) | VH7-IgG4(mut)-linker-ADA2 (wt) (SEQ NO. 282) |
| VL6 (SEQ ID NO: 13) | VH7-IgG4(mut)-linker-ADA2 (mut 7) (SEQ NO. 283) |

What is claimed is:

1. A method of treating cancer in a subject in need thereof, the method comprising administering to the subject a therapeutically effective amount of a fusion protein comprising:

(a) an antibody, or an antigen-binding fragment or variant thereof, that specifically binds to programmed cell death protein-1 (PD-1) and comprises either:

(1) a VH region having the sequence of SEQ ID NO: 6 and a VL region having the sequence of SEQ ID NO: 12; or (ii) a VH region having the sequence of SEQ ID NO: 7 and a VL region having the sequence of SEQ ID NO: 13;

and (b) a transforming growth factor beta (TGF-β) cytokine trap having the sequence of SEQ ID NO: 14;

wherein the components of (a) and (b) are connected by a peptide linker and the cancer is colorectal cancer, head and neck cancer, or ovarian cancer.

2. The method of claim 1, wherein the peptide linker comprises the sequence of any one of SEQ ID NOs: 17-34.

3. The method of claim 1, wherein the antibody is an immunoglobulin G (IgG) antibody.

4. The method of claim 3, wherein the IgG antibody comprises a mutation at position 108 of SEQ ID NO: 146 or 292.

5. The method of claim 4, wherein the mutation is S108P mutation.

6. The method of claim 1, wherein the peptide linker connects the VH region with the TGF-β cytokine trap.

7. The method of claim 1, wherein the antibody, or antigen-binding fragment or variant thereof, comprises a VH region having the sequence of SEQ ID NO: 6 and a VL region having the sequence of SEQ ID NO: 12.

8. The method of claim 1, wherein the antibody, or antigen-binding fragment or variant thereof, comprises a VH region having the sequence of SEQ ID NO: 7 and a VL region having the sequence of SEQ ID NO: 13.

9. The method of claim 1, wherein the subject is a human.

10. The method of claim 1, further comprising administering to the subject an effective amount of T cells engineered to express an exogenous receptor.

11. The method of claim 10, wherein the exogenous receptor is a chimeric antigen receptor comprising an antigen-binding domain that binds to an epitope on CD19, BCMA, CD44, α-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, MUC-1, MUC-4, MUC-16, MAGE-A1, h5T4, PSMA, TAG-72, EGFR, CD20, EGFRVIII, CD123, or VEGF-R2.

12. The method of claim 10, wherein the exogenous receptor is a chimeric antigen receptor and the engineered T cells further express a fusion protein comprising IL-15 and IL-15Rα.

13. The method of claim 1, wherein the fusion protein comprises either:

(a) the amino acid sequences of SEQ ID NO: 15 and SEQ ID NO: 294; or (b) the amino acid sequences of SEQ ID NO: 296 and SEQ ID NO: 144.

14. The method of claim 1, wherein the cancer is colorectal cancer.

15. The method of claim 11, wherein the chimeric antigen receptor comprises an antigen-binding domain that binds to an epitope on CD33.

16. The method of claim 1, wherein the fusion protein comprises either:

(a) (i) the amino acid sequence of SEQ ID NO: 15, and (ii) the sequence of SEQ ID NO: 16, 143, or 294; or (b) (i) the amino acid sequence of SEQ ID NO: 296, and (ii) the amino acid sequence of SEQ ID NO: 144, 145, or 295.

17. The method of claim 1, wherein the fusion protein comprises the amino acid sequence of SEQ ID NO: 296 and the amino acid sequence of SEQ ID NO: 144.

* * * * *

SEQUENCE LISTING

```
Sequence total quantity: 309
SEQ ID NO: 1            moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 1
QVQLVESGGG VVQPGRSLRL SCAASGFTFR SYGMHWVRQA PGKGLEWVAI IFYDGSNKYY  60
ADSVKGRFTI SRDNSKNTLY LQMNSLRAED TAVYYCARDD DYWGQGALVT VSS         113

SEQ ID NO: 2            moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 2
EVQLVQSGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCAGEG FDYWGQGTLV TVSS        114

SEQ ID NO: 3            moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 3
QVQLVQSGAE VKKPGASVKV SCKASGYTFT GYYMHWVRQA PGQGLEWMGA INPNSGGTNY  60
AQKFQGRVTM TRDTSISTAY MELSRLRSDD TAVYYCARRP DRANWHFDYW GQGTLVTVSS  120
```

-continued

```
SEQ ID NO: 4            moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 4
QVQLVQSGAE VKKPGASVKV SCKASGYTFT GYYMHWVRQA PGQGLEWMGA INPNSGGTNY  60
AQKLQGRVTM TTDTSTSTAY MELRSLRSDD TAVYYCARHG LKGDGYFDYW GQGTLVTVSS  120

SEQ ID NO: 5            moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 5
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATNN DYWGQGTLVT VSS         113

SEQ ID NO: 6            moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 6
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 7            moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 7
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 8            moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 8
EIVMTQSPAT LSLSPGERAT LSCRASQSVS SYLAWYQQKP GQAPRLLIYD ASNRATGIPA  60
RFSGSGSGTD FTLTISSLEP EDFAVYYCQQ YNNWPRTFGQ GTKVEIK                107

SEQ ID NO: 9            moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 9
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPKTFGQ GTKVEIK                107

SEQ ID NO: 10           moltype = AA  length = 114
FEATURE                 Location/Qualifiers
REGION                  1..114
                        note = Description of Artificial Sequence: Synthetic
                         polypeptide
source                  1..114
                        mol_type = protein
```

-continued

```
                          organism = synthetic construct
SEQUENCE: 10
RNVLTQSPLS LPVTPGEPAS ISCRSSQSLS SSGYTYLDWY LQKPGQSPQL LIYLASWRDS  60
GVPDRFSGSG SGTDFTLKIS RVEAEDVGVY YCMQAEQTPG PGNTFGQGTK LEIK        114

SEQ ID NO: 11             moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 11
DVVMTQSPLS LPVTPGEPAS ISCRSSQSLL HTNGYNYLHW YLQKPGQSPQ LLIYLGSWQD  60
SGVPDRFSGS GSGTDFTLKI SRVEAEDVGV YYCMQAEQTP RTFGQGTRLE VK          112

SEQ ID NO: 12             moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 12
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 13             moltype = AA  length = 111
FEATURE                   Location/Qualifiers
REGION                    1..111
                          note = Description of Artificial Sequence: Synthetic
                           polypeptide
source                    1..111
                          mol_type = protein
                          organism = synthetic construct
SEQUENCE: 13
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI K           111

SEQ ID NO: 14             moltype = AA  length = 136
FEATURE                   Location/Qualifiers
source                    1..136
                          mol_type = protein
                          organism = Homo sapiens
SEQUENCE: 14
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                  136

SEQ ID NO: 15             moltype = AA  length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 15
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 16             moltype = AA  length = 586
FEATURE                   Location/Qualifiers
REGION                    1..586
                          note = Description of Artificial Sequence: Synthetic
                           polypeptide
source                    1..586
                          mol_type = protein
                          organism = synthetic construct
SEQUENCE: 16
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP SCPAPEFLGG PSVFLFPPKP  240
KDTLMISRTP EVTCVVVDVS QEDPEVQFNW YVDGVEVHNA KTKPREEQFN STYRVVSVLT  300
```

-continued

```
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSPGK GGGGSGGGGS IPPHVQKSVN NDMIVTDNNG AVKFPQLCKF  480
CDVRFSTCDN QKSCMSNCSI TSICEKPQEV CVAVWRKNDE NITLETVCHD PKLPYHDFIL  540
EDAASPKCIM KEKKKPGETF FMCSCSSDEC NDNIIFSEEY NTSNPD                 586

SEQ ID NO: 17          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 17
DPGGGGSGGG GSNPGS                                                  16

SEQ ID NO: 18          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 18
GGGGSGGGGS GSDPGS                                                  16

SEQ ID NO: 19          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 19
DPGSGGGGSG GGGSGS                                                  16

SEQ ID NO: 20          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 20
GGGGSGGGGS GGGGSDPGS                                               19

SEQ ID NO: 21          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 21
DPGSGGGGSG GGGSGGGGS                                               19

SEQ ID NO: 22          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 22
DPGSGSVPLG SGSNPGS                                                 17

SEQ ID NO: 23          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 23
DPGSGGSVPL GSGGSNPGS                                               19

SEQ ID NO: 24          moltype = AA  length = 20
FEATURE                Location/Qualifiers
REGION                 1..20
```

-continued

```
                        note = Description of Artificial Sequence: Synthetic peptide
source                  1..20
                        mol_type = protein
                        organism = synthetic construct
SEQUENCE: 24
DPGVLEREDK PTTSKPNPGS                                                20

SEQ ID NO: 25           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 25
DPGVLEREDV PTTSYPNPGS                                                20

SEQ ID NO: 26           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 26
DPGVLEREDK VTTSKYNPGS                                                20

SEQ ID NO: 27           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 27
DPVLEREDKV TTSKNPGS                                                  18

SEQ ID NO: 28           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 28
DIEGRMD                                                              7

SEQ ID NO: 29           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 29
GEGKSSGSGS ESKAS                                                     15

SEQ ID NO: 30           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 30
GSTSGSGKPG SGEGSTKG                                                  18

SEQ ID NO: 31           moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 31
AEAAAKEAAA KEAAAKEAAA KALEAEAAAK EAAAKEAAAK EAAAKA                   46

SEQ ID NO: 32           moltype = AA  length = 50
```

```
FEATURE                 Location/Qualifiers
REGION                  1..50
                        note = Description of Artificial Sequence: Synthetic
                         polypeptide
REGION                  1..50
                        note = MISC_FEATURE - This sequence may encompass 1-10 "Gly
                         Gly Gly Gly Ser" repeating units
source                  1..50
                        mol_type = protein
                        organism = synthetic construct
SEQUENCE: 32
GGGGSGGGGS GGGGSGGGGS GGGGSGGGGS GGGGSGGGGS GGGGSGGGGS            50

SEQ ID NO: 33           moltype = AA  length = 8
FEATURE                 Location/Qualifiers
REGION                  1..8
                        note = Description of Artificial Sequence: Synthetic peptide
REGION                  1..8
                        note = MISC_FEATURE - This sequence may encompass 6-8
                         residues
source                  1..8
                        mol_type = protein
                        organism = synthetic construct
SEQUENCE: 33
GGGGGGGG                                                          8

SEQ ID NO: 34           moltype = AA  length = 30
FEATURE                 Location/Qualifiers
REGION                  1..30
                        note = Description of Artificial Sequence: Synthetic
                         polypeptide
REGION                  1..30
                        note = MISC_FEATURE - This sequence may encompass 1-6 "Glu
                         Ala Ala Ala Lys" repeating units
source                  1..30
                        mol_type = protein
                        organism = synthetic construct
SEQUENCE: 34
EAAAKEAAAK EAAAKEAAAK EAAAKEAAAK                                  30

SEQ ID NO: 35           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 35
DIQMTQSPSS LSASVGDRVT ITCRASESVD NYGISFMNWF QQKPGKAPKL LIYAASNQGS  60
GVPSRFSGSG SGTDFTLTIS SLQPDDFATY YCQQSKEVPW TFGQGTKVEI K           111

SEQ ID NO: 36           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 36
QVQLVQSGAE VKKPGSSVKV SCKASGYTFT DYNMHWVRQA PGQGLEWIGY IYPYNGGTGY  60
NQKFKSKATI TADESTNTAY MELSSLRSED TAVYYCARGR PAMDYWGQGT LVTVSS      116

SEQ ID NO: 37           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 37
QVQLQQSGPE LVRPGTFVKI SCKASGYTFT NYDINWVNQR PGQGLEWIGW IYPGDGSTKY  60
NEKFKAKATL TADKSSSTAY LQLNNLTSEN SAVYFCASGY EDAMDYWGQG TSVTVSS     117

SEQ ID NO: 38           moltype = AA  length = 108
FEATURE                 Location/Qualifiers
REGION                  1..108
```

```
                        note = Description of Artificial Sequence: Synthetic
                         polypeptide
source                  1..108
                        mol_type = protein
                        organism = synthetic construct
SEQUENCE: 38
DIKMTQSPSS MYASLGERVI INCKASQDIN SYLSWFQQKP GKSPKTLIYR ANRLVDGVPS  60
RFSGSGSGQD YSLTISSLEY EDMGIYYCLQ YDEFPLTFGA GTKLELKR               108

SEQ ID NO: 39           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 39
EVKLQESGPE LVKPGASVKM SCKASGYKFT DYVVHWLKQK PGQGLEWIGY INPYNDGTKY  60
NEKFKGKATL TSDKSSSTAY MEVSSLTSED SAVYYCARDY RYEVYGMDYW GQGTSVTVSS  120

SEQ ID NO: 40           moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 40
DIVLTQSPTI MSASPGERVT MTCTASSSVN YIHWYQQKSG DSPLRWIFDT SKVASGVPAR  60
FSGSGSGTSY SLTISTMEAE DAATYYCQQW RSYPLTFGDG TRLELKRADA APTVS       115

SEQ ID NO: 41           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 41
QVQLQQPGAE VVKPGASVKM SCKASGYTFT SYYIHWIKQT PGQGLEWVGV IYPGNDDISY  60
NQKFKGKATL TADKSSTTAY MQLSSLTSED SAVYYCAREV RLRYFDVWGA GTTVTVSS    118

SEQ ID NO: 42           moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 42
NIMLTQSPSS LAVSAGEKVT MSCKSSQSVF FSSSQKNYLA WYQQIPGQSP KLLIYWASTR  60
ESGVPDRFTG SGSGTDFTLT ISSVQSEDLA IYYCHQYLSS RTFGGGTKLE IKR         113

SEQ ID NO: 43           moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 43
DIELTQSPSS LAVSAGEKVT MSCKSSQSLL NSRTRKNQLA WYQQKPGQSP ELLIYWASTR  60
QSGVPDRFTG SGSGTDFTLT ISSVQAEDLA VYYCQQSYNL LTFGPGTKLE VKR         113

SEQ ID NO: 44           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 44
VKLQESGGGF VKPGGSLKVS CAASGFTFSS YAMSWVRLSP EMRLEWVATI SSAGGYIFYS  60
```

-continued

```
DSVQGRFTIS RDNAKNTLHL QMGSLRSGDT AMYYCARQGF GNYGDYYAMD YWGQGTTVTV  120
SS                                                                 122

SEQ ID NO: 45          moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 45
DIELTQSPSS LAVSAGEKVT MSCKSSQSLL NSRTRKNQLA WYQQKTGQSP ELLIYWASTR  60
QSGVPDRFTG SGSGTDFTLT ISSVQAEDLA VYYCQQSYNL LTFGPGTKLE IKR         113

SEQ ID NO: 46          moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 46
VKLEESGGGF VKPGGSLKIS CAASGFTFRN YAMSWVRLSP EMRLEWVATI SSAGGYIFYS  60
DSVQGRFTIS RDNAKNTHLQ MGSLRSGDTA MYYCARQGFG NYGDYYAMDY WGQGTTVTVS  120
S                                                                  121

SEQ ID NO: 47          moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 47
DIKMAQSPSS VNASLGERVT ITCKASRDIN NFLSWFHQKP GKSPKTLIYR ANRLVDGVPS  60
RFSGSGSGQD YSFTISSLEY EDVGIYYCLQ YGDLYTFGGG TKLEIK                 106

SEQ ID NO: 48          moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 48
DVQLLESGPG LVRPSQSLSL TCSVTGYSIV SHYYWNWIRQ FPGNKLEWMG YISSDGSNEY  60
NPSLKNRISI SLDTSKNQFF LKFDFVTTAD TATYFCVRGV DYWGQGTTLT VSS         113

SEQ ID NO: 49          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 49
DIQMTQSSSF LSVSLGGRVT ITCKASDLIH NWLAWYQQKP GNAPRLLISG ATSLETGVPS  60
RFSGSGSGND YTLSIASLQT EDAATYYCQQ YWTTPFTFGS GTKLEIK                107

SEQ ID NO: 50          moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 50
DVQLQESGPG LVNPSQSLSL TCTVTGYSIT NDYAWNWIRQ FPGNKLEWMG YINYSGYTTY  60
NPSLKSRISI TRDTSKNQFF LHLNSVTTED TATYYCARWD GGLTYWGQGT LVTVSA      116

SEQ ID NO: 51          moltype = AA  length = 108
FEATURE                Location/Qualifiers
REGION                 1..108
```

```
                        note = Description of Artificial Sequence: Synthetic
                         polypeptide
source                  1..108
                        mol_type = protein
                        organism = synthetic construct
SEQUENCE: 51
DIQMTQSPSS LSASVGDRVT ITCKASDLIH NWLAWYQQKP GKAPKLLISG ATSLETGVPS  60
RFSGSGSGTD FTLTISSLQP EDFATYYCQQ YWTTPFTFGQ GTKVEIKR               108

SEQ ID NO: 52           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 52
EVQLVESGGG LVQPGGSLRL SCAASGYSIT NDYAWNWVRQ APGKGLEWVG YINYSGYTTY  60
NPSLKSRFTI SRDNSKNTLY LQMNSLRAED TAVYYCARWD GGLTYWGQGT LVTVSS      116

SEQ ID NO: 53           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 53
EVQLVESGGG LVQPGGSLRL SCAASGYSIT NDYAWNWVRQ APGKGLEWVG YINYSGYTTY  60
NPSLKSRFTI SRDNSKNTFY LQMNSLRAED TAVYYCARWD GGLTYWGQGT LVTVSS      116

SEQ ID NO: 54           moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 54
DIVLTQSPAI MSASLGERVT MTCTASSSVS SSYLHWYQQK PGSSPKLWIY STSNLASGVP  60
GRFSGSGSGT SYSLTISSME AEDAATYYCH QYHRSPYTFG GGTKVEIKR              109

SEQ ID NO: 55           moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 55
DIQMTQSPSS LSASVGDRVT ITCTASSSVS SSYLHWYQQK PGKAPKLLIY STSNLASGVP  60
SRFSGSGSGT DFTLTISSLQ PEDFATYYCH QYHRSPYTFG QGTKVEIKR              109

SEQ ID NO: 56           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 56
EVQLVESGGG LVQPGGSLRL SCAASGFNIK DTYMHWVRQA PGKGLEWVGR VDPANGNTKY  60
DPKFQGRFTI SADTSKNTAY LQMNSLRAED TAVYYCVRDY YGHTYGFAFW GQGTLVTVSS  120

SEQ ID NO: 57           moltype = AA  length = 47
FEATURE                 Location/Qualifiers
REGION                  1..47
                        note = Description of Unknown: CD8-alpha hinge sequence
source                  1..47
                        mol_type = protein
                        organism = unidentified
SEQUENCE: 57
KPTTTPAPRP PTPAPTIASQ PLSLRPEACR PAAGGAVHTR GLDFACD                47
```

-continued

```
SEQ ID NO: 58           moltype = AA  length = 94
FEATURE                 Location/Qualifiers
REGION                  1..94
                        note = Description of Artificial Sequence: Synthetic
                         polypeptide
source                  1..94
                        mol_type = protein
                        organism = synthetic construct
SEQUENCE: 58
KPTTTPAPRP PTPAPTIASQ PLSLRPEASR PAAGGAVHTR GLDFASDKPT TTPAPRPPTP  60
APTIASQPLS LRPEACRPAA GGAVHTRGLD FACD                              94

SEQ ID NO: 59           moltype = AA  length = 141
FEATURE                 Location/Qualifiers
REGION                  1..141
                        note = Description of Artificial Sequence: Synthetic
                         polypeptide
source                  1..141
                        mol_type = protein
                        organism = synthetic construct
SEQUENCE: 59
KPTTTPAPRP PTPAPTIASQ PLSLRPEASR PAAGGAVHTR GLDFASDKPT TTPAPRPPTP  60
APTIASQPLS LRPEASRPAA GGAVHTRGLD FASDKPTTTP APRPPTPAPT IASQPLSLRP  120
EACRPAAGGA VHTRGLDFAC D                                            141

SEQ ID NO: 60           moltype = AA  length = 185
FEATURE                 Location/Qualifiers
REGION                  1..185
                        note = Description of Artificial Sequence: Synthetic
                         polypeptide
source                  1..185
                        mol_type = protein
                        organism = synthetic construct
SEQUENCE: 60
TTPAPRPPTP APTIASQPLS LRPEASRPAA GGAVHTRGLD FASDKPTTTP APRPPTPAPT  60
IASQPLSLRP EASRPAAGGA VHTRGLDFAS DKPTTTPAPR PPTPAPTIAS QPLSLRPEAS  120
RPAAGGAVHT RGLDFASDKP TTTPAPRPPT PAPTIASQPL SLRPEACRPA AGGAVHTRGL  180
DFACD                                                              185

SEQ ID NO: 61           moltype = AA  length = 28
FEATURE                 Location/Qualifiers
REGION                  1..28
                        note = Description of Unknown: CD8-alpha TM sequence
source                  1..28
                        mol_type = protein
                        organism = unidentified
SEQUENCE: 61
IYIWAPLAGT CGVLLLSLVI TLYCNHRN                                     28

SEQ ID NO: 62           moltype = AA  length = 27
FEATURE                 Location/Qualifiers
REGION                  1..27
                        note = Description of Unknown: CD28 TM sequence
source                  1..27
                        mol_type = protein
                        organism = unidentified
SEQUENCE: 62
FWVLVVVGGV LACYSLLVTV AFIIFWV                                      27

SEQ ID NO: 63           moltype = AA  length = 42
FEATURE                 Location/Qualifiers
REGION                  1..42
                        note = Description of Unknown: 4-1BB signaling domain
                         sequence
source                  1..42
                        mol_type = protein
                        organism = unidentified
SEQUENCE: 63
KRGRKKLLYI FKQPFMRPVQ TTQEEDGCSC RFPEEEEGGC EL                     42

SEQ ID NO: 64           moltype = AA  length = 41
FEATURE                 Location/Qualifiers
REGION                  1..41
                        note = Description of Unknown: CD28 signaling domain
                         sequence
source                  1..41
                        mol_type = protein
                        organism = unidentified
SEQUENCE: 64
```

-continued

```
RSKRSRGGHS DYMNMTPRRP GPTRKHYQPY APPRDFAAYR S                    41

SEQ ID NO: 65          moltype = AA  length = 24
FEATURE                Location/Qualifiers
REGION                 1..24
                       note = Description of Unknown: DNAX-activation protein 10
                        (DAP 10) signaling domain sequence
source                 1..24
                       mol_type = protein
                       organism = unidentified
SEQUENCE: 65
LCARPRRSPA QEDGKVYINM PGRG                                       24

SEQ ID NO: 66          moltype = AA  length = 52
FEATURE                Location/Qualifiers
REGION                 1..52
                       note = Description of Unknown: DNAX-activation protein 12
                        (DAP12) signaling domain sequence
source                 1..52
                       mol_type = protein
                       organism = unidentified
SEQUENCE: 66
YFLGRLVPRG RGAAEAATRK QRITETESPY QELQGQRSDV YSDLNTQRPY YK         52

SEQ ID NO: 67          moltype = AA  length = 112
FEATURE                Location/Qualifiers
REGION                 1..112
                       note = Description of Unknown: CD3-zeta signaling domain
                        sequence
source                 1..112
                       mol_type = protein
                       organism = unidentified
SEQUENCE: 67
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 68          moltype = AA  length = 335
FEATURE                Location/Qualifiers
REGION                 1..335
                       note = Description of Unknown: HER1t sequence
source                 1..335
                       mol_type = protein
                       organism = unidentified
SEQUENCE: 68
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSCRNVSRGR ECVDKCNLLE GEPREFVENS ECIQCHPECL PQAMNITCTG  240
RGPDNCIQCA HYIDGPHCVK TCPAGVMGEN NTLVWKYADA GHVCHLCHPN CTYGCTGPGL  300
EGCPTNGPKI PSIATGMVGA LLLLLVVALG IGLFM                           335

SEQ ID NO: 69          moltype = AA  length = 243
FEATURE                Location/Qualifiers
REGION                 1..243
                       note = Description of Unknown: Her1t-1 sequence
source                 1..243
                       mol_type = protein
                       organism = unidentified
SEQUENCE: 69
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSGGGGSGGG SGGGGSGGGG SFWVLVVVGG VLACYSLLVT VAFIIFWVRS  240
KRS                                                              243

SEQ ID NO: 70          moltype = AA  length = 297
FEATURE                Location/Qualifiers
REGION                 1..297
                       note = Description of Unknown: FL CD20 sequence
source                 1..297
                       mol_type = protein
                       organism = unidentified
SEQUENCE: 70
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEETETNFP EPPQDQESSP IENDSSP     297
```

-continued

```
SEQ ID NO: 71          moltype = AA  length = 263
FEATURE                Location/Qualifiers
REGION                 1..263
                       note = Description of Unknown: CD20t-1 sequence
source                 1..263
                       mol_type = protein
                       organism = unidentified
SEQUENCE: 71
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIE                                         263

SEQ ID NO: 72          moltype = DNA  length = 333
FEATURE                Location/Qualifiers
misc_feature           1..333
                       note = Description of Artificial Sequence: Synthetic
                        polynucleotide
source                 1..333
                       mol_type = other DNA
                       organism = synthetic construct
SEQUENCE: 72
gacattcaga tgacccagtc tccgagctct ctgtccgcat cagtaggaga cagggtcacc  60
atcacatgca gagccagcga aagtgtcgac aattatggca ttagctttat gaactggttc  120
caacagaaac ccgggaaggc tcctaagctt ctgatttacg ctgcatccaa ccaaggctcc  180
ggggtaccct ctcgcttctc aggcagtgga tctgggacag acttcactct caccatttca  240
tctctgcagc ctgatgactt cgcaacctat tactgtcagc aaagtaagga ggttccgtgg  300
acgttcggtc aagggaccaa ggtggagatc aaa                              333

SEQ ID NO: 73          moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 73
caggttcagc tggtgcagtc tggagctgag gtgaagaagc ctgggagctc agtgaaggtt  60
tcctgcaaag cttctggcta caccttcact gactacaaca tgcactgggt gaggcaggct  120
cctggccaag gcctggaatg gattggatat atttatcctt acaatggtgg taccggctac  180
aaccagaagt tcaagagcaa ggccacaatt acagcagacg agagtactaa cacagcctac  240
atggaactct ccagcctgag gtctgaggac actgcagtct attactgcgc aagagggcgc  300
cccgctatgg actactgggg ccaagggact ctggtcactg tctcttca              348

SEQ ID NO: 74          moltype = DNA  length = 339
FEATURE                Location/Qualifiers
misc_feature           1..339
                       note = Description of Artificial Sequence: Synthetic
                        polynucleotide
source                 1..339
                       mol_type = other DNA
                       organism = synthetic construct
SEQUENCE: 74
gacatcgagc tgacacagag cccatctagc ctggctgtgt ctgccggcga gaaagtgacc  60
atgagctgca agagcagcca gagcctgctg aacagccgga ccagaaagaa tcagctggcc  120
tggtatcagc agaagcccgg ccaatctcct gagctgctga tctactgggc cagcacaaga  180
cagagcggcg tgcccgatag attcacagga tctggcagcg gcaccgactt caccctgaca  240
atcagttctg tgcaggccga ggacctggcc gtgtactact gtcagcagag ctacaacctg  300
ctgaccttcg gacccggcac caagctggaa gtgaagaga                        339

SEQ ID NO: 75          moltype = DNA  length = 366
FEATURE                Location/Qualifiers
misc_feature           1..366
                       note = Description of Artificial Sequence: Synthetic
                        polynucleotide
source                 1..366
                       mol_type = other DNA
                       organism = synthetic construct
SEQUENCE: 75
gtgaagctgc aagagtccgg cggaggcttt gtgaagcctg gcggctctct gaaagtgtcc  60
tgtgccgcca gcggcttcac ctttagcagc tacgccatga gctgggtccg actgagccct  120
gagatgagac tggaatgggt cgccaccatc agtagcgcag gcggctacat cttctacagc  180
gactctgtgc agggcagatt caccatcagc cgggacaacg ccaagaacac cctgcacctc  240
cagatgggca gtctgagaag cggcgatacc gccatgtact actgcgccag acaaggcttc  300
ggcaactacg gcgactacta tgccatggat tactggggcc agggcaccac cgtgacagtc  360
tcttct                                                            366
```

-continued

```
SEQ ID NO: 76           moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 76
gacatcgagc tgacacagag cccatctagc ctggctgtgt ctgccggcga gaaagtgacc  60
atgagctgca agagcagcca gagcctgctg aacagccgga ccagaaagaa tcagctggcc  120
tggtatcagc agaaaaccgg acagagcccc gagctgctga tctactgggc cagcacaaga  180
cagagcggcg tgcccgatag attcacagga tctggcagcg gcaccgactt caccctgaca  240
atcagttctg tgcaggccga ggacctggcc gtgtactact gtcagcagag ctacaacctg  300
ctgaccttcg gacccggcac caagctggaa atcaagaga                         339

SEQ ID NO: 77           moltype = DNA  length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 77
gtgaagctgg aagagtccgg cggaggcttt gtgaagcctg gcggaagcct gaagatcagc  60
tgtgccgcca gcggcttcac cttcagaaac tacgccatga gctgggtccg actgagcccc  120
gagatgagac tggaatgggt cgccacaatc agcagcgcag gcggctacat cttctacagc  180
gatagcgtgc agggcagatt caccatcagc cgggacaacg ccaagaacac cctgcacctc  240
cagatgggca gtctgagatc tggcgacacc gccatgtact actgcgccag acaaggcttc  300
ggcaactacg gcgactacta tgccatggat tactggggcc agggcaccac cgtgacagtc  360
tcttct                                                             366

SEQ ID NO: 78           moltype = DNA  length = 318
FEATURE                 Location/Qualifiers
misc_feature            1..318
                        note = Description of Artificial Sequence: Synthetic
                         polynucleotide
source                  1..318
                        mol_type = other DNA
                        organism = synthetic construct
SEQUENCE: 78
gacatcaaga tggctcagtc cccttctagc gtgaatgctt cgctagggga gcgtgtgacc  60
atcacatgta aagcatcacg cgacataaat aatttccttt cctggtttca tcagaaaccg  120
ggcaagtcgc ctaagacgct gatttacaga gcaaatcggt tggtagatgg agtgccaagc  180
agattcagcg ggagcggaag tggacaggat tatagcttca ctatttcatc cctggaatac  240
gaggacgtag gtatctatta ttgcctccag tatggcgatc tttacacatt tggtgggggg  300
actaagctgg agattaag                                                318

SEQ ID NO: 79           moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 79
gacgtgcaac ttctggagag cgggccaggg ctagtcaggc cctcccagtc gctttcactg  60
acttgcagtg tgaccggtta ctctattgtg agtcactact attggaactg gattcggcag  120
ttcccaggca acaaactgga atggatgggg tacatatctt ccgatggctc gaatgaatat  180
aacccatcat tgaaaaatcg tatttccatc agtctggata cgagtaaaaa ccagtttttc  240
ctcaaattcg atttcgtgac tacagcagat actgccacat acttctgtgt acgaggtgtc  300
gattattggg gacagggcac aacgctgacc gtaagttct                         339

SEQ ID NO: 80           moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 80
gacatccaga tgacccagag cagcagcttc ctgagcgtgt cccttggcgg cagagtgacc  60
atcacctgta aagccagcga cctgatccac aactggctgg cctggtatca gcagaagcct  120
ggcaacgctc ccagactgct gattagcggc gccacctctc tggaaacagg cgtgccaagc  180
agatttccg gcagcggctc cggcaacgac tacacactgt ctattgccag cctgcagacc  240
gaggatgccg ccacctatta ctgccagcag tactggacca cacctttcac ctttggcagc  300
```

```
ggcaccaagc tggaaatcaa g                                            321

SEQ ID NO: 81          moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 81
gacgttcagc tgcaagagtc tggccctggc ctggtcaatc ctagccagag cctgagcctg  60
acatgtaccg tgaccggcta cagcatcacc aacgactacg cctggaactg gatcagacag  120
ttccccggca acaagctgga atggatgggc tacatcaact acagcggcta caccacctac  180
aatcccagcc tgaagtcccg gatctccatc accagagaca ccagcaagaa ccagttcttc  240
ctgcacctga acagcgtgac caccgaggat accgccacct actactgcgc tagatgggat  300
ggcggcctga catattgggg ccagggaaca ctggtcaccg tgtctgct               348

SEQ ID NO: 82          moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
SEQUENCE: 82
gacatccaga tgacccagag ccccagcagc ctgagcgcca gcgtgggcga cagggtgacc  60
atcacctgca aggccagcga cctgatccac aactggctgg cctggtacca gcagaagccc  120
ggcaaggccc ccaagctgct gatcagcggc gccaccagcc tggagaccgg cgtgcccagc  180
aggttcagcg gcagcggcag cggcaccgac ttcaccctga ccatcagcag cctgcagccc  240
gaggacttcg ccacctacta ctgccagcag tactggacca ccccccttcac cttcggccag  300
ggcaccaagg tggagatcaa gagg                                         324

SEQ ID NO: 83          moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 83
gaggtgcagc tggtggagag cggcggcggc ctggtgcagc ccggcggcag cctgaggctg  60
agctgcgccg ccagcggcta cagcatcacc aacgactacg cctggaactg ggtgaggcag  120
gcccccggca agggcctgga gtgggtgggc tacatcaact acagcggcta caccacctac  180
aaccccagcc tgaagagcag gttcaccatc agcagggaca acagcaagaa caccctgtac  240
ctgcagatga acagcctgag ggccgaggac accgccgtgt actactgcgc caggtgggac  300
ggcggcctga cctactgggg ccagggcacc ctggtgaccg tgagcagc               348

SEQ ID NO: 84          moltype = DNA  length = 348
FEATURE                Location/Qualifiers
misc_feature           1..348
                       note = Description of Artificial Sequence: Synthetic
                        polynucleotide
source                 1..348
                       mol_type = other DNA
                       organism = synthetic construct
SEQUENCE: 84
gaggtgcagc tggtggagag cggcggcggc ctggtgcagc ccggcggcag cctgaggctg  60
agctgcgccg ccagcggcta cagcatcacc aacgactacg cctggaactg ggtgaggcag  120
gcccccggca agggcctgga gtgggtgggc tacatcaact acagcggcta caccacctac  180
aaccccagcc tgaagagcag gttcaccatc agcagggaca acagcaagaa caccttctac  240
ctgcagatga acagcctgag ggccgaggac accgccgtgt actactgcgc caggtgggac  300
ggcggcctga cctactgggg ccagggcacc ctggtgaccg tgagcagc               348

SEQ ID NO: 85          moltype = DNA  length = 327
FEATURE                Location/Qualifiers
misc_feature           1..327
                       note = Description of Artificial Sequence: Synthetic
                        polynucleotide
source                 1..327
                       mol_type = other DNA
                       organism = synthetic construct
SEQUENCE: 85
gacatcgtgc tgacacagag ccctgccatc atgtctgcca gcctcggcga gcgagtgacc  60
atgacatgta cagccagcag cagcgtgtcc agcagctacc tgcattggta tcagcagaag  120
cccggcagca gccccaagct gtggatctac agcacaagca atctggccag cggcgtgcca  180
ggcagatttt ctggttctgg cagcggcacc agctacagcc tgacaatcag cagcatggaa  240
```

```
gccgaggatg ccgccaccta ctactgccac cagtaccaca gaagccccta cacctttggc  300
ggaggcacca aggtggaaat caagcgg                                      327

SEQ ID NO: 86          moltype = DNA  length = 327
FEATURE                Location/Qualifiers
misc_feature           1..327
                       note = Description of Artificial Sequence: Synthetic
                        polynucleotide
source                 1..327
                       mol_type = other DNA
                       organism = synthetic construct
SEQUENCE: 86
gacatccaga tgacacagag ccctagcagc ctgtctgcca gcgtgggaga cagagtgacc  60
atcacctgta cagccagcag cagcgtgtcc agcagctacc tgcattggta tcagcagaag  120
cccggcaagg cccctaagct gctgatctac agcaccagca atctggccag cggcgtgcca  180
agcagatttt ctggctctgg cagcggcacc gacttcaccc tgaccatatc tagcctgcag  240
cctgaggact tcgccaccta ctactgccac cagtaccaca gaagccccta cacctttggc  300
cagggcacca aggtggaaat caagcgg                                      327

SEQ ID NO: 87          moltype = DNA  length = 360
FEATURE                Location/Qualifiers
misc_feature           1..360
                       note = Description of Artificial Sequence: Synthetic
                        polynucleotide
source                 1..360
                       mol_type = other DNA
                       organism = synthetic construct
SEQUENCE: 87
gaggtgcagc tggttgaatc tggcggagga ctggttcagc ctggcggatc tctgagactg  60
tcttgtgccg ccagcggctt caacatcaag gacacctaca tgcactgggt ccgacaggcc  120
cctggcaaag gacttgagtg ggttggaaga gtggaccccg ccaacggcaa caccaaatac  180
gaccccaagt tccagggcag attcaccatc agcgccgaca ccagcaagaa caccgcctac  240
ctgcagatga acagcctgag agccgaggac accgccgtgt actattgcgt gcgggattac  300
tacggccata cctacggctt cgccttttgg ggccagggca cactggttac cgttagctct  360

SEQ ID NO: 88          moltype = DNA  length = 141
FEATURE                Location/Qualifiers
misc_feature           1..141
                       note = Description of Unknown: CD8-alpha hinge sequence
source                 1..141
                       mol_type = other DNA
                       organism = unidentified
SEQUENCE: 88
aagcccacca ccacccctgc ccctagacct ccaaccccag cccctacaat cgccagccag  60
cccctgagcc tgaggcccga agcctgtaga cctgccgctg gcggagccgt gcacaccaga  120
ggcctggatt tcgcctgcga c                                            141

SEQ ID NO: 89          moltype = DNA  length = 282
FEATURE                Location/Qualifiers
misc_feature           1..282
                       note = Description of Artificial Sequence: Synthetic
                        polynucleotide
source                 1..282
                       mol_type = other DNA
                       organism = synthetic construct
SEQUENCE: 89
aaacctacta caactcctgc ccccccggcct cctacaccag ctcctactat cgcctcccag  60
ccactcagtc tcagacccga ggcttctagg ccagcggccg gaggcgcggt ccacacccgc  120
gggctggact ttgcatccga taagcccacc accacccctg cccctagacc tccaacccca  180
gcccctacaa tcgccagcca gcccctgagc ctgaggcccg aagcctgtag acctgccgct  240
ggcggagccg tgcacaccag aggcctggat ttcgcctgcg ac                     282

SEQ ID NO: 90          moltype = DNA  length = 423
FEATURE                Location/Qualifiers
misc_feature           1..423
                       note = Description of Artificial Sequence: Synthetic
                        polynucleotide
source                 1..423
                       mol_type = other DNA
                       organism = synthetic construct
SEQUENCE: 90
aagcctacca ccacccccgc acctcgtcct ccaacccctg cacctacgat tgccagtcag  60
cctctttcac tgcggcctga ggccagcaga ccagctgccg gcggtgccgt ccatacaaga  120
ggactggact tcgcgtccga taaacctact accactccag ccccaaggcc cccaacccca  180
gcaccgacta tcgcatcaca gcctttgtca ctgcgtcctg aagccagccg gccagctgca  240
ggggggggccg tccacacaag gggactcgac tttgcgagtg ataagcccac caccacccct  300
gcccctagac ctccaacccc agcccctaca atcgccagcc agcccctgag cctgaggccc  360
gaagcctgta gacctgccgc tggcggagcc gtgcacacca gaggcctgga tttcgcctgc  420
gac                                                                423
```

-continued

```
SEQ ID NO: 91          moltype = DNA  length = 564
FEATURE                Location/Qualifiers
misc_feature           1..564
                       note = Description of Artificial Sequence: Synthetic
                        polynucleotide
source                 1..564
                       mol_type = other DNA
                       organism = synthetic construct
SEQUENCE: 91
aagcctacca ccacccccgc acctcgtcct ccaacccctg cacctacgat tgccagtcag  60
cctctttcac tgcggcctga ggccagcaga ccagctgccg gcggtgccgt ccatacaaga  120
ggactggact tcgcgtccga taaacctact accactccag ccccaaggcc cccaacccca  180
gcaccgacta tcgcatcaca gcctttgtca ctgcgtcctg aagccagccg gccagctgca  240
ggggggggccg tccacacaag gggactcgac tttgcgagtg ataaacctac tacaactcct  300
gccccccggc ctcctacacc agctcctact atcgcctccc agccactcag tctcagaccc  360
gaggcttcta ggccagcggc cggaggcgcg gtccacaccc gcgggctgga ctttgcatcc  420
gataagccca ccaccacccc tgcccctaga cctccaaccc cagcccctac aatcgccagc  480
cagcccctga gcctgaggcc cgaagcctgt agacctgccg ctggcggagc cgtgcacacc  540
agaggcctgg atttcgcctg cgac                                        564

SEQ ID NO: 92          moltype = DNA  length = 84
FEATURE                Location/Qualifiers
misc_feature           1..84
                       note = Description of Unknown: CD8-alpha TM sequence
source                 1..84
                       mol_type = other DNA
                       organism = unidentified
SEQUENCE: 92
atctacatct gggcccctct ggccggcacc tgtggcgtgc tgctgctgag cctggtcatc  60
accctgtact gcaaccaccg gaat                                        84

SEQ ID NO: 93          moltype = DNA  length = 81
FEATURE                Location/Qualifiers
misc_feature           1..81
                       note = Description of Unknown: CD28 TM sequence
source                 1..81
                       mol_type = other DNA
                       organism = unidentified
SEQUENCE: 93
ttttgggtgc tggtggtggt tggtggagtc ctggcttgct atagcttgct agtaacagtg  60
gcctttatta ttttctgggt g                                           81

SEQ ID NO: 94          moltype = DNA  length = 126
FEATURE                Location/Qualifiers
misc_feature           1..126
                       note = Description of Unknown: 4-1BB signaling domain
                        sequence
source                 1..126
                       mol_type = other DNA
                       organism = unidentified
SEQUENCE: 94
aagagaggcc ggaagaaact gctgtacatc ttcaagcagc ccttcatgcg gcccgtgcag  60
accacccagg aagaggacgg ctgcagctgc cggttccccg aggaagagga aggcggctgc  120
gaactg                                                            126

SEQ ID NO: 95          moltype = DNA  length = 123
FEATURE                Location/Qualifiers
misc_feature           1..123
                       note = Description of Unknown: CD28 signaling domain
                        sequence
source                 1..123
                       mol_type = other DNA
                       organism = unidentified
SEQUENCE: 95
aggagcaagc ggagcagagg cggccacagc gactacatga acatgacccc ccggaggcct  60
ggccccaccc ggaagcacta ccagccctac gcccctccca gggacttcgc cgcctaccgg  120
agc                                                               123

SEQ ID NO: 96          moltype = DNA  length = 72
FEATURE                Location/Qualifiers
misc_feature           1..72
                       note = Description of Unknown: DNAX-activation protein 10
                        (DAP 10) signaling domain sequence
source                 1..72
                       mol_type = other DNA
                       organism = unidentified
SEQUENCE: 96
ctgtgcgcac gcccacgccg cagccccgcc caagaagatg gcaaagtcta catcaacatg  60
```

-continued

```
ccaggcaggg gc                                                    72

SEQ ID NO: 97          moltype = DNA  length = 156
FEATURE                Location/Qualifiers
misc_feature           1..156
                       note = Description of Unknown: DNAX-activation protein 12
                        (DAP12) signaling domain sequence
source                 1..156
                       mol_type = other DNA
                       organism = unidentified
SEQUENCE: 97
tacttcctgg gccggctggt ccctcggggg cgaggggctg cggaggcagc gacccggaaa  60
cagcgtatca ctgagaccga gtcgccttat caggagctcc agggtcagag gtcggatgtc  120
tacagcgacc tcaacacaca gaggccgtat tacaaa                          156

SEQ ID NO: 98          moltype = DNA  length = 336
FEATURE                Location/Qualifiers
misc_feature           1..336
                       note = Description of Unknown: CD3-zeta signaling domain
                        sequence
source                 1..336
                       mol_type = other DNA
                       organism = unidentified
SEQUENCE: 98
cgggtgaagt tcagccggag cgccgacgcc cctgcctacc agcagggcca gaaccagctg  60
tacaacgagc tgaacctggg ccggagggag gagtacgacg tgctggacaa gcggagaggc  120
cgggaccctg agatgggcgg caagccccgg agaaagaacc ctcaggaggg cctgtataac  180
gaactgcaga aagacaagat ggccgaggcc tacagcgaga tcggcatgaa gggcgagcgg  240
cggaggggca agggccacga cggcctgtac cagggcctga gcaccgccac caaggatacc  300
tacgacgccc tgcacatgca ggccctgccc cccaga                          336

SEQ ID NO: 99          moltype = DNA  length = 1005
FEATURE                Location/Qualifiers
misc_feature           1..1005
                       note = Description of Unknown: HER1t sequence
source                 1..1005
                       mol_type = other DNA
                       organism = unidentified
SEQUENCE: 99
cgcaaagtgt gtaacggaat aggtattggt gaatttaaag actcactctc cataaatgct  60
acgaatatta aacacttcaa aaactgcacc tccatcagtg gcgatctcca catcctgccg  120
gtggcattta ggggtgactc cttcacacat actcctcctc tggatccaca ggaactggat  180
attctgaaaa ccgtaaagga aatcacaggg tttttgctga ttcaggcttg gcctgaaaac  240
aggacggacc tccatgcctt tgagaaccta gaaatcatac gcggcaggac caagcaacat  300
ggtcagtttt ctcttgcagt cgtcagcctg aacataacat ccttgggatt acgctccctc  360
aaggagataa gtgatggaga tgtgataatt tcaggaaaca aaaatttgtg ctatgcaaat  420
acaataaact ggaaaaaact gtttgggacc tccggtcaga aaaccaaaat tataagcaac  480
agaggtgaaa acagctgcaa ggccacaggc caggtctgcc atgccttgtg ctcccccgag  540
ggctgctggg gcccggagcc cagggactgc gtctcttgcc ggaatgtcag ccgaggcagg  600
gaatgcgtgg acaagtgcaa ccttctggag ggtgagccaa gggagtttgt ggagaactct  660
gagtgcatac agtgccaccc agagtgcctg cctcaggcca tgaacatcac ctgcacagga  720
cggggaccag acaactgtat ccagtgtgcc cactacattg acggccccca ctgcgtcaag  780
acctgcccgg caggagtcat gggagaaaac aacaccctgg tctggaagta cgcagacgcc  840
ggccatgtgt gccacctgtg ccatccaaac tgcacctacg gatgcactgg gccaggtctt  900
gaaggctgtc caacgaatgg gcctaagatc ccgtccatcg ccactgggat ggtgggggcc  960
ctcctcttgc tgctggtggt ggccctgggg atcggcctct tcatg                1005

SEQ ID NO: 100         moltype = DNA  length = 732
FEATURE                Location/Qualifiers
misc_feature           1..732
                       note = Description of Unknown: Her1t-1 sequence
source                 1..732
                       mol_type = other DNA
                       organism = unidentified
SEQUENCE: 100
cgcaaagtgt gtaacggaat aggtattggt gaatttaaag actcactctc cataaatgct  60
acgaatatta aacacttcaa aaactgcacc tccatcagtg gcgatctcca catcctgccg  120
gtggcattta ggggtgactc cttcacacat actcctcctc tggatccaca ggaactggat  180
attctgaaaa ccgtaaagga aatcacaggg tttttgctga ttcaggcttg gcctgaaaac  240
aggacggacc tccatgcctt tgagaaccta gaaatcatac gcggcaggac caagcaacat  300
ggtcagtttt ctcttgcagt cgtcagcctg aacataacat ccttgggatt acgctccctc  360
aaggagataa gtgatggaga tgtgataatt tcaggaaaca aaaatttgtg ctatgcaaat  420
acaataaact ggaaaaaact gtttgggacc tccggtcaga aaaccaaaat tataagcaac  480
agaggtgaaa acagctgcaa ggccacaggc caggtctgcc atgccttgtg ctcccccgag  540
ggctgctggg gcccggagcc cagggactgc gtctctggtg gcggtggctc gggcggtggt  600
gggtcgggtg gcggcggatc tggtggcggt ggctcgtttt gggtgctggt ggtggttggt  660
ggagtcctgg cttgctatag cttgctagta acagtggcct ttattatttt ctgggtgagg  720
agtaagagga gc                                                    732
```

-continued

```
SEQ ID NO: 101          moltype = DNA  length = 891
FEATURE                 Location/Qualifiers
misc_feature            1..891
                        note = Description of Unknown: FL CD20 sequence
source                  1..891
                        mol_type = other DNA
                        organism = unidentified
SEQUENCE: 101
atgacaacac ccagaaattc agtaaatggg actttcccgg cagagccaat gaaaggccct  60
attgctatgc aatctggtcc aaaaccactc ttcaggagga tgtcttcact ggtgggcccc  120
acgcaaagct tcttcatgag ggaatctaag actttggggg ctgtccagat tatgaatggg  180
ctcttccaca ttgccctggg gggtcttctg atgatcccag cagggatcta tgcacccatc  240
tgtgtgactg tgtggtaccc tctctgggga ggcattatgt atattatttc cggatcactc  300
ctggcagcaa cggagaaaaa ctccaggaag tgtttggtca aaggaaaaat gataatgaat  360
tcattgagcc tctttgctgc catttctgga atgattcttt caatcatgga catacttaat  420
attaaaattt cccatttttt aaaaatggag agtctgaatt ttattagagc tcacacacca  480
tatattaaca tatacaactg tgaaccagct aatccctctg agaaaaactc cccatctacc  540
caatactgtt acagcataca atctctgttc ttgggcattt tgtcagtgat gctgatcttt  600
gccttcttcc aggaacttgt aatagctggc atcgttgaga atgaatggaa aagaacgtgc  660
tccagaccca aatctaacat agttctcctg tcagcagaag aaaaaaaaga acagactatt  720
gaaataaaag aagaagtggt tgggctaact gaaacatctt cccaaccaaa gaatgaagaa  780
gacattgaaa ttattccaat ccaagaagag gaagaagaag aaacagagac gaactttcca  840
gaacctcccc aagatcagga atcctcacca atagaaaatg acagctctcc t           891

SEQ ID NO: 102          moltype = DNA  length = 789
FEATURE                 Location/Qualifiers
misc_feature            1..789
                        note = Description of Unknown: CD20t-1 sequence
source                  1..789
                        mol_type = other DNA
                        organism = unidentified
SEQUENCE: 102
atgaccacac cacggaactc tgtgaatggc accttcccag cagagccaat gaagggacca  60
atcgcaatgc agagcggacc caagcctctg tttcggagaa tgagctccct ggtgggccca  120
acccagtcct tctttatgag agagtctaag acactgggcg ccgtgcagat catgaacgga  180
ctgttccaca tcgccctggg aggactgctg atgatcccag ccggcatcta cgcccctatc  240
tgcgtgaccg tgtggtaccc tctgtggggc ggcatcatgt atatcatctc cggctctctg  300
ctggccgcca cagagaagaa cagcaggaag tgtctggtga agggcaagat gatcatgaat  360
agcctgtccc tgtttgccgc catctctggc atgatcctga gcatcatgga catcctgaac  420
atcaagatca gccacttcct gaagatggag agcctgaact tcatcagagc ccacacccct  480
tacatcaaca tctataattg cgagcctgcc aacccatccg agaagaattc tccaagcaca  540
cagtactgtt attccatcca gtctctgttc ctgggcatcc tgtctgtgat gctgatcttt  600
gccttctttc aggagctggt catcgccggc atcgtggaga acgagtggaa gaggacctgc  660
agccgcccca agtccaatat cgtgctgctg tccgccgagg agaagaagga gcagacaatc  720
gagatcaagg aggaggtggt gggcctgacc gagacatcta gccagcctaa gaatgaggag  780
gatatcgag                                                          789

SEQ ID NO: 103          moltype = AA  length = 395
FEATURE                 Location/Qualifiers
REGION                  1..395
                        note = Description of Unknown: mbIL15 sequence
source                  1..395
                        mol_type = protein
                        organism = unidentified
SEQUENCE: 103
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS  120
FVHIVQMFIN TSSGGGSGGG GSGGGGSGGG GSGGGSLQIT CPPPMSVEHA DIWVKSYSLY  180
SRERYICNSG FKRKAGTSSL TECVLNKATN VAHWTTPSLK CIRDPALVHQ RPAPPSTVTT  240
AGVTPQPESL SPSGKEPAAS SPSSNNTAAT TAAIVPGSQL MPSKSPSTGT TEISSHESSH  300
GTPSQTTAKN WELTASASHQ PPGVYPQGHS DTTVAISTST VLLCGLSAVS LLACYLKSRQ  360
TPPLASVEME AMEALPVTWG TSSRDEDLEN CSHHL                              395

SEQ ID NO: 104          moltype = AA  length = 114
FEATURE                 Location/Qualifiers
REGION                  1..114
                        note = Description of Unknown: IL-15 sequence
source                  1..114
                        mol_type = protein
                        organism = unidentified
SEQUENCE: 104
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 105          moltype = AA  length = 237
FEATURE                 Location/Qualifiers
REGION                  1..237
                        note = Description of Unknown: IL-15R-alpha sequence
source                  1..237
```

```
                        mol_type = protein
                        organism = unidentified
SEQUENCE: 105
ITCPPPMSVE HADIWVKSYS LYSRERYICN SGFKRKAGTS SLTECVLNKA TNVAHWTTPS  60
LKCIRDPALV HQRPAPPSTV TTAGVTPQPE SLSPSGKEPA ASSPSSNNTA ATTAAIVPGS  120
QLMPSKSPST GTTEISSHES SHGTPSQTTA KNWELTASAS HQPPGVYPQG HSDTTVAIST  180
STVLLCGLSA VSLLACYLKS RQTPPLASVE MEAMEALPVT WGTSSRDEDL ENCSHHL     237

SEQ ID NO: 106          moltype = DNA  length = 1185
FEATURE                 Location/Qualifiers
misc_feature            1..1185
                        note = Description of Unknown: mbIL15 sequence
source                  1..1185
                        mol_type = other DNA
                        organism = unidentified
SEQUENCE: 106
atggattgga cctggattct gtttctggtg gccgctgcca caagagtgca cagcaactgg  60
gtgaatgtga tcagcgacct gaagaagatc gaggatctga tccagagcat gcacattgat  120
gccaccctgt acacagaatc tgatgtgcac cctagctgta aagtgaccgc catgaagtgt  180
tttctgctgg agctgcaggt gatttctctg gaaagcggag atgcctctat ccacgacaca  240
gtggagaatc tgatcatcct ggccaacaat agcctgagca gcaatggcaa tgtgacagag  300
tctggctgta aggagtgtga ggagctggag gagaagaaca tcaaggagtt tctgcagagc  360
tttgtgcaca tcgtgcagat gttcatcaat acaagctctg gcggaggatc tggaggaggc  420
ggatctggag gaggaggcag tggaggcgga ggatctggcg gaggatctct gcagattaca  480
tgccctcctc caatgtctgt ggagcacgcc gatatttggg tgaagtccta cagcctgtac  540
agcagagaga gatacatctg caacagcggc tttaagagaa aggccggcac ctcttctctg  600
acagagtgcg tgctgaataa ggccacaaat gtggcccact ggacaacacc tagcctgaag  660
tgcattagag atcctgccct ggtccaccag aggcctgccc ctccatctac agtgacaaca  720
gccggagtga cacctcagcc tgaatctctg agcccttctg gaaaagaacc tgccgccagc  780
tctcctagct ctaataatac cgccgccaca acagccgcca ttgtgcctgg atctcagctg  840
atgcctagca agtctcctag cacaggcaca acagagatca gcagccacga atcttctcac  900
ggaacacctt ctcagaccac cgccaagaat tgggagctga cagcctctgc ctctcaccag  960
cctccaggag tgtatcctca gggccactct gatacaacag tggccatcag cacatctaca  1020
gtgctgctgt gtggactgtc tgccgtgtct ctgctggcct gttacctgaa gtctagacag  1080
acacctcctc tggcctctgt ggagatggag gccatggaag ccctgcctgt gacatgggga  1140
acaagcagca gagatgagga cctggagaat tgttctcacc acctg                1185

SEQ ID NO: 107          moltype = DNA  length = 342
FEATURE                 Location/Qualifiers
misc_feature            1..342
                        note = Description of Unknown: IL-15 sequence
source                  1..342
                        mol_type = other DNA
                        organism = unidentified
SEQUENCE: 107
aactgggtga atgtgatcag cgacctgaag aagatcgagg atctgatcca gagcatgcac  60
attgatgcca ccctgtacac agaatctgat gtgcacccta gctgtaaagt gaccgccatg  120
aagtgttttc tgctggagct gcaggtgatt tctctggaaa gcggagatgc ctctatccac  180
gacacagtgg agaatctgat catcctggcc aacaatagcc tgagcagcaa tggcaatgtg  240
acagagtctg gctgtaagga gtgtgaggag ctggaggaga agaacatcaa ggagtttctg  300
cagagctttg tgcacatcgt gcagatgttc atcaatacaa gc                    342

SEQ ID NO: 108          moltype = DNA  length = 711
FEATURE                 Location/Qualifiers
misc_feature            1..711
                        note = Description of Unknown: IL-15R-alpha sequence
source                  1..711
                        mol_type = other DNA
                        organism = unidentified
SEQUENCE: 108
attacatgcc ctcctccaat gtctgtggag cacgccgata tttgggtgaa gtcctacagc  60
ctgtacagca gagagagata catctgcaac agcggcttta agagaaaggc cggcacctct  120
tctctgacag agtgcgtgct gaataaggcc acaaatgtgg cccactggac aacacctagc  180
ctgaagtgca ttagagatcc tgccctggtc caccagaggc ctgcccctcc atctacagtg  240
acaacagccg gagtgacacc tcagcctgaa tctctgagcc cttctggaaa agaacctgcc  300
gccagctctc ctagctctaa taataccgcc gccacaacag ccgccattgt gcctggatct  360
cagctgatgc ctagcaagtc tcctagcaca ggcacaacag agatcagcag ccacgaatct  420
tctcacggaa caccttctca gaccaccgcc aagaattggg agctgacagc ctctgcctct  480
caccagcctc caggagtgta tcctcagggc cactctgata caacagtggc catcagcaca  540
tctacagtgc tgctgtgtgg actgtctgcc gtgtctctgc tggcctgtta cctgaagtct  600
agacagacac ctcctctggc ctctgtggag atggaggcca tggaagccct gcctgtgaca  660
tggggaacaa gcagcagaga tgaggacctg gagaattgtt ctcaccacct g          711

SEQ ID NO: 109          moltype = DNA  length = 339
FEATURE                 Location/Qualifiers
misc_feature            1..339
                        note = Description of Artificial Sequence: Synthetic
                         polynucleotide
source                  1..339
```

```
                        mol_type = other DNA
                        organism = synthetic construct
SEQUENCE: 109
caggtgcagc tggtcgaaag cggaggagga gtggtccagc caggacgatc cctgagactg  60
gattgtaagg cctctggaat cacattctct aacagtggaa tgcactgggt gcgccaggca  120
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttca                          339

SEQ ID NO: 110          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 110
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360

SEQ ID NO: 111          moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 111
gagatcgtcc tgacacagag tccagcaact ctgagcctgt cccccggcga acgagctact  60
ctgtcctgcc gggcatctca gagtgtgtct agttacctgg cctggtatca gcagaagccc  120
ggccaggctc ctaggctgct gatctacgac gccagcaaca gagctaccgg gattcctgcc  180
aggttctcag gcagcgggtc cggaacagac tttaccctga caatctcaag cctggagccc  240
gaagatttcg ctgtgtacta ttgccagcag tcctctaatt ggcctcgcac ctttggccag  300
gggacaaagg tcgagatcaa g                                              321

SEQ ID NO: 112          moltype = DNA  length = 333
FEATURE                 Location/Qualifiers
misc_feature            1..333
                        note = Description of Artificial Sequence: Synthetic
                         polynucleotide
source                  1..333
                        mol_type = other DNA
                        organism = synthetic construct
SEQUENCE: 112
gagatcgtcc tgactcagtc cccagcaacc ctgagtctgt caccaggaga aagggcaacc  60
ctgagctgcc gagcatccaa gggggtgagc acatccggat actcttatct gcactggtac  120
cagcagaaac ccggacaggc tcctcgactg ctgatctacc tggcatctta tctggagagt  180
ggcgtgcctg ctcggttctc tgggagtgga tcaggcaccg attttacact gactatttct  240
agtctggagc cagaagattt cgcagtgtac tattgccagc attctcgaga cctgcccctg  300
acatttggcg gggaactaa ggtcgagatc aaa                                  333

SEQ ID NO: 113          moltype = DNA  length = 1758
FEATURE                 Location/Qualifiers
misc_feature            1..1758
                        note = Description of Artificial Sequence: Synthetic
                         polynucleotide
source                  1..1758
                        mol_type = other DNA
                        organism = synthetic construct
SEQUENCE: 113
caggtgcagc tggtcgaaag cggaggagga gtggtccagc caggacgatc cctgagactg  60
gattgtaagg cctctggaat cacattctct aacagtggaa tgcactgggt gcgccaggca  120
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttcag ctagcaccaa gggcccatcg  360
gtcttccccc tggcgccctg ctccaggagc acctccgaga gcacagccgc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acgaagacct acacctgcaa cgtagatcac  600
aagcccagca acaccaaggt ggacaagaga gttgagtcca aatatggtcc cccatgccca  660
tcatgcccag cacctgagtt cctgggggga ccatcagtct tcctgttccc cccaaaaccc  720
```

```
aaggacactc tcatgatctc ccggacccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tccgggtaaa  1320
ggtggaggtg gttctggagg tggaggtagt atccctcctc acgtacagaa gtccgtgaac  1380
aatgacatga ttgtcactga caataacgga gccgtcaagt ttcctcagct atgtaagttc  1440
tgcgatgttc ggttctccac atgcgataat cagaaaagct gtatgtctaa ttgcagtatc  1500
actagtatat gcgaaaaacc tcaagaagtt tgcgtcgccg tgtggcggaa aaatgatgaa  1560
aatatcacgc ttgagactgt ctgccatgat ccaaagttac cctaccacga cttcatctta  1620
gaagacgccg catcacccaa gtgcattatg aaagagaaaa agaagccagg agaaacattc  1680
tttatgtgct catgctcctc tgacgaatgc aacgacaaca ttatcttctc tgaggagtat  1740
aacacctcaa atccagac                                                1758

SEQ ID NO: 114         moltype = DNA  length = 1758
FEATURE                Location/Qualifiers
misc_feature           1..1758
                       note = Description of Artificial Sequence: Synthetic
                        polynucleotide
source                 1..1758
                       mol_type = other DNA
                       organism = synthetic construct
SEQUENCE: 114
caggtgcagc tggtcgaaag cggaggagga gtggtccagc caggacgatc cctgagactg  60
gattgtaagg cctctggaat cacattctct aacagtggaa tgcactgggt gcgccaggca  120
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttcag ctagcaccaa gggcccatcg  360
gtcttccccc tggcgccctg ctccaggagc acctccgaga gcacagccgc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acgaagacct acacctgcaa cgtagatcac  600
aagcccagca acaccaaggt ggacaagaga gttgagtcca aatatggtcc cccatgccca  660
ccatgcccag cacctgagtt cctgggggga ccatcagtct tcctgttccc cccaaaaccc  720
aaggacactc tcatgatctc ccggacccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tccgggtaaa  1320
ggtggaggtg gttctggagg tggaggtagt atccctcctc acgtacagaa gtccgtgaac  1380
aatgacatga ttgtcactga caataacgga gccgtcaagt ttcctcagct atgtaagttc  1440
tgcgatgttc ggttctccac atgcgataat cagaaaagct gtatgtctaa ttgcagtatc  1500
actagtatat gcgaaaaacc tcaagaagtt tgcgtcgccg tgtggcggaa aaatgatgaa  1560
aatatcacgc ttgagactgt ctgccatgat ccaaagttac cctaccacga cttcatctta  1620
gaagacgccg catcacccaa gtgcattatg aaagagaaaa agaagccagg agaaacattc  1680
tttatgtgct catgctcctc tgacgaatgc aacgacaaca ttatcttctc tgaggagtat  1740
aacacctcaa atccagac                                                1758

SEQ ID NO: 115         moltype = DNA  length = 1779
FEATURE                Location/Qualifiers
misc_feature           1..1779
                       note = Description of Artificial Sequence: Synthetic
                        polynucleotide
source                 1..1779
                       mol_type = other DNA
                       organism = synthetic construct
SEQUENCE: 115
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360
gctagcacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
```

```
aaatatggtc ccccatgccc accatgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagagc  1320
ctctccctgt ctccgggtaa aggtggaggt ggttctggag gtggaggtag tatccctcct  1380
cacgtacaga agtccgtgaa caatgacatg attgtcactg acaataacgg agccgtcaag  1440
tttcctcagc tatgtaagtt ctgcgatgtt cggttctcca catgcgataa tcagaaaagc  1500
tgtatgtcta attgcagtat cactagtata tgcgaaaaac ctcaagaagt ttgcgtcgcc  1560
gtgtggcgga aaaatgatga aaatatcacg cttgagactg tctgccatga tccaaagtta  1620
ccctaccacg acttcatctt agaagacgcc gcatcaccca agtgcattat gaaagagaaa  1680
aagaagccag gagaaacatt ctttatgtgc tcatgctcct ctgacgaatg caacgacaac  1740
attatcttct ctgaggagta taacacctca aatccagac                        1779

SEQ ID NO: 116          moltype = DNA  length = 1779
FEATURE                 Location/Qualifiers
misc_feature            1..1779
                        note = Description of Artificial Sequence: Synthetic
                         polynucleotide
source                  1..1779
                        mol_type = other DNA
                        organism = synthetic construct
SEQUENCE: 116
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360
gctagcacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc atcatgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagagc  1320
ctctccctgt ctccgggtaa aggtggaggt ggttctggag gtggaggtag tatccctcct  1380
cacgtacaga agtccgtgaa caatgacatg attgtcactg acaataacgg agccgtcaag  1440
tttcctcagc tatgtaagtt ctgcgatgtt cggttctcca catgcgataa tcagaaaagc  1500
tgtatgtcta attgcagtat cactagtata tgcgaaaaac ctcaagaagt ttgcgtcgcc  1560
gtgtggcgga aaaatgatga aaatatcacg cttgagactg tctgccatga tccaaagtta  1620
ccctaccacg acttcatctt agaagacgcc gcatcaccca agtgcattat gaaagagaaa  1680
aagaagccag gagaaacatt ctttatgtgc tcatgctcct ctgacgaatg caacgacaac  1740
attatcttct ctgaggagta taacacctca aatccagac                        1779

SEQ ID NO: 117          moltype = DNA  length = 981
FEATURE                 Location/Qualifiers
misc_feature            1..981
                        note = Description of Artificial Sequence: Synthetic
                         polynucleotide
source                  1..981
                        mol_type = other DNA
                        organism = synthetic construct
SEQUENCE: 117
gctagcacca agggcccatc ggtcttcccc ctggcgccct gctccaggag cacctccgag  60
agcacagccg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacgaagacc  240
tacacctgca acgtagatca caagcccagc aacaccaagg tggacaagag agttgagtcc  300
aaatatggtc ccccatgccc accatgccca gcacctgagt tcctgggggg accatcagtc  360
ttcctgttcc ccccaaaacc caaggacact ctcatgatct cccggacccc tgaggtcacg  420
tgcgtggtgg tggacgtgag ccaggaagac cccgaggtcc agttcaactg gtacgtggat  480
ggcgtggagg tgcataatgc caagacaaag ccgcgggagg agcagttcaa cagcacgtac  540
cgtgtggtca gcgtcctcac cgtcctgcac caggactggc tgaacggcaa ggagtacaag  600
```

```
tgcaaggtct ccaacaaagg cctcccgtcc tccatcgaga aaaccatctc caaagccaaa  660
gggcagcccc gagagccaca ggtgtacacc ctgcccccat cccaggagga gatgaccaag  720
aaccaggtca gcctgacctg cctggtcaaa ggcttctacc ccagcgacat cgccgtggag  780
tgggagagca atgggcagcc ggagaacaac tacaagacca cgcctcccgt gctggactcc  840
gacggctcct tcttcctcta cagcaggctc accgtggaca agagcaggtg gcaggagggg  900
aatgtcttct catgctccgt gatgcatgag gctctgcaca accactacac acagaagagc  960
ctctccctgt ctccgggtaa a                                            981

SEQ ID NO: 118          moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 118
gagatagtta tgactcaaag ccccgctaca ttatccctgt ctccgggtga acgggccacc  60
ctgtcatgcc gggcttcaca gtcagtgtca agctatctgg catggtatca gcagaagcct  120
ggacaggccc caaggctact gatttatgac gccagcaacc gcgctacagg tattcctgct  180
aggttctcag ggtcaggctc tggaaccgac tttactctga ctatctcctc tcttgaaccc  240
gaggatttcg cggtgtacta ctgtcagcag tataataact ggccacgcac attcggccag  300
ggcactaaag tcgaaattaa g                                            321

SEQ ID NO: 119          moltype = DNA  length = 321
FEATURE                 Location/Qualifiers
misc_feature            1..321
                        note = Description of Artificial Sequence: Synthetic
                         polynucleotide
source                  1..321
                        mol_type = other DNA
                        organism = synthetic construct
SEQUENCE: 119
gagatcgtac tgactcagtc tccagccaca ttgtccctgt ccccagggga gcgcgccacc  60
ctgagctgta gagcttcaca gtccgtcagt tcttacctcg cgtggtatca gcaaaaacct  120
ggacaagctc cgaggttgct tatctatgac gcctccaacc gcgccactgg cataccagca  180
aggttcagcg gatctgggtc cggcacagat tttaccctca ctatttctag ccttgagccg  240
gaagatttcg ctgtttacta ctgccagcag cgatccaact ggcccaagac attcggccag  300
ggaactaaag tggaaatcaa a                                            321

SEQ ID NO: 120          moltype = DNA  length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 120
gaaattgtgt tgacacagtc tccagccacc ctgtctttgt ctccagggga aagagccacc  60
ctctcctgca gggccagtca gagtgttagt agttacttag cctggtacca acagaaacct  120
ggccaggctc ccaggctcct catctatgat gcatccaaca gggccaacgg catcccagcc  180
aggttcagtg gcagtgggtc tgggacagac ttcactctca ccatcagcag cctagagcct  240
gaagatttcg cagtttatta ctgtcagcag agtagcaact ggcctcggac gttcggccaa  300
gggaccaagg tggaaatcaa aaga                                         324

SEQ ID NO: 121          moltype = DNA  length = 342
FEATURE                 Location/Qualifiers
misc_feature            1..342
                        note = Description of Artificial Sequence: Synthetic
                         polynucleotide
source                  1..342
                        mol_type = other DNA
                        organism = synthetic construct
SEQUENCE: 121
cggaacgtgc tgacccagtc ccccttagc ctccccgtca cgcccggaga gcccgcaagt  60
atcagctgcc gcagttcaca aagtctgagt tcttctggat acacctattt ggactggtat  120
ttgcagaagc cagggcaatc cccacagctc ctgatatacc tcgcaagctg gagagatagc  180
ggagtacctg atcgcttttc tggtagcgga tctggtacgg atttcactct gaagatttct  240
agggtggagg cggaggacgt gggagtgtac tactgtatgc aagccgagca gactcccggc  300
ccaggtaaca cgttcggaca ggggaccaaa ctggagatta ag                     342

SEQ ID NO: 122          moltype = DNA  length = 336
FEATURE                 Location/Qualifiers
misc_feature            1..336
                        note = Description of Artificial Sequence: Synthetic
                         polynucleotide
source                  1..336
                        mol_type = other DNA
```

```
                        organism = synthetic construct
SEQUENCE: 122
gatgtggtaa tgacccagtc acctctttca ctgcctgtca ctcccggaga gccagcttca  60
atctcctgcc gtagctctca atcattgttg cacaccaatg gatacaacta cctccactgg  120
tatctccaga agcccggaca aagcccgcag ctgctgatct acctgggcag ctggcaggac  180
tccggggtgc ccgaccgatt tagcggcagt gggagcggca cggactttac actgaagatc  240
agccgagtag aggcggagga cgtgggcgtt tactactgta tgcaggcaga gcagaccccc  300
agaaccttcg gccagggcac ccggctggag gtgaaa                            336

SEQ ID NO: 123          moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 123
caggtgcagt tggttgaaag cggaggaggc gtggttcaac ccggtagaag cctacggctg  60
tcatgtgcgg cctccggctt cacatttcga tcttacggaa tgcactgggt caggcaggca  120
cccggcaagg gtctggagtg ggtcgccata attttctatg acggcagcaa caagtattac  180
gccgacagtg ttaaggggcg gtttaccatc agcagagaca actctaaaaa cactctttat  240
ctgcaaatga actctctgcg ggcagaggat accgctgttt actattgcgc cagagatgac  300
gactactggg ggcagggtgc cttggtgact gtgagcagc                         339

SEQ ID NO: 124          moltype = DNA  length = 342
FEATURE                 Location/Qualifiers
misc_feature            1..342
                        note = Description of Artificial Sequence: Synthetic
                         polynucleotide
source                  1..342
                        mol_type = other DNA
                        organism = synthetic construct
SEQUENCE: 124
gaggtccagt tagtccaaag cggcggaggc gtagtgcaac ctggcagaag cctgcggtta  60
tcgtgcgccg caagcggctt cacctttagc tcttatggta tgcactgggt cagacaggcc  120
cctgggaagg gcctggagtg ggtggccgtg atctggtatg acgggagcaa caagtattac  180
gcggattccg tcaagggacg gttcaccata tcccgcgata acagcaagaa tactctttac  240
ttacagatga acagcctgag ggccgaggac accgcagtat attattgcgc tggcgaaggc  300
tttgactatt ggggtcaggg cactctggtg actgtgagca gc                     342

SEQ ID NO: 125          moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 125
caggtgcagc tggtggagtc tgggggaggc gtggtccagc ctgggaggtc cctgagactc  60
gactgtaaag cgtctggaat caccttcagt aactctggca tgcactgggt ccgccaggct  120
ccaggcaagg ggctggagtg ggtggcagtt atttggtatg atggaagtaa aagatactat  180
gcagactccg tgaagggccg attcaccatc tccagagaca attccaagaa cacgctgttt  240
ctgcaaatga acagcctgag agccgaggac acggctgtgt attactgtgc gacaaacaac  300
gactactggg gccagggaac cctggtcacc gtctcctca                         339

SEQ ID NO: 126          moltype = DNA  length = 339
FEATURE                 Location/Qualifiers
misc_feature            1..339
                        note = Description of Artificial Sequence: Synthetic
                         polynucleotide
source                  1..339
                        mol_type = other DNA
                        organism = synthetic construct
SEQUENCE: 126
caggtgcagc tggtggagtc tgggggaggc gtggtccagc ctgggaggtc cctgagactc  60
gactgtaaag cgtctggaat caccttcagt aactctggca tgcactgggt ccgccaggct  120
ccaggcaagg ggctggagtg ggtggcagtt atttggtatg atggaagtaa aagatactat  180
gcagactccg tgaagggccg attcaccatc tccagagaca attccaagaa cacgctgttt  240
ctgcaaatga acagcctgag agccgaggac acggctgtgt attactgtgc gagaaacgac  300
gactactggg gccagggaac cctggtcacc gtctcctca                         339

SEQ ID NO: 127          moltype = DNA  length = 360
FEATURE                 Location/Qualifiers
misc_feature            1..360
                        note = Description of Artificial Sequence: Synthetic
                         polynucleotide
source                  1..360
```

```
                          mol_type = other DNA
                          organism = synthetic construct
SEQUENCE: 127
caggtacagc tggtgcagag cggcgcagag gtgaagaagc caggcgcttc tgtaaaggta  60
tcctgcaagg catccgggta tactttcacc ggctattaca tgcactgggt tcgtcaggca  120
cccggccagg gactagaatg gatgggggcc atcaacccta atagtggcgg tactaactac  180
gcacaaaagt ttcaggggcg agtgaccatg actcgggata cctccatctc cacggcatac  240
atggagctga gtcgcttgcg gtcagatgac actgcggtgt actactgcgc tcgcaggccc  300
gaccgagcta attggcactt tgactactgg ggacagggta cactggtgac cgtgtcatca  360

SEQ ID NO: 128          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 128
caggtgcagc tggtccagag cggcgcggaa gtgaaaaagc ccggcgcttc cgtgaaggtt  60
tcttgcaaag cctctggata cacattcact ggctattata tgcactgggt cagacaggcc  120
cccggccagg gattggagtg gatgggtgca atcaacccca attctggtgg gaccaattac  180
gcacagaaac tccagggccg agtgacaatg accaccgaca cttctaccag cactgcctac  240
atggagctgc ggtctctgcg atcagacgac accgctgtgt actattgtgc aagacacggg  300
ctgaagggcg acggctattt tgactactgg ggacagggca cgctggttac cgtgagttcc  360

SEQ ID NO: 129          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 129
caggtccagc tcgtgcaaag cggagtggaa gtgaaaaagc ctggcgcttc cgtcaaggtc  60
agctgtaagg ccagcggata cacattcaca aactattaca tgtactgggt gaggcaggct  120
cccggacagg gactggaatg gatgggcgga atcaatccct ccaacggagg cacaaacttt  180
aacgaaaagt ttaagaatag agtcaccctc accacagact ccagcacaac cacagcctat  240
atggaactga aaagcctcca gtttgacgat accgctgtgt attactgtgc caggagagat  300
tacaggttct acatgggatt cgattactgg ggccaaggca caaccgtcac cgtcagctcc  360

SEQ ID NO: 130          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 130
caggtccagc tcgtgcaaag cggagtggaa gtgaaaaagc ctggcgcttc cgtcaaggtc  60
agctgtaagg ccagcggata cacattcaca aactattaca tgtactgggt gaggcaggct  120
cccggacagg gactggaatg gatgggcgga atcaatccct ccaacggagg cacaaacttt  180
aacgaaaagt ttaagaatag agtcaccctc accacagact ccagcacaac cacagcctat  240
atggaactga aaagcctcca gtttgacgat accgctgtgt attactgtgc caggagagat  300
tacaggttca acatgggatt cgattactgg ggccaaggca caaccgtcac cgtcagctcc  360

SEQ ID NO: 131          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 131
caggtccagc tcgtgcaaag cggagtggaa gtgaaaaagc ctggcgcttc cgtcaaggtc  60
agctgtaagg ccagcggata cacattcaca aactattaca tgtactgggt gaggcaggct  120
cccggacagg gactggaatg gatgggcgga atccagccct ccaacggagg cacaaacttt  180
aacgaaaagt ttaagaatag agtcaccctc accacagact ccagcacaac cacagcctat  240
atggaactga aaagcctcca gtttgacgat accgctgtgt attactgtgc caggagagat  300
tacaggttct acatgggatt cgattactgg ggccaaggca caaccgtcac cgtcagctcc  360

SEQ ID NO: 132          moltype = DNA  length = 360
FEATURE                 Location/Qualifiers
misc_feature            1..360
                        note = Description of Artificial Sequence: Synthetic
                         polynucleotide
```

-continued

```
source                 1..360
                       mol_type = other DNA
                       organism = synthetic construct
SEQUENCE: 132
caggtccagc tcgtgcaaag cggagtggaa gtgaaaaagc ctggcgcttc cgtcaaggtc  60
agctgtaagg ccagcggata cacattcaca aactattaca tgtactgggt gaggcaggct  120
cccggacagg gactggaatg gatgggcgga atcgacccct ccaacggagg cacaaacttt  180
aacgaaaagt ttaagaatag agtcaccctc accacagact ccagcacaac cacagcctat  240
atggaactga aaagcctcca gtttgacgat accgctgtgt attactgtgc caggtacgat  300
tacaggttcg atatgggatt cgattactgg ggccaaggca caaccgtcac cgtcagctcc  360

SEQ ID NO: 133         moltype = DNA  length = 339
FEATURE                Location/Qualifiers
misc_feature           1..339
                       note = Description of Artificial Sequence: Synthetic
                        polynucleotide
source                 1..339
                       mol_type = other DNA
                       organism = synthetic construct
SEQUENCE: 133
caggtgcagc tggtggagtc tgggggaggc gtggtccagc ctgggaggtc cctgagactc  60
gactgtaaag cgtctggatt caccttcagt aactctggca tgcactgggt ccgccaggct  120
ccaggcaagg ggctggagtg ggtggcagtt atttggtatg atggaagtaa aagatactat  180
gcagactccg tgaagggccg attcaccatc tccagagaca attccaagaa cacgctgttt  240
ctgcaaatga acagcctgag agccgaggac acggctgtgt attactgtgc gacaaacaac  300
gactactggg gccagggaac cctggtcacc gtctcctca                         339

SEQ ID NO: 134         moltype = DNA  length = 339
FEATURE                Location/Qualifiers
misc_feature           1..339
                       note = Description of Artificial Sequence: Synthetic
                        polynucleotide
source                 1..339
                       mol_type = other DNA
                       organism = synthetic construct
SEQUENCE: 134
gaggtccagt tagtccaaag cggcggaggc gtagtgcaac ctggcagaag cctgcggtta  60
tcgtgcgccg caagcggctt cacctttagc tcttatggta tgcactgggt cagacaggcc  120
cctgggaagg gcctggagtg ggtggccgtg atctggtatg acgggagcaa caagtattac  180
gcggattccg tcaagggacg gttcaccata tcccgcgata acagcaagaa tactctttac  240
ttacagatga acagcctgag ggccgaggac accgcagtat attattgcgc taccaataat  300
gactattggg gtcagggcac tctggtgact gtgagcagc                         339

SEQ ID NO: 135         moltype = DNA  length = 336
FEATURE                Location/Qualifiers
misc_feature           1..336
                       note = Description of Artificial Sequence: Synthetic
                        polynucleotide
source                 1..336
                       mol_type = other DNA
                       organism = synthetic construct
SEQUENCE: 135
gaggtgcaac tggttcagtc cggcgggggc gtcgtccagc cggggcgcag tctgcgcttg  60
agctgtgctg cctctgggat tacctttagc aactccatgc attgggtgcg gcaggcaccc  120
gggaagggac tggaatgggt cgcagtgatc tggtacgatg gatcaaagcg gtattacgcc  180
gactccgtca aaggccggtt cacaatcagc cgcgacaaca gcaaaaatac tttatatctt  240
cagatgaatt cccttagggc agaggatact gctgtgtatt actgcgctac taacaacgat  300
tattgggggc aggggacact agtcactgtt tctagt                            336

SEQ ID NO: 136         moltype = DNA  length = 339
FEATURE                Location/Qualifiers
misc_feature           1..339
                       note = Description of Artificial Sequence: Synthetic
                        polynucleotide
source                 1..339
                       mol_type = other DNA
                       organism = synthetic construct
SEQUENCE: 136
gaggtccagt tagtccaaag cggcggaggc gtagtgcaac ctggcagaag cctgcggtta  60
tcgtgcgccg caagcggctt cacctttagc aattctggta tgcactgggt cagacaggcc  120
cctgggaagg gcctggagtg ggtggccgtg atctggtatg acgggagcaa caagtattac  180
gcggattccg tcaagggacg gttcaccata tcccgcgata acagcaagaa tactctttac  240
ttacagatga acagcctgag ggccgaggac accgcagtat attattgcgc taccaataat  300
gactattggg gtcagggcac tctggtgact gtgagcagc                         339

SEQ ID NO: 137         moltype = DNA  length = 336
FEATURE                Location/Qualifiers
misc_feature           1..336
                       note = Description of Artificial Sequence: Synthetic
```

-continued

```
                         polynucleotide
source                  1..336
                        mol_type = other DNA
                        organism = synthetic construct
SEQUENCE: 137
gaggtccagt tagtccaaag cggcggaggc gtagtgcaac ctggcagaag cctgcggtta  60
tcgtgcgccg caagcggctt cacctttagc tcttatggta tgcactgggt cagacaggcc  120
cctgggaagg gcctggagtg ggtggccgtg atctggtatg acgggagcaa gtattacgcg  180
gattccgtca agggacggtt caccatatcc cgcgataaca gcaagaatac tctttactta  240
cagatgaaca gcctgagggc cgaggacacc gcagtatatt attgcgctac caataatgac  300
tattggggtc agggcactct ggtgactgtg agcagc                            336

SEQ ID NO: 138          moltype = DNA  length = 342
FEATURE                 Location/Qualifiers
misc_feature            1..342
                        note = Description of Artificial Sequence: Synthetic
                         polynucleotide
source                  1..342
                        mol_type = other DNA
                        organism = synthetic construct
SEQUENCE: 138
caggtgcagc tggtggagtc tgggggaggc gtggtccagc ctgggaggtc cctgagactc  60
gactgtaaag cgtctggaat caccttcagt aactctggca tgcactgggt ccgccaggct  120
ccaggcaagg ggctggagtg ggtggcagtt atttggtatg atggaagtaa caaaagatac  180
tatgcagact ccgtgaaggg ccgattcacc atctccagag acaattccaa gaacacgctg  240
tttctgcaaa tgaacagcct gagagccgag gacacggctg tgtattactg tgcgacaaac  300
aacgactact ggggccaggg aaccctggtc accgtctcct ca                     342

SEQ ID NO: 139          moltype = DNA  length = 342
FEATURE                 Location/Qualifiers
misc_feature            1..342
                        note = Description of Artificial Sequence: Synthetic
                         polynucleotide
source                  1..342
                        mol_type = other DNA
                        organism = synthetic construct
SEQUENCE: 139
caggtgcagc tggtggagtc tgggggaggc gtggtccagc ctgggaggtc cctgagactc  60
gactgtaaag cgtctggatt caccttcagt aactctggca tgcactgggt ccgccaggct  120
ccaggcaagg ggctggagtg ggtggcagtt atttggtatg atggaagtaa caaaagatac  180
tatgcagact ccgtgaaggg ccgattcacc atctccagag acaattccaa gaacacgctg  240
tttctgcaaa tgaacagcct gagagccgag gacacggctg tgtattactg tgcgacaaac  300
aacgactact ggggccaggg aaccctggtc accgtctcct ca                     342

SEQ ID NO: 140          moltype = DNA  length = 336
FEATURE                 Location/Qualifiers
misc_feature            1..336
                        note = Description of Artificial Sequence: Synthetic
                         polynucleotide
source                  1..336
                        mol_type = other DNA
                        organism = synthetic construct
SEQUENCE: 140
gaggtgcaac ttgtgcaaag cggcggcgga gtcgtgcagc ccggtcgatc tcttcgcctg  60
agttgtgctg ccagcggcat tacctttagc aattctggta tgcactgggt acgtcaggcc  120
cccggtaagg ggctagaatg ggtggctgtg atttggtacg atggttctaa gtactacgcc  180
gacagcgtta aaggccgatt caccatcagt agagacaaca gtaagaacac cctctacctc  240
cagatgaaca gtctgcgagc tgaagacact gctgtgtact actgtgccac caacaacgac  300
tactggggac agggaaccct ggtcaccgtg agtagt                            336

SEQ ID NO: 141          moltype = AA  length = 161
FEATURE                 Location/Qualifiers
source                  1..161
                        mol_type = protein
                        organism = Homo sapiens
SEQUENCE: 141
IPPHVQKSDV EMEAQKDEII CPSCNRTAHP LRHINNDMIV TDNNGAVKFP QLCKFCDVRF  60
STCDNQKSCM SNCSITSICE KPQEVCVAVW RKNDENITLE TVCHDPKLPY HDFILEDAAS  120
PKCIMKEKKK PGETFFMCSC SSDECNDNII FSEEYNTSNP D                      161

SEQ ID NO: 142          moltype = AA  length = 112
FEATURE                 Location/Qualifiers
source                  1..112
                        mol_type = protein
                        organism = Homo sapiens
SEQUENCE: 142
PQLCKFCDVR FSTCDNQKSC MSNCSITSIC EKPQEVCVAV WRKNDENITL ETVCHDPKLP  60
YHDFILEDAA SPKCIMKEKK KPGETFFMCS CSSDECNDNI IFSEEYNTSN PD          112
```

```
SEQ ID NO: 143          moltype = AA  length = 586
FEATURE                 Location/Qualifiers
REGION                  1..586
                        note = Description of Artificial Sequence: Synthetic
                         polypeptide
source                  1..586
                        mol_type = protein
                        organism = synthetic construct
SEQUENCE: 143
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSPGK GGGGSGGGGS IPPHVQKSVN NDMIVTDNNG AVKFPQLCKF  480
CDVRFSTCDN QKSCMSNCSI TSICEKPQEV CVAVWRKNDE NITLETVCHD PKLPYHDFIL  540
EDAASPKCIM KEKKKPGETF FMCSCSSDEC NDNIIFSEEY NTSNPD                586

SEQ ID NO: 144          moltype = AA  length = 593
FEATURE                 Location/Qualifiers
REGION                  1..593
                        note = Description of Artificial Sequence: Synthetic
                         polypeptide
source                  1..593
                        mol_type = protein
                        organism = synthetic construct
SEQUENCE: 144
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSPGKGGG GSGGGGSIPP HVQKSVNNDM IVTDNNGAVK  480
FPQLCKFCDV RFSTCDNQKS CMSNCSITSI CEKPQEVCVA VWRKNDENIT LETVCHDPKL  540
PYHDFILEDA ASPKCIMKEK KKPGETFFMC SCSSDECNDN IIFSEEYNTS NPD        593

SEQ ID NO: 145          moltype = AA  length = 593
FEATURE                 Location/Qualifiers
REGION                  1..593
                        note = Description of Artificial Sequence: Synthetic
                         polypeptide
source                  1..593
                        mol_type = protein
                        organism = synthetic construct
SEQUENCE: 145
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPSCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSPGKGGG GSGGGGSIPP HVQKSVNNDM IVTDNNGAVK  480
FPQLCKFCDV RFSTCDNQKS CMSNCSITSI CEKPQEVCVA VWRKNDENIT LETVCHDPKL  540
PYHDFILEDA ASPKCIMKEK KKPGETFFMC SCSSDECNDN IIFSEEYNTS NPD        593

SEQ ID NO: 146          moltype = AA  length = 327
FEATURE                 Location/Qualifiers
source                  1..327
                        mol_type = protein
                        organism = Homo sapiens
SEQUENCE: 146
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 147          moltype = AA  length = 327
FEATURE                 Location/Qualifiers
REGION                  1..327
                        note = Description of Artificial Sequence: Synthetic
                         polypeptide
source                  1..327
```

```
                         mol_type = protein
                         organism = synthetic construct
SEQUENCE: 147
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSPGK                                     327

SEQ ID NO: 148           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 148
EIVLTQSPAT LSLSPGERAT LSCRASQSVS SYLAWYQQKP GQAPRLLIYD ASNRANGIPA  60
RFSGSGSGTD FTLTISSLEP EDFAVYYCQQ SSNWPRTFGQ GTKVEIKR               108

SEQ ID NO: 149           moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 149
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATNN DYWGQGTLVT VSS         113

SEQ ID NO: 150           moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 150
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCARND DYWGQGTLVT VSS         113

SEQ ID NO: 151           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 151
QVQLVQSGAE VKKPGASVKV SCKASGYTFT GYYMHWVRQA PGQGLEWMGA INPNSGGTNY  60
AQKFQGRVTM TRDTSISTAY MELSRLRSDD TAVYYCARRP DRANWHFDYW GQGTLVTVSS  120

SEQ ID NO: 152           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 152
QVQLVQSGAE VKKPGASVKV SCKASGYTFT GYYMHWVRQA PGQGLEWMGA INPNSGGTNY  60
AQKLQGRVTM TTDTSTSTAY MELRSLRSDD TAVYYCARHG LKGDGYFDYW GQGTLVTVSS  120

SEQ ID NO: 153           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 153
```

-continued

```
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFYMGFDYW GQGTTVTVSS  120

SEQ ID NO: 154         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 154
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFNMGFDYW GQGTTVTVSS  120

SEQ ID NO: 155         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 155
QVQLVQSGVE VKKPGASVKV SCKASGYTFT NYYMYWVRQA PGQGLEWMGG IQPSNGGTNF  60
NEKFKNRVTL TTDSSTTTAY MELKSLQFDD TAVYYCARRD YRFYMGFDYW GQGTTVTVSS  120

SEQ ID NO: 156         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 156
QVQLVQSGVE VKKPGASVKV SCKASGYTFT NYYMYWVRQA PGQGLEWMGG IDPSNGGTNF  60
NEKFKNRVTL TTDSSTTTAY MELKSLQFDD TAVYYCARYD YRFDMGFDYW GQGTTVTVSS  120

SEQ ID NO: 157         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 157
QVQLVESGGG VVQPGRSLRL DCKASGFTFS NSGMHWVRQA PGKGLEWVAV IWYDGSKRYY  60
ADSVKGRFTI SRDNSKNTLF LQMNSLRAED TAVYYCATNN DYWGQGTLVT VSS         113

SEQ ID NO: 158         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 158
EVQLVQSGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCATNN DYWGQGTLVT VSS         113

SEQ ID NO: 159         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 159
EVQLVQSGGG VVQPGRSLRL SCAASGITFS NSMHWVRQAP GKGLEWVAVI WYDGSKRYYA  60
DSVKGRFTIS RDNSKNTLYL QMNSLRAEDT AVYYCATNND YWGQGTLVTV SS          112

SEQ ID NO: 160         moltype = AA  length = 113
FEATURE                Location/Qualifiers
REGION                 1..113
                       note = Description of Artificial Sequence: Synthetic
```

-continued

```
                         polypeptide
source                  1..113
                        mol_type = protein
                        organism = synthetic construct
SEQUENCE: 160
EVQLVQSGGG VVQPGRSLRL SCAASGFTFS NSGMHWVRQA PGKGLEWVAV IWYDGSNKYY  60
ADSVKGRFTI SRDNSKNTLY LQMNSLRAED TAVYYCATNN DYWGQGTLVT VSS         113

SEQ ID NO: 161          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 161
EVQLVQSGGG VVQPGRSLRL SCAASGFTFS SYGMHWVRQA PGKGLEWVAV IWYDGSKYYA  60
DSVKGRFTIS RDNSKNTLYL QMNSLRAEDT AVYYCATNND YWGQGTLVTV SS          112

SEQ ID NO: 162          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 162
QVQLVESGGG VVQPGRSLRL DCKASGITFS NSGMHWVRQA PGKGLEWVAV IWYDGSNKRY  60
YADSVKGRFT ISRDNSKNTL FLQMNSLRAE DTAVYYCATN NDYWGQGTLV TVSS        114

SEQ ID NO: 163          moltype = AA  length = 45
FEATURE                 Location/Qualifiers
REGION                  1..45
                        note = Description of Artificial Sequence: Synthetic
                         polypeptide
source                  1..45
                        mol_type = protein
                        organism = synthetic construct
SEQUENCE: 163
QVQLVESGGG VVQPGRSLRL DCKASGFTFS NSGMHWVRQA PGKGL                  45

SEQ ID NO: 164          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 164
EVQLVQSGGG VVQPGRSLRL SCAASGITFS NSGMHWVRQA PGKGLEWVAV IWYDGSKYYA  60
DSVKGRFTIS RDNSKNTLYL QMNSLRAEDT AVYYCATNND YWGQGTLVTV SS          112

SEQ ID NO: 165          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 165
DIMMTQSPSS LAVSAGEKVT MSCKSSQSVL YSSNQKNYLA WYQQKPGQSP KLLIYWASTR  60
ESGVPDRFTG SGSGTDFTLT ISSVQAEDLA VYYCHQYLSS DTFGGGTKLE IKRTVA      116

SEQ ID NO: 166          moltype = AA  length = 124
FEATURE                 Location/Qualifiers
REGION                  1..124
                        note = Description of Artificial Sequence: Synthetic
                         polypeptide
MOD_RES                 3
                        note = Any amino acid
MOD_RES                 5
                        note = Any amino acid
source                  1..124
                        mol_type = protein
                        organism = synthetic construct
```

```
SEQUENCE: 166
QVXLXQSGAE LVRPGTSVKV SCKASGYAFT NYLIEWVKQR PGQGLEWIGV NNPGSGGSNY  60
NEKFKGKATL TADKSSSTAY MQLSSLTSDD SAVYFCARSG GFYFDYWGQG TTQSPSPQPK  120
RRAH                                                               124

SEQ ID NO: 167          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 167
DIQMTQSPSS LSASVGDRVT ITCRASQSVL YSSNQKNYLA WYQQKPGKAP KLLIYWASTR  60
ESGVPSRFSG SGSGTDFTLT ISSLQPEDFA TYYCHQYLSS DTFGQGTKVE IKRTVA      116

SEQ ID NO: 168          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 168
EVQLVESGGG LVQPGGSLRL SCAASGYAFT NYLIEWVRQA PGKGLEWVGV NNPGSGGSNY  60
NEKFKGRATI SADNSKNTLY LQMNSLRAED TAVYYCARSG GFYFDYWGQG TLVTVSSAST  120
KGPS                                                               124

SEQ ID NO: 169          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 169
LARPGASVKM SCKTSGYTFT NYWMHWVRQR PGQGLEWIGT IYPGNSDTNY NQKFKDKAKL  60
TAVTSATTAY MELSSLTNED SAVYFCTRED SRSLYYNGWD YFDYWGQGTT LTVSS       115

SEQ ID NO: 170          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 170
LTQSPASLAV SLGQRATISC RASESVDNYG ISFLNWFQQK PGQPPKLLIY AASNQGSGVP  60
ARFSGSGSGT DFSLNIHPME EDDTGMYFCQ QSKEVPRTFG GGTKLEII               108

SEQ ID NO: 171          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 171
QVQLVQSGAE VKKPGSSVKV SCKASGGTFS SYAISWVRQA PGQGLEWMGG IIPIFGTANY  60
AQKFQGRVTI TADESTSTAY MELSSLRSED TAVYYCARGL WEVRALPSVY WGQGTLVTVS  120
S                                                                  121

SEQ ID NO: 172          moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 172
SYELTQPPSV SVAPGQTARI TCGANDIGSK SVHWYQQKAG QAPVLVVSED IIRPSGIPER  60
ISGSNSGNTA TLTISRVEAG DEADYYCQVW DRDSDQYVFG TGTKVTVLG              109
```

-continued

```
SEQ ID NO: 173          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 173
QVQLVQSGAE VKKPGSSVKV SCKASGYTFS SNVISWVRQA PGQGLEWMGG VIPIVDIANY  60
AQRFKGRVTI TADESTSTTY MELSSLRSED TAVYYCASTL GLVLDAMDYW GQGTLVTVSS  120

SEQ ID NO: 174          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 174
ETVLTQSPGT LSLSPGERAT LSCRASQSLG SSYLAWYQQK PGQAPRLLIY GASSRAPGIP  60
DRFSGSGSGT DFTLTISRLE PEDFAVYYCQ QYADSPITFG QGTRLEIK               108

SEQ ID NO: 175          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 175
QVQLVQSGAE VKKPGSSVKV SCKASGYTFS SNVISWVRQA PGQGLEWMGG VIPIVDIANY  60
AQRFKGRVTI TADESTSTTY MELSSLRSED TAVYYCALPR AFVLDAMDYW GQGTLVTVSS  120

SEQ ID NO: 176          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 176
ETVLTQSPGT LSLSPGERAT LSCRASQSLG SSYLAWYQQK PGQAPRLLIY GASSRAPGIP  60
DRFSGSGSGT DFTLTISRLE PEDFAVYYCQ QYADSPITFG QGTRLEIK               108

SEQ ID NO: 177          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 177
QVQLVQSGAE VKKPGSSVKV SCKASGGTFS TSFINWVRQA PGQGLEWMGG IIPIFDITNY  60
AQKFQSRVTI TADKSTSTAY MELSSLRSED TAVYYCARGN GNYALDAMDY WGQGTLVTVS  120
S                                                                  121

SEQ ID NO: 178          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 178
EIVLTQSPGT LSLSPGERAT LSCRASQSVS SSYFAWYQQK PGQAPRLLIY GASSRATGIP  60
DRFSGSGSGT DFTLTISRLE PEDFAVYYCQ QYYDSPITFG QGTRLEIK               108

SEQ ID NO: 179          moltype = DNA  length = 348
FEATURE                 Location/Qualifiers
misc_feature            1..348
                        note = Description of Artificial Sequence: Synthetic
                         polynucleotide
source                  1..348
```

```
                        mol_type = other DNA
                        organism = synthetic construct
SEQUENCE: 179
gatataatga tgacacagag ccccagctct ctagctgtga gtgctggcga gaaggtgacc  60
atgagctgta agagcagtca aagcgtgctg tacagttcca atcagaaaaa ttacctcgca  120
tggtatcagc agaagccagg tcaaagccct aagctcctta tctactgggc ctcaacccgt  180
gaaagtggag tgcctgacag atttactggt tcagggagcg gcaccgattt cactctgact  240
attagctctg tgcaggcaga agaccttgcc gtgtattact gtcaccagta tctgtcttca  300
gacacgtttg gaggtgggac caaactagaa atcaaacgta ctgtcgca               348

SEQ ID NO: 180          moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
misc_difference         7..9
                        note = a, c, t, g, unknown or other
misc_difference         13..15
                        note = a, c, t, g, unknown or other
SEQUENCE: 180
caggtgnnnc tgnnncagag cggcgccgag ctggtgaggc ccggcaccag cgtgaaggtg  60
agctgcaagg ccagcggcta cgccttcacc aactacctga tcgagtgggt gaagcagagg  120
cccggccagg gcctggagtg gatcggcgtg aacaaccccg gcagcggcgg cagcaactac  180
aacgagaagt tcaagggcaa ggccaccctg accgccgaca agagcagcag caccgcctac  240
atgcagctga gcagcctgac cagcgacgac agcgccgtgt acttctgcgc caggagcggc  300
ggcttctact tcgactactg gggccagggc accacccaga gccccagccc ccagcccaag  360
aggagggccc ac                                                      372

SEQ ID NO: 181          moltype = DNA  length = 348
FEATURE                 Location/Qualifiers
misc_feature            1..348
                        note = Description of Artificial Sequence: Synthetic
                         polynucleotide
source                  1..348
                        mol_type = other DNA
                        organism = synthetic construct
SEQUENCE: 181
gacatccaga tgacccagag ccccagcagc ctgagcgcca gcgtgggcga cagggtgacc  60
atcacctgca gggccagcca gagcgtgctg tacagcagca accagaagaa ctacctggcc  120
tggtaccagc agaagcccgg caaggccccc aagctgctga tctactgggc cagcaccagg  180
gagagcggcg tgcccagcag gttcagcggc agcggcagcg gcaccgactt caccctgacc  240
atcagcagcc tgcagcccga ggacttcgcc acctactact gccaccagta cctgagcagc  300
gacaccttcg gccagggcac caaggtggag atcaagagga ccgtggcc               348

SEQ ID NO: 182          moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 182
gaggtgcagc tggtggagag cggcggcggc ctggtgcagc ccggcggcag cctgaggctg  60
agctgcgccg ccagcggcta cgccttcacc aactacctga tcgagtgggt gaggcaggcc  120
cccggcaagg gcctggagtg ggtgggcgtg aacaaccccg gcagcggcgg cagcaactac  180
aacgagaagt tcaagggcag ggccaccatc agcgccgaca acagcaagaa caccctgtac  240
ctgcagatga acagcctgag ggccgaggac accgccgtgt actactgcgc caggagcggc  300
ggcttctact tcgactactg gggccagggc accctggtga ccgtgagcag cgccagcacc  360
aagggcccca gc                                                      372

SEQ ID NO: 183          moltype = DNA  length = 345
FEATURE                 Location/Qualifiers
misc_feature            1..345
                        note = Description of Artificial Sequence: Synthetic
                         polynucleotide
source                  1..345
                        mol_type = other DNA
                        organism = synthetic construct
SEQUENCE: 183
ctggccaggc ccggcgccag cgtgaagatg agctgcaaga ccagcggcta caccttcacc  60
aactactgga tgcactgggt gaggcagagg cccggccagg gcctggagtg gatcggcacc  120
atctaccccg gcaacagcga caccaactac aaccagaagt tcaaggacaa ggccaagctg  180
accgccgtga ccagcgccac caccgcctac atggagctga gcagcctgac caacgaggac  240
agcgccgtgt acttctgcac cagggaggac agcaggagcc tgtactacaa cggctgggac  300
tacttcgact actggggcca gggcaccacc ctgaccgtga gcagc                  345
```

```
SEQ ID NO: 184          moltype = DNA  length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 184
ctgacccaga gccccgccag cctggccgtg agcctgggcc agagggccac catcagctgc  60
agggccagcg agagcgtgga caactacggc atcagcttcc tgaactggtt ccagcagaag  120
cccggccagc cccccaagct gctgatctac gccgccagca accagggcag cggcgtgccc  180
gccaggttca gcggcagcgg cagcggcacc gacttcagcc tgaacatcca ccccatggag  240
gaggacgaca ccggcatgta cttctgccag cagagcaagg aggtgcccag gaccttcggc  300
ggcggcacca agctggagat catc                                         324

SEQ ID NO: 185          moltype = DNA  length = 363
FEATURE                 Location/Qualifiers
misc_feature            1..363
                        note = Description of Artificial Sequence: Synthetic
                         polynucleotide
source                  1..363
                        mol_type = other DNA
                        organism = synthetic construct
SEQUENCE: 185
caggtgcagc tggtgcagag cggcgccgag gtgaagaagc ccggcagcag cgtgaaggtg  60
agctgcaagg ccagcggcgg caccttcagc agctacgcca tcagctgggt gaggcaggcc  120
cccggccagg gcctggagtg gatgggcggc atcatcccca tcttcggcac cgccaactac  180
gcccagaagt tccagggcag ggtgaccatc accgccgacg agagcaccag caccgcctac  240
atggagctga gcagcctgag gagcgaggac accgccgtgt actactgcgc caggggcctg  300
tgggaggtga gggccctgcc cagcgtgtac tggggccagg gcaccctggt gaccgtgagc  360
agc                                                                363

SEQ ID NO: 186          moltype = DNA  length = 327
FEATURE                 Location/Qualifiers
misc_feature            1..327
                        note = Description of Artificial Sequence: Synthetic
                         polynucleotide
source                  1..327
                        mol_type = other DNA
                        organism = synthetic construct
SEQUENCE: 186
agctacgagc tgacccagcc ccccagcgtg agcgtggccc ccggccagac cgccaggatc  60
acctgcggcg ccaacgacat cggcagcaag agcgtgcact ggtaccagca gaaggccggc  120
caggcccccg tgctggtggt gagcgaggac atcatcaggc ccagcggcat ccccgagagg  180
atcagcggca gcaacagcgg caacaccgcc accctgacca tcagcagggt ggaggccggc  240
gacgaggccg actactactg ccaggtgtgg gacagggaca gcgaccagta cgtgttcggc  300
accggcacca aggtgaccgt gctgggc                                      327

SEQ ID NO: 187          moltype = DNA  length = 360
FEATURE                 Location/Qualifiers
misc_feature            1..360
                        note = Description of Artificial Sequence: Synthetic
                         polynucleotide
source                  1..360
                        mol_type = other DNA
                        organism = synthetic construct
SEQUENCE: 187
caggtgcagc tggtgcagag cggcgccgag gtgaagaagc ccggcagcag cgtgaaggtg  60
agctgcaagg ccagcggcta caccttcagc agcaacgtga tcagctgggt gaggcaggcc  120
cccggccagg gcctggagtg gatgggcggc gtgatcccca tcgtggacat cgccaactac  180
gcccagaggt tcaagggcag ggtgaccatc accgccgacg agagcaccag caccacctac  240
atggagctga gcagcctgag gagcgaggac accgccgtgt actactgcgc cagcaccctg  300
ggcctggtgc tggacgccat ggactactgg ggccagggca ccctggtgac cgtgagcagc  360

SEQ ID NO: 188          moltype = DNA  length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 188
gagaccgtgc tgacccagag ccccggcacc ctgagcctga gccccggcga gagggccacc  60
ctgagctgca gggccagcca gagcctgggc agcagctacc tggcctggta ccagcagaag  120
cccggccagg cccccaggct gctgatctac ggcgccagca gcagggcccc cggcatcccc  180
gacaggttca gcggcagcgg cagcggcacc gacttcaccc tgaccatcag caggctggag  240
```

-continued

```
cccgaggact tcgccgtgta ctactgccag cagtacgccg acagccccat caccttcggc  300
cagggcacca ggctggagat caag                                          324

SEQ ID NO: 189         moltype = DNA  length = 360
FEATURE                Location/Qualifiers
misc_feature           1..360
                       note = Description of Artificial Sequence: Synthetic
                        polynucleotide
source                 1..360
                       mol_type = other DNA
                       organism = synthetic construct
SEQUENCE: 189
caggtgcagc tggtgcagag cggcgccgag gtgaagaagc ccggcagcag cgtgaaggtg  60
agctgcaagg ccagcggcta caccttcagc agcaacgtga tcagctgggt gaggcaggcc  120
cccggccagg gcctggagtg gatgggcggc gtgatcccca tcgtggacat cgccaactac  180
gcccagaggt tcaagggcag ggtgaccatc accgccgacg agagcaccag caccacctac  240
atggagctga gcagcctgag gagcgaggac accgccgtgt actactgcgc cctgcccagg  300
gccttcgtgc tggacgccat ggactactgg ggccagggca ccctggtgac cgtgagcagc  360

SEQ ID NO: 190         moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
SEQUENCE: 190
gagaccgtgc tgacccagag ccccggcacc ctgagcctga gccccggcga gagggccacc  60
ctgagctgca gggccagcca gagcctgggc agcagctacc tggcctggta ccagcagaag  120
cccggccagg cccccaggct gctgatctac ggcgccagca gcagggcccc cggcatcccc  180
gacaggttca gcggcagcgg cagcggcacc gacttcaccc tgaccatcag caggctggag  240
cccgaggact tcgccgtgta ctactgccag cagtacgccg acagccccat caccttcggc  300
cagggcacca ggctggagat caag                                          324

SEQ ID NO: 191         moltype = DNA  length = 363
FEATURE                Location/Qualifiers
misc_feature           1..363
                       note = Description of Artificial Sequence: Synthetic
                        polynucleotide
source                 1..363
                       mol_type = other DNA
                       organism = synthetic construct
SEQUENCE: 191
caggtgcagc tggtgcagag cggcgccgag gtgaagaagc ccggcagcag cgtgaaggtg  60
agctgcaagg ccagcggcgg caccttcagc accagcttca tcaactgggt gaggcaggcc  120
cccggccagg gcctggagtg gatgggcggc atcatcccca tcttcgacat caccaactac  180
gcccagaagt tccagagcag ggtgaccatc accgccgaca agagcaccag caccgcctac  240
atggagctga gcagcctgag gagcgaggac accgccgtgt actactgcgc caggggcaac  300
ggcaactacg ccctggacgc catggactac tggggccagg gcaccctggt gaccgtgagc  360
agc                                                                 363

SEQ ID NO: 192         moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
SEQUENCE: 192
gagatcgtgc tgacccagag ccccggcacc ctgagcctga gccccggcga gagggccacc  60
ctgagctgca gggccagcca gagcgtgagc agcagctact tcgcctggta ccagcagaag  120
cccggccagg cccccaggct gctgatctac ggcgccagca gcagggccac cggcatcccc  180
gacaggttca gcggcagcgg cagcggcacc gacttcaccc tgaccatcag caggctggag  240
cccgaggact tcgccgtgta ctactgccag cagtactacg acagccccat caccttcggc  300
cagggcacca ggctggagat caag                                          324

SEQ ID NO: 193         moltype =   length =
SEQUENCE: 193
000

SEQ ID NO: 194         moltype =   length =
SEQUENCE: 194
000

SEQ ID NO: 195         moltype =   length =
SEQUENCE: 195
000
```

```
SEQ ID NO: 196          moltype =   length =
SEQUENCE: 196
000

SEQ ID NO: 197          moltype =   length =
SEQUENCE: 197
000

SEQ ID NO: 198          moltype =   length =
SEQUENCE: 198
000

SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000

SEQ ID NO: 204          moltype =   length =
SEQUENCE: 204
000

SEQ ID NO: 205          moltype =   length =
SEQUENCE: 205
000

SEQ ID NO: 206          moltype =   length =
SEQUENCE: 206
000

SEQ ID NO: 207          moltype =   length =
SEQUENCE: 207
000

SEQ ID NO: 208          moltype =   length =
SEQUENCE: 208
000

SEQ ID NO: 209          moltype =   length =
SEQUENCE: 209
000

SEQ ID NO: 210          moltype =   length =
SEQUENCE: 210
000

SEQ ID NO: 211          moltype =   length =
SEQUENCE: 211
000

SEQ ID NO: 212          moltype =   length =
SEQUENCE: 212
000

SEQ ID NO: 213          moltype =   length =
SEQUENCE: 213
000

SEQ ID NO: 214          moltype =   length =
SEQUENCE: 214
000

SEQ ID NO: 215          moltype =   length =
SEQUENCE: 215
```

```
000

SEQ ID NO: 216         moltype =   length =
SEQUENCE: 216
000

SEQ ID NO: 217         moltype =   length =
SEQUENCE: 217
000

SEQ ID NO: 218         moltype =   length =
SEQUENCE: 218
000

SEQ ID NO: 219         moltype =   length =
SEQUENCE: 219
000

SEQ ID NO: 220         moltype =   length =
SEQUENCE: 220
000

SEQ ID NO: 221         moltype =   length =
SEQUENCE: 221
000

SEQ ID NO: 222         moltype =   length =
SEQUENCE: 222
000

SEQ ID NO: 223         moltype =   length =
SEQUENCE: 223
000

SEQ ID NO: 224         moltype =   length =
SEQUENCE: 224
000

SEQ ID NO: 225         moltype =   length =
SEQUENCE: 225
000

SEQ ID NO: 226         moltype =   length =
SEQUENCE: 226
000

SEQ ID NO: 227         moltype =   length =
SEQUENCE: 227
000

SEQ ID NO: 228         moltype =   length =
SEQUENCE: 228
000

SEQ ID NO: 229         moltype =   length =
SEQUENCE: 229
000

SEQ ID NO: 230         moltype =   length =
SEQUENCE: 230
000

SEQ ID NO: 231         moltype =   length =
SEQUENCE: 231
000

SEQ ID NO: 232         moltype =   length =
SEQUENCE: 232
000

SEQ ID NO: 233         moltype =   length =
SEQUENCE: 233
000

SEQ ID NO: 234         moltype =   length =
SEQUENCE: 234
000

SEQ ID NO: 235         moltype =   length =
```

-continued

```
SEQUENCE: 235
000

SEQ ID NO: 236         moltype =   length =
SEQUENCE: 236
000

SEQ ID NO: 237         moltype =   length =
SEQUENCE: 237
000

SEQ ID NO: 238         moltype =   length =
SEQUENCE: 238
000

SEQ ID NO: 239         moltype =   length =
SEQUENCE: 239
000

SEQ ID NO: 240         moltype =   length =
SEQUENCE: 240
000

SEQ ID NO: 241         moltype =   length =
SEQUENCE: 241
000

SEQ ID NO: 242         moltype =   length =
SEQUENCE: 242
000

SEQ ID NO: 243         moltype =   length =
SEQUENCE: 243
000

SEQ ID NO: 244         moltype =   length =
SEQUENCE: 244
000

SEQ ID NO: 245         moltype =   length =
SEQUENCE: 245
000

SEQ ID NO: 246         moltype =   length =
SEQUENCE: 246
000

SEQ ID NO: 247         moltype =   length =
SEQUENCE: 247
000

SEQ ID NO: 248         moltype =   length =
SEQUENCE: 248
000

SEQ ID NO: 249         moltype =   length =
SEQUENCE: 249
000

SEQ ID NO: 250         moltype =   length =
SEQUENCE: 250
000

SEQ ID NO: 251         moltype =   length =
SEQUENCE: 251
000

SEQ ID NO: 252         moltype =   length =
SEQUENCE: 252
000

SEQ ID NO: 253         moltype =   length =
SEQUENCE: 253
000

SEQ ID NO: 254         moltype =   length =
SEQUENCE: 254
000
```

-continued

```
SEQ ID NO: 255          moltype =   length =
SEQUENCE: 255
000

SEQ ID NO: 256          moltype =   length =
SEQUENCE: 256
000

SEQ ID NO: 257          moltype =   length =
SEQUENCE: 257
000

SEQ ID NO: 258          moltype =   length =
SEQUENCE: 258
000

SEQ ID NO: 259          moltype =   length =
SEQUENCE: 259
000

SEQ ID NO: 260          moltype =   length =
SEQUENCE: 260
000

SEQ ID NO: 261          moltype =   length =
SEQUENCE: 261
000

SEQ ID NO: 262          moltype =   length =
SEQUENCE: 262
000

SEQ ID NO: 263          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 263
HANFCLGPCP YIWSLA                                                    16

SEQ ID NO: 264          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 264
FCLGPCPYIW SLDTA                                                     15

SEQ ID NO: 265          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 265
SNPYSAFQVD IIVDIA                                                    16

SEQ ID NO: 266          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 266
TSLDATMIWT MMA                                                       13

SEQ ID NO: 267          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 267
TSLDASIWAM MQNA                                                  14

SEQ ID NO: 268          moltype = DNA  length = 48
FEATURE                 Location/Qualifiers
misc_feature            1..48
                        note = Description of Artificial Sequence: Synthetic
                         oligonucleotide
source                  1..48
                        mol_type = other DNA
                        organism = synthetic construct
SEQUENCE: 268
cacgccaact tctgcctggg cccctgcccc tacatctgga gcctggcc             48

SEQ ID NO: 269          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 269
ttctgcctgg gcccctgccc ctacatctgg agcctggaca ccgcc                45

SEQ ID NO: 270          moltype = DNA  length = 48
FEATURE                 Location/Qualifiers
misc_feature            1..48
                        note = Description of Artificial Sequence: Synthetic
                         oligonucleotide
source                  1..48
                        mol_type = other DNA
                        organism = synthetic construct
SEQUENCE: 270
agcaacccct acagcgcctt ccaggtggac atcatcgtgg acatcgcc             48

SEQ ID NO: 271          moltype = DNA  length = 39
FEATURE                 Location/Qualifiers
misc_feature            1..39
                        note = Description of Artificial Sequence: Synthetic
                         oligonucleotide
source                  1..39
                        mol_type = other DNA
                        organism = synthetic construct
SEQUENCE: 271
accagcctgg acgccaccat gatctggacc atgatggcc                       39

SEQ ID NO: 272          moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 272
accagcctgg acgccagcat ctgggccatg atgcagaacg cc                   42

SEQ ID NO: 273          moltype = AA  length = 442
FEATURE                 Location/Qualifiers
REGION                  1..442
                        note = Description of Artificial Sequence: Synthetic
                         polypeptide
source                  1..442
                        mol_type = protein
                        organism = synthetic construct
SEQUENCE: 273
IDETRAHLLL KEKMMRLGGR LVLNTKEELA NERLMTLKIA EMKEAMRTLI FPPSMHFFQA  60
KHLIERSQVF NILRMMPKGA ALHLHDIGIV TMDWLVRNVT YRPHGIALPG DSLLRNFTLV  120
TQHPEVIYTN QNVVLSKFET IFFTISGLIH YAPVFRDYVF RSMQEFYEDN VLYMEIRASL  180
LPVYELSGEH HDEEWSVKTY QEVAQDFVET HPEFIGIKII YSDHRSKDVA VIAESIRMAM  240
GLRIKFPTVV AGFDLVGHED TGHSLHDYKE ALMIPAKDGV KLPYFFHAGE TDWQGTSIDR  300
NILDALMLNT TRIGHGFALS KHPAVRTYSW KKDIPIEVCP ISNQVLKLVS DLRNHPVATL  360
MATGHPMVIS SDDPAMFGAK GLSYDFYEVF MGIGGMKADL RTLKQLAMNS IKYSTLLESE  420
KNTFMEIWKK RWDKFIADVA TK                                          442

SEQ ID NO: 274          moltype = AA  length = 442
FEATURE                 Location/Qualifiers
REGION                  1..442
```

```
                         note = Description of Artificial Sequence: Synthetic
                          polypeptide
source                   1..442
                         mol_type = protein
                         organism = synthetic construct
SEQUENCE: 274
IDETRAHLLL KEKMMRLGGR LVLNTKEELA NERLMTLKIA EMKEAMRTLI FPPSMHFFQA  60
KHLIERSQVF NILRMMPKGA ALHLHDIGIV TMDWLVRNVT YRPHGIALPG DSLLRNFTLV  120
TQHPEVIYTN QNVVWSKFET IVFTISGLIH YAPVFRDYVF RSMQEFYEDN VLYMEIRARL  180
LPVYELSGEH HDEEWSVKTY QEVAQDFVET HPEFIGIKII YSDHRSKDVA VIAESIRMAM  240
GLRIKFPTVV AGFDLAGHED TGHSLHDYKE ALMIPAKDGV KLPYFFHAGE TDWQGTSIDR  300
NILDALMLNT TRIGHGFALS KHPAVRTYSW KKDIPIEVCP ISNQVLKLVS DLRNHPVATL  360
MATGHPMVIS SDDPAMFGAK GLSYDFYEVF MGIGGMKADL RTLKQLAMNS IKYSTLLESE  420
KNTFMEIWKK RWDKFIADVA TK                                           442

SEQ ID NO: 275           moltype = AA  length = 402
FEATURE                  Location/Qualifiers
REGION                   1..402
                         note = Description of Artificial Sequence: Synthetic
                          polypeptide
source                   1..402
                         mol_type = protein
                         organism = synthetic construct
SEQUENCE: 275
EMKEAMRTLI FPPSMHFFQA KHLIERSQVF NILRMMPKGA ALHLHDIGIV TMDWLVRNVT  60
YRPHGIALPG DSLLRNFTLV TQHPEVIYTN QNVVLSKFET IVFTISGLIH YAPVFRDYVF  120
RSMQEFYEDN VLYMEIRARL LPVYELSGEH HDEEWSVKTY QEVAQDFVET HPEFIGIKII  180
YSDHRSKDVA VIAESIRMAM GLRIKFPTVV AGFDLVGHED TGHSLHDYKE ALMIPAKDGV  240
KLPYFFHAGE TDWQGTSIDR NILDALMLNT TRIGHGFALS KHPAVRTYSW KKDIPIEVCP  300
ISNQVLKLVS DLRNHPVATL MATGHPMVIS SDDPAMFGAK GLSYDFYEVF MGIGGMKADL  360
RTLKQLAMNS IKYSTLLESE KNTFMEIWKK RWDKFIADVA TK                     402

SEQ ID NO: 276           moltype = AA  length = 442
FEATURE                  Location/Qualifiers
REGION                   1..442
                         note = Description of Artificial Sequence: Synthetic
                          polypeptide
source                   1..442
                         mol_type = protein
                         organism = synthetic construct
SEQUENCE: 276
IDETRAHLLL KEKMMRLGGR LVLNTKEELA NERLMTLKIA EMKEAMRTLI FPPSMHFFQA  60
KHLIERSQVF NILRMMPKGA ALHLHDIGIV TMDWLGGGGS GGGGSVTEFD DSLLRNFTLV  120
TQHPEVIYTN QNVVWSKFET IFFTISGLIH YAPVFRDYVF RSMQEFYEDN VLYMEIRARL  180
LPVYELSGEH HDEEWSVKTY QEVAQEFVET HPEFIGIKII YSDHRSRDVA VIAESIRMAM  240
GLRIKFPTVV AGFDLSGHED TGHSLHDYKE ALMIPAKDGV KLPYFFHAGE TDWQGTSIDR  300
NILDALMLNT TRIGHGFALS KHPAVRTYSW KKDIPIEVCP ISNQVLKLVS DLRNHPVATL  360
MATGHPMVIS SDDPAMFGAK GLSYDFYEVF MGIGGMKADL RTLKQLAMNS IKYSTLLESE  420
KNTFMEIWKK RWDKFIADVA TK                                           442

SEQ ID NO: 277           moltype = AA  length = 442
FEATURE                  Location/Qualifiers
REGION                   1..442
                         note = Description of Artificial Sequence: Synthetic
                          polypeptide
source                   1..442
                         mol_type = protein
                         organism = synthetic construct
SEQUENCE: 277
IDETRAHLLL KEKMMRLGGR LVLNTKEELA NERLMTLKIA EMKEAMRTLI FPPSMHFFQA  60
KHLIERSQVF NILRMMPKGA ALHLHNIGIV TMDWLGGGGS GGGGSVTEFD DSLLRNFTLV  120
TQHPEVIYTN QNVVWSKFET IFFTISGLIH YAPVFRDYVF RSMQEFYEDN VLYMEIRARL  180
LPVYELSGEH HDEEWSVKTY QEVAQDFVET HPEFIGIKII YSDHRSYDVA VIAESIRMAM  240
GLRIKFPTVV AGFDLVGHED TGHSLHDYKE ALMIPAKDGV KLPYFFHAGE TDWQGTSIDR  300
NILDALMLNT TRIGHGFALS KHPAVRTYSW KKDIPIEVCP ISNQVLKLVS DLRNHPVATL  360
MATGHPMVIS SDDPAMFGAK GLSYDFYEVF MGIGGMKADL RTLKQLAMNS IKYSTLLESE  420
KNTFMEIWKK RWDKFIADVA TK                                           442

SEQ ID NO: 278           moltype = AA  length = 482
FEATURE                  Location/Qualifiers
REGION                   1..482
                         note = Description of Artificial Sequence: Synthetic
                          polypeptide
source                   1..482
                         mol_type = protein
                         organism = synthetic construct
SEQUENCE: 278
IDETRAHLLL KEKMMRLGGR LVLNTKEELA NERLMTLKIA EMKEAMRTLI FPPSMHFFQA  60
KHLIERSQVF NILRMMPKGA ALHLHDIGIV TMDWLVRNVT YRPHCHICFT PRGIMQFRFA  120
```

```
HPTPRPSEKC SKWILLEDYR KRVQNVTEFD DSLLRNFTLV TQHPEVIYTN QNVVWSKFET  180
IFFTISGLIH YAPVFRDYVF RSMQEFYEDN VLYMEIRARL LPVYELSGEH HDEEWSVKTY  240
QEVAQKFVET HPEFIGIKII YSDHRSKDVA VIAESIRMAM GLRIKFPTVV AGFDLVGHED  300
TGHSLHDYKE ALMIPAKDGV KLPYFFHAGE TDWQGTSIDR NILDALMLNT TRIGHGFALS  360
KHPAVRTYSW KKDIPIEVCP ISNQVLKLVS DLRNHPVATL MATGHPMVIS SDDPAMFGAK  420
GLSYDFYEVF MGIGGMKADL RTLKQLAMNS IKYSTLLESE KNTFMEIWKK RWDKFIADVA  480
TK                                                                 482

SEQ ID NO: 279         moltype = AA  length = 482
FEATURE                Location/Qualifiers
REGION                 1..482
                       note = Description of Artificial Sequence: Synthetic
                        polypeptide
source                 1..482
                       mol_type = protein
                       organism = synthetic construct
SEQUENCE: 279
IDETRAHLLL KEKMMRLGGR LVLNTKEELA NERLMTLKIA EMKEAMRTLI FPPSMHFFQA  60
KHLIERSQVF NILRMMPKGA ALHLHDIGIV TMDWLVRNVT YRPHCHICFT PRGIMQFRFA  120
HPTPRPSEKC SKWILLEDYR KRVQNVTEFD DSLLRNFTLV TQHPEVIYTN QNVVWSKFET  180
IFFTISGLIH YAPVFRDYVF RSMQEFYEDN VLYMEIRAQL LPVYELSGEH HDEEWSVKTY  240
QEVAQKFVET HPEFIGIKII YNDHRSKDVA VIAESIRMAM GLRIKFPTVV AGFDLVGHED  300
TGHSLHDYKE ALMIPAKDGV KLPYFFHAGE TDWQGTSIDR NILDALMLNT TRIGHGFALS  360
KHPAVRTYSW DKDIPIEVCP ISNQVLKLVS DLRNHPVATL MATGHPMVIS SDDPAMFGAK  420
GLSYDFYEVF MGIGGMKADL RTLKQLAMNS IKYSTLLESE KNTFMEIWKK RWDKFIADVA  480
TK                                                                 482

SEQ ID NO: 280         moltype = AA  length = 932
FEATURE                Location/Qualifiers
REGION                 1..932
                       note = Description of Artificial Sequence: Synthetic
                        polypeptide
source                 1..932
                       mol_type = protein
                       organism = synthetic construct
SEQUENCE: 280
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSPGK GGGGSGGGGS IDETRAHLLL KEKMMRLGGR LVLNTKEELA  480
NERLMTLKIA EMKEAMRTLI FPPSMHFFQA KHLIERSQVF NILRMMPKGA ALHLHDIGIV  540
TMDWLVRNVT YRPHCHICFT PRGIMQFRFA HPTPRPSEKC SKWILLEDYR KRVQNVTEFD  600
DSLLRNFTLV TQHPEVIYTN QNVVWSKFET IFFTISGLIH YAPVFRDYVF RSMQEFYEDN  660
VLYMEIRARL LPVYELSGEH HDEEWSVKTY QEVAQKFVET HPEFIGIKII YSDHRSKDVA  720
VIAESIRMAM GLRIKFPTVV AGFDLVGHED TGHSLHDYKE ALMIPAKDGV KLPYFFHAGE  780
TDWQGTSIDR NILDALMLNT TRIGHGFALS KHPAVRTYSW KKDIPIEVCP ISNQVLKLVS  840
DLRNHPVATL MATGHPMVIS SDDPAMFGAK GLSYDFYEVF MGIGGMKADL RTLKQLAMNS  900
IKYSTLLESE KNTFMEIWKK RWDKFIADVA TK                                932

SEQ ID NO: 281         moltype = AA  length = 932
FEATURE                Location/Qualifiers
REGION                 1..932
                       note = Description of Artificial Sequence: Synthetic
                        polypeptide
source                 1..932
                       mol_type = protein
                       organism = synthetic construct
SEQUENCE: 281
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSPGK GGGGSGGGGS IDETRAHLLL KEKMMRLGGR LVLNTKEELA  480
NERLMTLKIA EMKEAMRTLI FPPSMHFFQA KHLIERSQVF NILRMMPKGA ALHLHDIGIV  540
TMDWLVRNVT YRPHCHICFT PRGIMQFRFA HPTPRPSEKC SKWILLEDYR KRVQNVTEFD  600
DSLLRNFTLV TQHPEVIYTN QNVVWSKFET IFFTISGLIH YAPVFRDYVF RSMQEFYEDN  660
VLYMEIRAQL LPVYELSGEH HDEEWSVKTY QEVAQKFVET HPEFIGIKII YNDHRSKDVA  720
VIAESIRMAM GLRIKFPTVV AGFDLVGHED TGHSLHDYKE ALMIPAKDGV KLPYFFHAGE  780
TDWQGTSIDR NILDALMLNT TRIGHGFALS KHPAVRTYSW DKDIPIEVCP ISNQVLKLVS  840
DLRNHPVATL MATGHPMVIS SDDPAMFGAK GLSYDFYEVF MGIGGMKADL RTLKQLAMNS  900
IKYSTLLESE KNTFMEIWKK RWDKFIADVA TK                                932
```

```
SEQ ID NO: 282          moltype = AA  length = 939
FEATURE                 Location/Qualifiers
REGION                  1..939
                        note = Description of Artificial Sequence: Synthetic
                         polypeptide
source                  1..939
                        mol_type = protein
                        organism = synthetic construct
SEQUENCE: 282
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSPGKGGG GSGGGGSIDE TRAHLLLKEK MMRLGGRLVL  480
NTKEELANER LMTLKIAEMK EAMRTLIFPP SMHFFQAKHL IERSQVFNIL RMMPKGAALH  540
LHDIGIVTMD WLVRNVTYRP HCHICFTPRG IMQFRFAHPT PRPSEKCSKW ILLEDYRKRV  600
QNVTEFDDSL LRNFTLVTQH PEVIYTNQNV VWSKFETIFF TISGLIHYAP VFRDYVFRSM  660
QEFYEDNVLY MEIRARLLPV YELSGEHHDE EWSVKTYQEV AQKFVETHPE FIGIKIIYSD  720
HRSKDVAVIA ESIRMAMGLR IKFPTVVAGF DLVGHEDTGH SLHDYKEALM IPAKDGVKLP  780
YFFHAGETDW QGTSIDRNIL DALMLNTTRI GHGFALSKHP AVRTYSWKKD IPIEVCPISN  840
QVLKLVSDLR NHPVATLMAT GHPMVISSDD PAMFGAKGLS YDFYEVFMGI GGMKADLRTL  900
KQLAMNSIKY STLLESEKNT FMEIWKKRWD KFIADVATK                        939

SEQ ID NO: 283          moltype = AA  length = 939
FEATURE                 Location/Qualifiers
REGION                  1..939
                        note = Description of Artificial Sequence: Synthetic
                         polypeptide
source                  1..939
                        mol_type = protein
                        organism = synthetic construct
SEQUENCE: 283
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSPGKGGG GSGGGGSIDE TRAHLLLKEK MMRLGGRLVL  480
NTKEELANER LMTLKIAEMK EAMRTLIFPP SMHFFQAKHL IERSQVFNIL RMMPKGAALH  540
LHDIGIVTMD WLVRNVTYRP HCHICFTPRG IMQFRFAHPT PRPSEKCSKW ILLEDYRKRV  600
QNVTEFDDSL LRNFTLVTQH PEVIYTNQNV VWSKFETIFF TISGLIHYAP VFRDYVFRSM  660
QEFYEDNVLY MEIRAQLLPV YELSGEHHDE EWSVKTYQEV AQKFVETHPE FIGIKIIYND  720
HRSKDVAVIA ESIRMAMGLR IKFPTVVAGF DLVGHEDTGH SLHDYKEALM IPAKDGVKLP  780
YFFHAGETDW QGTSIDRNIL DALMLNTTRI GHGFALSKHP AVRTYSWDKD IPIEVCPISN  840
QVLKLVSDLR NHPVATLMAT GHPMVISSDD PAMFGAKGLS YDFYEVFMGI GGMKADLRTL  900
KQLAMNSIKY STLLESEKNT FMEIWKKRWD KFIADVATK                        939

SEQ ID NO: 284          moltype = AA  length = 483
FEATURE                 Location/Qualifiers
source                  1..483
                        mol_type = protein
                        organism = Homo sapiens
SEQUENCE: 284
SIDETRAHLL LKEKMMRLGG RLVLNTKEEL ANERLMTLKI AEMKEAMRTL IFPPSMHFFQ  60
AKHLIERSQV FNILRMMPKG AALHLHDIGI VTMDWLVRNV TYRPHCHICF TPRGIMQFRF  120
AHPTPRPSEK CSKWILLEDY RKRVQNVTEF DDSLLRNFTL VTQHPEVIYT NQNVVWSKFE  180
TIFFTISGLI HYAPVFRDYV FRSMQEFYED NVLYMEIRAR LLPVYELSGE HHDEEWSVKT  240
YQEVAQKFVE THPEFIGIKI IYSDHRSKDV AVIAESIRMA MGLRIKFPTV VAGFDLVGHE  300
DTGHSLHDYK EALMIPAKDG VKLPYFFHAG ETDWQGTSID RNILDALMLN TTRIGHGFAL  360
SKHPAVRTYS WKKDIPIEVC PISNQVLKLV SDLRNHPVAT LMATGHPMVI SSDDPAMFGA  420
KGLSYDFYEV FMGIGGMKAD LRTLKQLAMN SIKYSTLLES EKNTFMEIWK KRWDKFIADV  480
ATK                                                               483

SEQ ID NO: 285          moltype = DNA  length = 2796
FEATURE                 Location/Qualifiers
misc_feature            1..2796
                        note = Description of Artificial Sequence: Synthetic
                         polynucleotide
source                  1..2796
                        mol_type = other DNA
                        organism = synthetic construct
SEQUENCE: 285
caggtgcagc tggtcgaaag cggaggagga gtggtccagc caggacgatc cctgagactg  60
gattgtaagg cctctggaat cacattctct aacagtggaa tgcactgggt gcgccaggca  120
```

```
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttcag ctagcaccaa gggcccatcg  360
gtcttccccc tggcgccctg ctccaggagc acctccgaga gcacagccgc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acgaagacct acacctgcaa cgtagatcac  600
aagcccagca acaccaaggt ggacaagaga gttgagtcca aatatggtcc cccatgccca  660
ccatgcccag cacctgagtt cctgggggga ccatcagtct tcctgttccc cccaaaaccc  720
aaggacactc tcatgatctc ccggacccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tccgggtaaa  1320
ggtggaggtg gttctggagg tggaggtagt atcgacgaaa ccagagcaca cttactgctg  1380
aaagagaaaa tgatgcgcct gggcgggaga ttggtgttaa atactaagga agagctggca  1440
aatgaaagac tcatgacact gaagattgct gaaatgaagg aggcgatgag gacgctgatc  1500
tttccgcctt ccatgcactt cttccaagct aaacacctga tcgaaagatc ccaagtgttt  1560
aacatcctga ggatgatgcc taagggggcc gctctgcacc ttcacgatat tgggattgta  1620
acaatggact ggctggtaag gaacgtgaca tacagacctc attgccatat ttgttttact  1680
ccccgaggaa tcatgcaatt caggtttgcc cacccaactc ctcggccaag cgagaagtgt  1740
agtaagtgga ttttgctgga agattaccgt aagcgcgtgc agaatgtgac agagtttgat  1800
gactccctgc tccgcaattt taccctggtg acccagcacc ccgaagttat atacactaac  1860
caaaatgtcg tgtggtccaa gtttgagacg atcttcttca cgatttcagg cttgatccac  1920
tacgccccgg tctttcggga ttatgtgttt aggagtatgc aggagtttta tgaggataat  1980
gttctgtaca tggagatccg agcccggctg cttccagtct acgaactatc cggcgaacac  2040
catgacgagg aatggagcgt caagacctat caagaggtgg cccagaagtt cgtagaaacg  2100
catccagagt tcatcggtat taagattatc tactctgatc accgctcaaa ggatgtggct  2160
gtcatcgccg agtctatacg gatggccatg ggcctgcgga ttaagttccc taccgtcgtc  2220
gccggattcg acctcgttgg gcatgaggat actggccata gtctccatga ctataaagaa  2280
gcccttatga tcccagcaaa ggacggagtg aagctgccct acttcttcca cgcaggggag  2340
accgactggc agggaacgag catcgaccgg aacatacttg atgcactcat gcttaatacc  2400
acacgaatcg gccacggctt cgctctctcc aagcacccag ccgtgagaac ctacagctgg  2460
aagaaggata tccccatcga ggtttgtccc atcagcaatc aggtgctgaa attggtgagt  2520
gacctgagaa accacccagt cgcaacatta atggccactg gccaccctat ggtgatttca  2580
agcgatgatc cagccatgtt cggagcaaaa ggactcagtt acgacttcta tgaggtattc  2640
atgggtattg gtggtatgaa ggcagacctg cggactctta agcagttggc aatgaactca  2700
attaagtact ctaccttatt ggagtctgaa aagaacacat ttatggagat ctggaaaaag  2760
cgctgggaca aattcatcgc agatgttgcc acaaaa                           2796

SEQ ID NO: 286          moltype = DNA  length = 2796
FEATURE                 Location/Qualifiers
misc_feature            1..2796
                        note = Description of Artificial Sequence: Synthetic
                         polynucleotide
source                  1..2796
                        mol_type = other DNA
                        organism = synthetic construct
SEQUENCE: 286
caggtgcagc tggtcgaaag cggaggagga gtggtccagc caggacgatc cctgagactg  60
gattgtaagg cctctggaat cacattctct aacagtggaa tgcactgggt gcgccaggca  120
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttcag ctagcaccaa gggcccatcg  360
gtcttccccc tggcgccctg ctccaggagc acctccgaga gcacagccgc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acgaagacct acacctgcaa cgtagatcac  600
aagcccagca acaccaaggt ggacaagaga gttgagtcca aatatggtcc cccatgccca  660
ccatgcccag cacctgagtt cctgggggga ccatcagtct tcctgttccc cccaaaaccc  720
aaggacactc tcatgatctc ccggacccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tccgggtaaa  1320
ggtggaggtg gttctggagg tggaggtagt atcgacgaaa ccagagcaca cttactgctg  1380
aaagagaaaa tgatgcgcct gggcgggaga ttggtgttaa atactaagga agagctggca  1440
```

-continued

```
aatgaaagac tcatgacact gaagattgct gaaatgaagg aggcgatgag gacgctgatc  1500
tttccgcctt ccatgcactt cttccaagct aaacacctga tcgaaagatc ccaagtgttt  1560
aacatcctga ggatgatgcc taagggggcc gctctgcacc ttcacgatat tgggattgta  1620
acaatggact ggctggtaag gaacgtgaca tacagacctc attgccatat ttgttttact  1680
ccccgaggaa tcatgcaatt caggtttgcc cacccaactc ctcggccaag cgagaagtgt  1740
agtaagtgga ttttgctgga agattaccgt aagcgcgtgc agaatgtgac agagtttgat  1800
gactccctgc tccgcaattt taccctggtg acccagcacc ccgaagttat atacactaac  1860
caaaatgtcg tgtggtccaa gtttgagacg atcttcttca cgatttcagg cttgatccac  1920
tacgccccgg tctttcggga ttatgtgttt aggagtatgc aggagtttta tgaggataat  1980
gttctgtaca tggagatccg agcccagctg cttccagtct acgaactatc cggcgaacac  2040
catgacgagg aatggagcgt caagacctat caagaggtgg cccagaagtt cgtagaaacg  2100
catccagagt tcatcggtat taagattatc tacaatgatc accgctcaaa ggatgtggct  2160
gtcatcgccg agtctatacg gatggccatg ggcctgcgga ttaagttccc taccgtcgtc  2220
gccggattcg acctcgttgg gcatgaggat actggccata gtctccatga ctataaagaa  2280
gcccttatga tcccagcaaa ggacggagtg aagctgccct acttcttcca cgcaggggag  2340
accgactggc agggaacgag catcgaccgg aacatacttg atgcactcat gcttaatacc  2400
acacgaatcg gccacggctt cgctctctcc aagcacccag ccgtgagaac ctacagctgg  2460
gataaggata tccccatcga ggtttgtccc atcagcaatc aggtgctgaa attggtgagt  2520
gacctgagaa accacccagt cgcaacatta atggccactg gccaccctat ggtgatttca  2580
agcgatgatc cagccatgtt cggagcaaaa ggactcagtt acgacttcta tgaggtattc  2640
atgggtattg gtggtatgaa ggcagacctg cggactctta agcagttggc aatgaactca  2700
attaagtact ctaccttatt ggagtctgaa aagaacacat ttatggagat ctggaaaaag  2760
cgctgggaca aattcatcgc agatgttgcc acaaaa                            2796
```

```
SEQ ID NO: 287          moltype = DNA  length = 2817
FEATURE                 Location/Qualifiers
misc_feature            1..2817
                        note = Description of Artificial Sequence: Synthetic
                         polynucleotide
source                  1..2817
                        mol_type = other DNA
                        organism = synthetic construct
SEQUENCE: 287
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360
gctagcacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accatgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagagc  1320
ctctccctgt ctccgggtaa aggtggaggt ggttctggag gtggaggtag tatcgacgaa  1380
accagagcac acttactgct gaaagagaaa atgatgcgcc tgggcgggag attggtgtta  1440
aatactaagg aagagctggc aaatgaaaga ctcatgacac tgaagattgc tgaaatgaag  1500
gaggcgatga ggacgctgat ctttccgcct tccatgcact tcttccaagc taaacacctg  1560
atcgaaagat cccaagtgtt taacatcctg aggatgatgc ctaagggggc cgctctgcac  1620
cttcacgata ttgggattgt aacaatggac tggctggtaa ggaacgtgac atacagacct  1680
cattgccata tttgttttac tccccgagga atcatgcaat tcaggtttgc ccacccaact  1740
cctcggccaa gcgagaagtg tagtaagtgg attttgctgg aagattaccg taagcgcgtg  1800
cagaatgtga cagagtttga tgactccctg ctccgcaatt ttaccctggt gacccagcac  1860
cccgaagtta tatacactaa ccaaaatgtc gtgtggtcca agtttgagac gatcttcttc  1920
acgatttcag gcttgatcca ctacgccccg gtctttcggg attatgtgtt taggagtatg  1980
caggagtttt atgaggataa tgttctgtac atggagatcc gagcccggct gcttccagtc  2040
tacgaactat ccggcgaaca ccatgacgag gaatggagcg tcaagaccta tcaagaggtg  2100
gcccagaagt tcgtagaaac gcatccagag ttcatcggta ttaagattat ctactctgat  2160
caccgctcaa aggatgtggc tgtcatcgcc gagtctatac ggatggccat gggcctgcgg  2220
attaagttcc ctaccgtcgt cgccggattc gacctcgttg ggcatgagga tactggccat  2280
agtctccatg actataaaga agcccttatg atcccagcaa aggacggagt gaagctgccc  2340
tacttcttcc acgcagggga gaccgactgg cagggaacga gcatcgaccg gaacatactt  2400
gatgcactca tgcttaatac cacacgaatc ggccacggct tcgctctctc caagcaccca  2460
gccgtgagaa cctacagctg gaagaaggat atccccatcg aggtttgtcc catcagcaat  2520
caggtgctga aattggtgag tgacctgaga aaccacccag tcgcaacatt aatggccact  2580
ggccacccta tggtgatttc aagcgatgat ccagccatgt tcggagcaaa aggactcagt  2640
tacgacttct atgaggtatt catgggtatt ggtggtatga aggcagacct gcggactctt  2700
aagcagttgg caatgaactc aattaagtac tctaccttat tggagtctga aaagaacaca  2760
```

-continued

```
tttatggaga tctggaaaaa gcgctgggac aaattcatcg cagatgttgc cacaaaa     2817

SEQ ID NO: 288          moltype = DNA  length = 2817
FEATURE                 Location/Qualifiers
misc_feature            1..2817
                        note = Description of Artificial Sequence: Synthetic
                         polynucleotide
source                  1..2817
                        mol_type = other DNA
                        organism = synthetic construct
SEQUENCE: 288
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360
gctagcacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accatgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagagc  1320
ctctccctgt ctccgggtaa aggtggaggt ggttctggag gtggaggtag tatcgacgaa  1380
accagagcac acttactgct gaaagagaaa atgatgcgcc tgggcgggag attggtgtta  1440
aatactaagg aagagctggc aaatgaaaga ctcatgacac tgaagattgc tgaaatgaag  1500
gaggcgatga ggacgctgat ctttccgcct tccatgcact tcttccaagc taaacacctg  1560
atcgaaagat cccaagtgtt taacatcctg aggatgatgc ctaagggggc cgctctgcac  1620
cttcacgata ttgggattgt aacaatggac tggctggtaa ggaacgtgac atacagacct  1680
cattgccata tttgttttac tccccgagga atcatgcaat tcaggtttgc ccacccaact  1740
cctcggccaa gcgagaagtg tagtaagtgg attttgctgg aagattaccg taagcgcgtg  1800
cagaatgtga cagagtttga tgactccctg ctccgcaatt ttaccctggt gacccagcac  1860
cccgaagtta tatacactaa ccaaaatgtc gtgtggtcca agtttgagac gatcttcttc  1920
acgatttcag gcttgatcca ctacgccccg gtctttcggg attatgtgtt taggagtatg  1980
caggagtttt atgaggataa tgttctgtac atggagatcc gagcccagct gcttccagtc  2040
tacgaactat ccggcgaaca ccatgacgag gaatggagcg tcaagaccta tcaagaggtg  2100
gcccagaagt tcgtagaaac gcatccagag ttcatcggta ttaagattat ctacaatgat  2160
caccgctcaa aggatgtggc tgtcatcgcc gagtctatac ggatggccat gggcctgcgg  2220
attaagttcc ctaccgtcgt cgccggattc gacctcgttg ggcatgagga tactggccat  2280
agtctccatg actataaaga agcccttatg atcccagcaa aggacggagt gaagctgccc  2340
tacttcttcc acgcagggga gaccgactgg cagggaacga gcatcgaccg gaacatactt  2400
gatgcactca tgcttaatac cacacgaatc ggccacggct tcgctctctc caagcaccca  2460
gccgtgagaa cctacagctg ggataaggat atccccatcg aggtttgtcc catcagcaat  2520
caggtgctga aattggtgag tgacctgaga aaccacccag tcgcaacatt aatggccact  2580
ggccacccta tggtgatttc aagcgatgat ccagccatgt tcggagcaaa aggactcagt  2640
tacgacttct atgaggtatt catgggtatt ggtggtatga aggcagacct gcggactctt  2700
aagcagttgg caatgaactc aattaagtac tctaccttat tggagtctga aaagaacaca  2760
tttatggaga tctggaaaaa gcgctgggac aaattcatcg cagatgttgc cacaaaa     2817

SEQ ID NO: 289          moltype = AA  length = 592
FEATURE                 Location/Qualifiers
source                  1..592
                        mol_type = protein
                        organism = Homo sapiens
SEQUENCE: 289
MGRGLLRGLW PLHIVLWTRI ASTIPPHVQK SDVEMEAQKD EIICPSCNRT AHPLRHINND  60
MIVTDNNGAV KFPQLCKFCD VRFSTCDNQK SCMSNCSITS ICEKPQEVCV AVWRKNDENI  120
TLETVCHDPK LPYHDFILED AASPKCIMKE KKKPGETFFM CSCSSDECND NIIFSEEYNT  180
SNPDLLLVIF QVTGISLLPP LGVAISVIII FYCYRVNRQQ KLSSTWETGK TRKLMEFSEH  240
CAIILEDDRS DISSTCANNI NHNTELLPIE LDTLVGKGRF AEVYKAKLKQ NTSEQFETVA  300
VKIFPYEEYA SWKTEKDIFS DINLKHENIL QFLTAEERKT ELGKQYWLIT AFHAKGNLQE  360
YLTRHVISWE DLRKLGSSLA RGIAHLHSDH TPCGRPKMPI VHRDLKSSNI LVKNDLTCCL  420
CDFGLSLRLD PTLSVDDLAN SGQVGTARYM APEVLESRMN LENVESFKQT DVYSMALVLW  480
EMTSRCNAVG EVKDYEPPFG SKVREHPCVE SMKDNVLRDR GRPEIPSFWL NHQGIQMVCE  540
TLTECWDHDP EARLTAQCVA ERFSELEHLD RLSGRSCSEE KIPEDGSLNT TK          592

SEQ ID NO: 290          moltype = AA  length = 567
FEATURE                 Location/Qualifiers
source                  1..567
```

```
                        mol_type = protein
                        organism = Homo sapiens
SEQUENCE: 290
MGRGLLRGLW PLHIVLWTRI ASTIPPHVQK SVNNDMIVTD NNGAVKFPQL CKFCDVRFST  60
CDNQKSCMSN CSITSICEKP QEVCVAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQQKLSST WETGKTRKLM EFSEHCAIIL EDDRSDISST CANNINHNTE  240
LLPIELDTLV GKGRFAEVYK AKLKQNTSEQ FETVAVKIFP YEEYASWKTE KDIFSDINLK  300
HENILQFLTA EERKTELGKQ YWLITAFHAK GNLQEYLTRH VISWEDLRKL GSSLARGIAH  360
LHSDHTPCGR PKMPIVHRDL KSSNILVKND LTCCLCDFGL SLRLDPTLSV DDLANSGQVG  420
TARYMAPEVL ESRMNLENVE SFKQTDVYSM ALVLWEMTSR CNAVGEVKDY EPPFGSKVRE  480
HPCVESMKDN VLRDRGRPEI PSFWLNHQGI QMVCETLTEC WDHDPEARLT AQCVAERFSE  540
LEHLDRLSGR SCSEEKIPED GSLNTTK                                     567

SEQ ID NO: 291          moltype = AA  length = 327
FEATURE                 Location/Qualifiers
REGION                  1..327
                        note = Description of Artificial Sequence: Synthetic
                         polypeptide
source                  1..327
                        mol_type = protein
                        organism = synthetic construct
SEQUENCE: 291
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 292          moltype = AA  length = 327
FEATURE                 Location/Qualifiers
REGION                  1..327
                        note = Description of Artificial Sequence: Synthetic
                         polypeptide
source                  1..327
                        mol_type = protein
                        organism = synthetic construct
SEQUENCE: 292
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSPGK                                     327

SEQ ID NO: 293          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 293
GGGGSGGGS                                                         9

SEQ ID NO: 294          moltype = AA  length = 586
FEATURE                 Location/Qualifiers
REGION                  1..586
                        note = Description of Artificial Sequence: Synthetic
                         polypeptide
source                  1..586
                        mol_type = protein
                        organism = synthetic construct
SEQUENCE: 294
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK GGGGSGGGGS IPPHVQKSVN NDMIVTDNNG AVKFPQLCKF  480
CDVRFSTCDN QKSCMSNCSI TSICEKPQEV CVAVWRKNDE NITLETVCHD PKLPYHDFIL  540
EDAASPKCIM KEKKKPGETF FMCSCSSDEC NDNIIFSEEY NTSNPD                586

SEQ ID NO: 295          moltype = AA  length = 593
FEATURE                 Location/Qualifiers
REGION                  1..593
```

```
                         note = Description of Artificial Sequence: Synthetic
                          polypeptide
source                   1..593
                         mol_type = protein
                         organism = synthetic construct
SEQUENCE: 295
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGKGGG GSGGGGSIPP HVQKSVNNDM IVTDNNGAVK  480
FPQLCKFCDV RFSTCDNQKS CMSNCSITSI CEKPQEVCVA VWRKNDENIT LETVCHDPKL  540
PYHDFILEDA ASPKCIMKEK KKPGETFFMC SCSSDECNDN IIFSEEYNTS NPD         593

SEQ ID NO: 296           moltype = AA  length = 218
FEATURE                  Location/Qualifiers
REGION                   1..218
                         note = Description of Artificial Sequence: Synthetic
                          polypeptide
source                   1..218
                         mol_type = protein
                         organism = synthetic construct
SEQUENCE: 296
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 297           moltype = DNA  length = 1758
FEATURE                  Location/Qualifiers
misc_feature             1..1758
                         note = Description of Artificial Sequence: Synthetic
                          polynucleotide
source                   1..1758
                         mol_type = other DNA
                         organism = synthetic construct
SEQUENCE: 297
caggtgcagc tggtcgaaag cggaggagga gtggtccagc caggacgatc cctgagactg  60
gattgtaagg cctctggaat cacattctct aacagtggaa tgcactgggt gcgccaggca  120
ccaggaaaag gactggagtg ggtggccgtc atctggtacg acgggtcaaa gcgatactat  180
gcagatagcg tgaaaggaag gttcacaatt tcacgcgaca acagcaagaa tactctgttt  240
ctgcagatga actctctgag agcagaggat actgccgtgt actattgtgc taccaatgac  300
gattattggg ggcagggaac tctggtgacc gtcagttcag ctagcaccaa gggcccatcg  360
gtcttccccc tggcgccctg ctccaggagc acctccgaga gcacagccgc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acgaagacct acacctgcaa cgtagatcac  600
aagcccagca acaccaaggt ggacaagaga gttgagtcca aatatggtcc cccatgccca  660
ccatgcccag cacctgagtt cctgggggga ccatcagtct tcctgttccc cccaaaaccc  720
aaggacactc tcatgatctc ccggacccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tctgggtaaa  1320
ggtggaggtg gttctggagg tggaggtagt atccctcctc acgtacagaa gtccgtgaac  1380
aatgacatga ttgtcactga caataacgga gccgtcaagt ttcctcagct atgtaagttc  1440
tgcgatgttc ggttctccac atgcgataat cagaaaagct gtatgtctaa ttgcagtatc  1500
actagtatat gcgaaaaacc tcaagaagtt tgcgtcgccg tgtggcggaa aaatgatgaa  1560
aatatcacgc ttgagactgt ctgccatgat ccaaagttac cctaccacga cttcatctta  1620
gaagacgccg catcacccaa gtgcattatg aaagagaaaa agaagccagg agaaacattc  1680
tttatgtgct catgctcctc tgacgaatgc aacgacaaca ttatcttctc tgaggagtat  1740
aacacctcaa atccagac                                                1758

SEQ ID NO: 298           moltype = DNA  length = 1779
FEATURE                  Location/Qualifiers
misc_feature             1..1779
                         note = Description of Artificial Sequence: Synthetic
                          polynucleotide
source                   1..1779
                         mol_type = other DNA
                         organism = synthetic construct
```

```
SEQUENCE: 298
caggtgcagc tggtccagag cggcgtggaa gtcaagaaac ccggggcctc agtgaaggtc  60
agctgtaaag cttccggcta caccttcaca aactactata tgtattgggt gagacaggca  120
ccaggacagg gactggagtg gatgggcggg attaacccta gtaatggagg cactaacttc  180
aacgaaaagt ttaaaaacag ggtgaccctg accacagatt caagcactac cacagcttac  240
atggagctga agtccctgca gtttgacgat acagccgtgt actattgtgc tcggagagac  300
tacaggttcg atatgggctt tgactattgg ggccagggga ctaccgtgac cgtctcctct  360
gctagcacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accatgccca gcacctgagt tcctgggggg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagagc  1320
ctctccctgt ctctgggtaa aggtggaggt ggttctggag gtggaggtag tatccctcct  1380
cacgtacaga agtccgtgaa caatgacatg attgtcactg acaataacgg agccgtcaag  1440
tttcctcagc tatgtaagtt ctgcgatgtt cggttctcca catgcgataa tcagaaaagc  1500
tgtatgtcta attgcagtat cactagtata tgcgaaaaac ctcaagaagt ttgcgtcgcc  1560
gtgtggcgga aaaatgatga aaatatcacg cttgagactg tctgccatga tccaaagtta  1620
ccctaccacg acttcatctt agaagacgcc gcatcaccca agtgcattat gaaagagaaa  1680
aagaagccag gagaaacatt ctttatgtgc tcatgctcct ctgacgaatg caacgacaac  1740
attatcttct ctgaggagta taacacctca aatccagac                          1779

SEQ ID NO: 299         moltype = DNA  length = 642
FEATURE                Location/Qualifiers
misc_feature           1..642
                       note = Description of Artificial Sequence: Synthetic
                        polynucleotide
source                 1..642
                       mol_type = other DNA
                       organism = synthetic construct
SEQUENCE: 299
gagatcgtcc tgacacagag tccagcaact ctgagcctgt cccccggcga acgagctact  60
ctgtcctgcc gggcatctca gagtgtgtct agttacctgg cctggtatca gcagaagccc  120
ggccaggctc ctaggctgct gatctacgac gccagcaaca gagctaccgg gattcctgcc  180
aggttctcag gcagcgggtc cggaacagac tttaccctga caatctcaag cctggagccc  240
gaagatttcg ctgtgtacta ttgccagcag tcctctaatt ggcctcgcac ctttggccag  300
gggacaaagg tcgagatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                      642

SEQ ID NO: 300         moltype = DNA  length = 654
FEATURE                Location/Qualifiers
misc_feature           1..654
                       note = Description of Artificial Sequence: Synthetic
                        polynucleotide
source                 1..654
                       mol_type = other DNA
                       organism = synthetic construct
SEQUENCE: 300
gagatcgtcc tgactcagtc cccagcaacc ctgagtctgt caccaggaga aagggcaacc  60
ctgagctgcc gagcatccaa gggggtgagc acatccggat actcttatct gcactggtac  120
cagcagaaac ccggacaggc tcctcgactg ctgatctacc tggcatctta tctggagagt  180
ggcgtgcctg ctcggttctc tgggagtgga tcaggcaccg attttacact gactatttct  240
agtctggagc cagaagattt cgcagtgtac tattgccagc attctcgaga cctgcccctg  300
acatttggcg gggggaactaa ggtcgagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 301         moltype = AA  length = 30
FEATURE                Location/Qualifiers
REGION                 1..30
                       note = Description of Artificial Sequence: Synthetic
                        polypeptide
```

```
REGION                 1..30
                       note = MISC_FEATURE - This sequence may encompass 2-6 "Gly
                        Gly Gly Gly Ser" repeating units
source                 1..30
                       mol_type = protein
                       organism = synthetic construct
SEQUENCE: 301
GGGGSGGGGS GGGGSGGGGS GGGGSGGGGS                                   30

SEQ ID NO: 302         moltype = AA  length = 75
FEATURE                Location/Qualifiers
REGION                 1..75
                       note = Description of Artificial Sequence: Synthetic
                        polypeptide
REGION                 1..75
                       note = MISC_FEATURE - This sequence may encompass 0-15 "Gly
                        Gly Gly Gly Ser" repeating units
source                 1..75
                       mol_type = protein
                       organism = synthetic construct
SEQUENCE: 302
GGGGSGGGGS GGGGSGGGGS GGGGSGGGGS GGGGSGGGGS GGGGSGGGGS GGGGSGGGGS  60
GGGGSGGGGS GGGGS                                                   75

SEQ ID NO: 303         moltype = AA  length = 30
FEATURE                Location/Qualifiers
REGION                 1..30
                       note = Description of Artificial Sequence: Synthetic
                        polypeptide
REGION                 1..30
                       note = MISC_FEATURE - This sequence may encompass 0-15 "Gly
                        Ser" repeating units
source                 1..30
                       mol_type = protein
                       organism = synthetic construct
SEQUENCE: 303
GSGSGSGSGS GSGSGSGSGS GSGSGSGSGS                                   30

SEQ ID NO: 304         moltype = AA  length = 30
FEATURE                Location/Qualifiers
REGION                 1..30
                       note = Description of Artificial Sequence: Synthetic
                        polypeptide
REGION                 1..30
                       note = MISC_FEATURE - This sequence may encompass 0-15 "Ser
                        Gly" repeating units
source                 1..30
                       mol_type = protein
                       organism = synthetic construct
SEQUENCE: 304
SGSGSGSGSG SGSGSGSGSG SGSGSGSGSG                                   30

SEQ ID NO: 305         moltype = AA  length = 45
FEATURE                Location/Qualifiers
REGION                 1..45
                       note = Description of Artificial Sequence: Synthetic
                        polypeptide
REGION                 1..45
                       note = MISC_FEATURE - This sequence may encompass 0-15 "Gly
                        Ser Gly" repeating units
source                 1..45
                       mol_type = protein
                       organism = synthetic construct
SEQUENCE: 305
GSGGSGGSGG SGGSGGSGGS GGSGGSGGSG GSGGSGGSGG SGGSG                  45

SEQ ID NO: 306         moltype = AA  length = 60
FEATURE                Location/Qualifiers
REGION                 1..60
                       note = Description of Artificial Sequence: Synthetic
                        polypeptide
REGION                 1..60
                       note = MISC_FEATURE - This sequence may encompass 0-15 "Ser
                        Gly Ser Gly" repeating units
source                 1..60
                       mol_type = protein
                       organism = synthetic construct
SEQUENCE: 306
SGSGSGSGSG SGSGSGSGSG SGSGSGSGSG SGSGSGSGSG SGSGSGSGSG SGSGSGSGSG  60
```

-continued

```
SEQ ID NO: 307          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 307
ESKYGPPCPP CP                                                      12

SEQ ID NO: 308          moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 308
HHHHHH                                                             6

SEQ ID NO: 309          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 309
GGGGSGGGGS                                                         10
```